United States Patent
Lusso et al.

(10) Patent No.: US 11,760,790 B2
(45) Date of Patent: Sep. 19, 2023

(54) NEUTRALIZING ANTIBODIES TO HIV-1 ENV AND THEIR USE

(71) Applicant: The United States of America, as represented by the Secretary, Department of Health and Human Services, Bethesda, MD (US)

(72) Inventors: Paolo Lusso, Rockville, MD (US); Qingbo Liu, Rockville, MD (US); Peter Kwong, Washington, DC (US); John Mascola, Rockville, MD (US); Young Do Kwon, Kensington, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 325 days.

(21) Appl. No.: 16/971,826

(22) PCT Filed: Feb. 21, 2019

(86) PCT No.: PCT/US2019/019021
§ 371 (c)(1),
(2) Date: Aug. 21, 2020

(87) PCT Pub. No.: WO2019/165122
PCT Pub. Date: Aug. 29, 2019

(65) Prior Publication Data
US 2021/0079070 A1 Mar. 18, 2021

Related U.S. Application Data

(60) Provisional application No. 62/775,754, filed on Dec. 5, 2018, provisional application No. 62/633,517, filed on Feb. 21, 2018.

(51) Int. Cl.
*C07K 16/10* (2006.01)
*A61P 31/18* (2006.01)
*G01N 33/569* (2006.01)
*A61K 39/00* (2006.01)

(52) U.S. Cl.
CPC .......... *C07K 16/1063* (2013.01); *A61P 31/18* (2018.01); *G01N 33/56988* (2013.01); *A61K 2039/505* (2013.01); *C07K 2317/24* (2013.01); *C07K 2317/31* (2013.01); *C07K 2317/567* (2013.01); *C07K 2317/76* (2013.01); *C07K 2317/94* (2013.01); *G01N 2333/162* (2013.01)

(58) Field of Classification Search
None
See application file for complete search history.

(56) References Cited

U.S. PATENT DOCUMENTS

| 6,180,370 B1 * | 1/2001 | Queen .................... A61P 31/12 |
| | | 435/69.6 |
| 8,637,024 B2 | 1/2014 | Ho et al. |
| 2013/0209454 A1 | 8/2013 | Diskin et al. |
| 2015/0361160 A1 | 12/2015 | Burton et al. |

FOREIGN PATENT DOCUMENTS

| EP | 3783018 A1 * | 2/2021 | ............. A61K 39/42 |
| EP | 3390441 B1 * | 8/2021 | ........... A61K 39/395 |
| WO | WO 2015/128846 A1 | 9/2015 | |
| WO | WO 2016/154003 A1 | 9/2016 | |
| WO | WO 2016/205704 A2 | 12/2016 | |
| WO | WO 2017/133640 A1 | 8/2017 | |

OTHER PUBLICATIONS

Janeway, Charles A. "Immunobiology: The Immune System in Health and Disease." 2001 (Year: 2001).*
Sela-Culang, Inbal et al. Frontiers in immunology vol. 4 302. Oct. 8, 2013 (Year: 2013).*
Stryer, Biochemistry 4th, WH Freeman, New York. 1995 (Year: 1995).*
Xiang et al. J. Mol. Biol. (1995): 385-390 (Year: 1995).*
Zalevsky, Jonathan et al. "Enhanced antibody half-life improves in vivo activity." Nature biotechnology vol. 28,2 (2010): 157-9. doi:10.1038/nbt.1601 (Year: 2010).*
Monnier, Philippe P., Robin J. Vigouroux, and Nardos G. Tassew Antibodies 2.2 (2013): 193-208 (Year: 2013).*
Bournazos, Stylianos et al. "Bispecific Anti-HIV-1 Antibodies with Enhanced Breadth and Potency." Cell vol. 165,7 (2016): 1609-1620. doi:10.1016/j.cell.2016.04.050 (Year: 2016).*
Kipriyanov, Sergey M., and Fabrice Le Gall. "Generation and production of engineered antibodies." Molecular biotechnology 26.1 (2004): 39-60. (Year: 2004).*
Janeway, A. C., et al. "Immunobiology: the immune system in health and disease. London." Current Biology (1997): 3:1-3:11. (Year: 1997).*
Asokan et al., "Bispecific Antibodies Targeting Different Epitopes on the HIV-1 Envelope Exhibit Broad and Potent Neutralization," *J Virol*. 89.24: 12501-12512, Dec. 2015.
Diskin et al., "Increasing the Potency and Breadth of an HIV Antibody by using Structure-Based Rational Design," *Science* 334. 6060: 1289-1293, Dec. 2011.
Gaudinski et al., "A Phase-I Dose Escalation of Monoclonal Antibody VRC07-523LS in Healthy Adults," *Conference on Retroviruses and Opportunistic Infections, Boston, United States of America*, Mar. 2018.

(Continued)

*Primary Examiner* — Michael Szperka
*Assistant Examiner* — Lia E Taylor
(74) *Attorney, Agent, or Firm* — Klarquist Sparkman, LLP

(57) ABSTRACT

Antibodies and antigen binding fragments that specifically bind to HIV-1 Env and neutralize HIV-1 are disclosed. Nucleic acids encoding these antibodies, vectors and host cells are also provided. Methods for detecting HIV-1 using these antibodies are disclosed. In addition, the use of these antibodies, antigen binding fragment, nucleic acids and vectors to prevent and/or treat an HIV-1 infection is disclosed.

30 Claims, 39 Drawing Sheets

Specification includes a Sequence Listing.

(56) References Cited

OTHER PUBLICATIONS

Haynes et al., "Cardiolipin Polyspecific Autoreactivity in Two Broadly Neutralizing HIV-1 Antibodies," *Science* 308.5730: 1906-1908, Jun. 2005.
Huang et al., "Identification of a CD4-Binding-Site Antibody to HIV that Evolved Near-Pan Neutralization Breadth," *Immunity* 45.5: 1108-1121, Nov. 2016.
Kwon et al., "Surface-Matrix Screening Identifies Semi-Specific Interactions that Improve Potency of a Near Pan-Reactive HIV-1-Neutralizing Antibody," *Cell Rep.* 22.7: 1798-1809, Feb. 2018.
Li et al., "Mechanism of Neutralization of the Broadly Neutralizing HIV-1 Monoclonal Antibody VRC01," *J Virol.* 85.17: 8954-8967, Sep. 2011.
Li et al., "Human Immunodeficiency Virus Type 1 Env Clones from Acute and Early Subtype B Infections for Standardized Assessments of Vaccine-Elicited Neutralizing Antibodies," *J Virol.* 79.16: 10108-10125, Aug. 2005.
Liu et al., "Quaternary Contact in the Initial Interaction of CD4 with the HIV-1 Envelope Trimer," *Nat Struct Mol Biol.* 24.4: 370-378, Apr. 2017.
Lynch et al., "The Development of CD4 Binding Site Antibodies during HIV-1 Infection," *J Virol.* 86.14: 7588-7595, Jul. 2012.
Rudicell et al., "Enhanced Potency of a Broadly Neutralizing HIV-1 Antibody in Vitro Improves Protection Against Lentiviral Infection In Vivo," *J Virol.* 88.21: 12669-12682, Aug. 2014.
Sajadi et al., "Identification of Near Pan-Neutralizing Antibodies against HIV-1 by Deconvolution of Plasma Humoral Responses," *Cell* 173.7: 1783-1795, Jun. 2018.
Sun et al., "Recent Progress toward Engineering HIV-1-Specific Neutralizing Monoclonal Antibodies," *Frontiers in Immunology* 7.391: 1-8, Sep. 2016.
Third Party Observation from parent PCT Application No. PCT/US2019/019021, 13 pages, mailed Jun. 22, 2020.
Wu et al., "Rational Design of Envelope Identifies Broadly Neutralizing Human Monoclonal Antibodies to HIV-1," *Science* 329.5993: 856-861, Aug. 2010.
Wu et al., "Maturation and Diversity of the VRC01-Antibody Lineage over 15 Years of Chronic HIV-1 Infection," *Cell* 161.3: 470-485, Apr. 2015.
Pakula and Sauer, "Genetic analysis of protein stability and function," *Annual Review of Genetics* 23: 289-310 (1989).
A Study of the Safety and Pharmacokinetics of a Human Monoclonal Antibody, VRCHIVMAB0115-00-AB (VRC01.23LS), Administered Intravenously or Subcutaneously to Healthy Adults, https://clinicaltrials.gov/ct2/show/NCT05627258 (Nov. 25, 2022).
Kwon et al., "A matrix of structure-based designs yields improved VRC01-class antibodies for Hiv-1 therapy and prevention," *mAbs* 13:1, 1946918 (Jan.-Dec. 2021).
Leggat et al., "Vaccination induced HIV broadly neutralizing antibody precursors in humans," *Science* 378(6623): eadd6502 (e-Pub Dec. 2, 2022).
West et al., "Structural basis for germ-line gene usage of a potent class of antibodies targeting the CD4-binding site of HIV-1 gp120," *Proc. Natl. Acad. Sci. USA.* 109(30): E2083-E2090 (Jul. 24, 2012).
Zhou et al., "Multidonor analysis reveals structural elements, genetic determinants, and maturation pathway for HIV-1 neutralization by VRC01-Class antibodies," *Immunity* 39: 245-258 (Aug. 22, 2013).
Zhu et al., "De Novo identification of VRC01 class HIV-1 neutralizing antibodies by next generation sequencing of B-cell transcripts," *Proc. Natl, Acad. Sci. USA* 110(43):E4088- E4097 (e-PUB Oct. 8, 2013).
Zhu et al., "Mining the antibodyome for HIV-1-neutralizing antibodies with next-generation sequencing and phylogenetic pairing of heavy/light chains," *Proc. Natl, Acad. Sci. USA* 110(16): 6470-6475 (e-PUB Mar. 27, 2013).

\* cited by examiner

FIG. 1B

```
                 1         10        20        30         40
                 |          |         |         |          |
Heavy Chain  _____FR1_____  CDR1_  _____FR2_____
  IGHV1-2*02 QVQLVQSGAEVKKPGASVKVSCKAS-GYTFT       GYYMH   WVRQAPGQGLEWMG
          N6 RAHLVQSGTAMKKPGASVRVSCQTS-GYTFT       AHILF   WFRQAPGRGLEWVG
       VRC01 QVQLVQSCGQMKKPGESMRISCRAS-GYEFI       DCTLN   WIRLAPCKRPEWMG
       VRC07 QVRLSQSGGQMKKPGDSMRISCRAS-GYEFI       NCPIN   WIRLAPGKRPEWMG
   VRC07-523 QVRLSQSGGQMKKPGDSMRISCRAS-GYEFI       NCPIN   WIRLAPGKRPEWMG
     3BNC117 QVQLLQSGAAVTKPGASVRVSCEAS-GYNIR       DYFIH   WWRQAPGQGLQWVG
     VRC-PG04 QVQLVQSGSGVKKPGASVRVSCWTSEDIFER      TELIH   WVRQAPGQGLEWIG
       N49P7 -ADLVQSGAVVKKPGDSVRISCEAQ-GYRFP       DYIIH   WIRRAPGQGPEWMG
       VRC08 EVQLVQSGTQMKEPGASVTISCVTS-GYEFV       EILIN   WVRQVPGRGLEWMG
       VRC03 QVQLVQSGAVIKTPGSSVKISCRAS-GYNFR       DYSIH   WVRLIPDKGFEWIG
       VRC06 EVQLVESGPVMRKPGSSMKISCATS-GYNFR       DFSIH   WVRFNRRYGFEWIG 5052A  57 60                70                 8082ABC         90
               |  || |   |                 |                  | ||||          |
Heavy Chain  _____CDR2_____  _____FR3_____
  IGHV1-2*02 WINPNSGGTNYAQKFQG   RVTMTRDTSI--------STAYMELSRLRSDDTAVYYCAR
          N6 WIKPQYGAVNFGGGFRD   RVTLTRDVYR--------EIAYMDIRGLKPDDTAVYYCAR
       VRC01 WLKPRGGAVNYARPLQG   RVTMTRDVYS--------DTAFLELRSLTVDDTAVYFCTR
       VRC07 WMKPRGGAVSYARQLQG   RVTMTRDMYS--------ETAFLELRSLTSDDTAVYFCTR
   VRC07-523 WMKPRHGAVSYARQLQG   RVTMTRDMYS--------ETAFLELRSLTSDDTAVYFCTR
     3BNC117 WINPKTGQPNNPRQFQG   RVSLTRHASWDF---DTFSFYMDLKALRSDDTAVYFCAR
     VRC-PG04 WVKTVTGAVNFGSPDFRQ  RVSLTRDRDL--------FTAHMDIRGLTQGDTATYFCAR
       N49P7 WMNPMGGQVNIPWKFQG   RVSMTRDTSI--------ETAFLDLRGLKSDDTAVYYCVR
       VRC08 WMNPRGGGVNYARQFQG   KVTMTRDVYR--------DTAYLTLSGLTSGDTAKYFCVR
       VRC03 WIKPLWGAVSYARQLQG   RVSMTRQLSQDPDDPDWGVAYMEFSGLTSADTAEYFCVR
       VRC06 WIKPMWGAVNYARQLQG   RVSMSRLFSQDLYYPDRGTAYLEFSGLTSADTADYFCVR 99   100ABCD 102          113
                 |    |||||   |            |
Heavy Chain  _____CDR3_____  FR4(HJ5*01)
  IGHV1-2*02 AYCGG----DCYNWFDS      WGQGTLVTVSS
          N6 DRSYG----DSSWALDA      WGQGTTVVVSA
       VRC01 GKNCD-----YNWDFEH      WGRGTPVIVSS
       VRC07 GKYCTARDYYNWDFEH       WGQGTPVTVSS
   VRC07-523 GKYCTARDYYNWDFEH       WGQGTPVTVSS
     3BNC117 QRSDY-------WDFDV      WGSGTQVTVSS
     VRC-PG04 QKFYTGGQG--WYFDL       WGRGTLIVVSS
       N49P7 DRSNGSGKRFESSNWFLDL    WGRGTAVTIQS
       VRC08 GRSCCGGRRHCNGADCFN     WDFQHWGQGTLVIVSP
       VRC03 RGSCDYCGD--FPWQY       WGQGTWVVSSA
       VRC06 RGSSCPHCGD-FHFEH       WGQGTAVVVSA
```

FIG. 1C

| | Mutations | | |
|---|---|---|---|
| VRC03del | SQDPDDPD | → | GPG |
| VRC06del | SQDLYYPDR | → | GPG |
| VRC01 70-03 | DVYSD | → | QLSQDPDDPDWG |
| VRC01 70-06 | DVYSD | → | LFSQDLYYPDRG |
| N6 70-03 | DVYRE | → | QLSQDPDDPDWG |
| N6 70-06 | DVYRE | → | LFSQDLYYPDRG |
| VRC07 70-03 | DMYSE | → | QLSQDPDDPDWG |
| VRC07-523 70-03 | DMYSE | → | QLSQDPDDPDWG |
| 3BNC117 70-03 | HASWDFDTF | → | QLSQDPDDPDWG |
| VRC-PG04 70-03 | DRDLF | → | QLSQDPDDPDWG |
| N97P7 70-03 | DTSIE | → | QLSQDPDDPDWG |
| VRC08 70-03 | DVYRD | → | QLSQDPDDPDWG |

FIG. 1D

```
                       1         10         20         30              40              5052
                       |          |          |          |               |               | |
Kappa Chain   _____FR1_____ ____CDR1____  _____FR2_____  _CDR2__
IGKV1-33*01   DIQMTQSPSSLSASVGDRVTITC   QASQDISNYLN   WYQQKPGKAPKLLIY   DASNLET
         N6   YIHVTQSPSSLSVSIGDRVTINC   QTSQGVGSDLH   WYQHKPGRAPKLLIH   HTSSVED
      VRC01   EIVLTQSPGTLSLSPGETAIISC   RTSQYGSLA     WYQQRPGQAPRLVIY   SGSTRAA
      VRC07   EIVLTQSPGTLSLSPGETAIISC   RTSQYGSLA     WYQQRPGQAPRLVIY   SGSTRAA
  VRC07-523   --SLTQSPGTLSLSPGETAIISC   RTSQYGSLA     WYQQRPGQAPRLVIY   SGSTRAA
    3BNC117   DIQMTQSPSSLSASVGDTVTITC   QANGYLN       WYQQRRGKAPKLLIY   DGSKLER
    VRC-PG04  EIVLTQSPGTLSLSPGETASLSC   TAASYGHMT     WYQKKPGQPPKLLIF   ATSKRAS
      N49P7   QSALTQ-PRSVSASPGQSVTISC   TGTHNLVS      WCQHQPGRAPKLLIY   DFNKRPS
      VRC08   YIGVTQSPAILSVSLGERVTLSC   KTSQAITPRHLV  WHRQKGGQAPSLVMT   GTSERAS
      VRC03   EIVLTQSPGILSLSPGETATLFC   KASQGGNAMT    WYQKRRGQVPRLLIY   DTSRRAS
      VRC06   EIVLTQSPATLSLSPGERATLSC   RASQGGNSLN    WYQKRRGQTPRLLIY   DTSRRAS 60         70         80          90          100       107
                                 |          |          |           |           |          |
Kappa Chain   _____FR3_____   ___CDR3___  FR4(KJ5*01)
IGKV1-33*01   GVPSRFSGSGSGTDFTFTISSLQPEDIATYYC    QQYDNLPIT   FGQGTRLEIK
         N6   GVPSRFSGSGFHTSFNLTISDLQADDIATYYC    QVL----QF   FGRGSRLHIK
      VRC01   GIPDRFSGSRWGPDYNLTISNLESGDFGVYYC    QQY----EF   FGQGTKVQVDIK
      VRC07   GIPDRFSGSRWGPDYNLTISNLESGDFGVYYC    QQY----EF   FGQGTKVQVDIK
  VRC07-523   GIPDRFSGSRWGPDYNLTISNLESGDFGVYYC    QQY----EF   FGQGTKVQVDIK
    3BNC117   GVPSRFSGRRWGQEYNLTINNLQPEDIATYFC    QVY----EF   VVPGTRLDLK
    VRC-PG04  GIPDRFSGSQFGKQYTLTITRMEPEDFARYYC    QQL---EFF   GQGTRLEIRRTV
      N49P7   GVPDRFSGSGSGGTASLTITGLQDDDAEYFC     WAY----EA   FGGGTKLTVLGQPK
      VRC08   GIPDRFIGSGSTDFTLTITRLEAEDFAVYYC     QCL----EA   FGQGTKLEIK
      VRC03   GVPDRFVGSGSGTDFFLTINKLDREDFAVYYC    QQF----EF   FGLGSELEVH
      VRC06   DIPEKFVGSGSGTDFSLTITKVGPEDFAVYYC    QQF----EF   FGLGTTLEIN
```

FIG. 1E
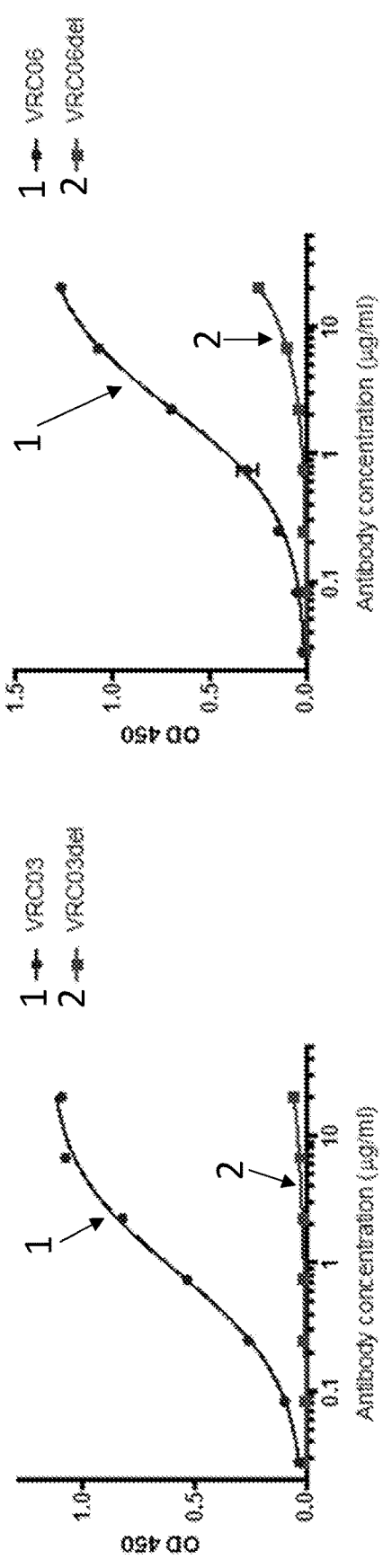
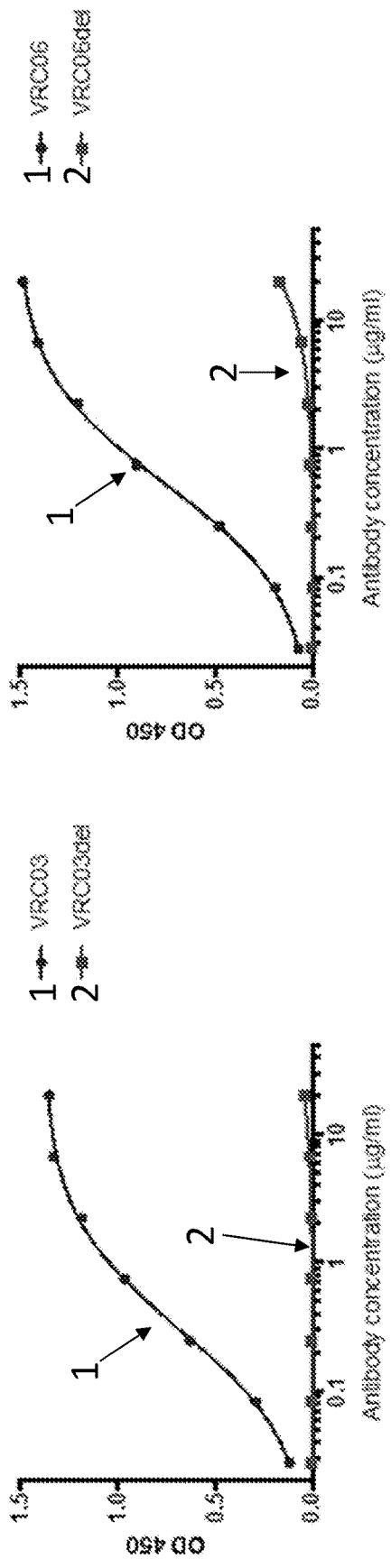

FIG. 1F
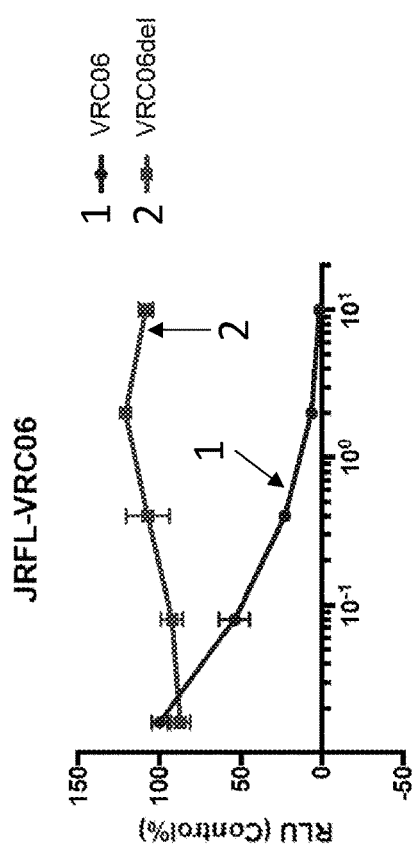
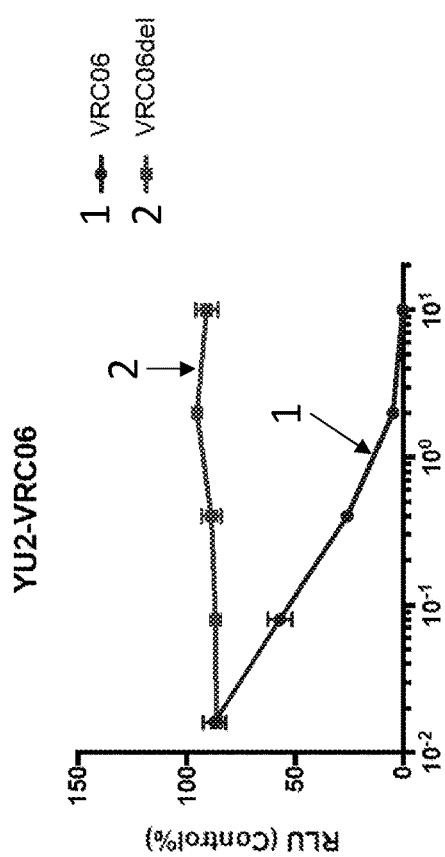
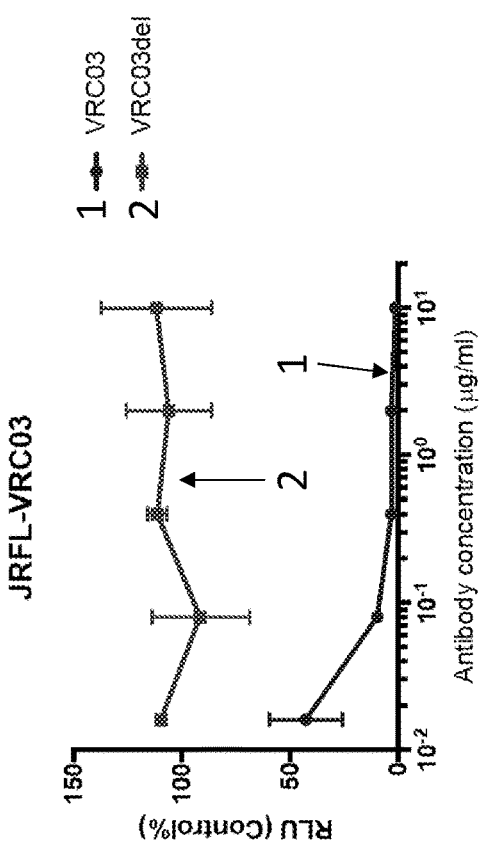
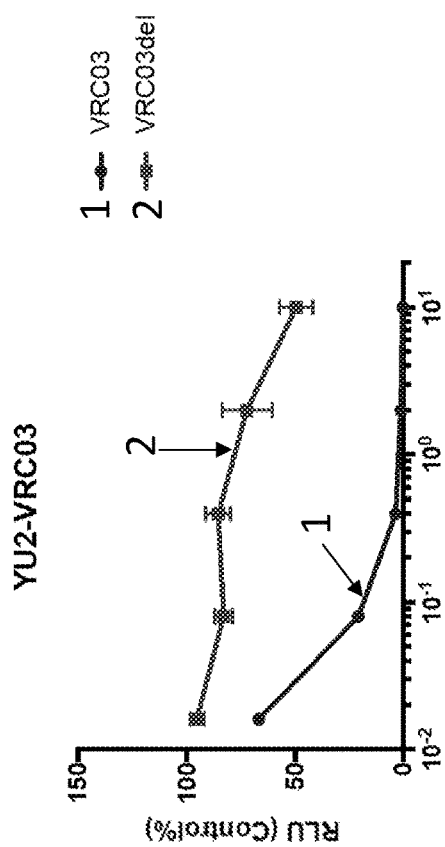

FIG. 2B
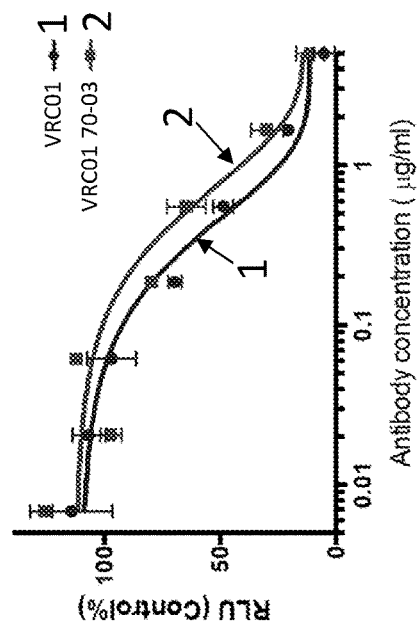
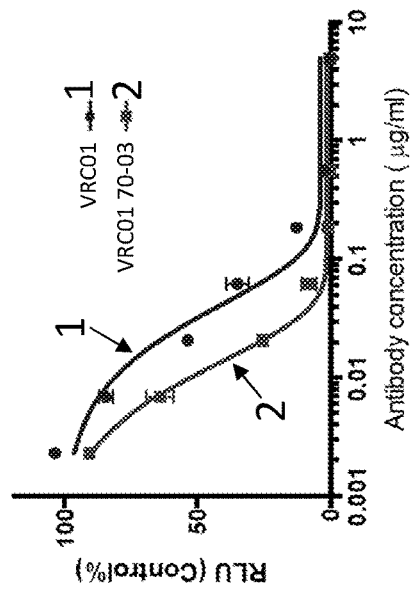
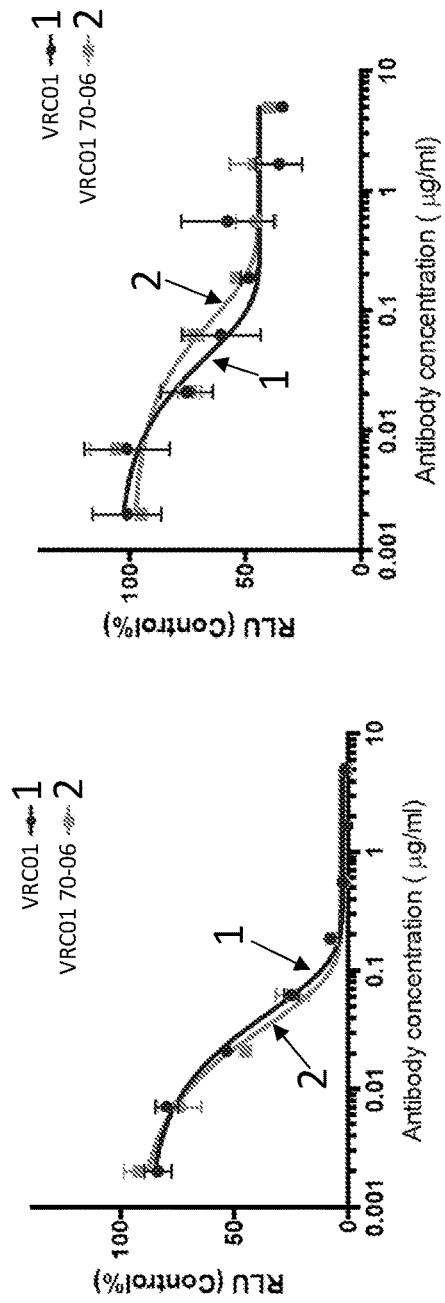

FIG. 3A

Neutralization potency (IC50, µg/mL)

| | Virus | Clade | Tier | N6 | N6 70-03 | VRC01 | VRC01 70-03 | VRC07 | VRC07 70-03 | 3BNC117 | 3BNC117 70-03 | VRC07-523-LS | VRC07-523-LS 70-03 |
|---|---|---|---|---|---|---|---|---|---|---|---|---|---|
| 1 | TRO11 | B | 1 | 0.190 | 0.067 | 0.532 | 0.090 | 0.362 | 0.062 | 0.045 | 0.091 | 0.124 | 0.018 |
| 2 | 25710 | C | 1B | 0.057 | 0.050 | 1.217 | 0.230 | 0.391 | 0.199 | 0.299 | 0.228 | 0.036 | 0.055 |
| 3 | 398F1 | A | 2 | 0.049 | 0.058 | 0.180 | 0.146 | 0.192 | 0.058 | 0.064 | 0.089 | 0.049 | 0.063 |
| 4 | CNE8 | AE | 2 | 0.044 | 0.034 | 0.448 | 0.248 | 0.195 | 0.271 | 0.099 | 0.150 | 0.045 | 0.035 |
| 5 | X2278 | B | 2 | 0.413 | 0.032 | 0.155 | 0.010 | 0.027 | 0.010 | 0.017 | 0.011 | 0.010 | 0.007 |
| 6 | BJOX002000 | BC | 2 | 0.064 | 0.072 | 2.129 | 0.771 | >10 | >10 | >10 | >10 | 0.215 | 0.065 |
| 7 | X1632 | G | 2 | 0.041 | 0.061 | 0.096 | 0.056 | 0.036 | 0.009 | 0.040 | 0.038 | 0.026 | 0.005 |
| 8 | CEA176 | C | 2 | 0.562 | 0.293 | 2.872 | 3.636 | 1.208 | 0.761 | 0.154 | 0.133 | 0.165 | 0.371 |
| 9 | 246F3 | AC | 2 | 0.105 | 0.104 | 0.538 | 0.294 | 0.414 | 0.373 | 0.190 | 0.133 | 0.274 | 0.082 |
| 10 | CH119 | BC | 2 | 0.107 | 0.144 | 0.464 | 0.850 | 0.232 | 0.425 | 5.041 | 1.007 | 0.075 | 0.116 |
| 11 | CEO217 | C | 2 | 0.063 | 0.039 | 0.141 | 0.165 | 0.144 | 0.084 | 0.038 | 0.064 | 0.117 | 0.021 |
| 12 | CNE55 | AE | 2 | 0.091 | 0.048 | 0.175 | 0.141 | 0.226 | 0.067 | 0.030 | 0.078 | 0.022 | 0.038 |

FIG. 3B

| | Virus | Clade | Tier | Neutralization potency (IC50, µg/ml) | | | |
|---|---|---|---|---|---|---|---|
| | | | | VRC01 | VRC01 70-03 | N6 | N6 70-03 |
| 1 | BG505 | A | 2 | 0.072 | 0.039 | 0.115 | 0.025 |
| 2 | Q168 | A | 2 | 0.09 | 0.014 | 0.072 | 0.043 |
| 3 | 398F1 | A | 2 | 0.18 | 0.146 | 0.049 | 0.058 |
| 4 | 246F3 | AC | 2 | 0.538 | 0.294 | 0.105 | 0.104 |
| 5 | BaL | B | 1B | 0.04 | 0.037 | 0.022 | 0.028 |
| 6 | JRFL | B | 2 | 0.017 | 0.01 | 0.007 | 0.004 |
| 7 | JRCSF | B | 2 | 0.162 | 0.089 | 0.13 | 0.032 |
| 8 | YU2 | B | 2 | 0.108 | 0.031 | 0.036 | 0.02 |
| 9 | CAAN | B | 2 | 1.138 | 2.877 | 0.322 | 0.665 |
| 10 | PVO | B | 3 | 0.423 | 0.105 | 0.37 | 0.128 |
| 11 | X2278 | B | 2 | 0.155 | 0.113 | 0.413 | 0.032 |
| 12 | TRO11 | B | 2 | 0.532 | 0.09 | 0.19 | 0.087 |
| 13 | BJOX002000 | BC | 2 | 2.129 | 0.771 | 0.064 | 0.072 |
| 14 | CH119 | BC | 2 | 0.464 | 0.85 | 0.107 | 0.144 |
| 15 | 25710 | C | 1B | 1.217 | 0.43 | 0.057 | 0.05 |
| 16 | CE1176 | C | 2 | 2.872 | 3.636 | 0.562 | 0.293 |
| 17 | CE0217 | C | 2 | 0.141 | 0.165 | 0.063 | 0.039 |
| 18 | ZM106 | C | 2 | 0.37 | 0.159 | 0.048 | 0.026 |
| 19 | DU422 | C | 2 | >5 | >5 | 0.045 | 0.17 |
| 20 | CNE8 | AE | 2 | 0.448 | 0.248 | 0.044 | 0.034 |
| 21 | CNE55 | AE | 2 | 0.175 | 0.141 | 0.091 | 0.034 |
| 22 | C1080 | AE | 2 | 0.408 | 0.891 | 0.166 | 0.118 |
| 23 | X1632 | G | 2 | 0.096 | 0.038 | 0.041 | 0.021 |
| | Increased neutralization: | | | | 16/23 (69.6%) | | 15/23 (65.2%) |

FIG. 4A
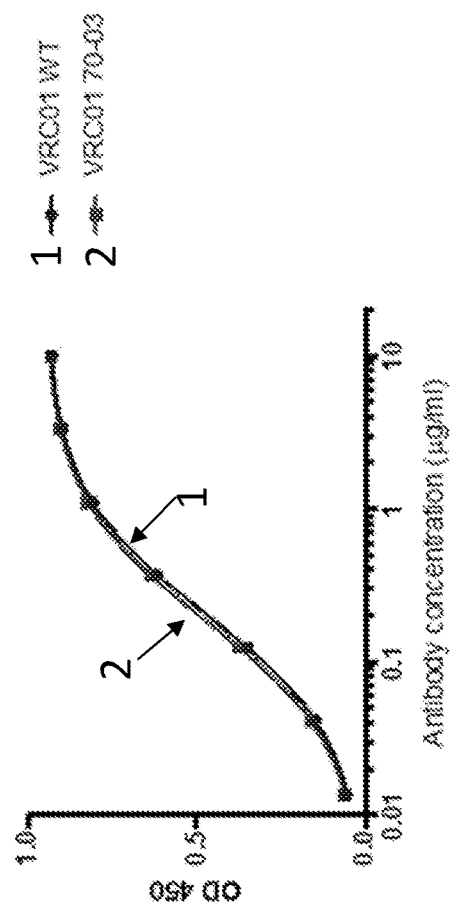
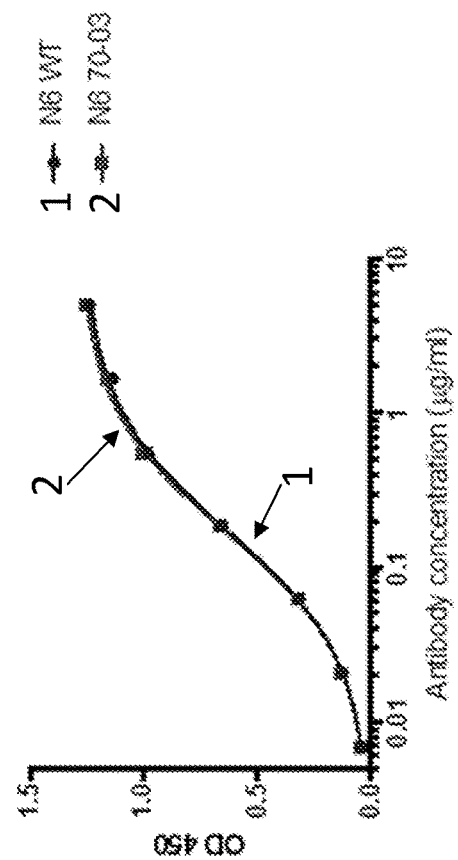
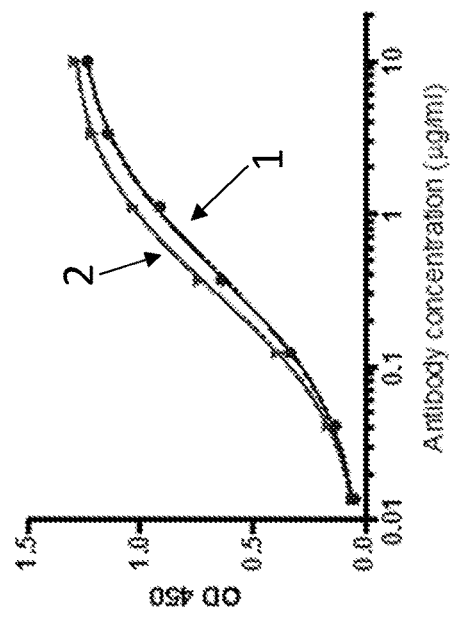
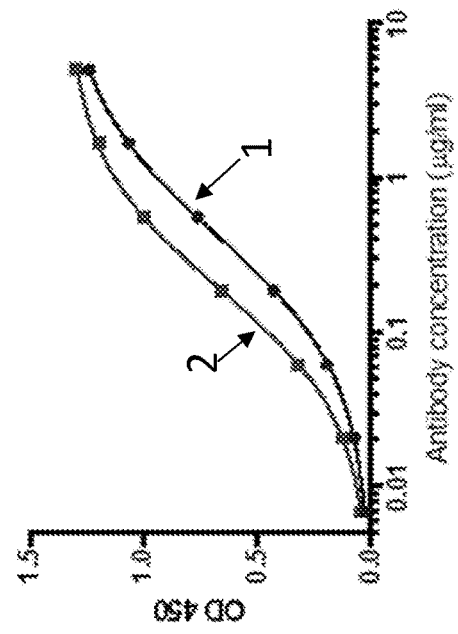

|  | ka | kd | KD |
|---|---|---|---|
| N6 Fab | 2.08E+04 | 7.41E-06 | 0.36 nM |
| N6 70-03 Fab | 1.07E+04 | 1.75E-07 | 0.016 nM |
| VRC01 Fab | 4.99E+03 | 1.10E-04 | 22.1 nM |
| VRC01 70-03 Fab | 5.62E+03 | 4.72E-05 | 8.4 nM |

20's loop:

GYEF→
EDDDY         (20loop, SEQ ID NO: 46)
GEDDDY        (G20, SEQ ID NO: 47)
GSGEDDDY      (GSG20, SEQ ID NO: 48)
EDDDYG        (20G, SEQ ID NO: 49)
GEDDDYG       (G20G, SEQ ID NO: 50)
GSGEDDDYG     (GSG20G, SEQ ID NO: 51)

FIG. 7B

BG505 vs VRC01 20loop mutants

1 — WT
2 — 20loop
3 — G20
4 — GSG20
5 — 20G
6 — G20G
7 — GSG20G

BaL vs VRC01 20loop mutants

1 — WT
2 — 20loop
3 — G20
4 — GSG20
5 — 20G
6 — G20G
7 — GSG20G

FIG. 8A
```
                Mutations
VRC01 70-03    DVYSD → QLSQDPDDPDWG
VRC01 70-G03   DVYSD → GQLSQDPDDPDWG
VRC01 70-GSG03 DVYSD → GSGQLSQDPDDPDWG
VRC01 70-G03S  DVYSD → GQLSQDPDDPDWGS
VRC01 70-03D   DVYSD → QLSQDPDDPDWGD
```
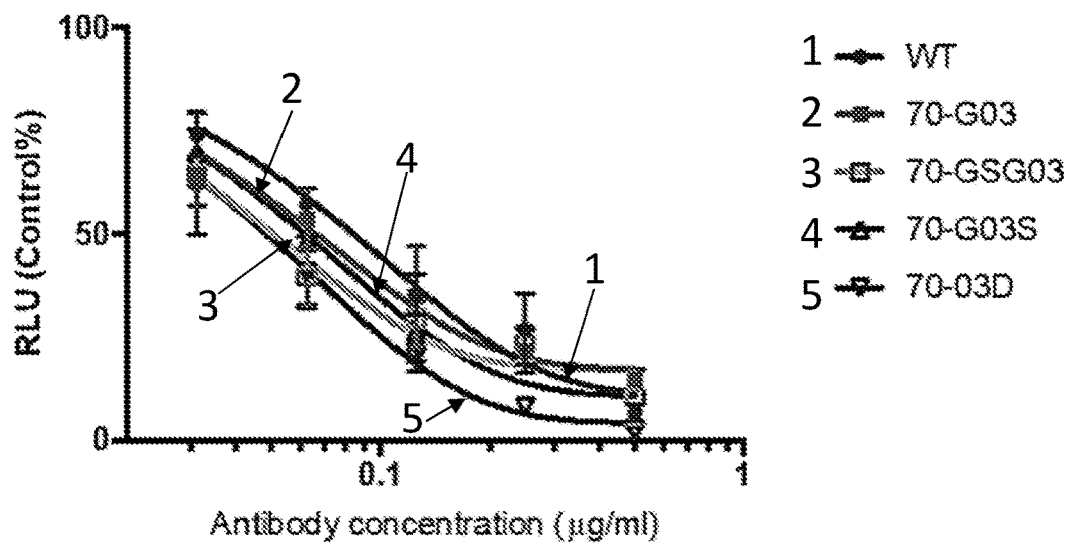
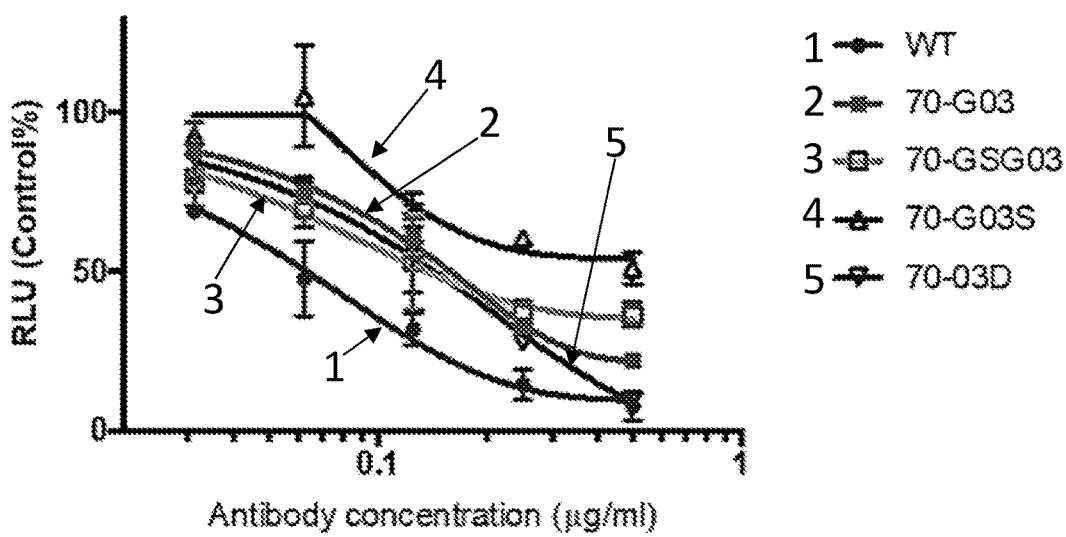

Point mutations

FIG. 9A

Neutralization IC50

IC50 (μg/ml)

| virus | clade | VRC01.11 YDK | VRC01.12 YDK | VRC01.13 YDK | VRC01.21 YDK | VRC01.22 YDK | VRC01.23 YDK | VRC01.31 YDK | VRC01.32 YDK | VRC01.33 YDK | VRC01.41 YDK | VRC01.42 YDK | VRC01.43 YDK | VRC07-523-LS YDK | VRC01 HiMC |
|---|---|---|---|---|---|---|---|---|---|---|---|---|---|---|---|
| Q23.17.SG3 | A | 0.088 | 0.062 | 0.061 | 0.022 | 0.024 | 0.023 | 0.117 | 0.102 | 0.100 | 0.061 | 0.032 | 0.031 | 0.083 | 0.184 |
| UG037.8.SG3 | A | 0.087 | 0.076 | 0.080 | 0.030 | 0.048 | 0.020 | 0.080 | 0.070 | 0.072 | 0.041 | 0.036 | 0.032 | 0.060 | 0.300 |
| 242-14.SG3 | AG | 50 | 9.01 | 11.7 | 7.83 | 1.06 | 0.614 | 50 | 50 | 50 | 44.1 | 1.53 | 1.91 | 0.381 | 50 |
| 7165.18.SG3 | B | 6.70 | 3.49 | 2.98 | 3.79 | 1.71 | 1.80 | 11.4 | 6.44 | 6.01 | 9.09 | 3.42 | 3.03 | 3.67 | 50 |
| AC10.29.SG3 | B | 0.785 | 0.487 | 0.416 | 0.733 | 0.394 | 0.436 | 1.17 | 0.885 | 0.708 | 1.48 | 0.793 | 0.849 | 0.602 | 3.26 |
| JRFL.JB.SG3 | B | 0.025 | 0.021 | 0.022 | 0.009 | 0.006 | 0.007 | 0.038 | 0.030 | 0.037 | 0.012 | 0.011 | 0.012 | 0.019 | 0.077 |
| QH0692.42.SG3 | B | 1.77 | 1.18 | 1.11 | 0.315 | 0.224 | 0.218 | 1.84 | 1.32 | 1.27 | 0.395 | 0.337 | 0.314 | 1.44 | 4.33 |
| DU151.02.SG3 | C | 0.281 | 0.191 | 0.131 | 0.070 | 0.051 | 0.044 | 0.530 | 0.289 | 0.199 | 0.139 | 0.094 | 0.087 | 0.184 | 40.6 |
| DU172.17.SG3 | C | 0.256 | 0.228 | 0.127 | 0.291 | 0.472 | 0.251 | 0.660 | 0.617 | 0.417 | 1.34 | 1.04 | 0.610 | 0.197 | 50 |
| TV1.29.SG3 | C | 50 | 50 | 50 | 50 | 50 | 50 | 50 | 50 | 50 | 50 | 50 | 50 | 3.45 | 50 |
| ZM53.12.SG3 | C | 1.75 | 1.63 | 1.16 | 2.53 | 2.21 | 1.94 | 2.06 | 1.56 | 1.61 | 4.87 | 3.40 | 2.01 | 0.529 | 3.93 |
| 57128.vrc15.SG3 | D | 13.5 | 1.97 | 1.85 | 8.17 | 2.86 | 2.64 | 21.3 | 5.04 | 2.52 | 50 | 4.66 | 3.51 | 1.90 | 50 |
| Median IC50 | | 1.268 | 0.834 | 0.763 | 0.524 | 0.433 | 0.344 | 1.505 | 1.103 | 0.989 | 1.410 | 0.917 | 0.730 | 0.455 | 22.465 |
| Geometric Mean IC50 | | 1.185 | 0.694 | 0.618 | 0.555 | 0.378 | 0.315 | 1.623 | 1.155 | 1.016 | 1.241 | 0.577 | 0.514 | 0.395 | 6.161 |

For geometric mean and median calculation, >50's were treated as 50.

FIG. 9B

Neutralization IC80

IC80 (μg/ml)

| virus | clade | VRC01 11 YDK | VRC01 12 YDK | VRC01 13 YDK | VRC01 21 YDK | VRC01 22 YDK | VRC01 23 YDK | VRC01 31 YDK | VRC01 32 YDK | VRC01 33 YDK | VRC01 41 YDK | VRC01 42 YDK | VRC01 43 YDK | VRC07-523-LS YDK | VRC01 HIMC YDK |
|---|---|---|---|---|---|---|---|---|---|---|---|---|---|---|---|
| Q23.17.SG3 | A | 0.197 | 0.154 | 0.141 | 0.056 | 0.058 | 0.058 | 0.283 | 0.242 | 0.256 | 0.113 | 0.091 | 0.083 | 0.188 | 0.555 |
| UG037.8.SG3 | A | 0.208 | 0.192 | 0.227 | 0.089 | 0.080 | 0.066 | 0.237 | 0.212 | 0.206 | 0.122 | 0.083 | 0.094 | 0.152 | 0.702 |
| 242-14.SG3 | AG | 50 | 50 | 50 | 50 | 7.07 | 6.95 | 50 | 50 | 50 | 50 | 21.0 | 36.3 | 1.70 | 50 |
| 7165.18.SG3 | B | 24.1 | 9.18 | 8.03 | 10.5 | 4.77 | 4.45 | 20.4 | 13.9 | 13.6 | 24.4 | 8.65 | 7.95 | 9.58 | 50 |
| AC10.29.SG3 | B | 2.20 | 1.29 | 1.17 | 2.21 | 1.13 | 1.11 | 3.82 | 2.57 | 1.94 | 3.63 | 2.18 | 1.99 | 1.38 | 7.30 |
| JRFL.JB.SG3 | B | 0.073 | 0.058 | 0.062 | 0.023 | 0.018 | 0.017 | 0.108 | 0.066 | 0.089 | 0.031 | 0.027 | 0.029 | 0.046 | 0.299 |
| QH0692.42.SG3 | B | 4.28 | 3.31 | 3.25 | 0.699 | 0.505 | 0.468 | 4.60 | 3.12 | 2.93 | 0.848 | 0.619 | 0.659 | 3.89 | 10.9 |
| DU151.02.SG3 | C | 0.715 | 0.418 | 0.339 | 0.169 | 0.133 | 0.104 | 1.92 | 0.793 | 0.629 | 0.332 | 0.203 | 0.210 | 0.541 | 50 |
| DU172.17.SG3 | C | 2.07 | 1.55 | 0.941 | 2.54 | 4.26 | 1.89 | 3.95 | 3.38 | 1.82 | 13.8 | 8.13 | 3.46 | 1.02 | 50 |
| TV1.29.SG3 | C | 50 | 50 | 50 | 50 | 50 | 50 | 50 | 50 | 50 | 50 | 50 | 50 | 24.5 | 50 |
| ZM53.12.SG3 | C | 3.81 | 2.25 | 2.59 | 6.35 | 5.16 | 4.53 | 4.32 | 3.33 | 3.30 | 11.5 | 7.31 | 5.76 | 1.24 | 9.48 |
| 57128.vrc15.SG3 | D | 50 | 7.02 | 5.41 | 32.6 | 8.33 | 6.66 | 50 | 21.8 | 8.33 | 50 | 12.9 | 11.7 | 5.45 | 50 |
| Median IC80 | | 3.005 | 1.900 | 1.880 | 2.375 | 2.695 | 1.500 | 4.135 | 3.225 | 2.435 | 7.565 | 4.745 | 2.725 | 1.310 | 30.450 |
| Geometric Mean IC80 | | 2.941 | 1.860 | 1.721 | 1.652 | 1.058 | 0.807 | 3.851 | 2.730 | 2.351 | 2.778 | 1.644 | 1.561 | 1.211 | 10.268 |

For geometric mean and median calculation, >50's were treated as 50.

FIG. 10A

Neutralization of a Multiclade Panel of 208 Viruses
*CD4bs mAb Improvements*

FIG. 10C

NVITAL/VRC Multiclade Panel

| IC50 | VRC01 | VRC01_7 0-03 | VRC01.23 | VRC07 | VRC07_7 0-03 | VRC07-523-LS | VRC07-523_70-03-LS | VRC07-523-LS N72Q R24D | N6-LS | N6_70-03 | 3BNC117 | 3BNC117_70-03 | VRC03 | VRC07-523LS.v3 |
|---|---|---|---|---|---|---|---|---|---|---|---|---|---|---|
| # Viruses | 208 | 208 | 208 | 208 | 208 | 208 | 208 | 208 | 208 | 208 | 208 | 208 | 208 | 207 |
| % VS Neutralized | | | | | | | | | | | | | | |
| IC50 <50ug/ml | 90 | 89 | 96 | 93 | 94 | 96 | 97 | 94 | 98 | 97 | 85 | 85 | 50 | 97 |
| IC50 <10ug/ml | 89 | 88 | 96 | 92 | 92 | 96 | 97 | 93 | 97 | 97 | 84 | 82 | 44 | 97 |
| IC50 <1.0ug/ml | 72 | 72 | 94 | 85 | 85 | 91 | 94 | 90 | 95 | 93 | 77 | 71 | 35 | 96 |
| IC50 <0.1ug/ml | 17 | 30 | 73 | 38 | 46 | 51 | 68 | 58 | 63 | 64 | 40 | 31 | 17 | 86 |
| *For Sensitive Viruses Only:* | | | | | | | | | | | | | | |
| Median IC50 | 0.330 | 0.207 | 0.041 | 0.143 | 0.106 | 0.090 | 0.063 | 0.068 | 0.069 | 0.056 | 0.110 | 0.149 | 0.290 | 0.023 |
| Geometric Mean | 0.337 | 0.228 | 0.042 | 0.140 | 0.123 | 0.098 | 0.058 | 0.076 | 0.072 | 0.063 | 0.125 | 0.202 | 0.359 | 0.024 |
| *For All Viruses:* | | | | | | | | | | | | | | |
| Median IC50 | 0.391 | 0.246 | 0.042 | 0.150 | 0.111 | 0.096 | 0.065 | 0.076 | 0.071 | 0.057 | 0.139 | 0.215 | 48.8 | 0.024 |
| Geometric Mean | 0.544 | 0.404 | 0.055 | 0.209 | 0.174 | 0.128 | 0.073 | 0.114 | 0.081 | 0.079 | 0.315 | 0.460 | 4.24 | 0.030 |

| IC80 | VRC01 | VRC01_7 0-03 | VRC01.23 | VRC07 | VRC07_7 0-03 | VRC07-523-LS | VRC07-523_70-03-LS | VRC07-523-LS N72Q R24D | N6-LS | N6_70-03 | 3BNC117 | 3BNC117_70-03 | VRC03 | VRC07-523LS.v3 |
|---|---|---|---|---|---|---|---|---|---|---|---|---|---|---|
| # Viruses | 208 | 208 | 208 | 208 | 208 | 208 | 208 | 208 | 208 | 208 | 208 | 208 | 208 | 207 |
| % VS Neutralized | | | | | | | | | | | | | | |
| IC80 <50ug/ml | 89 | 87 | 96 | 92 | 92 | 96 | 96 | 92 | 97 | 96 | 80 | 82 | 39 | 97 |
| IC80 <10ug/ml | 83 | 84 | 96 | 90 | 89 | 94 | 96 | 91 | 96 | 94 | 78 | 76 | 36 | 97 |
| IC80 <1.0ug/ml | 46 | 58 | 90 | 67 | 74 | 83 | 88 | 83 | 88 | 85 | 68 | 55 | 24 | 95 |
| IC80 <0.1ug/ml | 3 | 13 | 45 | 13 | 24 | 23 | 37 | 25 | 23 | 37 | 14 | 10 | 6 | 69 |
| *For Sensitive Viruses Only:* | | | | | | | | | | | | | | |
| Median IC80 | 0.980 | 0.534 | 0.107 | 0.435 | 0.270 | 0.240 | 0.153 | 0.192 | 0.221 | 0.135 | 0.298 | 0.456 | 0.567 | 0.061 |
| Geometric Mean | 1.06 | 0.570 | 0.120 | 0.444 | 0.294 | 0.269 | 0.146 | 0.217 | 0.231 | 0.165 | 0.318 | 0.558 | 0.625 | 0.060 |
| *For All Viruses:* | | | | | | | | | | | | | | |
| Median IC80 | 1.24 | 0.659 | 0.117 | 0.468 | 0.315 | 0.251 | 0.160 | 0.220 | 0.235 | 0.144 | 0.425 | 0.656 | 50 | 0.064 |
| Geometric Mean | 1.62 | 1.04 | 0.151 | 0.639 | 0.447 | 0.338 | 0.183 | 0.330 | 0.270 | 0.212 | 0.861 | 1.24 | 8.89 | 0.073 |

FIG. 12
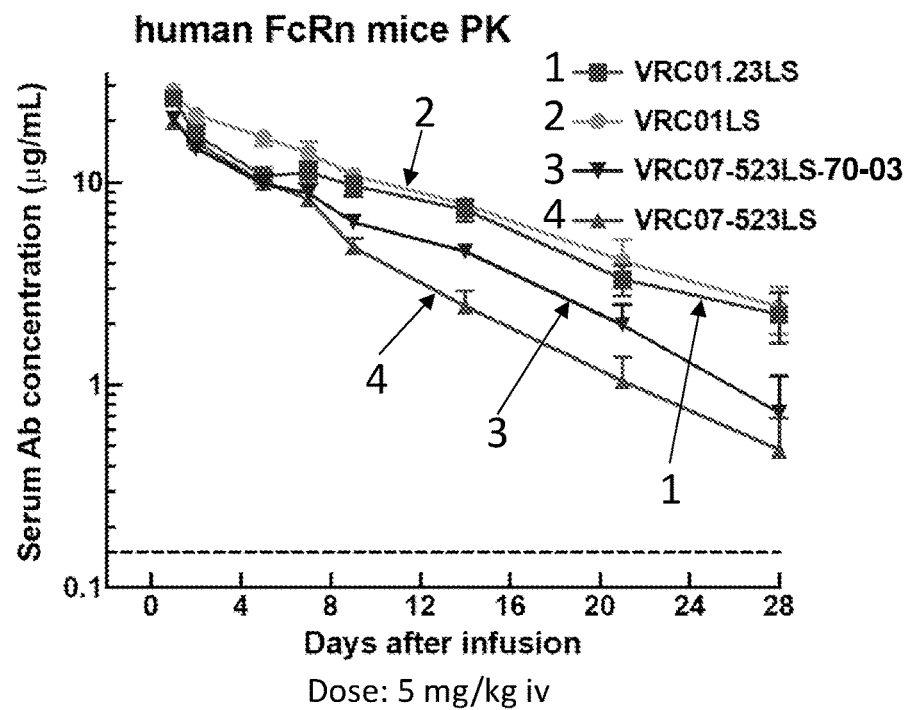
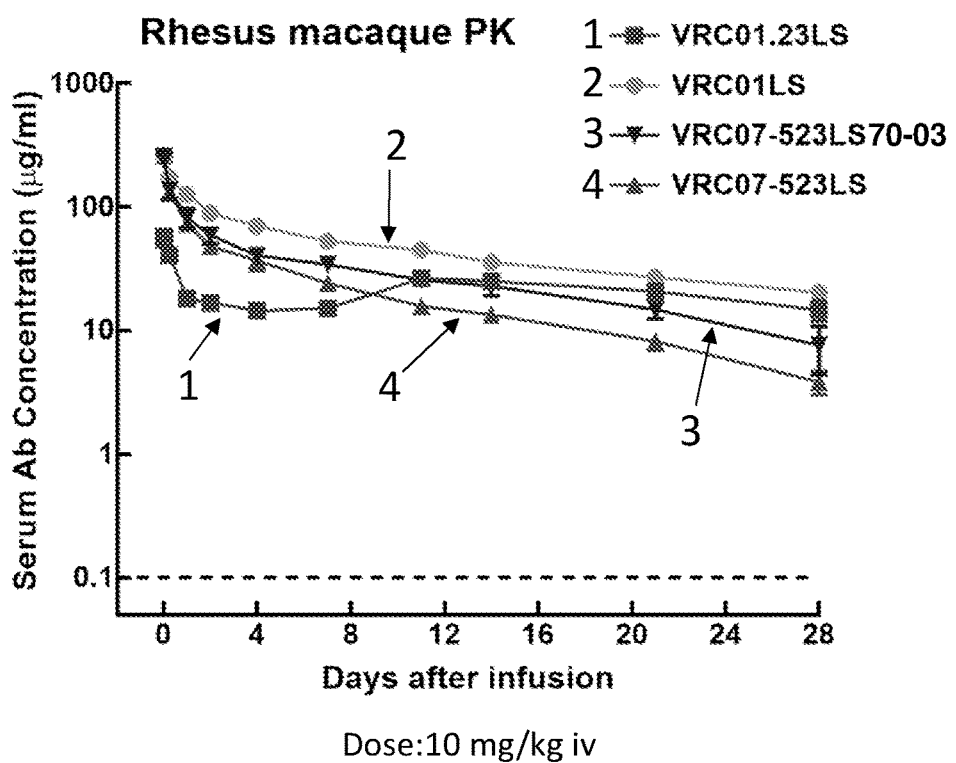

FIG. 13A

Neutralization IC 50 (μg/ml)

| | | N49.P7 | N49.P7.v1 | N49.P7.v2 | N49.P7.v3 | VRC08 | VRC08.v1 | VRC08.v2 | VRC08.v3 |
|---|---|---|---|---|---|---|---|---|---|
| Q23.17.SG3 | A | 0.191 | 0.024 | 0.030 | 0.032 | 0.157 | 0.240 | 0.098 | 0.068 |
| UG037.8.SG3 | A | 0.141 | 0.023 | 0.020 | 0.027 | 0.114 | 0.242 | 0.092 | 0.055 |
| 242-14.SG3 | AG | 7.28 | 0.066 | 0.053 | 0.066 | 50 | 50 | 50 | 50 |
| 7165.18.SG3 | B | 50 | 4.01 | 2.82 | 3.52 | 11.4 | 50 | 36.0 | 27.2 |
| AC10.29.SG3 | B | 17.8 | 1.08 | 1.03 | 0.918 | 0.935 | 13.7 | 50 | 50 |
| JRFL.JB.SG3 | B | 0.023 | 0.012 | 0.012 | 0.012 | 0.016 | 0.077 | 0.098 | 0.056 |
| QH0692.42.SG3 | B | 1.22 | 0.176 | 0.165 | 0.178 | 0.478 | 1.24 | 0.538 | 0.402 |
| DU151.02.SG3 | C | 1.60 | 0.062 | 0.061 | 0.067 | 0.490 | 0.862 | 0.837 | 0.411 |
| DU172.17.SG3 | C | 0.344 | 0.166 | 0.160 | 0.150 | 50 | 50 | 50 | 50 |
| TV1.29.SG3 | C | 50 | 50 | 50 | 50 | 50 | 50 | 50 | 50 |
| ZM53.12.SG3 | C | 0.918 | 1.33 | 1.28 | 1.37 | 0.610 | 9.31 | 50 | 50 |
| 5712B.wc15.SG3 | D | 4.18 | 2.03 | 1.97 | 1.86 | 50 | 50 | 50 | 50 |
| # Viruses | | 12 | 12 | 12 | 12 | 12 | 12 | 12 | 12 |
| Total VS Neutralized | | | | | | | | | |
| IC50 <50ug/ml | | 10 | 11 | 11 | 11 | 9 | 7 | 6 | 6 |
| IC50 <1ug/ml | | 5 | 7 | 7 | 8 | 7 | 4 | 5 | 5 |
| % VS Neutralized | | | | | | | | | |
| IC50 <50ug/ml | | 83 | 92 | 92 | 92 | 67 | 58 | 50 | 50 |
| IC50 <1ug/ml | | 42 | 58 | 58 | 67 | 58 | 33 | 42 | 42 |
| Median IC50 | | 1.410 | 0.171 | 0.163 | 0.164 | 0.773 | 1.505 | 43.000 | 38.600 |
| Geometric Mean | | 1.693 | 0.297 | 0.279 | 0.299 | 1.933 | 4.898 | 4.964 | 3.956 |

FIG. 13B

Neutralization IC 50 (μg/ml)

| | | 3BNC117 | 3BNC117 v1 | 3BNC117 v2 | 3BNC117 v3 | 3BNC117 v4 | 3BNC117 v5 | 3BNC117 v6 |
|---|---|---|---|---|---|---|---|---|
| Q23.17.SG3 | A | 0.027 | 0.023 | 0.031 | 0.033 | 0.016 | 0.018 | 0.017 |
| UG037.8.SG3 | A | 0.029 | 0.033 | 0.035 | 0.039 | 0.018 | 0.015 | 0.018 |
| 242-14.SG3 | AG | 50 | 50 | 50 | 50 | 50 | 50 | 50 |
| 7165.18.SG3 | B | 3.89 | 2.28 | 3.59 | 3.76 | 4.39 | 3.81 | 3.35 |
| AC10.29.SG3 | B | 17.5 | 2.19 | 50 | 50 | 1.63 | 26.3 | 27.2 |
| IRFL.8.SG3 | B | 0.006 | 0.008 | 0.008 | 0.010 | 0.004 | 0.005 | 0.005 |
| QH0692.42.SG3 | B | 0.325 | 0.244 | 0.225 | 0.228 | 0.137 | 0.114 | 0.112 |
| DU151.02.SG3 | C | 50 | 14.7 | 50 | 50 | 0.551 | 11.0 | 8.56 |
| DU172.17.SG3 | C | 0.546 | 0.191 | 50 | 50 | 0.172 | 50 | 50 |
| TV1.29.SG3 | C | 0.384 | 0.286 | 0.577 | 0.692 | 0.961 | 1.03 | 1.05 |
| ZM53.12.SG3 | C | 0.633 | 0.741 | 1.49 | 1.55 | 50 | 50 | 50 |
| SF128.wc15.SG3 | D | | | | | | | |
| # Viruses | | 12 | 12 | 12 | 12 | 12 | 12 | 12 |
| Total VS Neutralized | | | | | | | | |
| IC50 <50ug/ml | | 9 | 10 | 7 | 7 | 9 | 8 | 8 |
| IC50 <1ug/ml | | 7 | 7 | 5 | 5 | 7 | 4 | 4 |
| % VS Neutralized | | | | | | | | |
| IC50 <50ug/ml | | 75 | 83 | 58 | 58 | 75 | 67 | 67 |
| IC50 <1ug/ml | | 58 | 58 | 42 | 42 | 58 | 33 | 33 |
| Median IC50 | | 0.390 | 0.514 | 2.540 | 2.655 | 0.756 | 7.405 | 5.955 |
| Geometric Mean | | 1.045 | 0.697 | 1.875 | 1.983 | 0.696 | 1.791 | 1.759 |

FIG. 13C

Neutralization IC 50 (μg/ml)

| | | N6 | N6LS v1 | N6LS v2 | N6LS v3 | N6LS v4 | N6LS v5 | N6LS v6 | VRC01LS | VRC01 |
|---|---|---|---|---|---|---|---|---|---|---|
| Q23.17.SG3 | A | 0.101 | 0.028 | 0.034 | 0.035 | 0.042 | 0.046 | 0.042 | 0.112 | 0.125 |
| UG037.8.SG3 | A | 0.118 | 0.025 | 0.041 | 0.042 | 0.032 | 0.049 | 0.055 | 0.128 | 0.162 |
| 242-14.SG3 | AG | 0.331 | 1.92 | 50 | 50 | 7.40 | 50 | 50 | 50 | 50 |
| 7165.18.SG3 | B | 2.46 | 4.23 | 50 | 50 | 15.6 | 50 | 50 | 35.2 | 47.2 |
| AC10.29.SG3 | B | 0.355 | 0.453 | 8.00 | 6.54 | 0.720 | 10.2 | 9.92 | 1.30 | 1.55 |
| JRFL.JB.SG3 | B | 0.012 | 0.007 | 0.008 | 0.009 | 0.010 | 0.012 | 0.014 | 0.038 | 0.066 |
| QH0692.42.SG3 | B | 1.07 | 0.196 | 0.204 | 0.249 | 0.223 | 0.255 | 0.280 | 1.47 | 1.83 |
| DU151.02.SG3 | C | 0.102 | 0.054 | 1.18 | 0.442 | 0.124 | 6.69 | 3.87 | 9.54 | 10.8 |
| DU172.17.SG3 | C | 0.069 | 0.083 | 0.992 | 0.663 | 0.119 | 8.41 | 4.23 | 50 | 50 |
| TV1.29.SG3 | C | 50 | 50 | 50 | 50 | 50 | 50 | 50 | 50 | 50 |
| ZM53.12.SG3 | C | 0.487 | 1.08 | 1.12 | 1.21 | 1.13 | 1.53 | 1.71 | 1.47 | 1.67 |
| 6718.vrc15.SG3 | D | 2.79 | 4.55 | 27.0 | 17.8 | 5.69 | 50 | 40.3 | 50 | 50 |
| # Viruses | | 12 | 12 | 12 | 12 | 12 | 12 | 12 | 12 | 12 |
| Total VS Neutralized | | | | | | | | | | |
| IC50 <50μg/ml | | 11 | 11 | 9 | 9 | 11 | 8 | 9 | 8 | 8 |
| IC50 <1μg/ml | | 8 | 7 | 5 | 6 | 7 | 4 | 4 | 3 | 3 |
| % VS Neutralized | | | | | | | | | | |
| IC50 <50μg/ml | | 92 | 92 | 75 | 75 | 92 | 67 | 75 | 67 | 67 |
| IC50 <1μg/ml | | 67 | 58 | 42 | 50 | 58 | 33 | 33 | 25 | 25 |
| Median IC50 | | 0.343 | 0.325 | 1.150 | 0.937 | 0.472 | 7.550 | 4.050 | 5.505 | 6.315 |
| Geometric Mean | | 0.408 | 0.354 | 1.442 | 1.266 | 0.570 | 2.407 | 2.197 | 3.446 | 4.062 |

FIG. 13D

| | | VRC07-523LS.v1 YDK | VRC07-523LS.v2 YDK | VRC07-523LS.v3 YDK | VRC07-523LS.v4 YDK | VRC07-523LS YDK |
|---|---|---|---|---|---|---|
| Q23.17.SG3 | A | 0.011 | 0.017 | 0.009 | 0.016 | 0.069 |
| UG037.8.SG3 | A | 0.014 | 0.016 | 0.009 | 0.017 | 0.044 |
| 242-14.SG3 | AG | 0.029 | 0.092 | 0.016 | 0.093 | 0.242 |
| 7165.18.SG3 | B | 0.301 | 0.962 | 0.016 | 0.852 | 2.22 |
| AC10.29.SG3 | B | 0.201 | 0.307 | 0.114 | 0.312 | 0.315 |
| JRFL.JB.SG3 | B | 0.004 | 0.005 | 0.002 | 0.004 | 0.010 |
| QH0692.42.SG3 | B | 0.063 | 0.131 | 0.074 | 0.105 | 0.445 |
| DU151.02.SG3 | C | 0.025 | 0.059 | 0.016 | 0.034 | 0.096 |
| DU172.17.SG3 | C | 0.072 | 0.084 | 0.033 | 0.096 | 0.166 |
| TV1.29.SG3 | C | 0.244 | 1.15 | 0.103 | 1.36 | 1.98 |
| ZM53.12.SG3 | C | 0.312 | 0.474 | 0.188 | 0.504 | 0.274 |
| 57128.vrc15.SG3 | D | 1.09 | 1.23 | 0.684 | 1.09 | 1.24 |

| | | | | | | |
|---|---|---|---|---|---|---|
| # Viruses | | 12 | 12 | 12 | 12 | 12 |
| Total VS Neutralized | | | | | | |
| IC50 <50ug/ml | | 12 | 12 | 12 | 12 | 12 |
| IC50 <1ug/ml | | 11 | 10 | 12 | 10 | 9 |
| % VS Neutralized | | | | | | |
| IC50 <50ug/ml | | 100 | 100 | 100 | 100 | 100 |
| IC50 <1ug/ml | | 92 | 83 | 100 | 83 | 75 |
| Median IC50 | | 0.068 | 0.112 | 0.025 | 0.101 | 0.258 |
| Geometric Mean | | 0.068 | 0.126 | 0.034 | 0.117 | 0.232 |

Neutralization IC 50 (μg/ml)

FIG. 13E

Neutralization IC 80 (μg/ml)

| | | N49.P7 | N49.P7.v1 | N49.P7.v2 | N49.P7.v3 | VRC08 | VRC08.v1 | VRC08.v2 | VRC08.v3 |
|---|---|---|---|---|---|---|---|---|---|
| Q23.17.SG3 | A | 0.437 | 0.071 | 0.084 | 0.086 | 0.395 | 0.565 | 0.265 | 0.197 |
| UG037.8.SG3 | A | 0.369 | 0.063 | 0.066 | 0.074 | 0.351 | 0.474 | 0.251 | 0.169 |
| 242-14.SG3 | AG | 50 | 0.209 | 0.193 | 0.193 | 50 | 50 | 50 | 50 |
| 7165.18.SG3 | B | 50 | 11.1 | 8.75 | 8.6 | 31.6 | 50 | 50 | 50 |
| AC10.29.SG3 | B | 50 | 2.91 | 2.19 | 2.63 | 2.85 | 8.88 | 50 | 50 |
| JRFL.JB.SG3 | B | 0.066 | 0.027 | 0.028 | 0.032 | 0.038 | 0.206 | 0.933 | 1.06 |
| QH0692.42.SG3 | B | 3.14 | 0.400 | 0.421 | 0.439 | 1.53 | 3.43 | 1.68 | 1.20 |
| DU151.02.SG3 | C | 10.6 | 0.161 | 0.168 | 0.180 | 1.25 | 2.29 | 3.70 | 1.93 |
| DU172.17.SG3 | C | 1.25 | 0.449 | 0.457 | 0.515 | 50 | 50 | 50 | 50 |
| TV1.29.SG3 | C | 50 | 50 | 50 | 50 | 50 | 50 | 50 | 50 |
| ZM53.12.SG3 | C | 2.41 | 3.71 | 3.39 | 3.69 | 2.02 | 2.75 | 50 | 50 |
| 57128.vrc15.SG3 | D | 8.08 | 7.42 | 7.39 | 6.77 | 50 | 50 | 50 | 50 |
| # Viruses | | 12 | 12 | 12 | 12 | 12 | 12 | 12 | 12 |
| Total VS Neutralized | | | | | | | | | |
| IC80 <50ug/ml | | 8 | 11 | 11 | 11 | 8 | 7 | 5 | 5 |
| IC80 <1ug/ml | | 3 | 7 | 7 | 7 | 3 | 3 | 3 | 2 |
| % VS Neutralized | | | | | | | | | |
| IC80 <50ug/ml | | 67 | 92 | 92 | 92 | 67 | 58 | 42 | 42 |
| IC80 <1ug/ml | | 25 | 58 | 58 | 58 | 25 | 25 | 25 | 17 |
| Median IC80 | | 6.870 | 0.425 | 0.439 | 0.477 | 2.435 | 30.650 | 50.000 | 50.000 |
| Geometric Mean | | 4.583 | 0.752 | 0.721 | 0.796 | 3.886 | 8.353 | 9.049 | 7.951 |

FIG. 13F

Neutralization IC 80 (µg/ml)

| | | 3BNC117 | 3BNC117 v1 | 3BNC117 v2 | 3BNC117 v3 | 3BNC117 v4 | 3BNC117 v5 | 3BNC117 v6 |
|---|---|---|---|---|---|---|---|---|
| Q23.17.SG3 | A | 0.078 | 0.070 | 0.103 | 0.119 | 0.044 | 0.065 | 0.040 |
| UG037.8.SG3 | A | 0.111 | 0.117 | 0.117 | 0.114 | 0.055 | 0.044 | 0.046 |
| 242-14.SG3 | AG | 50 | 50 | 50 | 50 | 50 | 50 | 50 |
| 7165.18.SG3 | B | 8.10 | 8.10 | | | | | |
| AC10.29.SG3 | B | 50 | 9.15 | 50 | 50 | 8.11 | 50 | 50 |
| JRFL.JB.SG3 | B | 0.023 | 0.025 | 0.090 | 0.098 | 0.013 | 0.015 | 0.014 |
| QH0692.42.SG3 | B | 0.928 | 0.641 | 0.851 | 0.795 | 0.436 | 0.331 | 0.335 |
| DU151.02.SG3 | C | 50 | 50 | 50 | 50 | 5.19 | 50 | 50 |
| DU172.17.SG3 | C | 4.53 | 1.00 | 1.89 | 2.02 | 1.39 | 3.53 | 3.05 |
| TV1.29.SG3 | C | 50 | 50 | 50 | 50 | 50 | 50 | 50 |
| ZM53.12.SG3 | C | 1.92 | 0.937 | | | 3.47 | | |
| 5T128.wrc15.SG3 | D | 2.60 | 2.51 | 4.77 | 5.70 | | | |
| # Viruses | | 12 | 12 | 12 | 12 | 12 | 12 | 12 |
| Total VS Neutralized | | | | | | | | |
| IC80 <50µg/ml | | 8 | 9 | 7 | 7 | 9 | 6 | 6 |
| IC80 <1µg/ml | | 4 | 5 | 4 | 4 | 4 | 4 | 4 |
| % VS Neutralized | | | | | | | | |
| IC80 <50µg/ml | | 67 | 75 | 58 | 58 | 75 | 50 | 50 |
| IC80 <1µg/ml | | 33 | 42 | 33 | 33 | 33 | 33 | 33 |
| Median IC80 | | 3.315 | 1.755 | 7.935 | 7.950 | 4.330 | 30.600 | 30.200 |
| Geometric Mean | | 2.755 | 1.941 | 3.903 | 3.944 | 2.052 | 3.668 | 3.569 |

FIG. 13G

Neutralization IC 80 (μg/ml)

| | | N6 | N6LS.v1 | N6LS.v2 | N6LS.v3 | N6LS.v4 | N6LS.v5 | N6LS.v6 | VRC01LS | VRC01 |
|---|---|---|---|---|---|---|---|---|---|---|
| Q23.17.SG3 | A | 0.234 | 0.080 | 0.100 | 0.106 | 0.104 | 0.100 | 0.100 | 0.321 | 0.346 |
| UG037.8.SG3 | A | 0.108 | 0.074 | 0.102 | 0.113 | 0.089 | 0.099 | 0.116 | 0.426 | 0.519 |
| 242-14.SG3 | AG | 2.64 | 9.46 | 50 | 50 | 50 | 50 | 50 | 50 | 50 |

FIG. 13H

|  |  | VRC07-523LS.v1 YDK | VRC07-523LS.v2 YDK | VRC07-523LS.v3 YDK | VRC07-523LS.v4 YDK | VRC07-523LS YDK |
|---|---|---|---|---|---|---|
| Q23.17.SG3 | A | 0.029 | 0.036 | 0.020 | 0.040 | 0.171 |
| UG037.8.SG3 | A | 0.033 | 0.034 | 0.020 | 0.040 | 0.126 |
| 242-14.SG3 | AG | 0.093 | 0.328 | 0.046 | 0.373 | 0.817 |
| 7165.18.SG3 | B | 1.53 | 2.56 | 0.961 | 3.01 | 6.85 |
| AC10.29.SG3 | B | 0.555 | 0.770 | 0.338 | 0.869 | 0.943 |
| JRFL.JB.SG3 | B | 0.009 | 0.013 | 0.006 | 0.012 | 0.027 |
| QH0692.42.SG3 | B | 0.192 | 0.250 | 0.148 | 0.281 | 1.63 |
| DU151.02.SG3 | C | 0.061 | 0.118 | 0.124 | 0.124 | 0.376 |
| DU172.17.SG3 | C | 0.196 | 0.295 | 0.038 | 0.432 | 0.666 |
| TV1.29.SG3 | C | 0.732 | 7.96 | 0.238 | 8.38 | 16.3 |
| ZM53.12.SG3 | C | 0.923 | 1.22 | 0.528 | 1.37 | 0.680 |
| 57128.vrc15.SG3 | D | 3.57 | 3.93 | 1.92 | 3.71 | 4.70 |

|  | VRC07-523LS.v1 | VRC07-523LS.v2 | VRC07-523LS.v3 | VRC07-523LS.v4 | VRC07-523LS |
|---|---|---|---|---|---|
| # Viruses | 12 | 12 | 12 | 12 | 12 |
| Total VS Neutralized | | | | | |
| IC80 <50ug/ml | 12 | 12 | 12 | 12 | 12 |
| IC80 <1ug/ml | 10 | 8 | 11 | 8 | 8 |
| % VS Neutralized | | | | | |
| IC80 <50ug/ml | 100 | 100 | 100 | 100 | 100 |
| IC80 <1ug/ml | 83 | 67 | 92 | 67 | 67 |
| Median IC80 | 0.194 | 0.312 | 0.136 | 0.403 | 0.749 |
| Geometric Mean | 0.199 | 0.350 | 0.116 | 0.389 | 0.797 |

Neutralization IC 80 (µg/ml)

FIG. 14

Neutralization of a Multiclade Panel of 140 Viruses

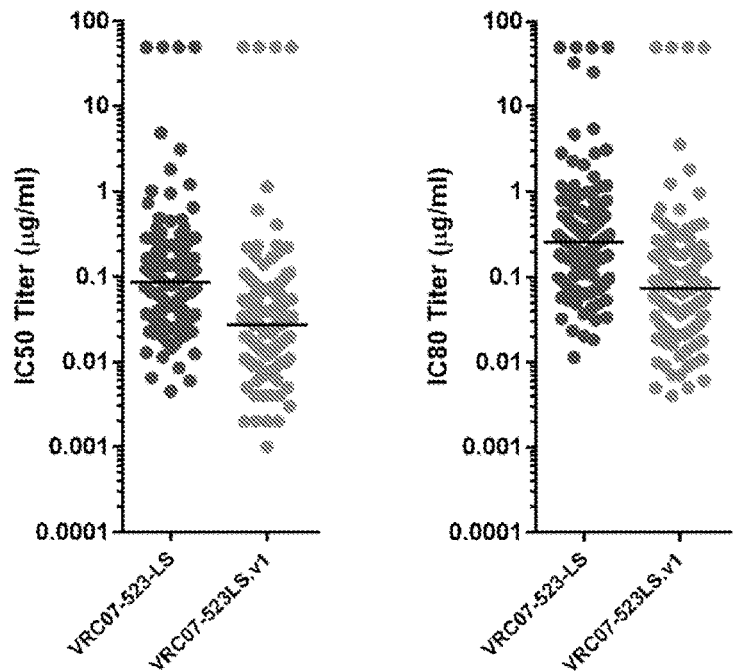

|  | VRC07-523LS.v1 | VRC01 |
|---:|:---:|:---:|
| # Viruses | 140 | 140 |
| Total VS Neutralized | | |
| IC50 <50ug/ml | 136 | 129 |
| IC50 <10ug/ml | 136 | 126 |
| IC50 <1.0ug/ml | 135 | 111 |
| IC50 <0.1ug/ml | 122 | 36 |
| IC50 <0.01ug/ml | 22 | 0 |
| % VS Neutralized | | |
| IC50 <50ug/ml | 97 | 92 |
| IC50 <10ug/ml | 97 | 90 |
| IC50 <1.0ug/ml | 96 | 79 |
| IC50 <0.1ug/ml | 87 | 26 |
| IC50 <0.01ug/ml | 16 | 0 |
| | | |
| Median IC50 | 0.027 | 0.249 |
| Geometric Mean | 0.026 | 0.256 |

|  | VRC07-523LS.v1 | VRC01 |
|---:|:---:|:---:|
| # Viruses | 140 | 140 |
| Total VS Neutralized | | |
| IC80 <50ug/ml | 136 | 126 |
| IC80 <10ug/ml | 136 | 119 |
| IC80 <1.0ug/ml | 133 | 74 |
| IC80 <0.1ug/ml | 85 | 6 |
| IC80 <0.01ug/ml | 8 | 0 |
| % VS Neutralized | | |
| IC80 <50ug/ml | 97 | 90 |
| IC80 <10ug/ml | 97 | 85 |
| IC80 <1.0ug/ml | 95 | 53 |
| IC80 <0.1ug/ml | 61 | 4 |
| IC80 <0.01ug/ml | 6 | 0 |
| | | |
| Median IC80 | 0.072 | 0.691 |
| Geometric Mean | 0.068 | 0.800 |

FIG. 15C

Summary of HEp-2 Staining

| mAb | Assay 1 | Assay 2 |
|---|---|---|
| VRC01-LS | 0 | 0 |
| 4E10 | 1 | 1 |
| VRC07-523-LS | 2 | 2 |
| VRC07-G54W | 3 | 3 |
| N49P7 | 1 | 1 |
| N49P7.v1 | 0/1 | 0/1 |
| N49P7.v2 | 0/1 | 0/1 |
| N49P7.v3 | 1 | 1 |
| VRC08 | 0/1 | 0/1 |
| VRC08.v1 | 0/1 | 0/1 |
| VRC08.v2 | 0/1 | 0/1 |
| VRC08.v3 | 0/1 | 0/1 |

FIG. 16A

Summary of anti-cardiolipin ELISA

| mAb | OD at 450 nm | | GPL units | | Interpretation |
|---|---|---|---|---|---|
| | 100 µg/ml | 33.3 µg/ml | 100 µg/ml | 33.3 µg/ml | |
| VRC01-LS | 0.0359 | 0.0365 | -4.83 | -4.74 | Negative |
| 4E10 | 1.6641 | 1.7992 | 225.70 | 240.31 | High positive |
| VRC07-523-LS | 0.0439 | 0.0389 | -3.71 | -4.41 | Negative |
| VRC07-G54W | 0.112 | 0.0558 | 5.75 | -2.06 | Negative |
| VRC07-523LS_v3 | 0.0612 | 0.0425 | -1.31 | -3.91 | Negative |
| VRC07-523LS_v1 | 0.0673 | 0.0431 | -0.46 | -3.83 | Negative |
| VRC01.23LS | 0.183 | 0.0884 | 15.62 | 2.47 | Negative |
| VRC07-523LS.v2 | 0.0593 | 0.0425 | -1.57 | -3.91 | Negative |
| VRC07-523LS.v4 | 0.1171 | 0.0556 | 6.46 | -2.09 | Negative |

FIG. 16B

Summary of anti-cardiolipin ELISA

| mAb | OD at 450 nm | | GPL units | | Interpretation |
|---|---|---|---|---|---|
| | 100 µg/ml | 33.3 µg/ml | 100 µg/ml | 33.3 µg/ml | |
| N49P7 | 0.1717 | 0.0716 | 4.71 | -4.39 | Negative |
| N49P7.v1 | 0.1136 | 0.0508 | -0.57 | -6.29 | Negative |
| N49P7.v2 | 0.2141 | 0.0876 | 8.57 | -2.94 | Negative |
| N49P7.v3 | 0.2461 | 0.0874 | 11.48 | -2.96 | Negative |
| VRC08 | 0.2007 | 0.0742 | 7.35 | -4.16 | Negative |
| VRC08.v1 | 0.7039 | 0.2434 | 53.13 | 11.24 | Negative |
| VRC08.v2 | 0.552 | 0.1906 | 39.32 | 6.43 | Negative |
| VRC08.v3 | 0.5225 | 0.2068 | 36.63 | 7.91 | Negative |
| VRC01-LS | 0.0366 | 0.0362 | -7.58 | -7.62 | Negative |
| 4E10 | 2.2974 | 2.2397 | 198.13 | 192.88 | High positive |
| VRC07-523-LS | 0.3454 | 0.1244 | 20.52 | 0.41 | Negative |
| VRC07-G54W | 0.7499 | 0.3186 | 57.30 | 18.08 | Indeterminate |
| N6 | 0.1491 | 0.0538 | 2.66 | -6.01 | Negative |
| N6.v1 | 0.0644 | 0.0416 | -5.05 | -7.12 | Negative |
| N6.v2 | 0.0818 | 0.0434 | -3.47 | -6.96 | Negative |
| N6.v3 | 0.1833 | 0.0677 | 3.95 | -4.75 | Negative |
| N6.v4 | 0.0543 | 0.0387 | -5.97 | -7.39 | Negative |
| N6.v5 | 0.0687 | 0.0492 | -2.84 | -6.43 | Negative |
| N6.v6 | 0.1057 | 0.0561 | -1.29 | -5.81 | Negative |

SEQUENCE LISTING

```
<160> NUMBER OF SEQ ID NOS: 123

<210> SEQ ID NO 1
<211> LENGTH: 122
<212> TYPE: PRT
<213> ORGANISM: homo sapiens

<400> SEQUENCE: 1

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
                20                  25                  30

Ile Leu Phe Trp Phe Arg Gln Ala Pro Gly Arg Gly Leu Glu Trp Val
            35                  40                  45

Gly Trp Ile Lys Pro Gln Tyr Gly Ala Val Asn Phe Gly Gly Gly Phe
        50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Asp Arg Ser Tyr Gly Asp Ser Ser Trp Ala Leu Asp Ala Trp
                100                 105                 110

Gly Gln Gly Thr Thr Val Val Val Ser Ala
            115                 120

<210> SEQ ID NO 2
<211> LENGTH: 103
<212> TYPE: PRT
<213> ORGANISM: homo sapiens

<400> SEQUENCE: 2

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
                20                  25                  30

Leu His Trp Tyr Gln His Lys Pro Gly Arg Ala Pro Lys Leu Leu Ile
            35                  40                  45

His His Thr Ser Ser Val Glu Asp Gly Val Pro Ser Arg Phe Ser Gly
        50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 3
<211> LENGTH: 121
```

<212> TYPE: PRT
<213> ORGANISM: homo sapiens

<400> SEQUENCE: 3

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 4
<211> LENGTH: 104
<212> TYPE: PRT
<213> ORGANISM: homo sapiens

<400> SEQUENCE: 4

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 5
<211> LENGTH: 125
<212> TYPE: PRT
<213> ORGANISM: homo sapiens

<400> SEQUENCE: 5

Gln Val Arg Leu Ser Gln Ser Gly Gly Gln Met Lys Lys Pro Gly Asp
1               5                   10                  15

Ser Met Arg Ile Ser Cys Arg Ala Ser Gly Tyr Glu Phe Ile Asn Cys
            20                  25                  30

Pro Ile Asn Trp Ile Arg Leu Ala Pro Gly Lys Arg Pro Glu Trp Met
        35                  40                  45

Gly Trp Met Lys Pro Arg Gly Gly Ala Val Ser Tyr Ala Arg Gln Leu
    50                  55                  60

Gln Gly Arg Val Thr Met Thr Arg Asp Met Tyr Ser Glu Thr Ala Phe

```
                65                  70                  75                  80
Leu Glu Leu Arg Ser Leu Thr Ser Asp Asp Thr Ala Val Tyr Phe Cys
                    85                  90                  95

Thr Arg Gly Lys Tyr Cys Thr Ala Arg Asp Tyr Tyr Asn Trp Asp Phe
                100                 105                 110

Glu His Trp Gly Gln Gly Thr Pro Val Thr Val Ser Ser
                115                 120                 125

<210> SEQ ID NO 6
<211> LENGTH: 125
<212> TYPE: PRT
<213> ORGANISM: Artificial Sequence
<220> FEATURE:
<223> OTHER INFORMATION: Recombinant antibody sequence

<400> SEQUENCE: 6

Gln Val Arg Leu Ser Gln Ser Gly Gly Gln Met Lys Lys Pro Gly Asp
1               5                   10                  15

Ser Met Arg Ile Ser Cys Arg Ala Ser Gly Tyr Glu Phe Ile Asn Cys
                20                  25                  30

Pro Ile Asn Trp Ile Arg Leu Ala Pro Gly Lys Arg Pro Glu Trp Met
                35                  40                  45

Gly Trp Met Lys Pro Arg His Gly Ala Val Ser Tyr Ala Arg Gln Leu
            50                  55                  60

Gln Gly Arg Val Thr Met Thr Arg Asp Met Tyr Ser Glu Thr Ala Phe
65                  70                  75                  80

Leu Glu Leu Arg Ser Leu Thr Ser Asp Asp Thr Ala Val Tyr Phe Cys
                    85                  90                  95

Thr Arg Gly Lys Tyr Cys Thr Ala Arg Asp Tyr Tyr Asn Trp Asp Phe
                100                 105                 110

Glu His Trp Gly Gln Gly Thr Pro Val Thr Val Ser Ser
                115                 120                 125

<210> SEQ ID NO 7
<211> LENGTH: 101
<212> TYPE: PRT
<213> ORGANISM: Artificial Sequence
<220> FEATURE:
<223> OTHER INFORMATION: Recombinant antibody sequence

<400> SEQUENCE: 7

Ser Leu Thr Gln Ser Pro Gly Thr Leu Ser Leu Ser Pro Gly Glu Thr
1               5                   10                  15

Ala Ile Ile Ser Cys Arg Thr Ser Gln Tyr Gly Ser Leu Ala Trp Tyr
                20                  25                  30

Gln Gln Arg Pro Gly Gln Ala Pro Arg Leu Val Ile Tyr Ser Gly Ser
            35                  40                  45

Thr Arg Ala Ala Gly Ile Pro Asp Arg Phe Ser Gly Ser Arg Trp Gly
        50                  55                  60

Pro Asp Tyr Asn Leu Thr Ile Ser Asn Leu Glu Ser Gly Asp Phe Gly
65                  70                  75                  80

Val Tyr Tyr Cys Gln Gln Tyr Glu Phe Phe Gly Gln Gly Thr Lys Val
                85                  90                  95

Gln Val Asp Ile Lys
            100

<210> SEQ ID NO 8
<211> LENGTH: 123
```

<212> TYPE: PRT
<213> ORGANISM: homo sapiens

<400> SEQUENCE: 8

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Leu Arg Ser Asp Asp Thr Ala
                85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser
        115                 120

<210> SEQ ID NO 9
<211> LENGTH: 99
<212> TYPE: PRT
<213> ORGANISM: homo sapiens

<400> SEQUENCE: 9

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
    50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Val Val Pro Gly Thr Arg Leu
                85                  90                  95

Asp Leu Lys

<210> SEQ ID NO 10
<211> LENGTH: 131
<212> TYPE: PRT
<213> ORGANISM: homo sapiens

<400> SEQUENCE: 10

Glu Val Gln Leu Val Glu Ser Gly Pro Val Met Arg Lys Pro Gly Ser
1               5                   10                  15

Ser Met Lys Ile Ser Cys Ala Thr Ser Gly Tyr Asn Phe Arg Asp Phe
            20                  25                  30

Ser Ile His Trp Val Arg Phe Asn Arg Arg Tyr Gly Phe Glu Trp Ile
        35                  40                  45

Gly Trp Ile Lys Pro Met Trp Gly Ala Val Asn Tyr Ala Arg Gln Leu
    50                  55                  60

Gln Gly Arg Val Ser Met Ser Arg Leu Phe Ser Gln Asp Leu Tyr Tyr
65                  70                  75                  80

```
Pro Asp Arg Gly Thr Ala Tyr Leu Glu Phe Ser Gly Leu Thr Ser Ala
            85                  90                  95

Asp Thr Ala Asp Tyr Phe Cys Val Arg Arg Gly Ser Ser Cys Pro His
            100                 105                 110

Cys Gly Asp Phe His Phe Glu His Trp Gly Gln Gly Thr Ala Val Val
            115                 120                 125

Val Ser Ala
    130

<210> SEQ ID NO 11
<211> LENGTH: 102
<212> TYPE: PRT
<213> ORGANISM: homo sapiens

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Gly Asn Ser Leu
            20                  25                  30

Asn Trp Tyr Gln Lys Arg Gly Gln Thr Pro Arg Leu Leu Ile Tyr
            35                  40                  45

Asp Thr Ser Arg Arg Ala Ser Asp Ile Pro Glu Lys Phe Val Gly Ser
    50                  55                  60

Gly Ser Gly Thr Asp Phe Ser Leu Thr Ile Thr Lys Val Gly Pro Glu
65                  70                  75                  80

Asp Phe Ala Val Tyr Tyr Cys Gln Gln Phe Glu Phe Phe Gly Leu Gly
            85                  90                  95

Thr Thr Leu Glu Ile Asn
            100

<210> SEQ ID NO 12
<211> LENGTH: 130
<212> TYPE: PRT
<213> ORGANISM: homo sapiens

<400> SEQUENCE: 12

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
            20                  25                  30

Ser Ile His Trp Val Arg Leu Ile Pro Asp Lys Gly Phe Glu Trp Ile
            35                  40                  45

Gly Trp Ile Lys Pro Leu Trp Gly Ala Val Ser Tyr Ala Arg Gln Leu
    50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Ser Ala
            85                  90                  95

Asp Thr Ala Glu Tyr Phe Cys Val Arg Arg Gly Ser Cys Asp Tyr Cys
            100                 105                 110

Gly Asp Phe Pro Trp Gln Tyr Trp Gly Gln Gly Thr Trp Val Val Ser
            115                 120                 125

Ser Ala
    130

<210> SEQ ID NO 13
```

```
<211> LENGTH: 102
<212> TYPE: PRT
<213> ORGANISM: homo sapiens

<400> SEQUENCE: 13

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
            20                  25                  30

Thr Trp Tyr Gln Lys Arg Gly Gln Val Pro Arg Leu Leu Ile Tyr
        35                  40                  45

Asp Thr Ser Arg Arg Ala Ser Gly Val Pro Asp Arg Phe Val Gly Ser
    50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Gly Leu Gly
                85                  90                  95

Ser Glu Leu Glu Val His
            100

<210> SEQ ID NO 14
<211> LENGTH: 111
<212> TYPE: PRT
<213> ORGANISM: homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Tyr Cys Gly Gly Asp Cys Tyr Asn Trp Phe Asp Ser
            100                 105                 110

<210> SEQ ID NO 15
<211> LENGTH: 97
<212> TYPE: PRT
<213> ORGANISM: homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Gln Tyr Asp Asn Leu Pro Ile
                85                  90                  95
Thr

<210> SEQ ID NO 16
<211> LENGTH: 129
<212> TYPE: PRT
<213> ORGANISM: Artificial Sequence
<220> FEATURE:
<223> OTHER INFORMATION: Recombinant antibody sequence

<400> SEQUENCE: 16

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
                20                  25                  30

Ile Leu Phe Trp Phe Arg Gln Ala Pro Gly Arg Gly Leu Glu Trp Val
            35                  40                  45

Gly Trp Ile Lys Pro Gln Tyr Gly Ala Val Asn Phe Gly Gly Gly Phe
        50                  55                  60

Arg Asp Arg Val Thr Leu Thr Arg Gln Leu Ser Gln Asp Pro Asp Asp
65                  70                  75                  80

Pro Asp Trp Gly Ile Ala Tyr Met Asp Ile Arg Gly Leu Lys Pro Asp
                85                  90                  95

Asp Thr Ala Val Tyr Tyr Cys Ala Arg Asp Arg Ser Tyr Gly Asp Ser
                100                 105                 110

Ser Trp Ala Leu Asp Ala Trp Gly Gln Gly Thr Thr Val Val Val Ser
            115                 120                 125

Ala

<210> SEQ ID NO 17
<211> LENGTH: 128
<212> TYPE: PRT
<213> ORGANISM: Artificial Sequence
<220> FEATURE:
<223> OTHER INFORMATION: Recombinant antibody sequence

<400> SEQUENCE: 17

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
                20                  25                  30

Thr Leu Asn Trp Ile Arg Leu Ala Pro Gly Lys Arg Pro Glu Trp Met
            35                  40                  45

Gly Trp Leu Lys Pro Arg Gly Gly Ala Val Asn Tyr Ala Arg Pro Leu
        50                  55                  60

Gln Gly Arg Val Thr Met Thr Arg Gln Leu Ser Gln Asp Pro Asp Asp
65                  70                  75                  80

Pro Asp Trp Gly Thr Ala Phe Leu Glu Leu Arg Ser Leu Thr Val Asp
                85                  90                  95

Asp Thr Ala Val Tyr Phe Cys Thr Arg Gly Lys Asn Cys Asp Tyr Asn
                100                 105                 110

Trp Asp Phe Glu His Trp Gly Arg Gly Thr Pro Val Ile Val Ser Ser
            115                 120                 125

<210> SEQ ID NO 18
<211> LENGTH: 132
<212> TYPE: PRT
```

<213> ORGANISM: Artificial Sequence
<220> FEATURE:
<223> OTHER INFORMATION: Recombinant antibody sequence

<400> SEQUENCE: 18

Gln Val Arg Leu Ser Gln Ser Gly Gly Gln Met Lys Lys Pro Gly Asp
1               5                   10                  15

Ser Met Arg Ile Ser Cys Arg Ala Ser Gly Tyr Glu Phe Ile Asn Cys
            20                  25                  30

Pro Ile Asn Trp Ile Arg Leu Ala Pro Gly Lys Arg Pro Glu Trp Met
        35                  40                  45

Gly Trp Met Lys Pro Arg Gly Gly Ala Val Ser Tyr Ala Arg Gln Leu
    50                  55                  60

Gln Gly Arg Val Thr Met Thr Arg Gln Leu Ser Gln Asp Pro Asp Asp
65                  70                  75                  80

Pro Asp Trp Gly Thr Ala Phe Leu Glu Leu Arg Ser Leu Thr Ser Asp
                85                  90                  95

Asp Thr Ala Val Tyr Phe Cys Thr Arg Gly Lys Tyr Cys Thr Ala Arg
            100                 105                 110

Asp Tyr Tyr Asn Trp Asp Phe Glu His Trp Gly Gln Gly Thr Pro Val
        115                 120                 125

Thr Val Ser Ser
    130

<210> SEQ ID NO 19
<211> LENGTH: 132
<212> TYPE: PRT
<213> ORGANISM: Artificial Sequence
<220> FEATURE:
<223> OTHER INFORMATION: Recombinant antibody sequence

<400> SEQUENCE: 19

Gln Val Arg Leu Ser Gln Ser Gly Gly Gln Met Lys Lys Pro Gly Asp
1               5                   10                  15

Ser Met Arg Ile Ser Cys Arg Ala Ser Gly Tyr Glu Phe Ile Asn Cys
            20                  25                  30

Pro Ile Asn Trp Ile Arg Leu Ala Pro Gly Lys Arg Pro Glu Trp Met
        35                  40                  45

Gly Trp Met Lys Pro Arg His Gly Ala Val Ser Tyr Ala Arg Gln Leu
    50                  55                  60

Gln Gly Arg Val Thr Met Thr Arg Gln Leu Ser Gln Asp Pro Asp Asp
65                  70                  75                  80

Pro Asp Trp Gly Thr Ala Phe Leu Glu Leu Arg Ser Leu Thr Ser Asp
                85                  90                  95

Asp Thr Ala Val Tyr Phe Cys Thr Arg Gly Lys Tyr Cys Thr Ala Arg
            100                 105                 110

Asp Tyr Tyr Asn Trp Asp Phe Glu His Trp Gly Gln Gly Thr Pro Val
        115                 120                 125

Thr Val Ser Ser
    130

<210> SEQ ID NO 20
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 20

Ala His Ile Leu Phe
1               5

<210> SEQ ID NO 21
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 21

Trp Ile Lys Pro Gln Tyr Gly Ala Val Asn Phe Gly Gly Gly Phe Arg
1               5                   10                  15

Asp

<210> SEQ ID NO 22
<211> LENGTH: 13
<212> TYPE: PRT
<213> ORGANISM: Artificial Sequence
<220> FEATURE:
<223> OTHER INFORMATION: Recombinant antibody sequence

<400> SEQUENCE: 22

Asp Arg Ser Tyr Gly Asp Ser Ser Trp Ala Leu Asp Ala
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Recombinant antibody sequence

<400> SEQUENCE: 23

Gln Thr Ser Gln Gly Val Gly Ser Asp Leu His
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Recombinant antibody sequence

<400> SEQUENCE: 24

His Thr Ser Ser Val Glu Asp
1               5

<210> SEQ ID NO 25
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 25

Gln Val Leu Gln Phe
1               5

<210> SEQ ID NO 26
<211> LENGTH: 5
<212> TYPE: PRT
<213> ORGANISM: Artificial Sequence
<220> FEATURE:
<223> OTHER INFORMATION: Recombinant antibody sequence -continued

```
<400> SEQUENCE: 26

Asp Cys Thr Leu Asn
1               5

<210> SEQ ID NO 27
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 27

Trp Leu Lys Pro Arg Gly Gly Ala Val Asn Tyr Ala Arg Pro Leu Gln
1               5                   10                  15

Gly

<210> SEQ ID NO 28
<211> LENGTH: 12
<212> TYPE: PRT
<213> ORGANISM: Artificial Sequence
<220> FEATURE:
<223> OTHER INFORMATION: Recombinant antibody sequence

<400> SEQUENCE: 28

Gly Lys Asn Cys Asp Tyr Asn Trp Asp Phe Glu His
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Recombinant antibody sequence

<400> SEQUENCE: 29

Arg Thr Ser Gln Tyr Gly Ser Leu Ala
1               5

<210> SEQ ID NO 30
<211> LENGTH: 7
<212> TYPE: PRT
<213> ORGANISM: Artificial Sequence
<220> FEATURE:
<223> OTHER INFORMATION: Recombinant antibody sequence

<400> SEQUENCE: 30

Ser Gly Ser Thr Arg Ala Ala
1               5

<210> SEQ ID NO 31
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 31

Gln Gln Tyr Glu Phe
1               5

<210> SEQ ID NO 32
<211> LENGTH: 5
<212> TYPE: PRT
<213> ORGANISM: Artificial Sequence
<220> FEATURE:
<223> OTHER INFORMATION: Recombinant antibody sequence
```

<400> SEQUENCE: 32

Asn Cys Pro Ile Asn
1               5

<210> SEQ ID NO 33
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 33

Trp Met Lys Pro Arg Gly Gly Ala Val Ser Tyr Ala Arg Gln Leu Gln
1               5                   10                  15

Gly

<210> SEQ ID NO 34
<211> LENGTH: 16
<212> TYPE: PRT
<213> ORGANISM: Artificial Sequence
<220> FEATURE:
<223> OTHER INFORMATION: Recombinant antibody sequence

<400> SEQUENCE: 34

Gly Lys Tyr Cys Thr Ala Arg Asp Tyr Tyr Asn Trp Asp Phe Glu His
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 35

Trp Met Lys Pro Arg His Gly Ala Val Ser Tyr Ala Arg Gln Leu Gln
1               5                   10                  15

Gly

<210> SEQ ID NO 36
<211> LENGTH: 12
<212> TYPE: PRT
<213> ORGANISM: Artificial Sequence
<220> FEATURE:
<223> OTHER INFORMATION: Recombinant antibody sequence

<400> SEQUENCE: 36

Gln Leu Ser Gln Asp Pro Asp Pro Asp Trp Gly
1               5                   10

<210> SEQ ID NO 37
<211> LENGTH: 856
<212> TYPE: PRT
<213> ORGANISM: human immunodeficiency virus

<400> SEQUENCE: 37

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

-continued

```
Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
        130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
                180                 185                 190

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
        210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
                260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
        290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
        370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
```

```
            465                 470                 475                 480
Ser Glu Leu Tyr Lys Tyr Lys Val Val Lys Ile Glu Pro Leu Gly Val
                485                 490                 495

Ala Pro Thr Lys Ala Lys Arg Val Val Gln Arg Glu Lys Arg Ala
            500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
        530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
            595                 600                 605

Pro Trp Asn Ala Ser Trp Ser Asn Lys Ser Leu Glu Gln Ile Trp Asn
        610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
            690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
        770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
        850                 855

<210> SEQ ID NO 38
<211> LENGTH: 387
<212> TYPE: PRT
<213> ORGANISM: Artificial Sequence
```

<220> FEATURE:
<223> OTHER INFORMATION: Recombinant antibody sequence

<400> SEQUENCE: 38

```
Cys Gly Ala Gly Cys Gly Cys Ala Cys Cys Thr Gly Thr Ala Cys
1               5                   10                  15

Ala Ala Thr Cys Ala Gly Gly Ala Cys Thr Gly Cys Gly Ala Thr
                20                  25                  30

Gly Ala Ala Gly Ala Ala Ala Cys Cys Gly Gly Gly Gly Cys Cys
                35                  40                  45

Thr Cys Ala Gly Thr Ala Ala Gly Ala Gly Thr Cys Thr Cys Thr
                50                  55                  60

Gly Cys Cys Ala Gly Ala Cys Cys Thr Cys Thr Gly Gly Ala Thr Ala
65                  70                  75                  80

Cys Ala Cys Cys Thr Thr Thr Ala Cys Cys Gly Cys Cys Ala Cys
                85                  90                  95

Ala Thr Ala Thr Thr Ala Thr Thr Thr Gly Gly Thr Thr Cys Cys
                100                 105                 110

Gly Ala Cys Ala Gly Gly Cys Cys Cys Cys Gly Gly Gly Cys Gly
                115                 120                 125

Ala Gly Gly Ala Cys Thr Thr Gly Ala Gly Thr Gly Gly Thr Gly
                130                 135                 140

Gly Gly Gly Thr Gly Gly Ala Thr Cys Ala Ala Gly Cys Ala Cys
145                 150                 155                 160

Ala Ala Thr Ala Thr Gly Gly Gly Cys Cys Gly Thr Gly Ala Ala
                165                 170                 175

Thr Thr Thr Thr Gly Gly Thr Gly Gly Thr Gly Thr Thr Thr Thr
                180                 185                 190

Cys Gly Gly Gly Ala Cys Ala Gly Gly Gly Thr Cys Ala Cys Ala
                195                 200                 205

Thr Gly Ala Cys Thr Cys Gly Ala Cys Ala Ala Thr Ala Thr Cys
                210                 215                 220

Thr Cys Ala Ala Gly Ala Cys Cys Cys Ala Gly Ala Cys Gly Ala Cys
225                 230                 235                 240

Cys Cys Gly Gly Ala Cys Thr Gly Gly Gly Cys Ala Thr Thr Gly
                245                 250                 255

Cys Gly Thr Ala Cys Ala Thr Gly Gly Ala Cys Ala Cys Ala Gly
                260                 265                 270

Ala Gly Gly Cys Cys Thr Thr Ala Ala Ala Cys Thr Gly Ala Cys
                275                 280                 285

Gly Ala Cys Ala Cys Gly Gly Cys Cys Gly Thr Cys Thr Ala Thr
                290                 295                 300

Ala Cys Thr Gly Thr Gly Cys Gly Ala Gly Gly Ala Cys Cys Gly
305                 310                 315                 320

Thr Thr Cys Cys Thr Ala Thr Gly Gly Cys Gly Ala Cys Thr Cys
                325                 330                 335

Thr Cys Thr Thr Gly Gly Gly Cys Cys Thr Thr Ala Gly Ala Thr Gly
                340                 345                 350

Cys Cys Thr Gly Gly Gly Ala Cys Ala Gly Gly Ala Ala Cys
                355                 360                 365

Gly Ala Cys Gly Gly Thr Cys Gly Thr Cys Gly Thr Cys Thr Cys Cys
                370                 375                 380

Gly Cys Gly
385
```

<210> SEQ ID NO 39
<211> LENGTH: 309
<212> TYPE: PRT
<213> ORGANISM: homo sapiens

<400> SEQUENCE: 39

```
Thr Ala Cys Ala Thr Cys Cys Ala Cys Gly Thr Gly Ala Cys Cys
1               5                   10                  15

Ala Gly Thr Cys Thr Cys Cys Gly Cys Cys Thr Cys Cys Cys Thr
                20                  25                  30

Gly Thr Cys Thr Gly Thr Gly Thr Cys Thr Ala Thr Gly Gly Ala
                35                  40                  45

Gly Ala Cys Ala Gly Ala Gly Thr Cys Ala Cys Ala Thr Cys Ala
                50                  55                  60

Ala Thr Thr Gly Cys Cys Ala Gly Ala Cys Gly Ala Gly Cys Ala
65                  70                  75                  80

Gly Gly Gly Thr Gly Thr Thr Gly Gly Cys Ala Gly Thr Gly Cys
                85                  90                  95

Cys Thr Ala Cys Ala Thr Thr Gly Gly Thr Ala Thr Cys Ala Ala
                100                 105                 110

Ala Cys Ala Ala Cys Cys Gly Gly Gly Ala Gly Ala Gly Cys
        115                 120                 125

Cys Cys Cys Thr Ala Ala Ala Cys Thr Cys Thr Thr Gly Ala Thr Cys
    130                 135                 140

Cys Ala Cys Cys Ala Thr Ala Cys Cys Thr Cys Thr Cys Thr Gly
145                 150                 155                 160

Thr Gly Gly Ala Ala Gly Ala Cys Gly Gly Thr Gly Thr Cys Cys Cys
                165                 170                 175

Cys Thr Cys Ala Ala Gly Ala Thr Thr Cys Ala Gly Cys Gly Gly Cys
                180                 185                 190

Thr Cys Thr Gly Gly Ala Thr Thr Cys Ala Cys Ala Cys Ala Thr
                195                 200                 205

Cys Thr Thr Thr Thr Ala Ala Thr Cys Thr Gly Ala Cys Cys Ala Thr
    210                 215                 220

Cys Ala Gly Cys Gly Ala Cys Cys Thr Cys Ala Gly Gly Cys Thr
225                 230                 235                 240

Gly Ala Cys Gly Ala Cys Ala Thr Thr Gly Cys Cys Ala Cys Ala Thr
                245                 250                 255

Ala Thr Thr Ala Cys Thr Gly Thr Cys Ala Ala Gly Thr Thr Thr Thr
    260                 265                 270

Ala Cys Ala Ala Thr Thr Thr Thr Cys Gly Gly Cys Cys Gly Ala
    275                 280                 285

Gly Gly Gly Ala Gly Thr Cys Gly Ala Cys Thr Cys Cys Ala Thr Ala
    290                 295                 300

Thr Thr Ala Ala Ala
305
```

<210> SEQ ID NO 40
<211> LENGTH: 384
<212> TYPE: PRT
<213> ORGANISM: Artificial Sequence
<220> FEATURE:
<223> OTHER INFORMATION: Recombinant antibody sequence

<400> SEQUENCE: 40

```
Cys Ala Gly Gly Thr Gly Cys Ala Gly Cys Thr Gly Gly Thr Gly Cys
1               5                   10                  15

Ala Gly Thr Cys Thr Gly Gly Ala Gly Gly Thr Cys Ala Gly Ala Thr
            20                  25                  30

Gly Ala Ala Gly Ala Ala Gly Cys Cys Thr Gly Gly Cys Gly Ala Gly
        35                  40                  45

Thr Cys Gly Ala Thr Gly Ala Gly Ala Ala Thr Thr Thr Cys Thr Thr
    50                  55                  60

Gly Thr Cys Gly Gly Gly Cys Thr Thr Cys Thr Gly Gly Ala Thr Ala
65                  70                  75                  80

Thr Gly Ala Ala Thr Thr Thr Ala Thr Thr Gly Ala Thr Thr Gly Thr
                85                  90                  95

Ala Cys Gly Cys Thr Ala Ala Ala Thr Thr Gly Gly Ala Thr Thr Cys
            100                 105                 110

Gly Thr Cys Thr Gly Gly Cys Cys Cys Cys Cys Gly Gly Ala Ala Ala
        115                 120                 125

Ala Ala Gly Gly Cys Cys Thr Gly Ala Gly Thr Gly Gly Ala Thr Gly
    130                 135                 140

Gly Gly Ala Thr Gly Gly Cys Thr Gly Ala Ala Gly Cys Cys Thr Cys
145                 150                 155                 160

Gly Gly Gly Gly Gly Gly Gly Gly Gly Cys Cys Gly Thr Cys Ala Ala
                165                 170                 175

Cys Thr Ala Cys Gly Cys Ala Cys Gly Thr Cys Cys Ala Cys Thr Thr
            180                 185                 190

Cys Ala Gly Gly Gly Cys Ala Gly Ala Gly Thr Gly Ala Cys Cys Ala
        195                 200                 205

Thr Gly Ala Cys Thr Cys Gly Ala Cys Ala Ala Thr Thr Ala Thr Cys
    210                 215                 220

Thr Cys Ala Ala Gly Ala Cys Cys Cys Ala Gly Ala Cys Gly Ala Cys
225                 230                 235                 240

Cys Cys Gly Gly Ala Cys Thr Gly Gly Gly Gly Cys Ala Cys Ala Gly
                245                 250                 255

Cys Cys Thr Thr Thr Thr Thr Gly Gly Ala Gly Cys Thr Gly Cys Gly
            260                 265                 270

Cys Thr Cys Gly Thr Thr Gly Ala Cys Ala Gly Thr Ala Gly Ala Cys
        275                 280                 285

Gly Ala Cys Ala Cys Gly Gly Cys Cys Gly Thr Cys Thr Ala Cys Thr
    290                 295                 300

Thr Thr Thr Gly Thr Ala Cys Thr Ala Gly Gly Gly Gly Ala Ala Ala
305                 310                 315                 320

Ala Ala Ala Cys Thr Gly Thr Gly Ala Thr Thr Ala Cys Ala Ala Thr
                325                 330                 335

Thr Gly Gly Gly Ala Cys Thr Thr Cys Gly Ala Ala Cys Ala Cys Thr
            340                 345                 350

Gly Gly Gly Gly Cys Cys Gly Gly Gly Gly Cys Ala Cys Cys Cys Cys
        355                 360                 365

Gly Gly Thr Cys Ala Thr Cys Gly Thr Cys Thr Cys Ala Thr Cys Ala
    370                 375                 380
```

```
<210> SEQ ID NO 41
<211> LENGTH: 309
<212> TYPE: PRT
<213> ORGANISM: homo sapiens

<400> SEQUENCE: 41
```

Gly Ala Ala Ala Thr Gly Thr Gly Thr Gly Ala Cys Ala Cys
1               5                   10                  15

Ala Gly Thr Cys Thr Cys Cys Ala Gly Gly Cys Ala Cys Cys Cys Thr
                20                  25                  30

Gly Thr Cys Thr Thr Thr Gly Thr Cys Thr Cys Ala Gly Gly Gly
            35                  40                  45

Gly Ala Ala Cys Ala Gly Cys Cys Ala Thr Cys Ala Thr Cys Thr
        50                  55                  60

Cys Thr Thr Gly Thr Cys Gly Ala Cys Cys Ala Gly Thr Cys Ala
65                  70                  75                  80

Gly Thr Ala Thr Gly Gly Thr Thr Cys Cys Thr Thr Ala Gly Cys Cys
                85                  90                  95

Thr Gly Gly Thr Ala Thr Cys Ala Ala Cys Ala Gly Ala Gly Gly Cys
                100                 105                 110

Cys Cys Gly Gly Cys Cys Ala Gly Gly Cys Cys Cys Cys Ala Gly
            115                 120                 125

Gly Cys Thr Cys Gly Thr Cys Ala Thr Cys Thr Ala Thr Cys Gly
        130                 135                 140

Gly Gly Cys Thr Cys Thr Ala Cys Thr Cys Gly Gly Gly Cys Cys Gly
145                 150                 155                 160

Cys Thr Gly Gly Cys Ala Thr Cys Cys Cys Ala Gly Ala Cys Ala Gly
                165                 170                 175

Gly Thr Thr Cys Ala Gly Cys Gly Gly Cys Ala Gly Thr Cys Gly Gly
                180                 185                 190

Thr Gly Gly Gly Gly Cys Cys Ala Gly Ala Cys Thr Ala Cys Ala
        195                 200                 205

Ala Thr Cys Thr Cys Ala Cys Cys Ala Thr Cys Ala Gly Cys Ala Ala
                210                 215                 220

Cys Cys Thr Gly Gly Ala Gly Thr Cys Thr Gly Gly Ala Gly Ala Thr
225                 230                 235                 240

Thr Thr Thr Gly Gly Thr Gly Thr Thr Thr Ala Thr Ala Thr Thr
            245                 250                 255

Gly Cys Cys Ala Gly Cys Ala Gly Thr Ala Thr Gly Ala Ala Thr Thr
                260                 265                 270

Thr Thr Thr Thr Gly Gly Cys Cys Ala Gly Gly Gly Ala Cys Cys
            275                 280                 285

Ala Ala Gly Gly Thr Cys Ala Gly Gly Thr Cys Gly Ala Cys Ala
        290                 295                 300

Thr Thr Ala Ala Ala
305

<210> SEQ ID NO 42
<211> LENGTH: 396
<212> TYPE: PRT
<213> ORGANISM: Artificial Sequence
<220> FEATURE:
<223> OTHER INFORMATION: Recombinant antibody sequence

<400> SEQUENCE: 42

Cys Ala Gly Gly Thr Gly Cys Gly Ala Cys Thr Gly Thr Cys Gly Cys
1               5                   10                  15

Ala Gly Thr Cys Thr Gly Gly Ala Gly Gly Thr Cys Ala Gly Ala Thr
                20                  25                  30

Gly Ala Ala Gly Ala Ala Gly Cys Cys Thr Gly Gly Cys Gly Ala Cys
            35                  40                  45

Thr Cys Gly Ala Thr Gly Ala Gly Ala Ala Thr Thr Cys Thr Thr
        50                  55                  60

Gly Thr Cys Gly Gly Gly Cys Thr Thr Cys Gly Gly Ala Thr Ala
65                  70                  75                  80

Cys Gly Ala Ala Thr Thr Thr Ala Thr Thr Ala Ala Thr Thr Gly Thr
                    85                  90                  95

Cys Cys Ala Ala Thr Ala Ala Ala Thr Thr Gly Gly Ala Thr Thr Cys
                100                 105                 110

Gly Gly Cys Thr Gly Gly Cys Cys Cys Cys Gly Gly Ala Ala Ala
                115                 120                 125

Ala Ala Gly Gly Cys Cys Thr Gly Ala Gly Thr Gly Ala Thr Gly
            130                 135                 140

Gly Gly Ala Thr Gly Gly Ala Thr Gly Ala Ala Gly Cys Cys Thr Ala
145                 150                 155                 160

Gly Gly Gly Gly Thr Gly Gly Gly Cys Cys Gly Thr Cys Ala Gly
                    165                 170                 175

Thr Thr Ala Cys Gly Cys Ala Cys Gly Thr Cys Ala Ala Cys Thr Thr
                180                 185                 190

Cys Ala Gly Gly Gly Cys Ala Gly Ala Gly Thr Gly Ala Cys Cys Ala
            195                 200                 205

Thr Gly Ala Cys Thr Cys Gly Ala Cys Ala Ala Thr Ala Thr Cys
210                 215                 220

Thr Cys Ala Ala Gly Ala Cys Cys Cys Ala Gly Ala Cys Gly Ala Cys
225                 230                 235                 240

Cys Cys Gly Gly Ala Cys Thr Gly Gly Gly Cys Ala Cys Ala Gly
                    245                 250                 255

Cys Cys Thr Thr Thr Thr Thr Gly Gly Ala Gly Cys Thr Cys Cys Gly
                260                 265                 270

Thr Thr Cys Cys Thr Thr Gly Ala Cys Ala Thr Cys Cys Gly Ala Cys
            275                 280                 285

Gly Ala Cys Ala Cys Gly Gly Cys Cys Gly Thr Cys Thr Ala Thr Thr
290                 295                 300

Thr Thr Thr Gly Thr Ala Cys Thr Cys Gly Gly Gly Ala Ala Ala
305                 310                 315                 320

Ala Thr Ala Thr Thr Gly Cys Ala Cys Thr Gly Cys Gly Cys Gly Cys
                    325                 330                 335

Gly Ala Cys Thr Ala Thr Thr Ala Thr Ala Ala Thr Thr Gly Gly Gly
            340                 345                 350

Ala Cys Thr Thr Cys Gly Ala Ala Cys Ala Cys Thr Gly Gly Gly Gly
            355                 360                 365

Cys Cys Ala Gly Gly Gly Cys Ala Cys Cys Cys Gly Gly Thr Cys
370                 375                 380

Ala Cys Cys Gly Thr Cys Thr Cys Gly Thr Cys Ala
385                 390                 395

<210> SEQ ID NO 43
<211> LENGTH: 309
<212> TYPE: PRT
<213> ORGANISM: homo sapiens

<400> SEQUENCE: 43

Gly Ala Ala Ala Thr Thr Gly Thr Gly Thr Thr Gly Ala Cys Ala Cys
1               5                   10                  15

Ala Gly Thr Cys Thr Cys Cys Ala Gly Gly Cys Ala Cys Cys Cys Thr

```
              20                  25                  30
Gly Thr Cys Thr Thr Thr Gly Thr Cys Thr Cys Cys Ala Gly Gly Gly
            35                  40                  45
Gly Ala Ala Cys Ala Gly Cys Cys Ala Thr Cys Ala Thr Cys Thr
        50                  55                  60
Cys Thr Thr Gly Thr Cys Gly Gly Ala Cys Cys Ala Gly Thr Cys Ala
65                  70                  75                  80
Gly Thr Ala Thr Gly Gly Thr Cys Cys Thr Thr Ala Gly Cys Cys
                85                  90                  95
Thr Gly Gly Thr Ala Thr Cys Ala Ala Cys Ala Gly Ala Gly Gly Cys
            100                 105                 110
Cys Cys Gly Gly Cys Cys Ala Gly Gly Cys Cys Cys Cys Cys Ala Gly

```
            65                  70                  75                  80
Cys Gly Ala Ala Thr Thr Ala Thr Thr Ala Ala Thr Thr Gly Thr
                85                  90                  95
Cys Cys Ala Ala Thr Ala Ala Ala Thr Thr Gly Gly Ala Thr Thr Cys
                100                 105                 110
Gly Gly Cys Thr Gly Gly Cys Cys Cys Cys Gly Gly Ala Ala Ala
                115                 120                 125
Ala Ala Gly Gly Cys Cys Thr Gly Ala Gly Thr Gly Gly Ala Thr Gly
                130                 135                 140
Gly Gly Ala Thr Gly Gly Ala Thr Gly Ala Ala Gly Cys Cys Thr Ala
145                 150                 155                 160
Gly Gly Cys Ala Thr Gly Gly Gly Cys Cys Gly Thr Cys Ala Gly
                165                 170                 175
Thr Thr Ala Cys Gly Cys Ala Cys Gly Thr Cys Ala Ala Cys Thr Thr
                180                 185                 190
Cys Ala Gly Gly Gly Cys Ala Gly Ala Gly Thr Gly Ala Cys Cys Ala
                195                 200                 205
Thr Gly Ala Cys Thr Cys Gly Ala Cys Ala Ala Thr Thr Ala Thr Cys
                210                 215                 220
Thr Cys Ala Ala Gly Ala Cys Cys Ala Gly Ala Cys Gly Ala Cys
225                 230                 235                 240
Cys Cys Gly Gly Ala Cys Thr Gly Gly Gly Cys Ala Cys Ala Gly
                245                 250                 255
Cys Cys Thr Thr Thr Thr Thr Gly Gly Ala Gly Cys Thr Cys Cys Gly
                260                 265                 270
Thr Thr Cys Cys Thr Thr Gly Ala Cys Ala Thr Cys Cys Gly Ala Cys
                275                 280                 285
Gly Ala Cys Ala Cys Gly Gly Cys Cys Gly Thr Cys Thr Ala Thr Thr
                290                 295                 300
Thr Thr Thr Gly Thr Ala Cys Thr Cys Gly Gly Gly Ala Ala Ala
305                 310                 315                 320
Ala Thr Ala Thr Thr Gly Cys Ala Cys Thr Gly Cys Gly Cys Gly Cys
                325                 330                 335
Gly Ala Cys Thr Ala Thr Thr Ala Thr Ala Ala Thr Thr Gly Gly Gly
                340                 345                 350
Ala Cys Thr Thr Cys Gly Ala Ala Cys Ala Cys Thr Gly Gly Gly Gly
                355                 360                 365
Cys Cys Ala Gly Gly Gly Cys Ala Cys Cys Cys Gly Gly Thr Cys
                370                 375                 380
Ala Cys Cys Gly Thr Cys Thr Cys Gly Thr Cys Ala
385                 390                 395

<210> SEQ ID NO 45
<211> LENGTH: 360
<212> TYPE: PRT
<213> ORGANISM: Artificial Sequence
<220> FEATURE:
<223> OTHER INFORMATION: Recombinant antibody sequence

<400> SEQUENCE: 45

Ala Thr Gly Gly Gly Ala Thr Gly Gly Thr Cys Ala Thr Gly Thr Ala
1                   5                   10                  15

Thr Cys Ala Thr Cys Cys Thr Thr Thr Thr Cys Thr Ala Gly Thr
                20                  25                  30

Ala Gly Cys Ala Ala Cys Thr Gly Cys Ala Ala Cys Cys Gly Gly Thr
```

```
            35                  40                  45
Gly Thr Ala Cys Ala Thr Thr Cys Ala Thr Cys Thr Thr Gly Ala
     50                  55                  60
Cys Ala Cys Ala Gly Thr Cys Thr Cys Ala Gly Gly Cys Ala Cys
 65                  70                  75                  80
Cys Cys Thr Gly Thr Cys Thr Thr Thr Gly Thr Cys Thr Cys Ala
                 85                  90                  95
Gly Gly Gly Gly Ala Ala Ala Cys Ala Gly Cys Ala Thr Cys Ala
                100                 105                 110
Thr Cys Thr Cys Thr Thr Gly Thr Cys Gly Ala Cys Cys Ala Gly
                115                 120                 125
Thr Cys Ala Gly Thr Ala Thr Gly Gly Thr Thr Cys Cys Thr Ala
            130                 135                 140
Gly Cys Cys Thr Gly Gly Thr Ala Thr Cys Ala Ala Cys Ala Gly
145                 150                 155                 160
Gly Gly Cys Cys Cys Gly Gly Cys Cys Ala Gly Cys Cys Cys Cys
                165                 170                 175
Cys Ala Gly Gly Cys Thr Cys Gly Thr Cys Ala Thr Cys Thr Ala
            180                 185                 190
Thr Cys Gly Gly Gly Cys Thr Cys Thr Ala Cys Thr Cys Gly Gly
            195                 200                 205
Cys Cys Gly Cys Thr Gly Gly Cys Ala Thr Cys Cys Ala Gly Ala
210                 215                 220
Cys Ala Gly Gly Thr Thr Cys Ala Gly Cys Gly Gly Cys Ala Gly
225                 230                 235                 240
Cys Gly Gly Thr Gly Gly Gly Cys Cys Ala Gly Ala Cys Thr
            245                 250                 255
Ala Cys Ala Ala Thr Cys Thr Cys Ala Cys Cys Ala Thr Cys Ala
            260                 265                 270
Cys Ala Ala Cys Cys Thr Gly Gly Ala Gly Thr Cys Gly Gly Ala
            275                 280                 285
Gly Ala Thr Thr Thr Thr Gly Gly Thr Gly Thr Thr Ala Thr Thr
            290                 295                 300
Ala Thr Thr Gly Cys Cys Ala Gly Cys Ala Gly Thr Ala Thr Ala
305                 310                 315                 320
Ala Thr Thr Thr Thr Thr Gly Gly Cys Cys Ala Gly Gly Gly
                325                 330                 335
Ala Cys Cys Ala Ala Gly Gly Thr Cys Cys Ala Gly Gly Thr Cys
            340                 345                 350
Ala Cys Ala Thr Thr Ala Ala Ala
        355                 360

<210> SEQ ID NO 46
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 46

Glu Asp Asp Asp Tyr
1               5

<210> SEQ ID NO 47
<211> LENGTH: 6
<212> TYPE: PRT
```

-continued

```
<213> ORGANISM: Artificial Sequence
<220> FEATURE:
<223> OTHER INFORMATION: Recombinant antibody sequence

<400> SEQUENCE: 47

Gly Glu Asp Asp Asp Tyr
1               5

<210> SEQ ID NO 48
<211> LENGTH: 8
<212> TYPE: PRT
<213> ORGANISM: Artificial Sequence
<220> FEATURE:
<223> OTHER INFORMATION: Recombinant antibody sequence

<400> SEQUENCE: 48

Gly Ser Gly Glu Asp Asp Asp Tyr
1               5

<210> SEQ ID NO 49
<211> LENGTH: 6
<212> TYPE: PRT
<213> ORGANISM: Artificial Sequence
<220> FEATURE:
<223> OTHER INFORMATION: Recombinant antibody sequence

<400> SEQUENCE: 49

Glu Asp Asp Asp Tyr Gly
1               5

<210> SEQ ID NO 50
<211> LENGTH: 7
<212> TYPE: PRT
<213> ORGANISM: Artificial Sequence
<220> FEATURE:
<223> OTHER INFORMATION: Recombinant antibody sequence

<400> SEQUENCE: 50

Gly Glu Asp Asp Asp Tyr Gly
1               5

<210> SEQ ID NO 51
<211> LENGTH: 9
<212> TYPE: PRT
<213> ORGANISM: Artificial Sequence
<220> FEATURE:
<223> OTHER INFORMATION: Recombinant antibody sequence

<400> SEQUENCE: 51

Gly Ser Gly Glu Asp Asp Asp Tyr Gly
1               5

<210> SEQ ID NO 52
<211> LENGTH: 13
<212> TYPE: PRT
<213> ORGANISM: Artificial Sequence
<220> FEATURE:
<223> OTHER INFORMATION: Recombinant antibody sequence

<400> SEQUENCE: 52

Gly Gln Leu Ser Gln Asp Pro Asp Asp Pro Asp Trp Gly
1               5                   10

<210> SEQ ID NO 53
<211> LENGTH: 15
<212> TYPE: PRT
<213> ORGANISM: Artificial Sequence
```

```
<220> FEATURE:
<223> OTHER INFORMATION: Recombinant antibody sequence

<400> SEQUENCE: 53

Gly Ser Gly Gln Leu Ser Gln Asp Pro Asp Asp Pro Asp Trp Gly
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: Recombinant antibody sequence

<400> SEQUENCE: 54

Gly Gln Leu Ser Gln Asp Pro Asp Asp Pro Asp Trp Gly Ser
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Recombinant antibody sequence

<400> SEQUENCE: 55

Gln Leu Ser Gln Asp Pro Asp Asp Pro Asp Trp Gly Asp
1               5                   10

<210> SEQ ID NO 56
<211> LENGTH: 125
<212> TYPE: PRT
<213> ORGANISM: homo sapiens

<400> SEQUENCE: 56

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
    50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Tyr Thr Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 57
<211> LENGTH: 104
<212> TYPE: PRT
<213> ORGANISM: homo sapiens

<400> SEQUENCE: 57

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30
```

Trp Tyr Gln Lys Lys Pro Gly Gln Pro Pro Lys Leu Leu Ile Phe Ala
            35                  40                  45

Thr Ser Lys Arg Ala Ser Gly Ile Pro Asp Arg Phe Ser Gly Ser Gln
    50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu Ile Arg Arg Thr Val
            100

<210> SEQ ID NO 58
<211> LENGTH: 132
<212> TYPE: PRT
<213> ORGANISM: Artificial Sequence
<220> FEATURE:
<223> OTHER INFORMATION: Recombinant antibody sequence

<400> SEQUENCE: 58

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
    50                  55                  60

Asp Phe Arg Gln Arg Val Ser Leu Thr Arg Gln Leu Ser Gln Asp Pro
65                  70                  75                  80

Asp Asp Pro Asp Trp Gly Thr Ala His Met Asp Ile Arg Gly Leu Thr
                85                  90                  95

Gln Gly Asp Thr Ala Thr Tyr Phe Cys Ala Arg Gln Lys Phe Tyr Thr
            100                 105                 110

Gly Gly Gln Gly Trp Tyr Phe Asp Leu Trp Gly Arg Gly Thr Leu Ile
        115                 120                 125

Val Val Ser Ser
    130

<210> SEQ ID NO 59
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 59

Thr Glu Leu Ile His
1               5

<210> SEQ ID NO 60
<211> LENGTH: 18
<212> TYPE: PRT
<213> ORGANISM: Artificial Sequence
<220> FEATURE:
<223> OTHER INFORMATION: Recombinant antibody sequence

<400> SEQUENCE: 60

Trp Val Lys Thr Val Thr Gly Ala Val Asn Phe Gly Ser Pro Asp Phe
1               5                   10                  15

Arg Gln

<210> SEQ ID NO 61
<211> LENGTH: 14
<212> TYPE: PRT
<213> ORGANISM: Artificial Sequence
<220> FEATURE:
<223> OTHER INFORMATION: Recombinant antibody sequence

<400> SEQUENCE: 61

Gln Lys Phe Tyr Thr Gly Gly Gln Gly Trp Tyr Phe Asp Leu
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Recombinant antibody sequence

<400> SEQUENCE: 62

Thr Ala Ala Ser Tyr Gly His Met Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Recombinant antibody sequence

<400> SEQUENCE: 63

Ala Thr Ser Lys Arg Ala Ser
1               5

<210> SEQ ID NO 64
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 64

Gln Gln Leu Glu Phe
1               5

<210> SEQ ID NO 65
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 65

Trp Leu Lys Pro Arg Trp Gly Ala Val Asn Tyr Ala Arg Pro Leu Gln
1               5                   10                  15

Gly

<210> SEQ ID NO 66
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 66

Asp Tyr Phe Ile His
1               5

<210> SEQ ID NO 67
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 67

Trp Ile Asn Pro Lys Thr Gly Gln Pro Asn Asn Pro Arg Gln Phe Gln
1               5                   10                  15
Gly

<210> SEQ ID NO 68
<211> LENGTH: 10
<212> TYPE: PRT
<213> ORGANISM: Artificial Sequence
<220> FEATURE:
<223> OTHER INFORMATION: Recombinant antibody sequence

<400> SEQUENCE: 68

Gln Arg Ser Asp Tyr Trp Asp Phe Asp Val
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Recombinant antibody sequence

<400> SEQUENCE: 69

Gln Ala Asn Gly Tyr Leu Asn
1               5

<210> SEQ ID NO 70
<211> LENGTH: 7
<212> TYPE: PRT
<213> ORGANISM: Artificial Sequence
<220> FEATURE:
<223> OTHER INFORMATION: Recombinant antibody sequence

<400> SEQUENCE: 70

Asp Gly Ser Lys Leu Glu Arg
1               5

<210> SEQ ID NO 71
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 71

Gln Val Tyr Glu Phe
1               5

<210> SEQ ID NO 72
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 72

-continued

Asp Tyr Ile Ile His
1               5

<210> SEQ ID NO 73
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 73

Trp Met Asn Pro Met Gly Gly Gln Val Asn Ile Pro Trp Lys Phe Gln
1               5                   10                  15

Gly

<210> SEQ ID NO 74
<211> LENGTH: 19
<212> TYPE: PRT
<213> ORGANISM: Artificial Sequence
<220> FEATURE:
<223> OTHER INFORMATION: Recombinant antibody sequence

<400> SEQUENCE: 74

Asp Arg Ser Asn Gly Ser Gly Lys Arg Phe Glu Ser Ser Asn Trp Phe
1               5                   10                  15

Leu Asp Leu

<210> SEQ ID NO 75
<211> LENGTH: 8
<212> TYPE: PRT
<213> ORGANISM: Artificial Sequence
<220> FEATURE:
<223> OTHER INFORMATION: Recombinant antibody sequence

<400> SEQUENCE: 75

Thr Gly Thr His Asn Leu Val Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Recombinant antibody sequence

<400> SEQUENCE: 76

Asp Phe Asn Lys Arg Pro Ser
1               5

<210> SEQ ID NO 77
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 77

Trp Ala Tyr Glu Ala
1               5

<210> SEQ ID NO 78
<211> LENGTH: 5
<212> TYPE: PRT
<213> ORGANISM: Artificial Sequence
<220> FEATURE:

```
<223> OTHER INFORMATION: Recombinant antibody sequence

<400> SEQUENCE: 78

Glu Ile Leu Ile Asn
1               5

<210> SEQ ID NO 79
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 79

Trp Met Asn Pro Arg Gly Gly Val Asn Tyr Ala Arg Gln Phe Gln
1               5                   10                  15

Gly

<210> SEQ ID NO 80
<211> LENGTH: 18
<212> TYPE: PRT
<213> ORGANISM: Artificial Sequence
<220> FEATURE:
<223> OTHER INFORMATION: Recombinant antibody sequence

<400> SEQUENCE: 80

Gly Arg Ser Cys Cys Gly Gly Arg Arg His Cys Asn Gly Ala Asp Cys
1               5                   10                  15

Phe Asn

<210> SEQ ID NO 81
<211> LENGTH: 12
<212> TYPE: PRT
<213> ORGANISM: Artificial Sequence
<220> FEATURE:
<223> OTHER INFORMATION: Recombinant antibody sequence

<400> SEQUENCE: 81

Lys Thr Ser Gln Ala Ile Thr Pro Arg His Leu Val
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Recombinant antibody sequence

<400> SEQUENCE: 82

Gly Thr Ser Glu Arg Ala Ser
1               5

<210> SEQ ID NO 83
<211> LENGTH: 5
<212> TYPE: PRT
<213> ORGANISM: Artificial Sequence
<220> FEATURE:
<223> OTHER INFORMATION: Recombinant antibody sequence

<400> SEQUENCE: 83

Gln Cys Leu Glu Ala
1               5

<210> SEQ ID NO 84
<211> LENGTH: 128
```

```
<212> TYPE: PRT
<213> ORGANISM: Artificial Sequence
<220> FEATURE:
<223> OTHER INFORMATION: Recombinant antibody sequence

<400> SEQUENCE: 84

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Trp Gly Ala Val Asn Tyr Ala Arg Pro Leu
    50                  55                  60

Gln Gly Arg Val Thr Met Thr Arg Gln Leu Ser Gln Asp Pro Asp Asp
65                  70                  75                  80

Pro Asp Trp Gly Thr Ala Phe Leu Glu Leu Arg Ser Leu Thr Val Asp
                85                  90                  95

Asp Thr Ala Val Tyr Phe Cys Thr Arg Gly Lys Asn Cys Asp Tyr Asn
            100                 105                 110

Trp Asp Phe Glu His Trp Gly Arg Gly Thr Pro Val Ile Val Ser Ser
        115                 120                 125

<210> SEQ ID NO 85
<211> LENGTH: 100
<212> TYPE: PRT
<213> ORGANISM: Artificial Sequence
<220> FEATURE:
<223> OTHER INFORMATION: Recombinant antibody sequence

<400> SEQUENCE: 85

Leu Thr Gln Ser Pro Gly Thr Leu Ser Leu Ser Pro Gly Glu Thr Ala
1               5                   10                  15

Ile Ile Ser Cys Arg Thr Ser Gln Tyr Gly Ser Leu Ala Trp Tyr Gln
            20                  25                  30

Gln Arg Pro Gly Gln Ala Pro Arg Leu Val Ile Tyr Ser Gly Ser Thr
        35                  40                  45

Arg Ala Ala Gly Ile Pro Asp Arg Phe Ser Gly Ser Arg Trp Gly Pro
    50                  55                  60

Asp Tyr Asn Leu Thr Ile Ser Asn Leu Glu Ser Gly Asp Phe Gly Val
65                  70                  75                  80

Tyr Tyr Cys Gln Gln Tyr Glu Phe Phe Gly Gln Gly Thr Lys Val Gln
                85                  90                  95

Val Asp Ile Lys
            100

<210> SEQ ID NO 86
<211> LENGTH: 126
<212> TYPE: PRT
<213> ORGANISM: Artificial Sequence
<220> FEATURE:
<223> OTHER INFORMATION: Recombinant antibody sequence

<400> SEQUENCE: 86

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
```

```
                35                  40                  45

Gly Trp Ile Asn Pro Lys Thr Gly Gln Pro Asn Asn Pro Arg Gln Phe
 50                  55                  60

Gln Gly Arg Val Ser Leu Thr Arg Gln Leu Ser Gln Asp Pro Asp Asp
 65                  70                  75                  80

Pro Asp Trp Gly Ser Phe Tyr Met Asp Leu Lys Ala Leu Arg Ser Asp
                 85                  90                  95

Asp Thr Ala Val Tyr Phe Cys Ala Arg Gln Arg Ser Tyr Trp Asp
                100                 105                 110

Phe Asp Val Trp Gly Ser Gly Thr Gln Val Thr Val Ser Ser
            115                 120                 125

<210> SEQ ID NO 87
<211> LENGTH: 134
<212> TYPE: PRT
<213> ORGANISM: Artificial Sequence
<220> FEATURE:
<223> OTHER INFORMATION: Recombinant antibody sequence

<400> SEQUENCE: 87

Ala Asp Leu Val Gln Ser Gly Ala Val Val Lys Lys Pro Gly Asp Ser
 1               5                  10                  15

Val Arg Ile Ser Cys Glu Ala Gln Gly Tyr Arg Phe Pro Asp Tyr Ile
                20                  25                  30

Ile His Trp Ile Arg Arg Ala Pro Gly Gln Gly Pro Glu Trp Met Gly
            35                  40                  45

Trp Met Asn Pro Met Gly Gly Gln Val Asn Ile Pro Trp Lys Phe Gln
 50                  55                  60

Gly Arg Val Ser Met Thr Arg Gln Leu Ser Gln Asp Pro Asp Pro
 65                  70                  75                  80

Asp Trp Gly Thr Ala Phe Leu Asp Leu Arg Gly Leu Lys Ser Asp Asp
                 85                  90                  95

Thr Ala Val Tyr Tyr Cys Val Arg Asp Arg Ser Asn Gly Ser Gly Lys
                100                 105                 110

Arg Phe Glu Ser Ser Asn Trp Phe Leu Asp Leu Trp Gly Arg Gly Thr
            115                 120                 125

Ala Val Thr Ile Gln Ser
            130

<210> SEQ ID NO 88
<211> LENGTH: 103
<212> TYPE: PRT
<213> ORGANISM: homo sapiens

<400> SEQUENCE: 88

Gln Ser Ala Leu Thr Gln Pro Arg Ser Val Ser Ala Ser Pro Gly Gln
 1               5                  10                  15

Ser Val Thr Ile Ser Cys Thr Gly Thr His Asn Leu Val Ser Trp Cys
                20                  25                  30

Gln His Gln Pro Gly Arg Ala Pro Lys Leu Leu Ile Tyr Asp Phe Asn
            35                  40                  45

Lys Arg Pro Ser Gly Val Pro Asp Arg Phe Ser Gly Ser Gly Ser Gly
 50                  55                  60

Gly Thr Ala Ser Leu Thr Ile Thr Gly Leu Gln Asp Asp Asp Ala
 65                  70                  75                  80

Glu Tyr Phe Cys Trp Ala Tyr Glu Ala Phe Gly Gly Gly Thr Lys Leu
                 85                  90                  95
```

Thr Val Leu Gly Gln Pro Lys
              100

<210> SEQ ID NO 89
<211> LENGTH: 139
<212> TYPE: PRT
<213> ORGANISM: Artificial Sequence
<220> FEATURE:
<223> OTHER INFORMATION: Recombinant antibody sequence

<400> SEQUENCE: 89

Glu Val Gln Leu Val Gln Ser Gly Thr Gln Met Lys Glu Pro Gly Ala
1               5                   10                  15

Ser Val Thr Ile Ser Cys Val Thr Ser Gly Tyr Glu Phe Val Glu Ile
            20                  25                  30

Leu Ile Asn Trp Val Arg Gln Val Pro Gly Arg Gly Leu Glu Trp Met
        35                  40                  45

Gly Trp Met Asn Pro Arg Gly Gly Val Asn Tyr Ala Arg Gln Phe
    50                  55                  60

Gln Gly Lys Val Thr Met Thr Arg Gln Leu Ser Gln Asp Pro Asp Asp
65                  70                  75                  80

Pro Asp Trp Gly Thr Ala Tyr Leu Thr Leu Ser Gly Leu Thr Ser Gly
                85                  90                  95

Asp Thr Ala Lys Tyr Phe Cys Val Arg Gly Arg Ser Cys Cys Gly Gly
            100                 105                 110

Arg Arg His Cys Asn Gly Ala Asp Cys Phe Asn Trp Asp Phe Gln His
        115                 120                 125

Trp Gly Gln Gly Thr Leu Val Ile Val Ser Pro
    130                 135

<210> SEQ ID NO 90
<211> LENGTH: 104
<212> TYPE: PRT
<213> ORGANISM: homo sapiens

<400> SEQUENCE: 90

Tyr Ile Gly Val Thr Gln Ser Pro Ala Ile Leu Ser Val Ser Leu Gly
1               5                   10                  15

Glu Arg Val Thr Leu Ser Cys Lys Thr Ser Gln Ala Ile Thr Pro Arg
            20                  25                  30

His Leu Val Trp His Arg Gln Lys Gly Gly Gln Ala Pro Ser Leu Val
        35                  40                  45

Met Thr Gly Thr Ser Glu Arg Ala Ser Gly Ile Pro Asp Arg Phe Ile
    50                  55                  60

Gly Ser Gly Ser Gly Thr Asp Phe Thr Leu Thr Ile Thr Arg Leu Glu
65                  70                  75                  80

Ala Glu Asp Phe Ala Val Tyr Tyr Cys Gln Cys Leu Glu Ala Phe Gly
                85                  90                  95

Gln Gly Thr Lys Leu Glu Ile Lys
            100

<210> SEQ ID NO 91
<211> LENGTH: 458
<212> TYPE: PRT
<213> ORGANISM: Artificial Sequence
<220> FEATURE:
<223> OTHER INFORMATION: Recombinant antibody sequence

<400> SEQUENCE: 91

```
Gln Val Gln Leu Val Gln Ser Gly Gly Gln Met Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
            35                  40                  45

Gly Trp Leu Lys Pro Arg Trp Gly Ala Val Asn Tyr Ala Arg Pro Leu
        50                  55                  60

Gln Gly Arg Val Thr Met Thr Arg Gln Leu Ser Gln Asp Pro Asp Asp
65                  70                  75                  80

Pro Asp Trp Gly Thr Ala Phe Leu Glu Leu Arg Ser Leu Thr Val Asp
                85                  90                  95

Asp Thr Ala Val Tyr Phe Cys Thr Arg Gly Lys Asn Cys Asp Tyr Asn
                100                 105                 110

Trp Asp Phe Glu His Trp Gly Arg Gly Thr Pro Val Ile Val Ser Ser
            115                 120                 125

Pro Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
        210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415
```

```
Leu Tyr Ser Lys Leu Thr Val Asp Lys Ser Arg Trp Gln Gln Gly Asn
            420                 425                 430

Val Phe Ser Cys Ser Val Leu His Glu Ala Leu His Ser His Tyr Thr
            435                 440                 445

Gln Lys Ser Leu Ser Leu Ser Pro Gly Lys
    450                 455

<210> SEQ ID NO 92
<211> LENGTH: 207
<212> TYPE: PRT
<213> ORGANISM: Artificial Sequence
<220> FEATURE:
<223> OTHER INFORMATION: Recombinant antibody sequence

<400> SEQUENCE: 92

Leu Thr Gln Ser Pro Gly Thr Leu Ser Leu Ser Pro Gly Glu Thr Ala
1               5                   10                  15

Ile Ile Ser Cys Arg Thr Ser Gln Tyr Gly Ser Leu Ala Trp Tyr Gln
            20                  25                  30

Gln Arg Pro Gly Gln Ala Pro Arg Leu Val Ile Tyr Ser Gly Ser Thr
        35                  40                  45

Arg Ala Ala Gly Ile Pro Asp Arg Phe Ser Gly Ser Arg Trp Gly Pro
    50                  55                  60

Asp Tyr Asn Leu Thr Ile Ser Asn Leu Glu Ser Gly Asp Phe Gly Val
65                  70                  75                  80

Tyr Tyr Cys Gln Gln Tyr Glu Phe Phe Gly Gln Gly Thr Lys Val Gln
                85                  90                  95

Val Asp Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val Gln Trp Lys Val Asp
    130                 135                 140

Asn Ala Leu Gln Ser Gly Asn Ser Gln Glu Ser Val Thr Glu Gln Asp
145                 150                 155                 160

Ser Lys Asp Ser Thr Tyr Ser Leu Ser Ser Thr Leu Thr Leu Ser Lys
                165                 170                 175

Ala Asp Tyr Glu Lys His Lys Val Tyr Ala Cys Glu Val Thr His Gln
            180                 185                 190

Gly Leu Ser Ser Pro Val Thr Lys Ser Phe Asn Arg Gly Glu Cys
        195                 200                 205

<210> SEQ ID NO 93
<211> LENGTH: 1431
<212> TYPE: PRT
<213> ORGANISM: Artificial Sequence
<220> FEATURE:
<223> OTHER INFORMATION: Recombinant antibody sequence

<400> SEQUENCE: 93

Ala Thr Gly Gly Gly Ala Thr Gly Gly Thr Cys Ala Thr Gly Thr Ala
1               5                   10                  15

Thr Cys Ala Thr Cys Cys Thr Thr Thr Thr Thr Cys Thr Ala Gly Thr
            20                  25                  30

Ala Gly Cys Ala Ala Cys Thr Gly Cys Ala Ala Cys Cys Gly Gly Thr
        35                  40                  45

Gly Thr Ala Cys Ala Thr Thr Cys Cys Cys Ala Gly Gly Thr Gly Cys
    50                  55                  60
```

```
Ala Gly Cys Thr Gly Gly Thr Gly Cys Ala Gly Thr Cys Thr Gly Gly
65                  70                  75                  80

Ala Gly Gly Thr Cys Ala Gly Ala Thr Gly Ala Ala Gly Ala Ala Gly
                85                  90                  95

Cys Cys Thr Gly Gly Cys Gly Ala Gly Thr Cys Gly Ala Thr Gly Ala
            100                 105                 110

Gly Ala Ala Thr Thr Thr Cys Thr Thr Gly Thr Cys Gly Gly Gly Cys
        115                 120                 125

Thr Thr Cys Thr Gly Gly Ala Thr Ala Thr Gly Ala Ala Thr Thr Thr
    130                 135                 140

Ala Thr Thr Gly Ala Thr Thr Gly Thr Ala Cys Gly Cys Thr Ala Ala
145                 150                 155                 160

Ala Thr Thr Gly Gly Ala Thr Thr Cys Gly Thr Cys Thr Gly Gly Cys
                165                 170                 175

Cys Cys Cys Cys Gly Gly Ala Ala Ala Ala Ala Gly Gly Cys Cys Thr
            180                 185                 190

Gly Ala Gly Thr Gly Gly Ala Thr Gly Gly Gly Ala Thr Gly Gly Cys
        195                 200                 205

Thr Gly Ala Ala Gly Cys Cys Thr Cys Gly Gly Thr Gly Gly Gly Gly
    210                 215                 220

Gly Gly Cys Cys Gly Thr Cys Ala Ala Cys Thr Ala Cys Gly Cys Ala
225                 230                 235                 240

Cys Gly Thr Cys Cys Ala Cys Thr Thr Cys Ala Gly Gly Gly Cys Ala
                245                 250                 255

Gly Ala Gly Thr Gly Ala Cys Cys Ala Thr Gly Ala Cys Thr Cys Gly
            260                 265                 270

Ala Cys Ala Gly Cys Thr Gly Ala Gly Cys Cys Ala Gly Gly Ala Cys
        275                 280                 285

Cys Cys Thr Gly Ala Cys Gly Ala Thr Cys Cys Cys Gly Ala Thr Thr
    290                 295                 300

Gly Gly Gly Gly Cys Ala Cys Ala Gly Cys Cys Thr Thr Thr Thr Thr
305                 310                 315                 320

Gly Gly Ala Gly Cys Thr Gly Cys Gly Cys Thr Cys Gly Thr Thr Gly
                325                 330                 335

Ala Cys Ala Gly Thr Ala Gly Ala Cys Gly Ala Cys Ala Cys Gly Gly
            340                 345                 350

Cys Cys Gly Thr Cys Thr Ala Cys Thr Thr Thr Thr Gly Thr Ala Cys
        355                 360                 365

Thr Ala Gly Gly Gly Gly Ala Ala Ala Ala Ala Cys Thr Gly Thr
    370                 375                 380

Gly Ala Thr Thr Ala Cys Ala Ala Thr Thr Gly Gly Gly Ala Cys Thr
385                 390                 395                 400

Thr Cys Gly Ala Ala Cys Ala Cys Thr Gly Gly Gly Gly Cys Cys Gly
                405                 410                 415

Gly Gly Gly Cys Ala Cys Cys Cys Cys Gly Gly Thr Cys Ala Thr Cys
            420                 425                 430

Gly Thr Cys Thr Cys Ala Thr Cys Ala Cys Cys Gly Thr Cys Gly Ala
        435                 440                 445

Cys Cys Ala Ala Gly Gly Gly Cys Cys Cys Ala Thr Cys Gly Gly Thr
    450                 455                 460

Cys Thr Thr Cys Cys Cys Cys Cys Thr Gly Gly Cys Ala Cys Cys Cys
465                 470                 475                 480

-continued

```
Thr Cys Cys Thr Cys Cys Ala Ala Gly Ala Gly Cys Ala Cys Cys Thr
            485                 490                 495
Cys Thr Gly Gly Gly Gly Cys Ala Cys Ala Gly Cys Gly Gly Cys
        500                 505                 510
Cys Cys Thr Gly Gly Gly Cys Thr Gly Cys Cys Thr Gly Gly Thr Cys
        515                 520                 525
Ala Ala Gly Gly Ala Cys Thr Ala Cys Thr Thr Cys Cys Cys Cys Gly
        530                 535                 540
Ala Ala Cys Cys Gly Gly Thr Gly Ala Cys Gly Gly Thr Gly Thr Cys
545                 550                 555                 560
Gly Thr Gly Gly Ala Ala Cys Thr Cys Ala Gly Gly Cys Gly Cys Cys
                565                 570                 575
Cys Thr Gly Ala Cys Cys Ala Gly Cys Gly Gly Cys Gly Thr Gly Cys
        580                 585                 590
Ala Cys Ala Cys Cys Thr Thr Cys Cys Cys Gly Gly Cys Thr Gly Thr
        595                 600                 605
Cys Cys Thr Ala Cys Ala Gly Thr Cys Cys Thr Cys Ala Gly Gly Ala
        610                 615                 620
Cys Thr Cys Thr Ala Cys Thr Cys Cys Cys Thr Cys Ala Gly Cys Ala
625                 630                 635                 640
Gly Cys Gly Thr Gly Gly Thr Gly Ala Cys Cys Gly Thr Gly Cys Cys
                645                 650                 655
Cys Thr Cys Cys Ala Gly Cys Ala Gly Cys Thr Thr Gly Gly Gly Cys
        660                 665                 670
Ala Cys Cys Cys Ala Gly Ala Cys Cys Thr Ala Cys Ala Thr Cys Thr
        675                 680                 685
Gly Cys Ala Ala Cys Gly Thr Gly Ala Ala Thr Cys Ala Cys Ala Ala
        690                 695                 700
Gly Cys Cys Cys Ala Gly Cys Ala Ala Cys Ala Cys Cys Ala Ala Gly
705                 710                 715                 720
Gly Thr Gly Gly Ala Cys Ala Ala Gly Ala Ala Gly Thr Thr Gly
                725                 730                 735
Ala Gly Cys Cys Cys Ala Ala Ala Thr Cys Thr Thr Gly Thr Gly Ala
        740                 745                 750
Cys Ala Ala Ala Cys Thr Cys Ala Cys Ala Cys Ala Thr Gly Cys
        755                 760                 765
Cys Cys Ala Cys Cys Gly Thr Gly Cys Cys Cys Ala Gly Cys Ala Cys
        770                 775                 780
Cys Thr Gly Ala Ala Cys Thr Cys Cys Thr Gly Gly Gly Gly Gly
785                 790                 795                 800
Ala Cys Cys Gly Thr Cys Ala Gly Thr Cys Thr Thr Cys Cys Thr Cys
                805                 810                 815
Thr Thr Cys Cys Cys Cys Cys Cys Ala Ala Ala Ala Cys Cys Cys Ala
        820                 825                 830
Ala Gly Gly Ala Cys Ala Cys Cys Cys Thr Cys Ala Thr Gly Ala Thr
        835                 840                 845
Cys Thr Cys Cys Cys Gly Gly Ala Cys Cys Cys Cys Thr Gly Ala Gly
        850                 855                 860
Gly Thr Cys Ala Cys Ala Thr Gly Cys Gly Thr Gly Gly Thr Gly Gly
865                 870                 875                 880
Thr Gly Gly Ala Cys Gly Thr Gly Ala Gly Cys Cys Ala Cys Gly Ala
                885                 890                 895
Ala Gly Ala Cys Cys Cys Thr Gly Ala Gly Gly Thr Cys Ala Ala Gly
```

-continued

```
                    900                 905                 910
Thr Thr Cys Ala Ala Cys Thr Gly Gly Thr Ala Cys Gly Thr Gly Gly
            915                 920                 925
Ala Cys Gly Gly Cys Gly Thr Gly Gly Ala Gly Gly Thr Gly Cys Ala
    930                 935                 940
Thr Ala Ala Thr Gly Cys Cys Ala Ala Gly Ala Cys Ala Ala Ala Gly
945                 950                 955                 960
Cys Cys Gly Cys Gly Gly Ala Gly Gly Ala Gly Cys Ala Gly Thr
                965                 970                 975
Ala Cys Ala Ala Cys Ala Gly Cys Ala Cys Gly Thr Ala Cys Cys Gly
                980                 985                 990
Thr Gly Thr Gly Gly Thr Cys Ala  Gly Cys Gly Thr Cys  Cys Thr Cys
            995                 1000                1005
Ala Cys  Cys Gly Thr Cys Cys  Thr Gly Cys Ala Cys  Cys Ala Gly
        1010                1015                1020
Gly Ala  Cys Thr Gly Gly Cys  Thr Gly Ala Ala Thr  Gly Gly Cys
        1025                1030                1035
Ala Ala  Gly Gly Ala Gly Thr  Ala Cys Ala Ala Gly  Thr Gly Cys
        1040                1045                1050
Ala Ala  Gly Gly Thr Cys Thr  Cys Cys Ala Ala Cys  Ala Ala Ala
        1055                1060                1065
Gly Cys  Cys Cys Thr Cys Cys  Cys Ala Gly Cys Cys  Cys Cys Cys
        1070                1075                1080
Ala Thr  Cys Gly Ala Gly Ala  Ala Ala Ala Cys Cys  Ala Thr Cys
        1085                1090                1095
Thr Cys  Cys Ala Ala Ala Gly  Cys Cys Ala Ala Ala  Gly Gly Gly
        1100                1105                1110
Cys Ala  Gly Cys Cys Cys Cys  Gly Ala Gly Ala Ala  Cys Cys Ala
        1115                1120                1125
Cys Ala  Gly Gly Thr Gly Thr  Ala Cys Ala Cys Cys  Cys Thr Gly
        1130                1135                1140
Cys Cys  Cys Cys Cys Ala Thr  Cys Cys Cys Gly Gly  Gly Ala Thr
        1145                1150                1155
Gly Ala  Gly Cys Thr Gly Ala  Cys Cys Ala Ala Gly  Ala Ala Cys
        1160                1165                1170
Cys Ala  Gly Gly Thr Cys Ala  Gly Cys Cys Thr Gly  Ala Cys Cys
        1175                1180                1185
Thr Gly  Cys Cys Thr Gly Gly  Thr Cys Ala Ala Ala  Gly Gly Cys
        1190                1195                1200
Thr Thr  Cys Thr Ala Thr Cys  Cys Cys Ala Gly Cys  Gly Ala Cys
        1205                1210                1215
Ala Thr  Cys Gly Cys Cys Gly  Thr Gly Gly Ala Gly  Thr Gly Gly
        1220                1225                1230
Gly Ala  Gly Ala Gly Cys Ala  Ala Thr Gly Gly Gly  Cys Ala Gly
        1235                1240                1245
Cys Cys  Gly Gly Ala Gly Ala  Ala Cys Ala Ala Cys  Thr Ala Cys
        1250                1255                1260
Ala Ala  Gly Ala Cys Cys Ala  Cys Gly Cys Cys Thr  Cys Cys Cys
        1265                1270                1275
Gly Thr  Gly Cys Thr Gly Gly  Ala Cys Thr Cys Cys  Gly Ala Cys
        1280                1285                1290
Gly Gly  Cys Thr Cys Cys Thr  Thr Cys Thr Thr Cys  Cys Thr Cys
        1295                1300                1305
```

Thr Ala Cys Ala Gly Cys Ala Ala Gly Cys Thr Cys Ala Cys Cys
            1310                1315                1320

Gly Thr Gly Gly Ala Cys Ala  Ala Gly Ala Gly Cys  Ala Gly Gly
            1325                1330                1335

Thr Gly Gly Cys Ala Gly Cys  Ala Gly Gly Gly Gly  Ala Ala Cys
            1340                1345                1350

Gly Thr Cys Thr Thr Cys Thr  Cys Ala Thr Gly Cys  Thr Cys Cys
            1355                1360                1365

Gly Thr Gly Cys Thr Gly Cys  Ala Thr Gly Ala Gly  Gly Cys Thr
            1370                1375                1380

Cys Thr Gly Cys Ala Cys Ala  Gly Cys Cys Ala Cys  Thr Ala Cys
            1385                1390                1395

Ala Cys Gly Cys Ala Gly Ala  Ala Gly Ala Gly Cys  Cys Thr Cys
            1400                1405                1410

Thr Cys Cys Cys Thr Gly Thr  Cys Thr Cys Cys Gly  Gly Gly Thr
            1415                1420                1425

Ala Ala Ala
    1430

<210> SEQ ID NO 94
<211> LENGTH: 678
<212> TYPE: PRT
<213> ORGANISM: Artificial Sequence
<220> FEATURE:
<223> OTHER INFORMATION: Recombinant antibody sequence

<400> SEQUENCE: 94

Ala Thr Gly Gly Gly Ala Thr Gly Gly Thr Cys Ala Thr Gly Thr Ala
1               5                   10                  15

Thr Cys Ala Thr Cys Cys Thr Thr Thr Thr Thr Cys Thr Ala Gly Thr
            20                  25                  30

Ala Gly Cys Ala Ala Cys Thr Gly Cys Ala Ala Cys Cys Gly Gly Thr
        35                  40                  45

Gly Thr Ala Cys Ala Thr Thr Cys Ala Thr Gly Ala Cys Ala Cys
    50                  55                  60

Ala Gly Thr Cys Thr Cys Cys Ala Gly Gly Cys Ala Cys Cys Cys Thr
65                  70                  75                  80

Gly Thr Cys Thr Thr Thr Gly Thr Cys Thr Cys Cys Ala Gly Gly Gly
                85                  90                  95

Gly Ala Ala Ala Cys Ala Gly Cys Cys Ala Cys Cys Cys Thr Cys Thr
                100                 105                 110

Cys Thr Thr Gly Thr Gly Gly Ala Cys Cys Ala Gly Thr Cys Ala
            115                 120                 125

Gly Thr Ala Thr Gly Gly Thr Thr Cys Thr Thr Ala Gly Cys Cys
        130                 135                 140

Thr Gly Gly Thr Ala Cys Ala Ala Cys Ala Gly Ala Gly Gly Cys
145                 150                 155                 160

Cys Cys Gly Gly Cys Cys Ala Gly Cys Cys Cys Cys Cys Ala Gly
                165                 170                 175

Gly Cys Thr Cys Gly Thr Cys Ala Thr Cys Thr Ala Thr Thr Cys Gly
                180                 185                 190

Gly Gly Cys Thr Cys Thr Ala Cys Thr Cys Gly Gly Gly Cys Cys Gly
            195                 200                 205

Cys Thr Gly Gly Cys Ala Thr Cys Cys Cys Ala Gly Ala Cys Ala Gly
        210                 215                 220

```
Gly Thr Thr Cys Ala Gly Cys Gly Cys Ala Gly Cys Gly Gly
225                 230                 235                 240

Thr Gly Gly Gly Gly Cys Cys Ala Gly Ala Cys Thr Ala Cys Ala
                245                 250                 255

Ala Thr Cys Thr Cys Ala Cys Cys Ala Thr Cys Ala Gly Cys Ala Ala
            260                 265                 270

Cys Cys Thr Gly Gly Ala Gly Thr Cys Gly Gly Ala Gly Ala Thr
        275                 280                 285

Thr Thr Thr Gly Gly Thr Gly Thr Thr Ala Thr Thr Ala Thr Thr
    290                 295                 300

Gly Cys Cys Ala Gly Cys Ala Gly Thr Ala Thr Gly Ala Ala Thr Thr
305                 310                 315                 320

Thr Thr Thr Thr Gly Gly Cys Cys Ala Gly Gly Gly Ala Cys Cys
            325                 330                 335

Ala Ala Gly Gly Thr Cys Cys Ala Gly Gly Thr Cys Gly Ala Cys Ala
        340                 345                 350

Thr Thr Ala Ala Ala Cys Gly Thr Ala Cys Gly Gly Thr Gly Gly Cys
    355                 360                 365

Thr Gly Cys Ala Cys Cys Ala Thr Cys Thr Gly Thr Cys Thr Thr Cys
370                 375                 380

Ala Thr Cys Thr Thr Cys Cys Cys Gly Cys Cys Ala Thr Cys Thr Gly
385                 390                 395                 400

Ala Thr Gly Ala Gly Cys Ala Gly Thr Thr Gly Ala Ala Ala Thr Cys
            405                 410                 415

Thr Gly Gly Ala Ala Cys Thr Gly Cys Cys Thr Cys Thr Gly Thr Thr
        420                 425                 430

Gly Thr Gly Thr Gly Cys Cys Thr Gly Cys Thr Gly Ala Ala Thr Ala
    435                 440                 445

Ala Cys Thr Thr Cys Thr Ala Cys Cys Cys Cys Ala Gly Ala Gly Ala
450                 455                 460

Ala Gly Cys Cys Ala Ala Ala Gly Thr Gly Cys Ala Gly Thr Gly Gly
465                 470                 475                 480

Ala Ala Gly Gly Thr Gly Gly Ala Cys Ala Ala Cys Gly Cys Cys Cys
            485                 490                 495

Thr Gly Cys Ala Gly Ala Gly Cys Gly Gly Ala Ala Cys Ala Gly
        500                 505                 510

Cys Cys Ala Gly Gly Ala Ala Ala Gly Cys Gly Thr Gly Ala Cys Ala
    515                 520                 525

Gly Ala Gly Cys Ala Gly Gly Ala Thr Thr Cys Cys Ala Ala Gly Gly
530                 535                 540

Ala Thr Thr Cys Cys Ala Cys Ala Cys Ala Gly Cys Cys Thr
545                 550                 555                 560

Gly Ala Gly Cys Ala Gly Cys Ala Cys Ala Thr Gly Ala Cys Ala
            565                 570                 575

Cys Thr Gly Thr Cys Cys Ala Ala Gly Gly Cys Gly Ala Cys Thr
        580                 585                 590

Ala Cys Gly Ala Gly Ala Ala Gly Cys Ala Cys Ala Ala Gly Gly Thr
    595                 600                 605

Gly Thr Ala Cys Gly Cys Cys Thr Gly Cys Gly Ala Ala Gly Thr Gly
610                 615                 620

Ala Cys Ala Cys Ala Cys Cys Ala Gly Gly Gly Ala Cys Thr Gly Thr
625                 630                 635                 640
```

```
Cys Cys Thr Cys Cys Cys Thr Gly Thr Gly Ala Cys Ala Ala Ala
                645                 650                 655

Gly Ala Gly Cys Thr Thr Cys Ala Ala Cys Ala Gly Ala Gly Ala
        660                 665                 670

Gly Ala Ala Thr Gly Cys
        675

<210> SEQ ID NO 95
<211> LENGTH: 129
<212> TYPE: PRT
<213> ORGANISM: Artificial Sequence
<220> FEATURE:
<223> OTHER INFORMATION: Recombinant antibody sequence

<400> SEQUENCE: 95

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Trp Gly Ala Val Asn Phe Gly Gly Phe
    50                  55                  60

Arg Asp Arg Val Thr Leu Thr Arg Gln Leu Ser Gln Asp Pro Asp Asp
65                  70                  75                  80

Pro Asp Trp Gly Ile Ala Tyr Met Asp Ile Arg Gly Leu Lys Pro Asp
                85                  90                  95

Asp Thr Ala Val Tyr Tyr Cys Ala Arg Asp Arg Ser Tyr Gly Asp Ser
            100                 105                 110

Ser Trp Ala Leu Asp Ala Trp Gly Gln Gly Thr Thr Val Val Val Ser
        115                 120                 125

Ala

<210> SEQ ID NO 96
<211> LENGTH: 129
<212> TYPE: PRT
<213> ORGANISM: Artificial Sequence
<220> FEATURE:
<223> OTHER INFORMATION: Recombinant antibody sequence

<400> SEQUENCE: 96

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Phe
    50                  55                  60

Arg Asp Arg Val Thr Leu Thr Arg Gln Leu Ser Gln Asp Pro Asp Asp
65                  70                  75                  80

Pro Asp Trp Gly Ile Ala Tyr Met Asp Ile Arg Gly Leu Lys Pro Asp
                85                  90                  95

Asp Thr Ala Val Tyr Tyr Cys Ala Arg Asp Arg Ser Ser Gly Asp Ser
            100                 105                 110

Ser Trp Ala Leu Asp Ala Trp Gly Gln Gly Thr Thr Val Val Val Ser
        115                 120                 125
```

```
<210> SEQ ID NO 97
<211> LENGTH: 101
<212> TYPE: PRT
<213> ORGANISM: Artificial Sequence
<220> FEATURE:
<223> OTHER INFORMATION: Recombinant antibody sequence

<400> SEQUENCE: 97

His Val Thr Gln Ser Pro Ser Ser Leu Ser Val Ser Ile Gly Asp Arg
1               5                   10                  15

Val Thr Ile Asn Cys Gln Thr Ser Gln Gly Val Gly Ser Asp Leu His
            20                  25                  30

Trp Tyr Gln His Lys Pro Gly Arg Ala Pro Lys Leu Leu Ile His His
        35                  40                  45

Thr Ser Ser Val Glu Asp Gly Val Pro Ser Arg Phe Ser Gly Ser Gly
    50                  55                  60

Phe His Thr Ser Phe Asn Leu Thr Ile Ser Asp Leu Gln Ala Asp Asp
65                  70                  75                  80

Ile Ala Thr Tyr Tyr Cys Gln Val Leu Gln Phe Phe Gly Arg Gly Ser
                85                  90                  95

Arg Leu His Ile Lys
            100

<210> SEQ ID NO 98
<211> LENGTH: 100
<212> TYPE: PRT
<213> ORGANISM: Artificial Sequence
<220> FEATURE:
<223> OTHER INFORMATION: Recombinant antibody sequence

<400> SEQUENCE: 98

Val Thr Gln Ser Pro Ser Ser Leu Ser Val Ser Ile Gly Asp Arg Val
1               5                   10                  15

Thr Ile Asn Cys Gln Thr Ser Gln Gly Val Gly Ser Asp Leu His Trp
            20                  25                  30

Tyr Gln His Lys Pro Gly Arg Ala Pro Lys Leu Leu Ile His His Thr
        35                  40                  45

Ser Ser Val Glu Asp Gly Val Pro Ser Arg Phe Ser Gly Ser Gly Phe
    50                  55                  60

His Thr Ser Phe Asn Leu Thr Ile Ser Asp Leu Gln Ala Asp Asp Ile
65                  70                  75                  80

Ala Thr Tyr Tyr Cys Gln Val Leu Gln Phe Phe Gly Arg Gly Ser Arg
                85                  90                  95

Leu His Ile Lys
            100

<210> SEQ ID NO 99
<211> LENGTH: 458
<212> TYPE: PRT
<213> ORGANISM: Artificial Sequence
<220> FEATURE:
<223> OTHER INFORMATION: Recombinant antibody sequence

<400> SEQUENCE: 99

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30
```

```
Ile Leu Phe Trp Phe Arg Gln Ala Pro Gly Arg Gly Leu Glu Trp Val
         35                  40                  45

Gly Trp Ile Lys Pro Gln Tyr Gly Ala Val Asn Phe Gly Gly Gly Phe
     50                  55                  60

Arg Asp Arg Val Thr Leu Thr Arg Gln Leu Ser Gln Asp Pro Asp Asp
 65                  70                  75                  80

Pro Asp Trp Gly Ile Ala Tyr Met Asp Ile Arg Gly Leu Lys Pro Asp
                 85                  90                  95

Asp Thr Ala Val Tyr Tyr Cys Ala Arg Asp Arg Ser Tyr Gly Asp Ser
                100                 105                 110

Ser Trp Ala Leu Asp Ala Trp Gly Gln Gly Thr Thr Val Val Val Ser
            115                 120                 125

Ala Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
            195                 200                 205

Thr Tyr Ile Cys Asn Val Asn His Lys Pro Ser Asn Thr Lys Val Asp
            210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
            290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
                340                 345                 350

Gly Gln Pro Arg Glu Pro Gln Val Tyr Thr Leu Pro Pro Ser Arg Asp
            355                 360                 365

Glu Leu Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Leu His Ala Leu His Ser His Tyr Thr
            435                 440                 445
```

```
Gln Lys Ser Leu Ser Leu Ser Pro Gly Lys
    450                 455

<210> SEQ ID NO 100
<211> LENGTH: 210
<212> TYPE: PRT
<213> ORGANISM: homo sapiens

<400> SEQUENCE: 100

Tyr Ile His Val Thr Gln Ser Pro Ser Leu Ser Val Ser Ile Gly
1               5                   10                  15

Asp Arg Val Thr Ile Asn Cys Gln Thr Ser Gln Gly Val Gly Ser Asp
                20                  25                  30

Leu His Trp Tyr Gln His Lys Pro Gly Arg Ala Pro Lys Leu Leu Ile
            35                  40                  45

His His Thr Ser Ser Val Glu Asp Gly Val Pro Ser Arg Phe Ser Gly
        50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210

<210> SEQ ID NO 101
<211> LENGTH: 132
<212> TYPE: PRT
<213> ORGANISM: Artificial Sequence
<220> FEATURE:
<223> OTHER INFORMATION: Recombinant antibody sequence

<400> SEQUENCE: 101

Gln Val Arg Leu Ser Gln Ser Gly Gly Gln Met Lys Lys Pro Gly Asp
1               5                   10                  15

Ser Met Arg Ile Ser Cys Arg Ala Ser Gly Tyr Glu Phe Ile Asn Cys
                20                  25                  30

Pro Ile Asn Trp Ile Arg Leu Ala Pro Gly Lys Arg Pro Glu Trp Met
            35                  40                  45

Gly Trp Met Lys Pro Arg Trp Gly Ala Val Ser Tyr Ala Arg Gln Leu
        50                  55                  60

Gln Gly Arg Val Thr Met Thr Arg Gln Leu Ser Gln Asp Pro Asp Asp
65                  70                  75                  80

Pro Asp Trp Gly Thr Ala Phe Leu Glu Leu Arg Ser Leu Thr Ser Asp
```

```
                85                  90                  95
Asp Thr Ala Val Tyr Phe Cys Thr Arg Gly Lys Tyr Cys Thr Ala Arg
            100                 105                 110
Asp Tyr Tyr Asn Trp Asp Phe Glu His Trp Gly Gln Gly Thr Pro Val
        115                 120                 125
Thr Val Ser Ser
    130

<210> SEQ ID NO 102
<211> LENGTH: 132
<212> TYPE: PRT
<213> ORGANISM: Artificial Sequence
<220> FEATURE:
<223> OTHER INFORMATION: Recombinant antibody sequence

<400> SEQUENCE: 102

Gln Val Arg Leu Ser Gln Ser Gly Gly Gln Met Lys Lys Pro Gly Asp
1               5                   10                  15
Ser Met Arg Ile Ser Cys Arg Ala Ser Gly Tyr Glu Phe Ile Asn Cys
            20                  25                  30
Pro Ile Asn Trp Ile Arg Leu Ala Pro Gly Lys Arg Pro Glu Trp Met
        35                  40                  45
Gly Trp Met Lys Pro Arg Phe Gly Ala Val Ser Tyr Ala Arg Gln Leu
    50                  55                  60
Gln Gly Arg Val Thr Met Thr Arg Gln Leu Ser Gln Asp Pro Asp Asp
65                  70                  75                  80
Pro Asp Trp Gly Thr Ala Phe Leu Glu Leu Arg Ser Leu Thr Ser Asp
                85                  90                  95
Asp Thr Ala Val Tyr Phe Cys Thr Arg Gly Lys Tyr Cys Thr Ala Arg
            100                 105                 110
Asp Tyr Tyr Asn Trp Asp Phe Glu His Trp Gly Gln Gly Thr Pro Val
        115                 120                 125
Thr Val Ser Ser
    130

<210> SEQ ID NO 103
<211> LENGTH: 100
<212> TYPE: PRT
<213> ORGANISM: Artificial Sequence
<220> FEATURE:
<223> OTHER INFORMATION: Recombinant antibody sequence

<400> SEQUENCE: 103

Leu Thr Gln Ser Pro Gly Thr Leu Ser Leu Ser Pro Gly Glu Thr Ala
1               5                   10                  15
Ile Ile Ser Cys Arg Thr Ser Gln Tyr Gly Ser Leu Ala Trp Tyr Gln
            20                  25                  30
Gln Arg Pro Gly Gln Ala Pro Arg Leu Val Ile Tyr Ser Gly Ser Thr
        35                  40                  45
Arg Ala Ala Gly Ile Pro Asp Arg Phe Ser Gly Ser Arg Trp Gly Pro
    50                  55                  60
Asp Tyr Asn Leu Thr Ile Ser Asn Leu Glu Ser Gly Asp Phe Gly Val
65                  70                  75                  80
Tyr Tyr Cys Gln Gln Tyr Glu Phe Phe Gly Gln Gly Thr Lys Val Gln
                85                  90                  95
Val Asp Ile Lys
    100
```

<210> SEQ ID NO 104
<211> LENGTH: 100
<212> TYPE: PRT
<213> ORGANISM: Artificial Sequence
<220> FEATURE:
<223> OTHER INFORMATION: Recombinant antibody sequence

<400> SEQUENCE: 104

Leu Thr Gln Ser Pro Gly Thr Leu Ser Leu Ser Pro Gly Glu Thr Ala
1               5                   10                  15

Ile Ile Ser Cys Asp Thr Ser Gln Tyr Gly Ser Leu Ala Trp Tyr Gln
            20                  25                  30

Gln Arg Pro Gly Gln Ala Pro Arg Leu Val Ile Tyr Gly Ser Ser Thr
        35                  40                  45

Arg Ala Ala Gly Ile Pro Asp Arg Phe Ser Gly Ser Arg Trp Gly Pro
    50                  55                  60

Asp Tyr Gln Leu Thr Ile Ser Asn Leu Glu Ser Gly Asp Phe Gly Val
65                  70                  75                  80

Tyr Tyr Cys Gln Gln Tyr Glu Phe Phe Gly Gln Gly Thr Lys Val Gln
                85                  90                  95

Val Asp Ile Lys
            100

<210> SEQ ID NO 105
<211> LENGTH: 134
<212> TYPE: PRT
<213> ORGANISM: Artificial Sequence
<220> FEATURE:
<223> OTHER INFORMATION: Recombinant antibody sequence

<400> SEQUENCE: 105

Ala Asp Leu Val Gln Ser Gly Ala Val Val Lys Lys Pro Gly Asp Ser
1               5                   10                  15

Val Arg Ile Ser Cys Glu Ala Gln Gly Tyr Arg Phe Pro Asp Tyr Ile
            20                  25                  30

Ile His Trp Ile Arg Arg Ala Pro Gly Gln Gly Pro Glu Trp Met Gly
        35                  40                  45

Trp Met Asn Pro Met Trp Gly Gln Val Asn Ile Pro Trp Lys Phe Gln
    50                  55                  60

Gly Arg Val Ser Met Thr Arg Gln Leu Ser Gln Asp Pro Asp Pro
65                  70                  75                  80

Asp Trp Gly Thr Ala Phe Leu Asp Leu Arg Gly Leu Lys Ser Asp Asp
                85                  90                  95

Thr Ala Val Tyr Tyr Cys Val Arg Asp Arg Ser Asn Gly Ser Gly Lys
                100                 105                 110

Arg Phe Glu Ser Ser Asn Trp Phe Leu Asp Leu Trp Gly Arg Gly Thr
            115                 120                 125

Ala Val Thr Ile Gln Ser
        130

<210> SEQ ID NO 106
<211> LENGTH: 101
<212> TYPE: PRT
<213> ORGANISM: Artificial Sequence
<220> FEATURE:
<223> OTHER INFORMATION: Recombinant antibody sequence

<400> SEQUENCE: 106

Ala Leu Thr Gln Pro Arg Ser Val Ser Ala Ser Pro Gly Gln Ser Val

```
                1               5                  10                  15
Thr Ile Ser Cys Thr Gly Thr His Asn Leu Val Ser Trp Cys Gln His
                20                  25                  30

Gln Pro Gly Arg Ala Pro Lys Leu Leu Ile Tyr Asp Phe Asn Lys Arg
                35                  40                  45

Pro Ser Gly Val Pro Asp Arg Phe Ser Gly Ser Gly Ser Gly Gly Thr
            50                  55                  60

Ala Ser Leu Thr Ile Thr Gly Leu Gln Asp Asp Asp Ala Glu Tyr
65                  70                  75                  80

Phe Cys Trp Ala Tyr Glu Ala Phe Gly Gly Gly Thr Lys Leu Thr Val
                    85                  90                  95

Leu Gly Gln Pro Lys
                100

<210> SEQ ID NO 107
<211> LENGTH: 100
<212> TYPE: PRT
<213> ORGANISM: Artificial Sequence
<220> FEATURE:
<223> OTHER INFORMATION: Recombinant antibody sequence

<400> SEQUENCE: 107

Leu Thr Gln Pro Arg Ser Val Ser Ala Ser Pro Gly Gln Ser Val Thr
1               5                   10                  15

Ile Ser Cys Thr Gly Thr His Asn Leu Val Ser Trp Cys Gln His Gln
                20                  25                  30

Pro Gly Arg Ala Pro Lys Leu Leu Ile Tyr Asp Phe Asn Lys Arg Pro
            35                  40                  45

Ser Gly Val Pro Asp Arg Phe Ser Gly Ser Gly Ser Gly Gly Thr Ala
        50                  55                  60

Ser Leu Thr Ile Thr Gly Leu Gln Asp Asp Asp Ala Glu Tyr Phe
65                  70                  75                  80

Cys Trp Ala Tyr Glu Ala Phe Gly Gly Gly Thr Lys Leu Thr Val Leu
                85                  90                  95

Gly Gln Pro Lys
            100

<210> SEQ ID NO 108
<211> LENGTH: 139
<212> TYPE: PRT
<213> ORGANISM: Artificial Sequence
<220> FEATURE:
<223> OTHER INFORMATION: Recombinant antibody sequence

<400> SEQUENCE: 108

Glu Val Gln Leu Val Gln Ser Gly Thr Gln Met Lys Glu Pro Gly Ala
1               5                   10                  15

Ser Val Thr Ile Ser Cys Val Thr Ser Gly Tyr Glu Phe Val Glu Ile
                20                  25                  30

Leu Ile Asn Trp Val Arg Gln Val Pro Gly Arg Gly Leu Glu Trp Met
            35                  40                  45

Gly Trp Met Asn Pro Arg Trp Gly Gly Val Asn Tyr Ala Arg Gln Phe
        50                  55                  60

Gln Gly Lys Val Thr Met Thr Arg Gln Leu Ser Gln Asp Pro Asp Asp
65                  70                  75                  80

Pro Asp Trp Gly Thr Ala Tyr Leu Thr Leu Ser Gly Leu Thr Ser Gly
                85                  90                  95
```

```
Asp Thr Ala Lys Tyr Phe Cys Val Arg Gly Arg Ser Cys Cys Gly Gly
            100                 105                 110

Arg Arg His Cys Asn Gly Ala Asp Cys Phe Asn Trp Asp Phe Gln His
        115                 120                 125

Trp Gly Gln Gly Thr Leu Val Ile Val Ser Pro
    130                 135
```

```
<210> SEQ ID NO 109
<211> LENGTH: 102
<212> TYPE: PRT
<213> ORGANISM: Artificial Sequence
<220> FEATURE:
<223> OTHER INFORMATION: Recombinant antibody sequence

<400> SEQUENCE: 109
```

```
Gly Val Thr Gln Ser Pro Ala Ile Leu Ser Val Ser Leu Gly Glu Arg
1               5                   10                  15

Val Thr Leu Ser Cys Lys Thr Ser Gln Ala Ile Thr Pro Arg His Leu
            20                  25                  30

Val Trp His Arg Gln Lys Gly Gly Gln Ala Pro Ser Leu Val Met Thr
        35                  40                  45

Gly Thr Ser Glu Arg Ala Ser Gly Ile Pro Asp Arg Phe Ile Gly Ser
    50                  55                  60

Gly Ser Gly Thr Asp Phe Thr Leu Thr Ile Thr Arg Leu Glu Ala Glu
65                  70                  75                  80

Asp Phe Ala Val Tyr Tyr Cys Gln Cys Leu Glu Ala Phe Gly Gln Gly
                85                  90                  95

Thr Lys Leu Glu Ile Lys
            100
```

```
<210> SEQ ID NO 110
<211> LENGTH: 101
<212> TYPE: PRT
<213> ORGANISM: Artificial Sequence
<220> FEATURE:
<223> OTHER INFORMATION: Recombinant antibody sequence

<400> SEQUENCE: 110
```

```
Val Thr Gln Ser Pro Ala Ile Leu Ser Val Ser Leu Gly Glu Arg Val
1               5                   10                  15

Thr Leu Ser Cys Lys Thr Ser Gln Ala Ile Thr Pro Arg His Leu Val
            20                  25                  30

Trp His Arg Gln Lys Gly Gly Gln Ala Pro Ser Leu Val Met Thr Gly
        35                  40                  45

Thr Ser Glu Arg Ala Ser Gly Ile Pro Asp Arg Phe Ile Gly Ser Gly
    50                  55                  60

Ser Gly Thr Asp Phe Thr Leu Thr Ile Thr Arg Leu Glu Ala Glu Asp
65                  70                  75                  80

Phe Ala Val Tyr Tyr Cys Gln Cys Leu Glu Ala Phe Gly Gln Gly Thr
                85                  90                  95

Lys Leu Glu Ile Lys
            100
```

```
<210> SEQ ID NO 111
<211> LENGTH: 123
<212> TYPE: PRT
<213> ORGANISM: Artificial Sequence
<220> FEATURE:
<223> OTHER INFORMATION: Recombinant antibody sequence
```

```
<400> SEQUENCE: 111

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Trp Gly Gln Pro Asn Asn Pro Arg Gln Phe
    50                  55                  60

Gln Gly Arg Val Ser Leu Thr Arg His Ala Ser Trp Asp Phe Asp Thr
65                  70                  75                  80

Tyr Ser Phe Tyr Met Asp Leu Lys Ala Leu Arg Ser Asp Asp Thr Ala
                85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser
            115                 120

<210> SEQ ID NO 112
<211> LENGTH: 126
<212> TYPE: PRT
<213> ORGANISM: Artificial Sequence
<220> FEATURE:
<223> OTHER INFORMATION: Recombinant antibody sequence

<400> SEQUENCE: 112

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Trp Gly Gln Pro Asn Asn Pro Arg Gln Phe
    50                  55                  60

Gln Gly Arg Val Ser Leu Thr Arg Gln Leu Ser Gln Asp Pro Asp Asp
65                  70                  75                  80

Pro Asp Trp Gly Ser Phe Tyr Met Asp Leu Lys Ala Leu Arg Ser Asp
                85                  90                  95

Asp Thr Ala Val Tyr Phe Cys Ala Arg Gln Arg Ser Asp Tyr Trp Asp
            100                 105                 110

Phe Asp Val Trp Gly Ser Gly Thr Gln Val Thr Val Ser Ser
        115                 120                 125

<210> SEQ ID NO 113
<211> LENGTH: 97
<212> TYPE: PRT
<213> ORGANISM: Artificial Sequence
<220> FEATURE:
<223> OTHER INFORMATION: Recombinant antibody sequence

<400> SEQUENCE: 113

Gln Met Thr Gln Ser Pro Ser Ser Leu Ser Ala Ser Val Gly Asp Thr
1               5                   10                  15

Val Thr Ile Thr Cys Gln Ala Asn Gly Tyr Leu Asn Trp Tyr Gln Gln
            20                  25                  30

Arg Arg Gly Lys Ala Pro Lys Leu Leu Ile Tyr Asp Gly Ser Lys Leu
        35                  40                  45
```

```
Glu Arg Gly Val Pro Ser Arg Phe Ser Gly Arg Trp Gly Gln Glu
 50                  55                  60

Tyr Asn Leu Thr Ile Asn Asn Leu Gln Pro Glu Asp Ile Ala Thr Tyr
 65                  70                  75                  80

Phe Cys Gln Val Tyr Glu Phe Val Val Pro Gly Thr Arg Leu Asp Leu
                 85                  90                  95

Lys

<210> SEQ ID NO 114
<211> LENGTH: 96
<212> TYPE: PRT
<213> ORGANISM: Artificial Sequence
<220> FEATURE:
<223> OTHER INFORMATION: Recombinant antibody sequence

<400> SEQUENCE: 114

Met Thr Gln Ser Pro Ser Ser Leu Ser Ala Ser Val Gly Asp Thr Val
 1               5                  10                  15

Thr Ile Thr Cys Gln Ala Asn Gly Tyr Leu Asn Trp Tyr Gln Gln Arg
                20                  25                  30

Arg Gly Lys Ala Pro Lys Leu Leu Ile Tyr Asp Gly Ser Lys Leu Glu
             35                  40                  45

Arg Gly Val Pro Ser Arg Phe Ser Gly Arg Trp Gly Gln Glu Tyr
 50                  55                  60

Asn Leu Thr Ile Asn Asn Leu Gln Pro Glu Asp Ile Ala Thr Tyr Phe
 65                  70                  75                  80

Cys Gln Val Tyr Glu Phe Val Val Pro Gly Thr Arg Leu Asp Leu Lys
                 85                  90                  95

<210> SEQ ID NO 115
<211> LENGTH: 126
<212> TYPE: PRT
<213> ORGANISM: Artificial Sequence
<220> FEATURE:
<223> OTHER INFORMATION: Recombinant antibody sequence

<400> SEQUENCE: 115

Gln Val Gln Leu Leu Gln Ser Gly Ala Ala Val Thr Lys Pro Gly Ala
 1               5                  10                  15

Ser Val Arg Val Ser Cys Glu Ala Ser Gly Tyr Asn Ile Arg Asp Tyr
                20                  25                  30

Phe Ile His Trp Trp Arg Gln Ala Pro Gly Gln Gly Leu Gln Trp Val
             35                  40                  45

Gly Trp Ile Asn Pro Lys Phe Gly Gln Pro Asn Asn Pro Arg Gln Phe
 50                  55                  60

Gln Gly Arg Val Ser Leu Thr Arg Gln Leu Ser Gln Asp Pro Asp Asp
 65                  70                  75                  80

Pro Asp Trp Gly Ser Phe Tyr Met Asp Leu Lys Ala Leu Arg Ser Asp
                 85                  90                  95

Asp Thr Ala Val Tyr Phe Cys Ala Arg Gln Arg Ser Asp Tyr Trp Asp
                100                 105                 110

Phe Asp Val Trp Gly Ser Gly Thr Gln Val Thr Val Ser Ser
            115                 120                 125

<210> SEQ ID NO 116
<211> LENGTH: 127
<212> TYPE: PRT
<213> ORGANISM: homo sapiens
```

-continued

```
<400> SEQUENCE: 116

Ala Asp Leu Val Gln Ser Gly Ala Val Lys Lys Pro Gly Asp Ser
1               5                   10                  15

Val Arg Ile Ser Cys Glu Ala Gln Gly Tyr Arg Phe Pro Asp Tyr Ile
                20                  25                  30

Ile His Trp Ile Arg Arg Ala Pro Gly Gln Gly Pro Glu Trp Met Gly
            35                  40                  45

Trp Met Asn Pro Met Gly Gly Gln Val Asn Ile Pro Trp Lys Phe Gln
    50                  55                  60

Gly Arg Val Ser Met Thr Arg Asp Thr Ser Ile Glu Thr Ala Phe Leu
65                  70                  75                  80

Asp Leu Arg Gly Leu Lys Ser Asp Thr Ala Val Tyr Tyr Cys Val
                85                  90                  95

Arg Asp Arg Ser Asn Gly Ser Gly Lys Arg Phe Glu Ser Asn Trp
                100                 105                 110

Phe Leu Asp Leu Trp Gly Arg Gly Thr Ala Val Thr Ile Gln Ser
            115                 120                 125

<210> SEQ ID NO 117
<211> LENGTH: 132
<212> TYPE: PRT
<213> ORGANISM: homo sapiens

<400> SEQUENCE: 117

Glu Val Gln Leu Val Gln Ser Gly Thr Gln Met Lys Glu Pro Gly Ala
1               5                   10                  15

Ser Val Thr Ile Ser Cys Val Thr Ser Gly Tyr Glu Phe Val Glu Ile
                20                  25                  30

Leu Ile Asn Trp Val Arg Gln Val Pro Gly Arg Gly Leu Glu Trp Met
            35                  40                  45

Gly Trp Met Asn Pro Arg Gly Gly Val Asn Tyr Ala Arg Gln Phe
    50                  55                  60

Gln Gly Lys Val Thr Met Thr Arg Asp Val Tyr Arg Asp Thr Ala Tyr
65                  70                  75                  80

Leu Thr Leu Ser Gly Leu Thr Ser Asp Thr Ala Lys Tyr Phe Cys
                85                  90                  95

Val Arg Gly Arg Ser Cys Cys Gly Gly Arg Arg His Cys Asn Gly Ala
                100                 105                 110

Asp Cys Phe Asn Trp Asp Phe Gln His Trp Gly Gln Gly Thr Leu Val
            115                 120                 125

Ile Val Ser Pro
        130

<210> SEQ ID NO 118
<211> LENGTH: 329
<212> TYPE: PRT
<213> ORGANISM: Artificial Sequence
<220> FEATURE:
<223> OTHER INFORMATION: Recombinant antibody sequence

<400> SEQUENCE: 118

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

-continued

```
Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Ala Leu His Ser His Tyr Thr Gln
305                 310                 315                 320

Lys Ser Leu Ser Leu Ser Pro Gly Lys
                325

<210> SEQ ID NO 119
<211> LENGTH: 107
<212> TYPE: PRT
<213> ORGANISM: homo sapiens

<400> SEQUENCE: 119

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
```

```
                85                  90                  95
Pro Val Thr Lys Ser Phe Asn Arg Gly Glu Cys
            100                 105

<210> SEQ ID NO 120
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 120

Trp Met Asn Pro Met Trp Gly Gln Val Asn Ile Pro Trp Lys Phe Gln
1               5                   10                  15

Gly

<210> SEQ ID NO 121
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 121

Trp Met Lys Pro Arg Phe Gly Ala Val Ser Tyr Ala Arg Gln Leu Gln
1               5                   10                  15

Gly

<210> SEQ ID NO 122
<211> LENGTH: 17
<212> TYPE: PRT
<213> ORGANISM: Artificial Sequence
<220> FEATURE:
<223> OTHER INFORMATION: Recombinant antibody sequence

<400> SEQUENCE: 122

Trp Met Lys Pro Arg Trp Gly Ala Val Ser Tyr Ala Arg Gln Leu Gln
1               5                   10                  15

Gly

<210> SEQ ID NO 123
<211> LENGTH: 9
<212> TYPE: PRT
<213> ORGANISM: Artificial Sequence
<220> FEATURE:
<223> OTHER INFORMATION: Recombinant antibody sequence

<400> SEQUENCE: 123

Asp Thr Ser Gln Tyr Gly Ser Leu Ala
1               5
```

# NEUTRALIZING ANTIBODIES TO HIV-1 ENV AND THEIR USE

CROSS-REFERENCE TO RELATED APPLICATIONS

This is the U.S. National Stage of International Application No. PCT/US2019/019021, filed on Feb. 21, 2020, which was published in English under PCT Article 21(2), which in turn claims priority to U.S. Provisional Application No. 62/633,517, filed Feb. 21, 2018, and U.S. Provisional Patent Application No. 62/775,754, filed Dec. 5, 2018. The provisional applications are herein incorporated by reference in their entirety.

FIELD OF THE DISCLOSURE

This relates to monoclonal antibodies and antigen binding fragments that specifically bind to HIV-1 Env and their use, for example, in methods of treating a subject with HIV-1 infection.

BACKGROUND

Human Immunodeficiency Virus type 1 (HIV-1) infection, and the resulting Acquired Immunodeficiency Syndrome (AIDS), remain threats to global public health, despite extensive efforts to develop anti-HIV-1 therapeutic agents.

An enveloped virus, HIV-1 hides from humoral recognition behind a wide array of protective mechanisms. The major HIV-1 envelope protein (HIV-1 Env) is a glycoprotein of approximately 160 kD (gp160). During infection, proteases of the host cell cleave gp160 into gp120 and gp41. Together gp120 and gp41 make up the HIV-1 envelope spike, which interacts with the host-cell receptor CD4 to facilitate virus infection, and is a target for neutralizing antibodies.

In addition to the "classic" CD4 binding site on the gp120 outer domain of HIV-1 Env ("CD4-BS1 domain"), CD4 also binds to residues of the neighboring protomer including residues of the α-1 helix (e.g., E62, E64, H66) and β3-β4 loop (e.g., K207) from the gp120 inner domain "CD4-B52." CD4 interaction with the CD4-BS2 facilitates stability of the CD4-HIV-1 Env interaction, triggering of HIV-1 Env conformational changes that enable coreceptor binding, and progression of the fusogenic process.

Neutralizing antibodies that bind to HIV-1 Env have been identified, including VRC01, which is the prototypical member of the "VRC01-class" of antibodies that specifically bind to the CD4 binding site of HIV-1 Env and neutralize a high percentage of HIV-1 strains. Non-limiting examples of VRC01-class antibodies include VRC01, N6, VRC07, VRC07-523, and VRC-PG04.

However, there is a need to develop additional neutralizing antibodies for HIV-1 with varying recognition and neutralization profiles for commercial production.

SUMMARY

Disclosed herein are modified forms of VRC01-class antibodies that specifically bind to the CD4 binding site of HIV-1 Env via a quaternary interaction with multiple protomers of the HIV-1 Env trimer. Surprisingly, a single modification to the heavy chain variable region framework region (HFR) 3 of VRC01-class antibodies promotes the quaternary interaction, and is shown herein to improve both HIV-1 Env binding and HIV-1 neutralization of VRC01-class antibodies.

In some embodiments, a monoclonal antibody is provided comprising a heavy chain variable region ($V_H$) comprising a heavy chain complementarity determining region (HCDR) 1, a HCDR2, and a HCDR3 of a parent VRC01-class antibody, and a light chain variable region ($V_L$) comprising a light chain complementarity determining region (LCDR) 1, a LCDR2, and a LCDR3 of the parent VRC01-class antibody. The HFR3 of the monoclonal antibody comprises a modification compared to the corresponding HFR3 of the parent VRC01-class antibody, wherein the modification is a substitution of the amino acids of Kabat positions 72-76 of the parent VRC01-class antibody with the sequence set forth as QLSQDPDDPDWG (SEQ ID NO: 36). The parent VRC01-class antibody does not contain an amino acid insertion between Kabat positions 75/76 compared to an IGHV1-2*02 germline sequence. As shown in the examples, replacement of the Kabat positions 72-76 of VRC01-class antibodies that lack an insertion at this position with SEQ ID NO: 36 confers a surprising improvement in HIV-1 neutralization to the modified VRC01-class antibody compared to the corresponding patent VRC01-class antibody. In some embodiments, the parent VRC01-class antibody is any one of N6, VRC01, VRC07, VRC07-523, and VRC-PG04.

In some embodiments, the monoclonal antibody further comprises a tryptophan or phenylalanine substitution at Kabat position 54 of the $V_H$. In some embodiments, the monoclonal antibody further comprises a tyrosine substitution at Kabat position 54 of the $V_H$. In some embodiments, the monoclonal antibody further comprises a two or three-amino acid deletion at the N-terminus of the $V_L$. In some embodiments, the monoclonal antibody further comprises the tryptophan substitution at Kabat position 54 of the $V_H$ and the three-amino acid deletion at the N-terminus of the $V_L$. In some embodiments, the HCDR1, the HCDR2, the HCDR3, the LCDR1, the LCDR2, and the LCDR3 of the monoclonal antibody comprise the amino acids sequences set forth as SEQ ID NOs: 26, 65, 28, 29, 30, and 31, respectively (VRC01.23 CDRs).

In some embodiments, the HCDR1, the HCDR2, the HCDR3, the LCDR1, the LCDR2, and the LCDR3 of the monoclonal antibody comprise the amino acids sequences set forth as SEQ ID NOs: 72, 120, 74, 75, 76, 77, respectively (N49P7.v2 and .v3 CDRs). In some embodiments, the $V_H$ and $V_L$ of the antibody comprise amino acid sequences at least 90% identical to SEQ ID NOs: 105 and 106, respectively, and the HCDR1, the HCDR2, the HCDR3, the LCDR1, the LCDR2, and the LCDR3 of the monoclonal antibody comprise the amino acids sequences set forth as SEQ ID NOs: 72, 120, 74, 75, 76, 77, respectively, and the HFR3 comprises the substitution of Kabat positions 72-76 for QLSQDPDDPDWG (SEQ ID NO: 36). In some embodiments, the $V_H$ and $V_L$ of the antibody comprise amino acid sequences at least 90% identical to SEQ ID NOs: 105 and 107, respectively, and the HCDR1, the HCDR2, the HCDR3, the LCDR1, the LCDR2, and the LCDR3 of the monoclonal antibody comprise the amino acids sequences set forth as SEQ ID NOs: 72, 120, 74, 75, 76, 77, respectively, and the HFR3 comprises the substitution of Kabat positions 72-76 for QLSQDPDDPDWG (SEQ ID NO: 36).

In some embodiments, the HCDR1, the HCDR2, the HCDR3, the LCDR1, the LCDR2, and the LCDR3 of the monoclonal antibody comprise the amino acids sequences set forth as SEQ ID NOs: 32, 121, 34, 29, 30, 31, respectively (VRC07-523.v1 CDRs). In some embodiments, the $V_H$ and $V_L$ of the antibody comprise amino acid sequences at least 90% identical to SEQ ID NOs: 102 and 103, respectively, and the HCDR1, the HCDR2, the HCDR3, the LCDR1, the LCDR2, and the LCDR3 of the monoclonal antibody comprise the amino acids sequences set forth as SEQ ID NOs: 32, 121, 34, 29, 30, 31, respectively, and the HFR3 comprises the substitution of Kabat positions 72-76 for QLSQDPDDPDWG (SEQ ID NO: 36).

In some embodiments, the HCDR1, the HCDR2, the HCDR3, the LCDR1, the LCDR2, and the LCDR3 of the monoclonal antibody comprise the amino acids sequences set forth as SEQ ID NOs: 32, 121, 34, 123, 30, 31, respectively (VRC07-523.v2 CDRs). In some embodiments, the $V_H$ and $V_L$ of the antibody comprise amino acid sequences at least 90% identical to SEQ ID NOs: 102 and 104, respectively, and the HCDR1, the HCDR2, the HCDR3, the LCDR1, the LCDR2, and the LCDR3 of the monoclonal antibody comprise the amino acids sequences set forth as SEQ ID NOs: 32, 121, 34, 123, 30, 31, respectively, and the HFR3 comprises the substitution of Kabat positions 72-76 for QLSQDPDDPDWG (SEQ ID NO: 36).

In some embodiments, the HCDR1, the HCDR2, the HCDR3, the LCDR1, the LCDR2, and the LCDR3 of the monoclonal antibody comprise the amino acids sequences set forth as SEQ ID NOs: 32, 122, 34, 29, 30, 31, respectively (VRC07-523.v3 CDRs). In some embodiments, the $V_H$ and $V_L$ of the antibody comprise amino acid sequences at least 90% identical to SEQ ID NOs: 101 and 103, respectively, and the HCDR1, the HCDR2, the HCDR3, the LCDR1, the LCDR2, and the LCDR3 of the monoclonal antibody comprise the amino acids sequences set forth as SEQ ID NOs: 32, 122, 34, 29, 30, 31, respectively, and the HFR3 comprises the substitution of Kabat positions 72-76 for QLSQDPDDPDWG (SEQ ID NO: 36).

In some embodiments, the HCDR1, the HCDR2, the HCDR3, the LCDR1, the LCDR2, and the LCDR3 of the monoclonal antibody comprise the amino acids sequences set forth as SEQ ID NOs: 32, 122, 34, 123, 30, 31, respectively (VRC07-523.v4 CDRs). In some embodiments, the $V_H$ and $V_L$ of the antibody comprise amino acid sequences at least 90% identical to SEQ ID NOs: 101 and 104, respectively, and the HCDR1, the HCDR2, the HCDR3, the LCDR1, the LCDR2, and the LCDR3 of the monoclonal antibody comprise the amino acids sequences set forth as SEQ ID NOs: 32, 122, 34, 123, 30, 31, respectively, and the HFR3 comprises the substitution of Kabat positions 72-76 for QLSQDPDDPDWG (SEQ ID NO: 36).

In additional embodiments, an antigen binding fragment of the monoclonal antibody is provided.

In some embodiments, the monoclonal antibody or antigen binding fragment comprises a $V_H$ and a $V_L$ comprising the amino acid sequences set forth as SEQ ID NOs: 16 and 2, respectively. In some embodiments, the monoclonal antibody or antigen binding fragment comprises a $V_H$ and a $V_L$ comprising the amino acid sequences set forth as SEQ ID NOs: 17 and 4, respectively. In some embodiments, the monoclonal antibody or antigen binding fragment comprises a $V_H$ and a $V_L$ comprising the amino acid sequences set forth as SEQ ID NOs: 18 and 4, respectively. In some embodiments, the monoclonal antibody or antigen binding fragment comprises a $V_H$ and a $V_L$ comprising the amino acid sequences set forth as SEQ ID NOs: 19 and 7, respectively. In some embodiments, the $V_H$ and $V_L$ of the monoclonal antibody comprise the amino acid sequences set forth as SEQ ID NOs: 84 and 85, respectively.

Also disclosed are compositions including the antibodies and antigen binding fragments, as well as related nucleic acid molecules and expression vectors.

The disclosed antibodies and antigen binding fragments potently neutralize HIV-1 in an accepted in vitro model of HIV-1 infection. Accordingly, a method is disclosed for inhibiting an HIV-1 infection in a subject, comprising administering a therapeutically effective amount of one or more of the disclosed antibodies, antigen binding fragments, nucleic acid molecules, vectors, or compositions, to the subject, wherein the subject is at risk of or has an HIV-1 infection.

The antibodies, antigen binding fragments, nucleic acid molecules, vectors, and compositions disclosed herein can be used for a variety of additional purposes, such as for detecting an HIV-1 infection or diagnosing HIV-1 infection in a subject, or detecting HIV-1 in a sample.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1F. Extended 70s' loop in framework 3 (FR3) of some VRC01-class antibodies is predicted to interact with the neighboring protomer of HIV-1 Env. (1A) Structure alignment shows that VRC03 (green) and VRC06 (orange) have a much longer HFR3 loop than N6 (red) and VRC01 (pink). The loop reaches the second CD4 binding site (CD4BS2) in the neighboring protomer. (1B) The length of HFR3 loop from VRC03 and VRC06 is unique across VRC01-class antibodies. Loop-deletion variants were designed, VRC03del and VRC06del, from these two antibodies by replacing the HFR3 loop with a short GPG linker. Additional mutations are shown where the Loop sequence from VRC03 or VRC06 was substituted for Kabat residues 72-76 of VRC01, N6, VRC07 or VRC07-523. The $V_H$ sequences of IGHV1-2*02 (SEQ ID NO: 14), N6 (SEQ ID NO: 1), VRC01 (SEQ ID NO: 3), VRC07 (SEQ ID NO: 5), VRC07-523 (SEQ ID NO: 6), 3BNC117 (SEQ ID NO: 8), VRC-PG04 (SEQ ID NO: 56), N49P7 (SEQ ID NO: 116), VRC08 (SEQ ID NO: 117), VRC03 (SEQ ID NO: 12), and VRC06 (SEQ ID NO: 10) are shown. (1C) The "Mutations" table shows the following sequences: SQDPDDPD (SEQ ID NO: 12, residues 74-81), SQDLYYPDR (SEQ ID NO: 10, residues 74-82), DVYSD (SEQ ID NO: 3, residues 72-76), DVYRE (SEQ ID NO: 1, residues 72-76), DMYSE (SEQ ID NO: 5, residues 72-76), HASWDFDTF (SEQ ID NO: 8, residues 72-80), DRDLF (SEQ ID NO: 56, residues 75-79), DTSIE (SEQ ID NO: 116, residues 72-76), DVYRD (SEQ ID NO: 117, residues 72-76), LFSQDLYYPDRG (SEQ ID NO: 10, residues 72-83), QLSQDPDDPDWG (SEQ ID NO: 12, residues 72-83). (1D) light chain variable regions sequences of VRC01-class antibodies. The $V_L$ sequences of IGKV1-33*01 (SEQ ID NO: 15), N6 (SEQ ID NO: 2), VRC01 (SEQ ID NO: 4), VRC07 (SEQ ID NO: 4), VRC07-523 (SEQ ID NO: 7), 3BNC117 (SEQ ID NO: 9), VRC-PG04 (SEQ ID NO: 57), N49P7 (SEQ ID NO: 88), VRC08 (SEQ ID NO: 90), VRC03 (SEQ ID NO: 13), VRC06 (SEQ ID NO: 11) are shown. (1E) Binding of the loop-deletion variants (shown in red) to BG505 SOSIP664 is impaired, as tested by ELISA. (1F) Neutralizing capacity of the loop-deletion variants is dramatically reduced relative of the parent antibody, indicating the critical role of the HFR3 loop in the interaction with HIV-1 Env.

FIGS. 2A and 2B. Introduction of HFR3 loop into VRC01: design and increased neutralizing potency. VRC01 has a shorter HFR3, which does not allow the antibody to contact with the neighboring protomer of the Env trimer like VRC03 and VRC06. To introduce quaternary interaction between VRC01 and the HIV Env, the long FR3 loop in VRC03 and VRC06 was transplanted to VRC01 respectively, creating 2 chimeric antibodies, VRC01 70-03 and VRC01 70-06 (see FIG. 1B). (2A-2B) The chimeric antibodies were tested against several HIV-1 isolates by TZM-bl neutralizing assay. VRC01 70-03 showed an increased neutralizing potency, while the 70-06 chimera was similar to the wild type (WT) form. This assay showed that engrafting HFR3 loop could improve neutralization potency of some VRC01-class antibodies, and the HFR3 loop from VRC03 instead of VRC06 is a better option.

FIGS. 3A and 3B. Introduction of the VRC03 HFR3 loop into more VRC01-class antibodies. To test if other VRC01-class antibodies can also benefit from the elongation of HFR3, the N6, VRC07, and 3BNC117 antibodies (IgG format) were selected for modification. N6, VRC07, and 3BNC117 are potent VRC01-class antibodies. Using the same substitution strategy discussed above for VRC01, the HFR3 loop of VRC03 (red) was transplanted onto Kabat positions 72-76 of N6, VRC07, and 3BNC117, creating 3 chimeric 70-03 antibodies (see FIG. 1B). (3A) A small global panel of HIV-1 isolates was used to evaluate the neutralizing capacity of the chimeric antibodies. VRC07 70-03's potency was markedly increased, with better neutralization than unmodified VRC07 against 9 out of 11 isolates. Nearly 60% of the whole panel became more sensitive to N6 70-03, which is striking considering that the WT N6 is already very potent. For VRC01, the chimeric form had a better neutralizing capacity against more than 70% of the tested isolates Similar results were obtained when the N6 70-03 and VRC01 70-03 chimeras were also tested against a larger panel of HIV-1 pseudoviruses (FIG. 3B). In contrast, introduction of the VRC03 HFR3 loop to 3BNC117 caused reduced antibody neutralization against most isolates in the tested panel. Interestingly, N6, VRC01, VRC07, and VRC-PG04 do not have any amino acid insertions relative to germline sequence in the HFR3 loop between Kabat positions 75 and 76, whereas 3BNC117 does include insertions in this loop. Accordingly, it appears that the modification of the HFR3 loop with VRC03 sequence can be used to improve VRC01-class antibodies that lack any insertions relative to germline sequence in the HFR3 loop between Kabat positions 75 and 76.

FIGS. 4A and 4B. VRC01-class antibodies with the 70-03 modification have a higher binding affinity to soluble HIV-1 Env trimers. (4A) To investigate the interaction of the chimeric antibodies with HIV-1 Env, their binding to soluble Env trimers was tested by ELISA. BG505 Env-pseudovirus is more sensitive to chimeric N6 70-03 and VRC01 70-03 than to their corresponding unmodified form. Consistently, the BG505-derived SOSIP trimer bound chimeric form with higher affinity. For JRFL, the WT and chimeric antibodies bound soluble SOSIP.664 equally well, and their neutralization against JRFL is also comparable (see FIG. 3B). (4B) SPR kinetics assays were performed for N6 70-03 Fab and VRC01 70-03 Fab binding to BG505 SOSIP.664. In both cases, the binding affinity to BG505 SOSIP.664 was higher for the 70-03 chimeric form of these antibodies than for the unmodified form. The on rate was hardly altered, while the off rate was much lower for the 70-03 chimeric forms. Taken together, the results show that introduced HFR3 loop stabilizes the interaction between the chimeric antibody and HIV-1 Env trimer, which translates to a better neutralizing potency.

FIG. 5. Crystal structure of N6 70-03 complexed with BG505 SOSIP.664. The elongated HFR3 loop in the chimeric N6 is clearly visible in the crystal structure. The loop stretched out to the V3 base and part of the CD4BS2 in the neighboring protomer. The residues K207, R304 and Y318 are involved in the contact with the FR3 loop.

FIGS. 7A and 7B. Introduction of the 20s' loop (EDDDY, SEQ ID NO: 46) of VRC-CH31 to VRC01. (7A) VRC-CH31 contains a longer 20s' loop in CDRH1 region than VRC01. Part of this 20s' loop was transplanted to VRC01 with linkers of various length. As shown in FIG. 7A, the sequence of VRC01 that was replaced is GYEF (residues 26-29 of SEQ ID NO: 3). All the designs are listed in the lower panel. (7B) Compared to the WT VRC01, all the 20s' loop chimeras are less potent against BG505 and BaL isolates.

FIGS. 8A and 8B. Further optimization of HFR3 loop in chimeric VRC01 is not successful. The length (8A) or the composition (8B) of the HFR3 loop in the VRC01 70-03 was varied, but all loop-modified mutants were less potent than the original VRC01 70-03 design. FIG. 8A shows the following sequences: DVYSD (SEQ ID NO: 3, residues 73-77), QLSQDPDDPDWG (SEQ ID NO: 12, residues 73-84), GQLSQDPDDPDWG (SEQ ID NO: 52), GSGQLSQDPDDPDWG (SEQ ID NO: 53), GQLSQDPDDPDWGS (SEQ ID NO: 54), and QLSQDPDDPDWGD (SEQ ID NO: 55).

FIGS. 9A and 9B show the results of an assay of several different VRC01 variants on the neutralization of a small panel of 12 HIV-1 pseudoviruses.

FIGS. 10A-10C show the results of an assay of several different VRC01 variants on the neutralization of a large panel of 208 HIV-1 pseudoviruses.

FIG. 12 shows a set of graphs illustrating the in vivo half-life of the VRC01.23LS, VRC01LS, VRC07-523LS 70-03, and VRC07-523LS antibodies in mice with a humanized neonatal Fc receptor (FcRn) and in Rhesus macaques.

FIGS. 13A-13H show the results of an assay of several different VRC01-class variants on the neutralization of a small panel HIV-1 pseudoviruses. FIGS. 13A-13D show IC50 (μg/ml) values and FIGS. 13E-13H show IC80 (μg/ml) values.

FIG. 14 shows the results of an assay of the VRC07-523LS.v1 antibody on the neutralization of a large panel of 140 HIV-1 pseudoviruses.

FIGS. 15A-15C show results of an in vitro auto-reactivity assay. Several different VRC01-class variants were assessed for autoreactivity in a HEp-2 cell staining assay. The staining score (on a scale of 0-4) for reference antibodies, as well as the VRC01-class variants is shown for assays completed at 25 µg/ml antibody and 50 µg/ml antibody.

FIGS. 16A-16B show results from ELISA binding assays of the indicated monoclonal antibodies to cardiolipin. Anti-cardiolipin assays are in vitro assays used to indicate if an antibody is self-reactive.

SEQUENCES

Figure 1A:
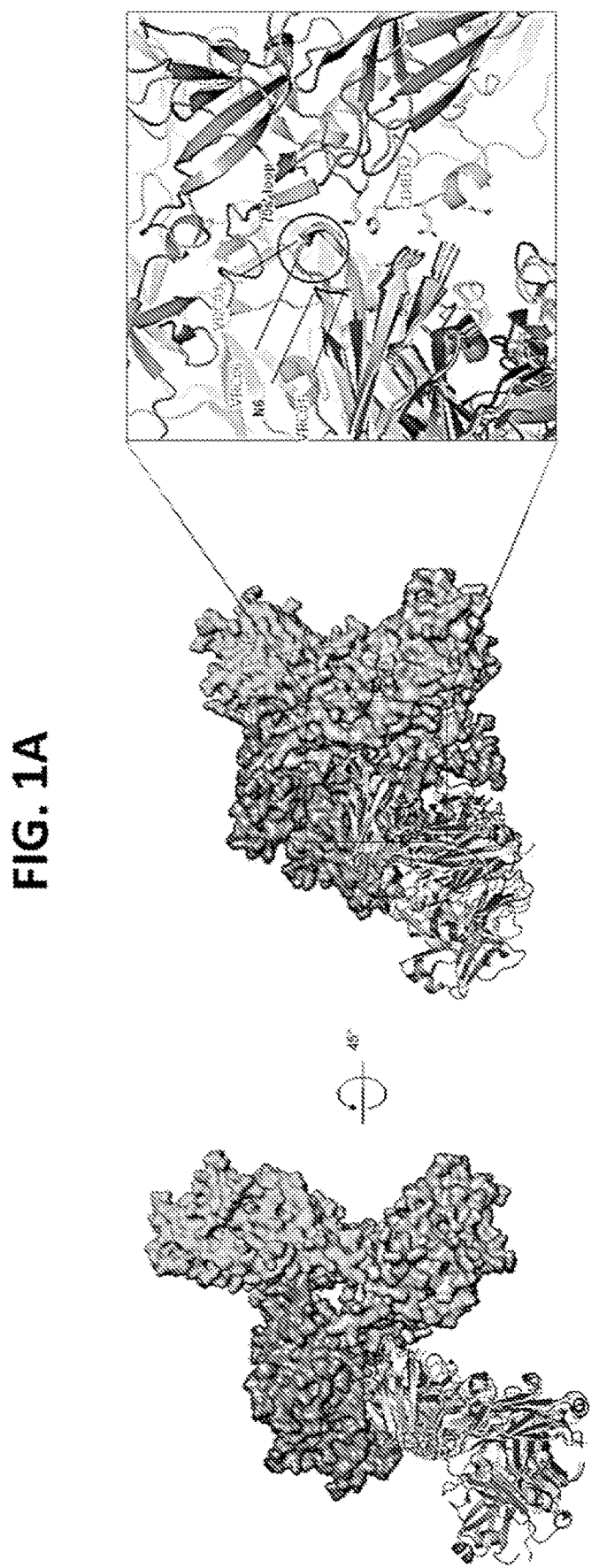

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~132 kb), which was created on Jul. 31, 2020, which is incorporated by reference herein. In the accompanying sequence listing:

```
SEQ ID NO: 1 is the amino acid sequence of the N6 V_H.
RAHLVQSGTAMKKPGASVRVSCQTSGYTFTAHILFWFRQAPGRGLEWVGWIKPQYGAVNFGGGFRDRVTLTRDVYREIAY

MDIRGLKPDDTAVYYCARDRSYGDSSWALDAWGQGTTVVVSA

SEQ ID NO: 2 is the amino acid sequence of the N6 V_L.
YIHVTQSPSSLSVSIGDRVTINCQTSQGVGSDLHWYQHKPGRAPKLLIHHTSSVEDGVPSRFSGSGFHTSFNLTISDLQA

DDIATYYCQVLQFFGRGSRLHIK

SEQ ID NO: 3 is the amino acid sequence of the VRC01 V_H.
QVQLVQSGGQMKKPGESMRISCRASGYEFIDCTLNWIRLAPGKRPEWMGWLKPRGGAVNYARPLQGRVTMTRDVYSDTAF

LELRSLTVDDTAVYFCTRGKNCDYNWDFEHWGRGTPVIVSS

SEQ ID NO: 4 is the amino acid sequence of the VRC01 V_L.
EIVLTQSPGTLSLSPGETAIISCRTSQYGSLAWYQQRPGQAPRLVIYSGSTRAAGIPDRFSGSRWGPDYNLTISNLESGD

FGVYYCQQYEFFGQGTKVQVDIKR

SEQ ID NO: 5 is the amino acid sequence of the VRC07 V_H.
QVRLSQSGGQMKKPGDSMRISCRASGYEFINCPINWIRLAPGKRPEWMGWMKPRGGAVSYARQLQGRVTMTRDMYSETAF

LELRSLTSDDTAVYFCTRGKYCTARDYYNWDFEHWGQGTPVTVSS

SEQ ID NO: 6 is the amino acid sequence of the VRC07-523 V_H.
QVRLSQSGGQMKKPGDSMRISCRASGYEFINCPINWIRLAPGKRPEWMGWMKPRHGAVSYARQLQGRVTMTRDMYSETAF

LELRSLTSDDTAVYFCTRGKYCTARDYYNWDFEHWGQGTPVTVSS

SEQ ID NO: 7 is the amino acid sequence of the VRC07-523 V_L.
SLTQSPGTLSLSPGETAIISCRTSQYGSLAWYQQRPGQAPRLVIYSGSTRAAGIPDRFSGSRWGPDYNLTISNLESGDFG

VYYCQQYEFFGQGTKVQVDIK

SEQ ID NO: 8 is the amino acid sequence of the 3BNC117 V_H.
QVQLLQSGAAVTKPGASVRVSCEASGYNIRDYFIHWWRQAPGQGLQWVGWINPKTGQPNNPRQFQGRVSLTRHASWDFDT

FSFYMDLKALRSDDTAVYFCARQRSDYWDFDVWGSGTQVTVSS

SEQ ID NO: 9 is the amino acid sequence of the 3BNC117 V_L.
DIQMTQSPSSLSASVGDTVTITCQANGYLNWYQQRRGKAPKLLIYDGSKLERGVPSRFSGRRWGQEYNLTINNLQPEDIA

TYFCQVYEFVVPGTRLDLK

SEQ ID NO: 10 is the amino acid sequence of the VRC06 V_H.
EVQLVESGPVMRKPGSSMKISCATSGYNFRDFSIHWVRFNRRYGFEWIGWIKPMWGAVNYARQLQGRVSMSRLFSQDLYY

PDRGTAYLEFSGLTSADTADYFCVRRGSSCPHCGDFHFEHWGQGTAVVVSA

SEQ ID NO: 11 is the amino acid sequence of the VRC06 V_L.
EIVLTQSPATLSLSPGERATLSCRASQGGNSLNWYQKRRGQTPRLLIYDTSRRASDIPEKFVGSGSGTDFSLTITKVGPE

DFAVYYCQQFEFFGLGTTLEIN

SEQ ID NO: 12 is the amino acid sequence of the VRC03 V_H.
QVQLVQSGAVIKTPGSSVKISCRASGYNFRDYSIHWVRLIPDKGFEWIGWIKPLWGAVSYARQLQGRVSMTRQLSQDPDD

PDWGVAYMEFSGLTSADTAEYFCVRRGSCDYCGDFPWQYWGQGTWVVSSA

SEQ ID NO: 13 is the amino acid sequence of the VRC03 V_L.
EIVLTQSPGILSLSPGETATLFCKASQGGNAMTWYQKRRGQVPRLLIYDTSRRASGVPDRFVGSGSGTDFFLTINKLDRE

DFAVYYCQQFEFFGLGSELEVH
```

SEQ ID NO: 14 is the amino acid sequence of IGHV1-2*02.
QVQLVQSGAEVKKPGASVKVSCKASGYTFTGYYMHWVRQAPGQGLEWMGWINPNSGGTNYAQKFQGRVTMTRDTSISTAY

MELSRLRSDDTAVYYCARAYCGGDCYNWFDS

SEQ ID NO: 15 is the amino acid sequence of IGKV1-33*01.
DIQMTQSPSSLSASVGDRVTITCQASQDISNYLNWYQQKPGKAPKLLIYDASNLETGVPSRFSGSGSGTDFTFTISSLQP

EDIATYYCQQYDNLPIT

SEQ ID NO: 16 is the amino acid sequence of the N6 70-03 $V_H$.
RAHLVQSGTAMKKPGASVRVSCQTSGYTFTAHILFWFRQAPGRGLEWVGWIKPQYGAVNFGGGFRDRVTLTRQLSQDPDD

PDWGIAYMDIRGLKPDDTAVYYCARDRSYGDSSWALDAWGQGTTVVVSA

SEQ ID NO: 17 is the amino acid sequence of the VRC01 70-03 $V_H$.
QVQLVQSGGQMKKPGESMRISCRASGYEFIDCTLNWIRLAPGKRPEWMGWLKPRGGAVNYARPLQGRVTMTRQLSQDPDD

PDWGTAFLELRSLTVDDTAVYFCTRGKNCDYNWDFEHWGRGTPVIVSS

SEQ ID NO: 18 is the amino acid sequence of the VRC07 70-03 $V_H$.
QVRLSQSGGQMKKPGDSMRISCRASGYEFINCPINWIRLAPGKRPEWMGWMKPRGGAVSYARQLQGRVTMTRQLSQDPDD

PDWGTAFLELRSLTSDDTAVYFCTRGKYCTARDYYNWDFEHWGQGTPVTVSS

SEQ ID NO: 19 is the amino acid sequence of the VRC07-523 70-03 $V_H$.
QVRLSQSGGQMKKPGDSMRISCRASGYEFINCPINWIRLAPGKRPEWMGWMKPRHGAVSYARQLQGRVTMTRQLSQDPDD

PDWGTAFLELRSLTSDDTAVYFCTRGKYCTARDYYNWDFEHWGQGTPVTVSS

SEQ ID NOs: 20-35 are CDR sequences.

SEQ ID NO: 36 is the amino acid sequence of the 70-03 insertion.
QLSQDPDDPDWG

SEQ ID NO: 37 is the amino acid sequence of HIV-1 Env from the HXB2 strain of HIV-1.

SEQ ID NO: 38 is an exemplary nucleic acid sequence encoding the N6 70-03 $V_H$.
Cgagcgcacctggtacaatcagggactgcgatgaagaaaccgggggcctcagtaagagtctcctgccagacctctggata cacctttaccgcccacatattattttggttccgacaggcccccgggcgaggacttgagtgggtggggtggatcaagccac aatatggggccgtgaattttggtggtggttttcgggacagggtcacattgactcgacaattatctcaagacccagacgac ccggactggggcattgcgtacatggacatcagaggccttaaacctgacgacacgccgtctattactgtgcgagagaccg ttcctatggcgactcctcttgggccttagatgcctggggacagggaacgacggtcgtcgtctccgcg SEQ ID NO: 39 is an exemplary nucleic acid sequence encoding the N6 $V_L$.
Tacatccacgtgacccagtctccgtcctccctgtctgtgtctattggagacagagtcaccatcaattgccagacgagtca gggtgttggcagtgacctacattggtatcaacacaaaccggggagagcccctaaactcttgatccaccatacctcttctg tggaagacggtgtcccctcaagattcagcggctctggatttcacacatcttttaatctgaccatcagcgacctacaggct gacgacattgccacatattactgtcaagttttacaattttttcggccgagggagtcgactccatattaaa SEQ ID NO: 40 is an exemplary nucleic acid sequence encoding the VRC01 70-03 $V_H$.
Caggtgcagctggtgcagtctggaggtcagatgaagaagcctggcgagtcgatgagaatttcttgtcgggcttctggata tgaatttattgattgtacgctaaattggattcgtctggcccccggaaaaaggcctgagtggatgggatggctgaagcctc gggggggggccgtcaactacgcacgtccacttcagggcagagtgaccatgactcgacaattatctcaagacccagacgac ccggactggggcacagcctttttggagctgcgctcgttgacagtagacgacacgccgtctacttttgtactagggaaa aaactgtgattacaattgggacttcgaacactggggccggggcacccggtcatcgtctcatca SEQ ID NO: 41 is an exemplary nucleic acid sequence encoding the VRC01 $V_L$.
Gaaattgtgttgacacagtctccaggcaccctgtctttgtctccaggggaaacagccatcatctcttgtcggaccagtca gtatggttccttagcctggtatcaacagaggcccggccaggcccccaggctcgtcatctattcgggctctactcgggccg ctggcatcccagacaggttcagcggcagtcggtggggccagactacaatctccaccatcagcaacctggagtcgggagat tttggtgtttattattgccagcagtatgaattttttggccaggggaccaaggtccaggtcgacattaaa SEQ ID NO: 42 is an exemplary nucleic acid sequence encoding the VRC07 70-03 $V_H$.
caggtgcgactgtcgcagtctggaggtcagatgaagaagcctggcgactcgatgagaatttcttgtcgggcttcgggata cgaatttattaattgtccaataaattggattcggctggccccgaaaaaggcctgagtggatgggatggatgaagccta ggggtggggccgtcagttacgcacgtcaacttcagggcagagtgaccatgactcgacaattatctcaagacccagacgac ccggactggggcacagccttttggagctccgttccttgacatccgacgacacggccgtctattttgtactggggaaa atattgcactgcgcgcgactattataattgggacttcgaacactggggccagggcaccccggtcaccgtctcgtca SEQ ID NO: 43 is an exemplary nucleic acid sequence encoding the VRC07 $V_L$.
Gaaattgtgttgacacagtctccaggcaccctgtctttgtctccaggggaaacagccatcatctcttgtcggaccagtca gtatggttccttagcctggtatcaacagaggcccggccaggcccccaggctcgtcatctattcgggctctactcgggccg ctggcatcccagacaggttcagcggcagtcggtggggccagactacaatctcaccatcagcaacctggagtcgggagat tttggtgtttattattgccagcagtatgaattttttggccaggggaccaaggtccaggtcgacattaaa SEQ ID NO: 44 is an exemplary nucleic acid sequence encoding the VRC07-523 70-03
$V_H$.
caggtgcgactgtcgcagtctggaggtcagatgaagaagcctggcgactcgatgagaatttcttgtcgggcttcgggata cgaatttattaattgtccaataaattggattcggctggccccgaaaaaggcctgagtggatgggatggatgaagccta ggcatggggccgtcagttacgcacgtcaacttcagggcagagtgaccatgactcgacaattatctcaagacccagacgac ccggactggggcacagccttttggagctccgttccttgacatccgacgacacggccgtctattttgtactggggaaa atattgcactgcgcgcgactattataattgggacttcgaacactggggccagggcaccccggtcaccgtctcgtca SEQ ID NO: 45 is an exemplary nucleic acid sequence encoding the VRC07-523 $V_L$.
Atgggatggtcatgtatcatccttttctagtagcaactgcaaccggtgtacattcatctttgacacagtctccaggcac cctgtctttgtctccaggggaaacagccatcatctcttgtcggaccagtcagtatggttccttagcctggtatcaacaga ggcccggccaggcccccaggctcgtcatctattcgggctctactcgggccgctggcatcccagacaggttcagcggcagt cggtggggccagactacaatctcaccatcagcaacctggagtcgggagattttggtgtttattattgccagcagtatga atttttggccaggggaccaaggtccaggtcgacattaaa SEQ ID NOs: 46-51 are peptide insertion sequences shown in FIG. 7A.

Figure 8B:
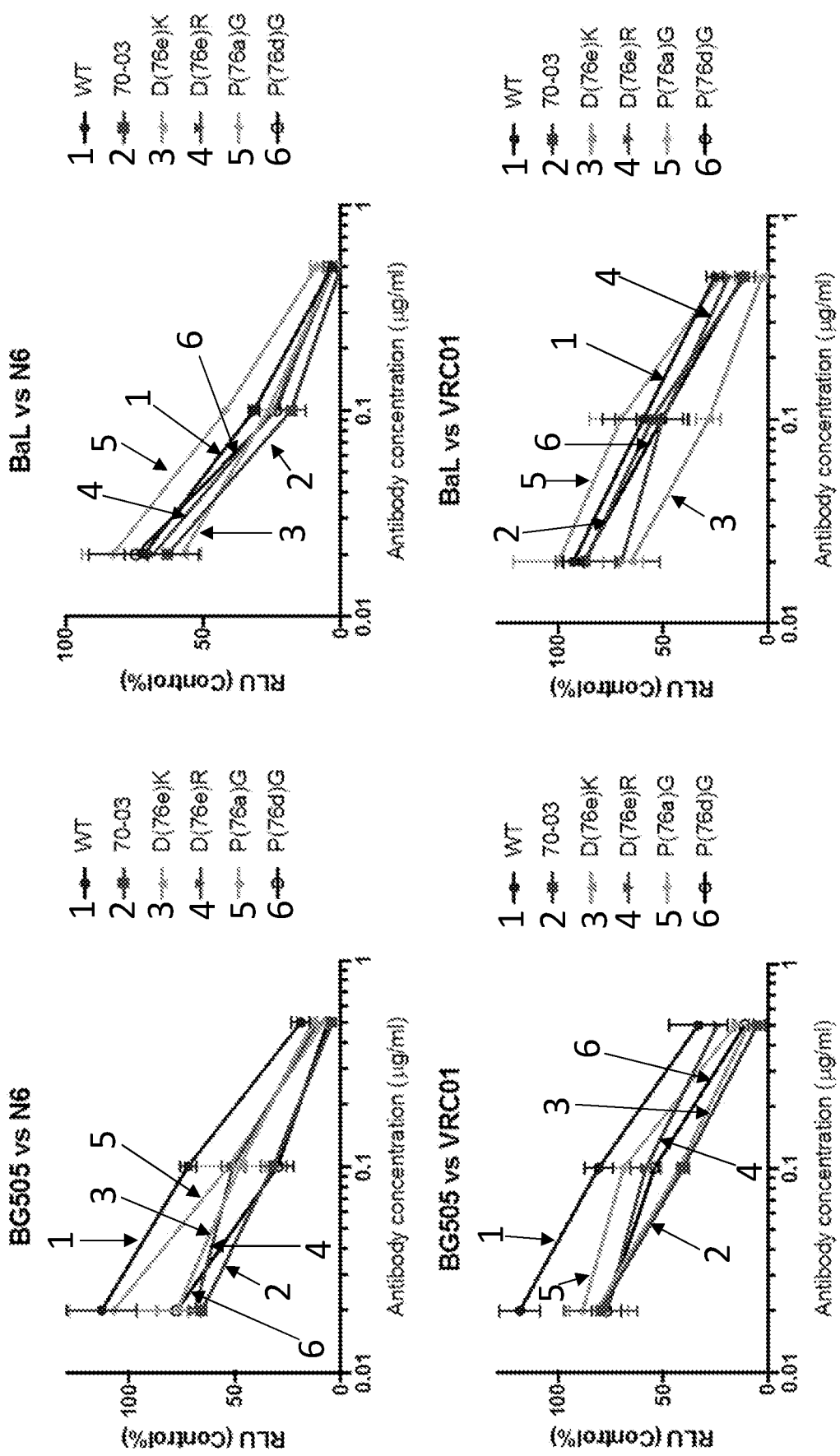

SEQ ID NOs: 52-55 are peptide insertion sequences shown in FIG. 8A.

SEQ ID NO: 56 is the amino acid sequence of the VRC-PG04 VH.
QVQLVQSGSGVKKPGASVRVSCWTSEDIFERTELIHWVRQAPGQGLEWIGWVKTVTGAVNFGSPDFRQRVSLTRDRDLFT

AHMDIRGLTQGDTATYFCARQKFYTGGQGWYFDLWGRGTLIVVSS

SEQ ID NO: 57 is the amino acid sequence of the VRC-PG04mAb $V_L$.
EIVLTQSPGTLSLSPGETASLSCTAASYGHMTWYQKKPGQPPKLLIFATSKRASGIPDRFSGSQFGKQYTLTITRMEPED

FARYYCQQLEFFGQGTRLEIRRTV

SEQ ID NO: 58 is the amino acid sequence of the VRC-PG04 70-03 $V_H$.
QVQLVQSGSGVKKPGASVRVSCWTSEDIFERTELIHWVRQAPGQGLEWIGWVKTVTGAVNFGSPDFRQRVSLTRQLSQDP

DDPDWGTAHMDIRGLTQGDTATYFCARQKFYTGGQGWYFDLWGRGTLIVVSS

SEQ ID NOs: 59-83 are CDR sequences.

SEQ ID NO: 84 is the amino acid sequence of the VRC01.23 $V_H$.
QVQLVQSGGQMKKPGESMRISCRASGYEFIDCTLNWIRLAPGKRPEWMGWLKPRWGAVNYARPLQGRVTMTRQLSQDPDD

PDWGTAFLELRSLTVDDTAVYFCTRGKNCDYNWDFEHWGRGTPVIVSS

SEQ ID NO: 85 is the amino acid sequence of the VRC01.23 $V_L$.
LTQSPGTLSLSPGETAIISCRTSQYGSLAWYQQRPGQAPRLVIYSGSTRAAGIPDRFSGSRWGPDYNLTISNLESGDFGV

YYCQQYEFFGQGTKVQVDIK

SEQ ID NO: 86 is the amino acid sequence of the 3BNC117 70-03 $V_H$.
QVQLLQSGAAVTKPGASVRVSCEASGYNIRDYFIHWWRQAPGQGLQWVGWINPKTGQPNNPRQFQGRVSLTRQLSQDPDD

PDWGSFYMDLKALRSDDTAVYFCARQRSDYWDFDVWGSGTQVTVSS

SEQ ID NO: 87 is the amino acid sequence of the N49P7 70-03 V$_H$.
ADLVQSGAVVKKPGDSVRISCEAQGYRFPDYIIHWIRRAPGQGPEWMGWMNPMGGQVNIPWKFQGRVSMTRQLSQDP DDP

DWGTAFLDLRGLKSDDTAVYYCVRDRSNGSGKRFESSNWELDLWGRGTAVTIQS

SEQ ID NO: 88 is the amino acid sequence of the N49P7 V$_L$.
QSALTQPRSVSASPGQSVTISCTGTHNLVSWCQHQPGRAPKLLIYDFNKRPSGVPDRFSGSGSGGTASLTITGLQDDDDA

EYFCWAYEAFGGGTKLTVLGQPK

SEQ ID NO: 89 is the amino acid sequence of the VRC08 70-03 V$_H$.
EVQLVQSGTQMKEPGASVTISCVTSGYEFVEILINWVRQVPGRGLEWMGWMNPRGGGVNYARQFQGKVTMTRQLSQDPDD

PDWGTAYLTLSGLTSGDTAKYFCVRGRSCCGGRRHCNGADCFNWDFQHWGQGTLVIVSP

SEQ ID NO: 90 is the amino acid sequence of the VRC08 V$_L$.
YIGVTQSPAILSVSLGERVTLSCKTSQAITPRHLVWHRQKGGQAPSLVMTGTSERASGIPDRFIGSGSGTDFTLTITRLE

AEDFAVYYCQCLEAFGQGTKLEIK

SEQ ID NO: 91 is an exemplary amino acid sequence of an antibody heavy chain comprising the VRC01.23 V$_H$ and a constant region with the "LS" mutation.
QVQLVQSGGQMKKPGESMRISCRASGYEFIDCTLNWIRLAPGKRPEWMGWLKPRWGAVNYARPLQGRVTMTRQLSQDPDD

PDWGTAFLELRSLTVDDTAVYFCTRGKNCDYNWDFEHWGRGTPVIVSSPSTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVKGFYPSDIAVEWESNGQPEN

NYKTTPPVLDSDGSFFLYSKLTVDKSRWQQGNVFSCSVLHEALHSHYTQKSLSLSPGK

SEQ ID NO: 92 is an exemplary amino acid sequence of an antibody light chain comprising the VRC01.23 V$_L$.
LTQSPGTLSLSPGETAIISCRTSQYGSLAWYQQRPGQAPRLVIYSGSTRAAGIPDRFSGSRWGPDYNLTISNLESGDFGV YYCQQYEFFGQGTKVQVDIKRTVAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

SEQ ID NO: 93 is an exemplary nucleic acid sequence encoding an antibody heavy chain comprising the VRC01.23 V$_H$.
atgggatggtcatgtatcatcctttttctagtagcaactgcaaccggtgtacattcccaggtgcagctggtgcagtctgg aggtcagatgaagaagcctggcgagtcgatgagaatttcttgtcgggcttctggatatgaatttattgattgtacgctaa attggattcgtctggccccggaaaaaggcctgagtggatgggatggctgaagcctcggtgggggccgtcaactacgca cgtccacttcagggcagagtgaccatgactcgacagctgagccaggaccctgacgatcccgattggggcacagcctttt ggagctgcgctcgttgacagtagacgacacggccgtctactttgtactaggggaaaaaactgtgattacaattgggact tcgaacactggggccggggcaccccggtcatcgtctcatcaccgtcgaccaagggcccatcggtcttcccctggcaccc tcctccaagagcacctctggggcacagcggcctgggctgcctggtcaaggactacttccccgaaccggtgacggtgtc gtggaactcaggcgccctgaccagcggcgtgcacaccttcccggctgtcctacagtcctcaggactctactccctcagca gcgtggtgaccgtgccctccagcagcttgggcacccagacctacatctgcaacgtgaatcacaagcccagcaacaccaag gtggacaagaaagttgagcccaaatcttgtgacaaaactcacacatgcccaccgtgcccagcacctgaactcctggggg accgtcagtcttcctcttccccccaaaacccaaggacaccctcatgatctcccggacccctgaggtcacatgcgtggtgg tggacgtgagccacgaagaccctgaggtcaagttcaactggtacgtggacggcgtggaggtgcataatgccaagacaaag ccgcggggaggagcagtacaacagcacgtaccgtgtggtcagcgtcctcaccgtcctgcaccaggactggctgaatggcaa ggagtacaagtgcaaggtctccaacaaagccctcccagcccccatcgagaaaaccatctccaaagccaaagggcagcccc gagaaccacaggtgtacaccctgcccccatcccgggatgagctgaccaagaaccaggtcagcctgacctgcctggtcaaa ggcttctatcccagcgacatcgccgtggagtgggagagcaatgggcagccggagaacaactacaagaccacgcctcccgt gctggactccgacggctccttcttcctctacagcaagctcaccgtggacaagagcaggtggcagcaggggaacgtcttct catgctccgtgctgcatgaggctctgcacagccactacacgcagaagagcctctccctgtctccgggtaaa SEQ ID NO: 94 is an exemplary nucleic acid sequence encoding an antibody light chain comprising the VRC01.23 $V_L$.
atgggatggtcatgtatcatcctttttctagtagcaactgcaaccggtgtacattcattgacacagtctccaggcaccct gtctttgtctccaggggaaacagccatcatctcttgtcggaccagtcagtatggttccttagcctggtatcaacagaggc ccggccaggcccccaggctcgtcatctattcgggctctactcgggccgctggcatcccagacaggttcagcggcagtcgg tgggggccagactacaatctcaccatcagcaacctggagtcgggagattttggtgtttattattgccagcagtatgaatt ttttggccaggggaccaaggtccaggtcgacattaaacgtacggtggctgcaccatctgtcttcatcttcccgccatctg atgagcagttgaaatctggaactgcctctgttgtgtgcctgctgaataacttctacccagagaagccaaagtgcagtgg aaggtggacaacgccctgcagagcggaaacagccaggaaagcgtgacagagcaggattccaaggattccacatacagcct gagcagcacactgacactgtccaaggccgactacgagaagcacaaggtgtacgcctgcgaagtgacacaccagggactgt cctcccctgtgacaaagagcttcaacagaggagaatgc SEQ ID NO: 95 is the amino acid sequence of the N6 70-03 Y54W $V_H$.
RAHLVQSGTAMKKPGASVRVSCQTSGYTFTAHILFWFRQAPGRGLEWVGWIKPQWGAVNFGGGFRDRVTLTRQLSQDPDD

PDWGIAYMDIRGLKPDDTAVYYCARDRSYGDSSWALDAWGQGTTVVVSA

SEQ ID NO: 96 is the amino acid sequence of the N6 70-03 Y98S $V_H$.
RAHLVQSGTAMKKPGASVRVSCQTSGYTFTAHILFWFRQAPGRGLEWVGWIKPQYGAVNFGGGFRDRVTLTRQLSQDPDD

PDWGIAYMDIRGLKPDDTAVYYCARDRSSGDSSWALDAWGQGTTVVVSA

SEQ ID NO: 97 is the amino acid sequence of the N6 $V_L$ with a 2-amino acid N-terminal deletion.
HVTQSPSSLSVSIGDRVTINCQTSQGVGSDLHWYQHKPGRAPKLLIHHTSSVEDGVPSRFSGSGFHTSFNLTISDLQADD

IATYYCQVLQFFGRGSRLHIK

SEQ ID NO: 98 is the amino acid sequence of the N6 $V_L$ with a 3-amino acid N-terminal deletion.
VTQSPSSLSVSIGDRVTINCQTSQGVGSDLHWYQHKPGRAPKLLIHHTSSVEDGVPSRFSGSGFHTSFNLTISDLQADDI

ATYYCQVLQFFGRGSRLHIK

SEQ ID NO: 99 is an exemplary amino acid sequence of an antibody heavy chain comprising the N6 70-03 $V_H$ and a constant region with the "LS" mutation.
RAHLVQSGTAMKKPGASVRVSCQTSGYTFTAHILFWFRQAPGRGLEWVGWIKPQYGAVNFGGGFRDRVTLTRQLSQDPDD

PDWGIAYMDIRGLKPDDTAVYYCARDRSYGDSSWALDAWGQGTTVVVSAASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVLHALHSHYTQKSLSLSPGK

SEQ ID NO: 100 is an exemplary amino acid sequence of an antibody light chain comprising the N6 $V_L$.
YIHVTQSPSSLSVSIGDRVTINCQTSQGVGSDLHWYQHKPGRAPKLLIHHTSSVEDGVPSRFSGSGFHTSFNLTISDLQA

DDIATYYCQVLQFFGRGSRLHIKRTVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

SEQ ID NO: 101 is the amino acid sequence of the VRC07-523 70-03 H54W $V_H$.
QVRLSQSGGQMKKPGDSMRISCRASGYEFINCPINWIRLAPGKRPEWMGWMKPRWGAVSYARQLQGRVTMTRQLSQDPDD

PDWGTAFLELRSLTSDDTAVYFCTRGKYCTARDYYNWDFEHWGQGTPVTVSS

SEQ ID NO: 102 is the amino acid sequence of the VRC07-523 70-03 H54F $V_H$.
QVRLSQSGGQMKKPGDSMRISCRASGYEFINCPINWIRLAPGKRPEWMGWMKPRFGAVSYARQLQGRVTMTRQLSQDPDD

PDWGTAFLELRSLTSDDTAVYFCTRGKYCTARDYYNWDFEHWGQGTPVTVSS

SEQ ID NO: 103 is the amino acid sequence of the VRC07-523 $V_L$ with a 3-amino acid N-terminal deletion relative to VRC01 VL.
LTQSPGTLSLSPGETAIISCRTSQYGSLAWYQQRPGQAPRLVIYSGSTRAAGIPDRFSGSRWGPDYNLTISNLESGDFGV

YYCQQYEFFGQGTKVQVDIK

SEQ ID NO: 104 is the amino acid sequence of the VRC07-523 V$_L$ with a 3-amino acid N-terminal deletion relative to VRC01 VL and R24D and N72Q substitutions.
LTQSPGTLSLSPGETAIISCDTSQYGSLAWYQQRPGQAPRLVIYSGSTRAAGIPDRFSGSRWGPDYQLTISNLESGDFGV

YYCQQYEFFGQGTKVQVDIK

SEQ ID NO: 105 is the amino acid sequence of the N49P7 70-03 G54W V$_H$.
ADLVQSGAVVKKPGDSVRISCEAQGYRFPDYIIHWIRRAPGQGPEWMGWMNPMWGQVNIPWKFQGRVSMTRQLSQDPDDP

DWGTAFLDLRGLKSDDTAVYYCVRDRSNGSGKRFESSNWFLDLWGRGTAVTIQS

SEQ ID NO: 106 is the amino acid sequence of the N49P7 V$_L$ with a 2-amino acid N-terminal deletion.
ALTQPRSVSASPGQSVTISCTGTHNLVSWCQHQPGRAPKLLIYDFNKRPSGVPDRFSGSGSGGTASLTITGLQDDDDAEY

FCWAYEAFGGGTKLTVLGQPK

SEQ ID NO: 107 is the amino acid sequence of the N49P7 V$_L$ with a 3-amino acid N-terminal deletion.
LTQPRSVSASPGQSVTISCTGTHNLVSWCQHQPGRAPKLLIYDFNKRPSGVPDRFSGSGSGGTASLTITGLQDDDDAEYF

CWAYEAFGGGTKLTVLGQPK

SEQ ID NO: 108 is the amino acid sequence of the VRC08 70-03 G54W V$_H$.
EVQLVQSGTQMKEPGASVTISCVTSGYEFVEILINWVRQVPGRGLEWMGWMNPRWGGVNYARQFQGKVTMTRQLSQDPDD

PDWGTAYLTLSGLTSGDTAKYFCVRGRSCCGGRRHCNGADCFNWDFQHWGQGTLVIVSP

SEQ ID NO: 109 is the amino acid sequence of the VRC08 V$_L$ with a 2-amino acid N-terminal deletion.
GVTQSPAILSVSLGERVTLSCKTSQAITPRHLVWHRQKGGQAPSLVMTGTSERASGIPDRFIGSGSGTDFTLTITRLEAE

DFAVYYCQCLEAFGQGTKLEIK

SEQ ID NO: 110 is the amino acid sequence of the VRC08 V$_L$ with a 3-amino acid N-terminal deletion.
VTQSPAILSVSLGERVTLSCKTSQAITPRHLVWHRQKGGQAPSLVMTGTSERASGIPDRFIGSGSGTDFTLTITRLEAED

FAVYYCQCLEAFGQGTKLEIK

SEQ ID NO: 111 is the amino acid sequence of the 3BNC117 T54W V$_H$.
QVQLLQSGAAVTKPGASVRVSCEASGYNIRDYFIHWWRQAPGQGLQWVGWINPKWGQPNNPRQFQGRVSLTRHASWDFDT

YSFYMDLKALRSDDTAVYFCARQRSDYWDFDVWGSGTQVTVSS

SEQ ID NO: 112 is the amino acid sequence of the 3BNC117 70-03 T54W V$_H$.
QVQLLQSGAAVTKPGASVRVSCEASGYNIRDYFIHWWRQAPGQGLQWVGWINPKWGQPNNPRQFQGRVSLTRQLSQDPDD

PDWGSFYMDLKALRSDDTAVYFCARQRSDYWDFDVWGSGTQVTVSS

SEQ ID NO: 113 is the amino acid sequence of the 3BNC117 V$_L$ with a 2-amino acid N-terminal deletion.
QMTQSPSSLSASVGDTVTITCQANGYLNWYQQRRGKAPKLLIYDGSKLERGVPSRFSGRRWGQEYNLTINNLQPEDIATY

FCQVYEFVVPGTRLDLK

SEQ ID NO: 114 is the amino acid sequence of the 3BNC117 V$_L$ with a 3-amino acid N-terminal deletion.
MTQSPSSLSASVGDTVTITCQANGYLNWYQQRRGKAPKLLIYDGSKLERGVPSRFSGRRWGQEYNLTINNLQPEDIATYF

CQVYEFVVPGTRLDLK

SEQ ID NO: 115 is the amino acid sequence of the 3BNC117 70-03 G54F V$_H$.
QVQLLQSGAAVTKPGASVRVSCEASGYNIRDYFIHWWRQAPGQGLQWVGWINPKFGQPNNPRQFQGRVSLTRQLSQDPDD

PDWGSFYMDLKALRSDDTAVYFCARQRSDYWDFDVWGSGTQVTVSS

SEQ ID NO: 116 is the amino acid sequence of the N49P7 V$_H$.
ADLVQSGAVVKKPGDSVRISCEAQGYRFPDYIIHWIRRAPGQGPEWMGWMNPMGGQVNIPWKFQGRVSMTRDTSIETAFL

DLRGLKSDDTAVYYCVRDRSNGSGKRFESSNWFLDLWGRGTAVTIQS

SEQ ID NO: 117 is the amino acid sequence of the VRC08 V$_H$.
EVQLVQSGTQMKEPGASVTISCVTSGYEFVEILINWVRQVPGRGLEWMGWMNPRGGVNYARQFQGKVTMTRDVYRDTAY

LTLSGLTSGDTAKYFCVRGRSCCGGRRHCNGADCFNWDFQHWGQGTLVIVSP

-continued

SEQ ID NO: 118 is the amino acid sequence of a heavy chain IgG1 constant region
with the "LS" mutation.
ASTKGPSVFPLAPSSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRWQQGNVFSCSVLHALHSHYTQ

KSLSLSPGK

SEQ ID NO: 119 is the amino acid sequence of a light chain constant region.
RTVAAPSVFIFPPSDEQLKSGTASVVCLLNNFYPREAKVQWKVDNALQSGNSQESVTEQDSKDSTYSLSSTLTLSKADYE

KHKVYACEVTHQGLSSPVTKSFNRGEC

DETAILED DESCRIPTION

I. Summary of Terms

Unless otherwise noted, technical terms are used according to conventional usage. Definitions of many common terms in molecular biology may be found in Krebs et al. (eds.), *Lewin's genes XII*, published by Jones & Bartlett Learning, 2017. As used herein, the singular forms "a," "an," and "the," refer to both the singular as well as plural, unless the context clearly indicates otherwise. For example, the term "an antigen" includes singular or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody and Antigen Binding Fragment: An immunoglobulin, antigen-binding fragment, or derivative thereof, that specifically binds and recognizes an analyte (antigen) such as HIV-1 gp120. The term "antibody" is used herein in the broadest sense and encompasses various antibody structures, including but not limited to monoclonal antibodies, polyclonal antibodies, multispecific antibodies (e.g., bispecific and trispecific antibodies), and antigen-binding fragment, so long as they exhibit the desired antigen-binding activity.

Non-limiting examples of antibodies include, for example, intact immunoglobulins and variants and fragments thereof known in the art that retain binding affinity for the antigen. Examples of antigen-binding fragment include but are not limited to Fv, Fab, Fab', Fab'-SH, F(ab')$_2$; diabodies; linear antibodies; single-chain antibody molecules (e.g. scFv); and multispecific antibodies formed from antibody fragments. Antigen-binding fragments include those produced by the modification of whole antibodies and those synthesized de novo using recombinant DNA methodologies (see, e.g., Kontermann and Dübel (Eds.), *Antibody Engineering*, Vols. 1-2, $2^{nd}$ ed., Springer-Verlag, 2010).

Antibodies also include genetically engineered forms such as chimeric antibodies (such as humanized murine antibodies) and heteroconjugate antibodies (such as bispecific antibodies).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain). In combination, the heavy and the light chain variable regions specifically bind the antigen.

References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, $5^{th}$ ed., NIH Publication No. 91-3242, Public Health Service, National Institutes of Health, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. (*Sequences of Proteins of Immunological Interest*, 5th ed., NIH Publication No. 91-3242, Public Health Service, National Institutes of Health, U.S. Department of Health and Human Services, 1991; "Kabat" numbering scheme), Al-Lazikani et al., ("Standard conformations for the canonical structures of immunoglobulins," *J. Mol. Bio.*, 273(4):927-948, 1997; "Chothia" numbering scheme), and Lefranc et al. ("IMGT unique numbering for immunoglobulin and T cell receptor variable domains and Ig superfamily V-like domains," *Dev. Comp. Immunol.*, 27(1):55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

In some embodiments, a disclosed antibody includes a heterologous constant domain. For example the antibody includes a constant domain that is different from a native constant domain, such as a constant domain including one or more modifications (such as the "LS" mutations) to increase half-life.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Greenfield (Ed.), *Antibodies: A Laboratory Manual*, 2nd ed. New York: Cold Spring Harbor Laboratory Press, 2014.)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manual*. 1st ed. New York: Cold Spring Harbor Laboratory Press, 2004; Lonberg, *Nat. Biotechnol.*, 23(9): 1117-1125, 2005; Lonberg, *Curr. Opin. Immunol.*, 20(4): 450-459, 2008).

A "bispecific antibody" is a recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody can include one or more constant domains, but does not necessarily include a constant domain.

A "parent" antibody is an antibody that is used as a reference or comparison when referring to another antibody that is not the parent antibody. For example, a test antibody that has the same CDRs as a particular parent antibody has CDRs that are identical to the CDRs of the parent antibody, but the remainder of the test antibody could be different from the parent antibody.

Antibody or antigen binding fragment that neutralizes HIV-1: An antibody or antigen binding fragment that specifically binds to HIV-1 Env (for example, that binds gp120) in such a way as to inhibit a biological function associated with HIV-1 Env (such as binding to its target receptor). In several embodiments, an antibody or antigen binding fragment that neutralizes HIV-1 reduces the infectious titer of HIV-1.

Broadly neutralizing antibodies to HIV-1 are distinct from other antibodies to HIV-1 in that they neutralize a high percentage of the many types of HIV-1 in circulation. In some embodiments, broadly neutralizing antibodies to HIV-1 are distinct from other antibodies to HIV-1 in that they neutralize a high percentage (such as at least 90%, at least 95%, at least 96%, at least 97%, at least 98%, at least 99%) of the many types of HIV-1 in circulation. Non-limiting examples of HIV-1 broadly neutralizing antibodies include N6, 2G12, PGT122, VRC01, 35022, VRC07, VRC07-523, and VRC-PG04.

Biological sample: A sample obtained from a subject. Biological samples include all clinical samples useful for detection of disease or infection (for example, HIV-1 infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having an HIV-1 infection.

CD4: Cluster of differentiation factor 4 polypeptide; a T-cell surface protein that mediates interaction with the MHC class II molecule. CD4 also serves as the primary receptor site for HIV-1 on T-cells during HIV-1 infection. CD4 is known to bind to gp120 from HIV-1. The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, Cell 42:93, 1985).

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Greenfield (Ed.), *Antibodies: A Laboratory Manual*, 2$^{nd}$ ed. New York: Cold Spring Harbor Laboratory Press, 2014, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intraorganismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods, for instance immunohistochemistry (IHC), immunoprecipitation (IP), flow cytometry, immunofluorescence microscopy, ELISA, immunoblotting (for example, Western blot), magnetic resonance imaging (MRI), computed tomography (CT) scans, radiography, and affinity chromatography. Immunological binding properties of selected antibodies may be quantified using known methods.

Conjugate: A complex of two molecules linked together, for example, linked together by a covalent bond. In one embodiment, an antibody is linked to an effector molecule; for example, an antibody that specifically binds to HIV-1 Env covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative amino acid substitution: "Conservative" amino acid substitutions are those substitutions that do not substantially affect a function of a protein, such as the ability of the protein to interact with a target protein.

In some embodiments, a conservative amino acid substitution in an HIV Env-specific antibody is one that does not reduce binding of the antibody to HIV Env by more than 10% (such as by more than 5%) compared to the HIV Env binding of the corresponding antibody lacking the conservative amino acid substitution. In some embodiments, the HIV Env-specific antibody includes no more than 10 (such as no more than 5, no more than 3, no more than 2, or no more than 1) conservative substitutions compared to a reference antibody and retain specific binding activity for HIV Env, and/or HIV-1 neutralization activity.

Typically, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient not infected with HIV-1. In other embodiments, the control is a positive control, such as a tissue sample obtained from a patient diagnosed with HIV-1 infection. In still other embodiments, the control is a historical control or standard reference value or range of values (such as a previously tested control sample, such as a group of HIV-1 patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Detecting: To identify the existence, presence, or fact of something.

Effector molecule: A molecule intended to have or produce a desired effect; for example, a desired effect on a cell to which the effector molecule is targeted. Effector molecules can include, for example, polypeptides and small molecules. In one non-limiting example, the effector molecule is a toxin. Some effector molecules may have or produce more than one desired effect.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on gp120.

Expression: Transcription or translation of a nucleic acid sequence. For example, an encoding nucleic acid sequence (such as a gene) can be expressed when its DNA is transcribed into RNA or an RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcriptional terminators, a start codon (ATG) in front of a protein-encoding gene, splice signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

HIV-1 Envelope protein (Env): The HIV-1 envelope protein is initially synthesized as a precursor protein of 845-870 amino acids in size, designated gp160. Individual gp160 polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp120/gp41 protomers within the homotrimer. The ectodomain (that is, the extracellular portion) of the HIV-1 Env trimer undergoes several structural rearrangements from a prefusion mature (cleaved) closed conformation that evades antibody recognition, through intermediate conformations that bind to receptors CD4 and co-receptor (either CCR5 or CXCR4), to a postfusion conformation.

The numbering used in the disclosed HIV-1 Env proteins and fragments thereof is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, N. Mex., which is incorporated by reference herein in its entirety.

HIV-1 gp120: A polypeptide that is part of the HIV-1 Env protein. Mature gp120 includes approximately HIV-1 Env residues 31-511, contains most of the external, surface-exposed, domains of the HIV-1 Env trimer, and it is gp120 which binds both to cellular CD4 receptors and to cellular chemokine receptors (such as CCR5). A mature gp120 polypeptide is an extracellular polypeptide that interacts with the gp41 ectodomain to form an HIV-1 Env protomer that trimerizes to form the HIV-1 Env trimer.

HIV-1 gp41: A polypeptide that is part of the HIV-1 Env protein. Mature gp41 includes approximately HIV-1 Env residues 512-860, and includes cytosolic-, transmembrane-, and ecto-domains. The gp41 ectodomain (including approximately HIV-1 Env residues 512-644) can interact with gp120 to form an HIV-1 Env protomer that trimerizes to form the HIV-1 Env trimer.

Human Immunodeficiency Virus type 1 (HIV-1): A retrovirus that causes immunosuppression in humans (HIV-1 disease), and leads to a disease complex known as the acquired immunodeficiency syndrome (AIDS). "HIV-1 disease" refers to a well-recognized constellation of signs and symptoms (including the development of opportunistic infections) in persons who are infected by an HIV-1 virus, as determined by antibody or western blot studies. Laboratory findings associated with this disease include a progressive decline in T cells. Related viruses that are used as animal models include simian immunodeficiency virus (SIV) and feline immunodeficiency virus (FIV). Treatment of HIV-1 with HAART has been effective in reducing the viral burden and ameliorating the effects of HIV-1 infection in infected individuals.

HXB2 numbering system: A reference numbering system for HIV-1 protein and nucleic acid sequences, using HIV-1 HXB2 strain sequences as a reference for all other HIV-1 strain sequences. The person of ordinary skill in the art is familiar with the HXB2 numbering system, and this system is set forth in "Numbering Positions in HIV Relative to HXB2CG," Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex., which is incorporated by reference herein in its entirety. HXB2 is also known as: HXBc2, for HXB clone 2; HXB2R, in the Los Alamos HIV database, with the R for revised, as it was slightly revised relative to the original HXB2 sequence; and HXB2CG in GENBANK™, for HXB2 complete genome. The numbering used in gp120 polypeptides disclosed herein is relative to the HXB2 numbering scheme. For reference, the amino acid sequence of HIV-1 Env of HXB2 is set forth below:

```
(SEQ ID NO: 37; GENBANK® Accession No. K03455)
MRVKEKYQHLWRWGWRWGTMLLGMLMICSATEKLWVTVYYGVPVWKEATT

TLFCASDAKAYDTEVHNVWATHACVPTDPNPQEVVLVNVTENFNMWKNDM

VEQMHEDIISLWDQSLKPCVKLTPLCVSLKCTDLKNDTNTNSSSGRMIME

KGEIKNCSFNISTSIRGKVQKEYAFFYKLDIIPIDNDTTSYKLTSCNTSV

ITQACPKVSFEPIPIHYCAPAGFAILKCNNKTFNGTGPCTNVSTVQCTHG

IRPVVSTQLLLNGSLAEEEVVIRSVNFTDNAKTIIVQLNTSVEINCTRPN

NNTRKRIRIQRGPGRAFVTIGKIGNMRQAHCNISRAKWNNTLKQIASKLR

EQFGNNKTIIFKQSSGGDPEIVTHSFNCGGEFFYCNSTQLFNSTWFNSTW

STEGSNNTEGSDTITLPCRIKQIINMWQKVGKAMYAPPISGQIRCSSNIT

GLLLTRDGGNSNNESEIFRPGGGDMRDNWRSELYKYKVVKIEPLGVAPTK

AKRRVVQREKRAVGIGALFLGFLGAAGSTMGAASMTLTVQARQLLSGIVQ

QQNNLLRAIEAQQHLLQLTVWGIKQLQARILAVERYLKDQQLLGIWGCSG

KLICTTAVPWNASWSNKSLEQIWNHTTWMEWDREINNYTSLIHSLIEESQ

NQQEKNEQELLELDKWASLWNWFNITNWLWYIKLFIMIVGGLVGLRIVFA

VLSIVNRVRQGYSPLSFQTHLPTPRGPDRPEGIEEEGGERDRDRSIRLVN

GSLALIWDDLRSLCLFSYHRLRDLLLIVTRIVELLGRRGWEALKYWWNLL

QYWSQELKNSAVSLLNATAIAVAEGTDRVIEVVQGACRAIRHIPRRIRQG

LERILL.
```

IgA: A polypeptide belonging to the class of antibodies that are substantially encoded by a recognized immunoglobulin alpha gene. In humans, this class or isotype comprises IgA$_1$ and IgA$_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class comprises IgG$_1$, IgG$_2$, IgG$_3$, and IgG$_4$.

Immune complex: The binding of antibody or antigen binding fragment (such as a scFv) to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Inhibiting a disease or condition: Reducing the full development of a disease or condition in a subject, for example, reducing the development of AIDS in a subject infected with HIV-1 or reducing symptoms associated with the HIV-1 infection. This includes neutralizing, antagonizing, prohibiting, preventing, restraining, slowing, disrupting, stopping, or reversing progression or severity of the disease or condition.

Inhibiting a disease or condition includes a prophylactic intervention administered before the disease or condition has begun to develop (for example a treatment initiated in a subject at risk of an HIV-1 infection, but not infected by HIV-1) that reduces subsequent development of the disease or condition and also to amelioration of one or more signs or symptoms of the disease or condition following development. Additionally, inhibiting a disease or condition includes a therapeutic intervention administered after a disease or condition has begun to develop (for example, a treatment administered following diagnosis of a subject with HIV-1 infection) that ameliorates one or more signs or symptoms of the disease or condition in the subject. The term "ameliorating," with reference to inhibiting a disease or condition refers to any observable beneficial effect of the intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters that are specific to the particular disease or condition.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Kabat position: A position of a residue in an amino acid sequence that follows the numbering convention delineated by Kabat et al. (*Sequences of Proteins of Immunological Interest*, 5$^{th}$ ed., NIH Publication No. 91-3242, Public Health Service, National Institutes of Health, U.S. Department of Health and Human Services, 1991).

Linker: A bi-functional molecule that can be used to link two molecules into one contiguous molecule, for example, to link an effector molecule to an antibody. Non-limiting examples of peptide linkers include glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. The linkage can be either by chemical or recombinant means. "Chemical means" refers to a reaction between the antibody moiety and the effector molecule such that there is a covalent bond formed between the two molecules to form one molecule.

Nucleic acid (molecule or sequence): A deoxyribonucleotide or ribonucleotide polymer or combination thereof including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides.

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and the non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy*, 22$^{nd}$ ed., London, UK: Pharmaceutical Press, 2013, describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as non-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal (C-terminal) end. In some embodiments, the polypeptide is a disclosed antibody or a fragment thereof.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences. Homologs and variants of a $V_L$ or a $V_H$ of an antibody that specifically binds a target antigen are typically characterized by possession of at least about 75% sequence identity, for example at least about 80%, 85%, 90%, 91%, 92%, 93%, 94%, 95%, 96%, 97%, 98% or 99% sequence identity counted over the full-length alignment with the amino acid sequence of interest.

Methods of alignment of sequences for comparison are well known in the art. Various programs and alignment algorithms are described in: Smith and Waterman, *Adv. Appl. Math.* 2(4):482-489, 1981; Needleman and Wunsch, *J. Mol. Biol.* 48(3):443-453, 1970; Pearson and Lipman, *Proc. Natl. Acad. Sci. U.S.A.* 85(8):2444-2448, 1988; Higgins and Sharp, *Gene,* 73(1):237-244, 1988; Higgins and Sharp, *Bioinformatics,* 5(2):151-3, 1989; Corpet, *Nucleic Acids Res.* 16(22):10881-10890, 1988; Huang et al. *Bioinformatics,* 8(2):155-165, 1992; and Pearson, *Methods Mol. Biol.* 24:307-331, 1994. Altschul et al., *J. Mol. Biol.* 215(3):403-410, 1990, presents a detailed consideration of sequence alignment methods and homology calculations. The NCBI Basic Local Alignment Search Tool (BLAST) (Altschul et al., *J. Mol. Biol.* 215(3):403-410, 1990) is available from several sources, including the National Center for Biological Information and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Generally, once two sequences are aligned, the number of matches is determined by counting the number of positions where an identical nucleotide or amino acid residue is present in both sequences. The percent sequence identity between the two sequences is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

Specifically bind: When referring to an antibody or antigen binding fragment, refers to a binding reaction which determines the presence of a target protein in the presence of a heterogeneous population of proteins and other biologics. Thus, under designated conditions, an antibody binds preferentially to a particular target protein, peptide or polysaccharide (such as an antigen present on the surface of a pathogen, for example HIV-1 Env) and does not bind in a significant amount to other proteins present in the sample or subject. A limited degree of non-specific interaction may occur between an antibody (such as an antibody that specifically binds to HIV-1 Env) and a non-target (such as a cell that does not express HIV-1 Env). Specific binding can be determined by methods known in the art. See Greenfield (Ed.), *Antibodies: A Laboratory Manual,* $2^{nd}$ ed. New York: Cold Spring Harbor Laboratory Press, 2014, for a description of immunoassay formats and conditions that can be used to determine specific immunoreactivity.

With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar. $K_D$ refers to the dissociation constant for a given interaction, such as a polypeptide-ligand interaction or an antibody-antigen interaction. For example, for the bimolecular interaction of an antibody or antigen binding fragment and an antigen it is the concentration of the individual components of the bimolecular interaction divided by the concentration of the complex.

Subject: Living multicellular vertebrate organisms, a category that includes human and non-human mammals. In an example, a subject is a human. In a particular example, the subject is a newborn infant. In an additional example, a subject is selected that is in need of inhibiting an HIV-1 infection. For example, the subject is uninfected and at risk of HIV-1 infection.

Therapeutically effective amount: A quantity of a specific substance sufficient to achieve a desired effect in a subject being treated. For instance, this can be the amount necessary to prevent, treat (including prophylaxis), reduce and/or ameliorate the symptoms or underlying causes of a disorder or disease, such as HIV-1 infection. In some embodiments, a therapeutically effective amount is sufficient to reduce or eliminate a symptom of HIV-1 infection, such as AIDS. For instance, this can be the amount necessary to inhibit or prevent HIV-1 replication or to measurably alter outward symptoms of the HIV-1 infection. Ideally, a therapeutically effective amount provides a therapeutic effect without causing a substantial cytotoxic effect in the subject.

In some embodiments, administration of a therapeutically effective amount of a disclosed antibody or antigen binding fragment that binds to HIV-1 Env can reduce or inhibit an HIV-1 infection (for example, as measured by infection of cells, or by number or percentage of subjects infected by HIV-1, or by an increase in the survival time of infected subjects) by a desired amount, for example by at least 10%, at least 20%, at least 50%, at least 60%, at least 70%, at least 80%, at least 90%, at least 95%, at least 98%, or even at least 100% (elimination or prevention of detectable HIV-1 infection), as compared to a suitable control.

A therapeutically effective amount of an antibody or antigen binding fragment that specifically binds gp120 that is administered to a subject will vary depending upon a number of factors associated with that subject, for example the overall health and/or weight of the subject. A therapeutically effective amount can be determined by varying the dosage and measuring the resulting therapeutic response, such as, for example, a reduction in viral titer. Therapeutically effective amounts also can be determined through various in vitro, in vivo or in situ immunoassays.

A therapeutically effective amount encompasses a fractional dose that contributes in combination with previous or subsequent administrations to attaining a therapeutic response. For example, a therapeutically effective amount of an agent can be administered in a single dose, or in several doses, for example daily, during a course of treatment lasting several days or weeks. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Transformed: A transformed cell is a cell into which a nucleic acid molecule has been introduced by molecular biology techniques. As used herein, the term transformed and the like (e.g., transformation, transfection, transduction, etc.) encompasses all techniques by which a nucleic acid molecule might be introduced into such a cell, including transduction with viral vectors, transformation with plasmid vectors, and introduction of DNA by electroporation, lipofection, and particle gun acceleration.

Vector: An entity containing a nucleic acid molecule (such as a DNA or RNA molecule) bearing a promoter(s) that is operationally linked to the coding sequence of a protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. In some embodiments, a viral vector comprises a nucleic acid molecule encoding a disclosed antibody or antigen binding fragment that specifically binds to HIV-1 gp120 and neutralizes HIV-1. In some embodiments, the viral vector can be an adeno-associated virus (AAV) viral vector.

VRC01-class antibody, heavy chain or light chain: A class of antibodies that bind to the CD4 binding site on gp120 and can neutralize HIV-1, as well as heavy and light chains thereof. The prototypical member of the VRC01-class of antibodies—VRC01—can neutralize over 90% of circulating HIV-1 isolates with an average 50% inhibitory concentration ($IC_{50}$) of ~0.3 µg/ml. Despite overall sequence differences between VRC01-class antibodies, antibody-gp120 co-crystal structures revealed VRC01-class recognition of gp120 to be consistent across the class. Indeed, three-dimensional structure analysis of HIV-1 gp120 from different HIV-1 clades in complexes with different VRC01-class antibodies from multiple donors show that the VRC01-class antibodies share striking similarity in physical structure, and revealed several antibody features that contribute to gp120 binding and HIV-1 neutralization. The substantial structural and ontogenetic characterization of VRC01-class of antibodies allows recognition of the members of this class by interrogation of antibody sequence.

For example, the $V_H$ of a VRC01-class antibody has a VH1-2 germline origin, wherein the VRC01-class $V_H$ encoding sequence is from 20-35% (such as 25-30%) divergent from the corresponding germline gene sequence. The VRC01-class $V_H$ includes a tryptophan residue at Kabat position 50 ($V_H$ $Trp_{50}$), a serine or asparagine residue at Kabat position 58 ($V_H$ $Asn_{58}$), an arginine residue at Kabat position 71 ($V_H$ $Arg_{71}$), and a tryptophan or phenylalanine at position 100B. These residues form specific interactions with amino acids on gp120 that contribute to the VRC01-class specificity and neutralization properties. When a VRC01-class antibody is bound to gp120, $V_H$ $Trp_{50}$ forms a hydrogen bond with gp120 $Asn_{280}$, $V_H$ $Asp_{58}$ forms hydrogen bonds with gp120 $Arg_{456}$ and $Gly_{458}$, $V_H$ $Arg_{71}$ forms salt bridges with gp120 $Asp_{368}$, and $V_H$ Trp100B forms a hydrogen bond with gp120 $Asn_{279}$.

Further, the $V_L$ of a VRC01-class antibody has an IGKV1-33, IGKV3-11, IGKV3-15, IGKV3-20, or IGLV2-14 germline origin, wherein the VRC01-class $V_L$ encoding sequence is from 15-35% (such as 25-30%) divergent from the corresponding germline gene sequence. The VRC01-class $V_L$ includes either a LCDR1 (Kabat positioning) with a 2-6 amino acid deletion, or a LCDR1 with glycine residues for at least two of Kabat positions 28-30. The deletion or the presence of the glycine residues provides flexibility that allows the LCDR1 to avoid structural clash with the D loop of gp120 when the antibody is bound to the CD4 binding site. Further, the VRC01-class $V_L$ includes an LCDR3 that is five amino acids in length (according to Kabat positioning) and includes a hydrophobic residue (such as leucine or tyrosine) at Kabat position 91, deletion of Kabat positions 92-95, and a glutamate or glutamine residue at Kabat position 96. The hydrophobic residue at position 91 packs against the backbone of gp120 loop D, and the glutamate or glutamine residue at Kabat position 96 interacts with a conserved electropositive region on the base of the gp120 V5 domain.

Non-limiting examples of antibodies that fall within the VRC01-class include the N6, VRC01, VRC03, VRC07, VRC07-523, VRC13, 3BCN117, 12A12, 12A21, VRC-PG04, NIH45-46, VRC23, VRC-CH30, VRC-CH31, and VRC-PG20 antibodies. Description, characterization, and productions of these antibodies, as well as the VRC01-class of antibodies is available and familiar to the person of ordinary skill in the art (see, e.g., Diskin et al., *Science*, 334(6060):1289-93, 2011; Kwong and Mascola, *Immunity*, 37, 412-425, 2012; Li et al., *J. Virol.*, 85, 8954-8967, 2011; Rudicell et al., *J. Virol.*, 88, 12669-12682, 2012; Scheid et al., *Science*, 333(6049):1633-1637, 2011; West et al., *PNAS*, 109:E2083-2090, 2012; Wu et al., *Science*, 329(5993):856-861, 2010; Wu et al., *Science*, 333(6049):1593-1602, 2011; Zhou et al., *Immunity*, 39:245-258, 2013; Georgiev et al., *Science*, 340:751-756, 2013; Zhu et al., *PNAS*, 110, E4088-E4097, 2013; and WIPO Pub. Nos. WO 2012/158948, WO2011038290, WO2012154312, WO2013142324, and WO2013016468, each of which is incorporated by reference herein in its entirety).

II. Description of Several Embodiments

Isolated monoclonal antibodies and antigen binding fragments that specifically bind to the CD4 binding site on HIV-1 Env are provided. In some embodiments, the antibody or antigen binding fragment is fully human. In several embodiments, the antibodies and antigen binding fragments are used to neutralize HIV-1. Also disclosed herein are compositions including the antibodies and antigen binding fragments and a pharmaceutically acceptable carrier. Nucleic acids encoding the antibodies or antigen binding fragments, expression vectors (such as adeno-associated virus (AAV) viral vectors) including these nucleic acids are also provided.

The antibodies, antigen binding fragments, nucleic acid molecules, and compositions can be used for research, diagnostic and therapeutic purposes. For example, the monoclonal antibodies and antigen binding fragments can be used to diagnose or treat a subject with an HIV-1 infection, or can be administered prophylactically to prevent HIV-1 infection in a subject. In some embodiments, the antibodies can be used to determine HIV-1 titer in a subject.

A. Antibodies and Antigen Binding Fragments

In addition to the "classic" CD4 binding site on the gp120 outer domain ("CD4-BS1 domain"), CD4 binds to residues of the neighboring protomer including residues of the α-1 helix (e.g., E62, T63, E64, H66) and β3-β4 loop (e.g., K207) from the gp120 inner domain "CD4-BS2." CD4 interaction with the CD4-BS2 facilitates stability of the CD4-gp120 interaction, triggering of gp120 conformational changes that enable coreceptor binding, and progression of the fusogenic process. Based on the complete CD4 binding site (including the CD4-BS1 and CD4-BS2) on the HIV-1 Env trimer, antibodies that target the CD4-BS1 were modified to also bind to CD4-BS2 and neighboring residues on the HIV-1 Env trimer. As shown herein, embodiments of such antibodies provide improved HIV-1 Env binding and HIV-1 neutralization compared to the corresponding unmodified, CD4-BS1 specific, parent antibodies.

In some embodiments, a monoclonal antibody is provided, comprising $V_H$ comprising a HCDR 1, a HCDR2, and a HCDR3 of a parent VRC01-class antibody, and a $V_L$ comprising a LCDR1, a LCDR2, and a LCDR3 of the parent VRC01-class antibody. The HFR3 of the monoclonal antibody comprises a modification compared to the corresponding HFR3 of the parent VRC01-class antibody, wherein the modification is a substitution of the amino acids of Kabat positions 72-76 of the parent VRC01-class antibody with the sequence set forth as QLSQDPDDPDWG (SEQ ID NO: 36). The parent VRC01-class antibody does not contain an amino acid insertion between Kabat positions 75/76 compared to an IGHV1-2*02 germline sequence. SEQ ID NO: 36 is the 70s Loop sequence from Kabat positions 72-76 of the VRC03 antibody. As shown in the examples, replacement of the Kabat positions 72-76 of VRC01-class antibodies that lack a 70s Loop insertion with SEQ ID NO: 36 from VRC03 (which contains a 70s Loop insertion) confers a surprising improvement in HIV-1 Env binding and HIV-1 neutralization to the modified VRC01-class antibodies. In this disclosure, replacement of the Kabat positions 72-76 of VRC01-class antibodies that lack a 70s Loop insertion with SEQ ID NO: 36 is also referred to as a "70-03 insertion."

In some embodiments, a HFR1, a HFR2, the HFR3, and a HFR4 of the monoclonal antibody comprise, in aggregate and not including the modification, no more than 10 amino acid substitutions (such as conservative amino acid substitutions) compared to the corresponding sequences of the parent VRC01-class antibody. In some embodiments, a LFR1, a LFR2, a LFR3, and a LFR4 of the monoclonal antibody comprise, in aggregate, no more than 10 amino acid substitutions (such as conservative amino acid substitutions) compared to the corresponding sequences of the parent VRC01-class antibody.

In some embodiments, the parent VRC01-class antibody is any one of N6, VRC01, VRC07, VRC07-523, VRC-PG04, 3BNC117, N49P7, or VRC08. The CDRs and variable region sequences of these VRC01-class antibodies are set forth below.

TABLE 1

Kabat CDRs of recombinant VRC01-class antibodies including a 70-03 insertion.

N6 70-03 $V_H$

| $V_H$ | SEQ ID NO: 16 positions | CDR protein sequence | CDR SEQ ID NO |
|---|---|---|---|
| HCDR1 | 31-35 | AHILF | 20 |
| HCDR2 | 50-66 | WIKPQYGAVNEGGGERD | 21 |
| HCDR3 | 106-118 | DRSYGDSSWALDA | 22 |

N6 70-03 $V_L$

| $V_L$ | SEQ ID NO: 2 positions | A.A. Sequence | CDR SEQ ID NO |
|---|---|---|---|
| LCDR1 | 24-34 | QTSQGVGSDLH | 23 |
| LCDR2 | 50-56 | HTSSVED | 24 |
| LCDR3 | 89-93 | QVLQF | 25 |

TABLE 1-continued

Kabat CDRs of recombinant VRC01-class antibodies including a 70-03 insertion.

VRC01 70-03 $V_H$

| $V_H$ | SEQ ID NO: 17 positions | CDR protein sequence | CDR SEQ ID NO |
|---|---|---|---|
| HCDR1 | 31-35 | DCTLN | 26 |
| HCDR2 | 50-66 | WLKPRGGAVNYARPLQG | 27 |
| HCDR3 | 106-117 | GKNCDYNWDFEH | 28 |

VRC01 70-03 $V_L$

| $V_L$ | SEQ ID NO: 4 positions | A.A. Sequence | CDR SEQ ID NO |
|---|---|---|---|
| LCDR1 | 24-32 | RTSQYGSLA | 29 |
| LCDR2 | 48-54 | SGSTRAA | 30 |
| LCDR3 | 87-92 | QQYEF | 31 |

VRC07 70-03 $V_H$

| $V_H$ | SEQ ID NO: 18 positions | CDR protein sequence | CDR SEQ ID NO |
|---|---|---|---|
| HCDR1 | 31-35 | NCPIN | 32 |
| HCDR2 | 50-66 | WMKPRGGAVSYARQLQG | 33 |
| HCDR3 | 106-121 | GKYCTARDYYNWDFEH | 34 |

VRC07 70-03 $V_L$

| $V_L$ | SEQ ID NO: 4 positions | A.A. Sequence | CDR SEQ ID NO |
|---|---|---|---|
| LCDR1 | 24-32 | RTSQYGSLA | 29 |
| LCDR2 | 48-54 | SGSTRAA | 30 |
| LCDR3 | 87-92 | QQYEF | 31 |

VRC07-523 70-03 $V_H$

| $V_H$ | SEQ ID NO: 19 positions | CDR protein sequence | CDR SEQ ID NO |
|---|---|---|---|
| HCDR1 | 31-35 | NCPIN | 32 |
| HCDR2 | 50-66 | WMKPRHGAVSYARQLQG | 35 |
| HCDR3 | 106-121 | GKYCTARDYYNWDFEH | 34 |

VRC07-523 70-03 H54F $V_H$

| $V_H$ | SEQ ID NO: 102 positions | CDR protein sequence | CDR SEQ ID NO |
|---|---|---|---|
| HCDR1 | 31-35 | NCPIN | 32 |
| HCDR2 | 50-66 | WMKPRFGAVSYARQLQG | 121 |
| HCDR3 | 106-121 | GKYCTARDYYNWDFEH | 34 |

VRC07-523 70-03 H54W $V_H$

| $V_H$ | SEQ ID NO: 101 positions | CDR protein sequence | CDR SEQ ID NO |
|---|---|---|---|
| HCDR1 | 31-35 | NCPIN | 32 |
| HCDR2 | 50-66 | WMKPRWGAVSYARQLQG | 122 |
| HCDR3 | 106-121 | GKYCTARDYYNWDFEH | 34 |

TABLE 1-continued

Kabat CDRs of recombinant VRC01-class antibodies including a 70-03 insertion.

VRC07-523 70-03 V_L

| V_L | SEQ ID NO: 7 positions | A.A. Sequence | CDR SEQ ID NO |
|---|---|---|---|
| LCDR1 | 22-30 | RTSQYGSLA | 29 |
| LCDR2 | 46-52 | SGSTRAA | 30 |
| LCDR3 | 85-90 | QQYEF | 31 |

VRC07-523 R24D N72Q V_L

| V_L | SEQ ID NO: 104 positions | A.A. Sequence | CDR SEQ ID NO |
|---|---|---|---|
| LCDR1 | 22-30 | DTSQYGSLA | 123 |
| LCDR2 | 46-52 | SGSTRAA | 30 |
| LCDR3 | 85-90 | QQYEF | 31 |

VRC-PG04 V_H 70-03 V_H

| V_H | SEQ ID NO: 58 positions | CDR protein sequence | CDR SEQ ID NO |
|---|---|---|---|
| HCDR1 | 32-36 | TELIH | 59 |
| HCDR2 | 51-68 | WVKTVTGAVNEGSPDFRQ | 60 |
| HCDR3 | 108-121 | QKFYTGGQGWYFDL | 61 |

VRC-PG04 V_L

| V_L | SEQ ID NO: 57 positions | A.A. Sequence | CDR SEQ ID NO |
|---|---|---|---|
| LCDR1 | 24-32 | TAASYGHMT | 62 |
| LCDR2 | 48-54 | ATSKRAS | 63 |
| LCDR3 | 87-91 | QQLEF | 64 |

VRC01.23 V_H

| V_H | SEQ ID NO: 84 positions | CDR protein sequence | CDR SEQ ID NO |
|---|---|---|---|
| HCDR1 | 31-35 | DCTLN | 26 |
| HCDR2 | 50-66 | WLKPRWGAVNYARPLQG | 65 |
| HCDR3 | 106-117 | GKNCDYNWDFEH | 28 |

VRC01.23 V_L

| V_L | SEQ ID NO: 85 positions | A.A. Sequence | CDR SEQ ID NO |
|---|---|---|---|
| LCDR1 | 22-30 | RTSQYGSLA | 29 |
| LCDR2 | 46-52 | SGSTRAA | 30 |
| LCDR3 | 85-90 | QQYEF | 31 |

3BNC117 70-03 V_H

| V_H | SEQ ID NO: 86 positions | CDR protein sequence | CDR SEQ ID NO |
|---|---|---|---|
| HCDR1 | 31-35 | DYFIH | 66 |
| HCDR2 | 50-66 | WINPKTGQPNNPRQFQG | 67 |
| HCDR3 | 103-112 | QRSDYWDFDV | 68 |

TABLE 1-continued

Kabat CDRs of recombinant VRC01-class antibodies including a 70-03 insertion.

3BNC117 V_L

| V_L | SEQ ID NO: 9 positions | A.A. Sequence | CDR SEQ ID NO |
|---|---|---|---|
| LCDR1 | 24-30 | QANGYLN | 69 |
| LCDR2 | 46-52 | DGSKLER | 70 |
| LCDR3 | 85-89 | QVYEF | 71 |

N49P7 70-03 V_H

| V_H | SEQ ID NO: 87 positions | CDR protein sequence | CDR SEQ ID NO |
|---|---|---|---|
| HCDR1 | 30-34 | DYIIH | 72 |
| HCDR2 | 49-65 | WMNPMGGQVNIPWKFQG | 73 |
| HCDR3 | 105-123 | DRSNGSGKRFESSNWFLDL | 74 |

N49P7 70-03 G54W V_H

| V_H | SEQ ID NO: 105 positions | CDR protein sequence | CDR SEQ ID NO |
|---|---|---|---|
| HCDR1 | 30-34 | DYIIH | 72 |
| HCDR2 | 49-65 | WMNPMWGQVNIPWKFQG | 120 |
| HCDR3 | 105-123 | DRSNGSGKRFESSNWFLDL | 74 |

N49P7 V_L

| V_L | SEQ ID NO: 88 positions | A.A. Sequence | CDR SEQ ID NO |
|---|---|---|---|
| LCDR1 | 23-30 | TGTHNLVS | 75 |
| LCDR2 | 46-52 | DFNKRPS | 76 |
| LCDR3 | 85-89 | WAYEA | 77 |

VRC08 70-03 V_H

| V_H | SEQ ID NO: 89 positions | CDR protein sequence | CDR SEQ ID NO |
|---|---|---|---|
| HCDR1 | 31-35 | EILIN | 78 |
| HCDR2 | 50-66 | WMNPRGGGVNYARQFQG | 79 |
| HCDR3 | 106-123 | GRSCCGGRRHCNGADCFN | 80 |

VRC08 V_L

| V_L | SEQ ID NO: 90 positions | A.A. Sequence | CDR SEQ ID NO |
|---|---|---|---|
| LCDR1 | 25-36 | KTSQAITPRHLV | 81 |
| LCDR2 | 52-58 | GTSERAS | 82 |
| LCDR3 | 91-95 | QCLEA | 83 |

N6 70-03

In some embodiments, the antibody or antigen binding fragment is based on a N6 antibody or antigen binding fragment. For example, the monoclonal antibody or antigen binding fragment comprises a V_H and a V_L comprising a HCDR1, a HCDR2, a HCDR3, a LCDR1, a LCDR2, and a LCDR3 set forth as SEQ ID NOs: 20, 21, 22, 23, 24, and 25, respectively, and a modification of a HFR3 compared to the N6 HFR3, wherein the modification is a substitution of the amino acids of Kabat positions 72-76 of N6 HFR3 with the sequence set forth as QLSQDPDDPDWG (SEQ ID NO: 36). The antibody or antigen binding fragment specifically binds to HIV-1 Env and neutralizes HIV-1.

In some embodiments, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 20, 21, 22, 23, 24, and 25, respectively, and a modification of a heavy chain framework region (HFR) 3 compared to the N6 antibody, wherein the modification is a substitution of the amino acids of Kabat positions 72-76 of N6 HFR3 with the sequence set forth as QLSQDPDDPDWG (SEQ ID NO: 36), and wherein a HFR1, a HFR2, the HFR3, and a HFR4 of the monoclonal antibody comprise, in aggregate and not including the modification, no more than 10 (such as no more than 5, no more than 4, no more than 3, no more than 2, or no more than 1) amino acid substitutions compared to the corresponding N6 sequences, and a LFR1, a LFR2, a LFR3, and a LFR4 of the monoclonal antibody comprise, in aggregate and not including the modification, no more than 10 (such as no more than 5, no more than 4, no more than 3, no more than 2, or no more than 1) amino acid substitutions (such as conservative amino acid substitutions) compared to the corresponding N6 sequences. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 16 and 2, respectively, wherein the $V_H$ and the $V_L$ comprise the HCDR1, HCDR2, HCDR3, LCDR1, LCDR2, and LCDR3 set forth as SEQ ID NOs: 20, 21, 22, 23, 24, and 25, respectively, and the HFR3 modification of the substitution of Kabat positions 72-76 for QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 16 and 2, respectively, 16 and 97, respectively, or 16 and 98, respectively and specifically binds to HIV-1 Env and neutralizes HIV-1.

In some embodiments, the $V_H$ of the monoclonal antibody or antigen binding fragment based on the N6 antibody further comprises a phenylalanine, tyrosine, or tryptophan substitution (such as a phenylalanine or tryptophan substitution) at Kabat position 54 (such as a Y54F substitution or a Y54W substitution) and/or a serine substitution at Kabat position 98 (such as a Y98S substitution), and/or the N-terminus of the $V_L$ of the monoclonal antibody or antigen binding fragment based on the N6 antibody further comprises a two or three-amino acid deletion, such as a deletion of the YI or YIH residues at the N-terminus of the $V_L$. In some embodiments, the $V_H$ of the monoclonal antibody or antigen binding fragment based on the N6 antibody further comprises a Y54W substitution (Kabat numbering) and the N-terminus of the $V_L$ of the monoclonal antibody or antigen binding fragment based on the N6 antibody further comprises a deletion of the YIH residues at the N-terminus of the $V_L$.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 16 and 2, respectively, wherein the $V_H$ and the $V_L$ comprise the HCDR1, HCDR2, HCDR3, LCDR1, LCDR2, and LCDR3 set forth as SEQ ID NOs: 20, 21, 22, 23, 24, and 25, respectively, the HCDR2 (SEQ ID NO: 21) further comprises the Y54W or Y54H substitution, the HFR3 comprises the substitution of Kabat positions 72-76 for QLSQDPDDPDWG (SEQ ID NO: 36), and the N-terminus of the $V_L$ further comprises the two or three-amino acid deletion relative to the N6 $V_L$. The antibody or antigen binding fragment specifically binds to HIV-1 Env and neutralizes HIV-1.

In some embodiments, the $V_H$ and the $V_L$ of the monoclonal antibody or antigen binding fragment comprise the amino acid sequences set forth as SEQ ID NOs: 95 and 97, respectively, 95 and 98, respectively, 96 and 2, respectively, 96 and 97, respectively, or 96 and 98, respectively, and specifically binds to HIV-1 Env and neutralizes HIV-1.

VRC01 70-03

In some embodiments, the antibody or antigen binding fragment is based on a VRC01 antibody or antigen binding fragment. For example, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 26, 27, 28, 29, 30, and 31, respectively, and a modification of a HFR3 compared to the VRC01 HFR3, wherein the modification is a substitution of the amino acids of Kabat positions 72-76 of VRC01 HFR3 with the sequence set forth as QLSQDPDDPDWG (SEQ ID NO: 36). The antibody or antigen binding fragment specifically binds to HIV-1 Env and neutralizes HIV-1.

In some embodiments, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 26, 27, 28, 29, 30, and 31, respectively, and a modification of a heavy chain framework region (HFR) 3 compared to the VRC01 antibody, wherein the modification is a substitution of the amino acids of Kabat positions 72-76 of VRC01 HFR3 with the sequence set forth as QLSQDPDDPDWG (SEQ ID NO: 36), and wherein a HFR1, a HFR2, the HFR3, and a HFR4 of the monoclonal antibody comprise, in aggregate and not including the modification, no more than 10 (such as no more than 5, no more than 4, no more than 3, no more than 2, or no more than 1) amino acid substitutions compared to the corresponding VRC01 sequences, and a LFR1, a LFR2, a LFR3, and a LFR4 of the monoclonal antibody comprise, in aggregate and not including the modification, no more than 10 (such as no more than 5, no more than 4, no more than 3, no more than 2, or no more than 1) amino acid substitutions (such as conservative amino acid substitutions) compared to the corresponding VRC01 sequences. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 17 and 4, respectively, wherein the $V_H$ and the $V_L$ comprise the HCDR1, HCDR2, HCDR3, LCDR1, LCDR2, and LCDR3 set forth as SEQ ID NOs: 26, 27, 28, 29, 30, and 31, respectively, and the HFR3 modification of the substitution of Kabat positions 72-76 for QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 17 and 4, respectively, and specifically binds to HIV-1 Env and neutralizes HIV-1.

In some embodiments, the $V_H$ of the monoclonal antibody or antigen binding fragment based on the VRC01 antibody further comprises a phenylalanine, tyrosine, or tryptophan substitution (such as a phenylalanine or tryptophan substitution) at Kabat position 54, such as a G54F substitution or a G54W substitution, and/or the N-terminus of the $V_L$ of the monoclonal antibody or antigen binding fragment based on the VRC01 antibody further comprises a two or three-amino acid deletion, such as a deletion of the EI or EIV residues at the N-terminus of the $V_L$. In some embodiments, the $V_H$ of the monoclonal antibody or antigen binding fragment based on the VRC01 antibody further comprises a G54W substitution (Kabat numbering) and the N-terminus of the $V_L$ of the monoclonal antibody or antigen binding fragment based on the VRC01 antibody further comprises a deletion of the EIV residues at the N-terminus of the $V_L$.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 17 and 4, respectively, wherein the $V_H$ and the $V_L$ comprise the HCDR1, HCDR2, HCDR3, LCDR1, LCDR2, and LCDR3 set forth as SEQ ID NOs: 26, 27, 28, 29, 30, and 31, respectively, the HCDR2 (SEQ ID NO: 27) further comprises the G54W or G54H substitution, the HFR3 comprises the substitution of Kabat positions 72-76 for QLSQDPDDPDWG (SEQ ID NO: 36), and the N-terminus of the $V_L$ further comprises the two or three-amino acid deletion relative to the VRC01 $V_L$. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 84 and 85, respectively, wherein the $V_H$ and the $V_L$ comprise the HCDR1, HCDR2, HCDR3, LCDR1, LCDR2, and LCDR3 set forth as SEQ ID NOs: 26, 65, 28, 28, 30, and 31, respectively, the HFR3 comprises the substitution of Kabat positions 72-76 for QLSQDPDDPDWG (SEQ ID NO: 36), and the N-terminus of the $V_L$ further comprises the three-amino acid deletion relative to the VRC01 $V_L$. The antibody or antigen binding fragment specifically binds to HIV-1 Env and neutralizes HIV-1.

In some embodiments, the parent VRC01-class antibody is VRC01, and the light chain variable region comprises a R24D substitution, a N72Q substitution, or a R24D substitution and a N72Q substitution, according to Kabat positioning.

In some embodiments, the $V_H$ and the $V_L$ of the monoclonal antibody or antigen binding fragment comprise the amino acid sequences set forth as SEQ ID NOs: 84 and 85, respectively, and specifically binds to HIV-1 Env and neutralizes HIV-1.

VRC07 70-03

In some embodiments, the antibody or antigen binding fragment is based on a VRC07 antibody or antigen binding fragment. For example, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 32, 33, 34, 29, 30, and 31, respectively, and a modification of a HFR3 compared to the VRC07 HFR3, wherein the modification is a substitution of the amino acids of Kabat positions 72-76 of VRC07 HFR3 with the sequence set forth as QLSQDPDDPDWG (SEQ ID NO: 36). The antibody or antigen binding fragment specifically binds to HIV-1 Env and neutralizes HIV-1.

In some embodiments, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 32, 33, 34, 29, 30, and 31, respectively, and a modification of a heavy chain framework region (HFR) 3 compared to the VRC07 antibody, wherein the modification is a substitution of the amino acids of Kabat positions 72-76 of VRC07 HFR3 with the sequence set forth as QLSQDPDDPDWG (SEQ ID NO: 36), and wherein a HFR1, a HFR2, the HFR3, and a HFR4 of the monoclonal antibody comprise, in aggregate and not including the modification, no more than 10 (such as no more than 5, no more than 4, no more than 3, no more than 2, or no more than 1) amino acid substitutions compared to the corresponding VRC07 sequences, and a LFR1, a LFR2, a LFR3, and a LFR4 of the monoclonal antibody comprise, in aggregate and not including the modification, no more than 10 (such as no more than 5, no more than 4, no more than 3, no more than 2, or no more than 1) amino acid substitutions (such as conservative amino acid substitutions) compared to the corresponding VRC07 sequences. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 18 and 4, respectively, wherein the $V_H$ and the $V_L$ comprise the HCDR1, HCDR2, HCDR3, LCDR1, LCDR2, and LCDR3 set forth as SEQ ID NOs: 32, 33, 34, 29, 30, and 31, respectively, and the HFR3 modification of the substitution of Kabat positions 72-76 for QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 18 and 4, respectively, and specifically binds to HIV-1 Env and neutralizes HIV-1.

In some embodiments, the $V_H$ of the monoclonal antibody or antigen binding fragment based on the VRC07 antibody further comprises a phenylalanine, tyrosine, or tryptophan substitution (such as a phenylalanine or tryptophan substitution) at Kabat position 54, such as a G54F substitution or a G54W substitution, and/or the N-terminus of the $V_L$ of the monoclonal antibody or antigen binding fragment based on the VRC07 antibody further comprises a two or three-amino acid deletion, such as a deletion of the EI or EIV residues at the N-terminus of the $V_L$. In some embodiments, the $V_H$ of the monoclonal antibody or antigen binding fragment based on the VRC07 antibody further comprises a G54W substitution (Kabat numbering) and the N-terminus of the $V_L$ of the monoclonal antibody or antigen binding fragment based on the VRC07 antibody further comprises a deletion of the EIV residues at the N-terminus of the $V_L$.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 18 and 4, respectively, wherein the $V_H$ and the $V_L$ comprise the HCDR1, HCDR2, HCDR3, LCDR1, LCDR2, and LCDR3 set forth as SEQ ID NOs: 32, 33, 34, 29, 30, and 31, respectively, the HCDR2 (SEQ ID NO: 33) further comprises the G54W or G54H substitution, the HFR3 comprises the substitution of Kabat positions 72-76 for QLSQDPDDPDWG (SEQ ID NO: 36), and the N-terminus of the $V_L$ further comprises the two or three amino acid deletion relative to the VRC07 $V_L$. The antibody or antigen binding fragment specifically binds to HIV-1 Env and neutralizes HIV-1.

VRC07-523 70-03

In some embodiments, the antibody or antigen binding fragment is based on a VRC07-523 antibody or antigen binding fragment. For example, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 32, 35, 34, 29, 30, and 31, respectively, and a modification of a HFR3 compared to the VRC07-523 HFR3, wherein the modification is a substitution of the amino acids of Kabat positions 72-76 of VRC07-523 HFR3 with the sequence set forth as QLSQDPDDPDWG (SEQ ID NO: 36). The antibody or antigen binding fragment specifically binds to HIV-1 Env and neutralizes HIV-1.

In some embodiments, the monoclonal antibody or antigen binding fragment comprises a $V_H$ and a $V_L$ comprising a HCDR1, a HCDR2, a HCDR3, a LCDR1, a LCDR2, a LCDR3 set forth as SEQ ID NOs: 32, 35, 34, 29, 30, and 31, respectively, and a modification of a heavy chain framework region (HFR) 3 compared to the VRC07-523 antibody, wherein the modification is a substitution of the amino acids of Kabat positions 72-76 of VRC07-523 HFR3 with the sequence set forth as QLSQDPDDPDWG (SEQ ID NO: 36), and wherein a HFR1, a HFR2, the HFR3, and a HFR4 of the monoclonal antibody comprise, in aggregate and not including the modification, no more than 10 (such as no more than 5, no more than 4, no more than 3, no more than 2, or no more than 1) amino acid substitutions compared to the corresponding VRC07-523 sequences, and a LFR1, a LFR2, a LFR3, and a LFR4 of the monoclonal antibody comprise, in aggregate and not including the modification, no more than 10 (such as no more than 5, no more than 4, no more than 3, no more than 2, or no more than 1) amino acid substitutions (such as conservative amino acid substitutions) compared to the corresponding VRC07-523 sequences. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 18 and 4, respectively, wherein the $V_H$ and the $V_L$ comprise the HCDR1, HCDR2, HCDR3, LCDR1, LCDR2, and LCDR3 set forth as SEQ ID NOs: 32, 35, 34, 29, 30, and 31, respectively, and the HFR3 modification of the substitution of Kabat positions 72-76 for QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 18 and 4, respectively, and specifically binds to HIV-1 Env and neutralizes HIV-1.

In some embodiments, the $V_H$ of the monoclonal antibody or antigen binding fragment based on the VRC07-523 antibody further comprises a phenylalanine, tyrosine, or tryptophan substitution (such as a phenylalanine or tryptophan substitution) at Kabat position 54, such as a H54F substitution or a H54W substitution, and/or the N-terminus of the $V_L$ of the monoclonal antibody or antigen binding fragment based on the VRC07-523 antibody further comprises a one amino acid deletion, such as a deletion of the S residue at the N-terminus of the $V_L$. In some embodiments, the $V_H$ of the monoclonal antibody or antigen binding fragment based on the VRC07-523 antibody further comprises a H54W substitution (Kabat numbering) and the N-terminus of the $V_L$ of the monoclonal antibody or antigen binding fragment based on the VRC07-523 antibody further comprises a deletion of the S residue at the N-terminus of the $V_L$.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 19 and 7, respectively, wherein the $V_H$ and the $V_L$ comprise the HCDR1, HCDR2, HCDR3, LCDR1, LCDR2, and LCDR3 set forth as SEQ ID NOs: 32, 35, 34, 29, 30, and 31, respectively, with the HCDR2 (SEQ ID NO: 35) further comprising the H54W or H54F substitution, the HFR3 comprises the substitution of Kabat positions 72-76 for QLSQDPDDPDWG (SEQ ID NO: 36), and the N-terminus of the $V_L$ further comprises the one amino acid deletion relative to the VRC07-523 $V_L$. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 102 and 103, respectively, wherein the $V_H$ and the $V_L$ comprise the HCDR1, HCDR2, HCDR3, LCDR1, LCDR2, and LCDR3 set forth as SEQ ID NOs: 32, 121, 34, 29, 30, 31, and the sequence of HFR3 Kabat positions 72-76 is QLSQDPDDPDWG (SEQ ID NO: 36). The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 102 and 104, respectively, wherein the $V_H$ and the $V_L$ comprise the HCDR1, HCDR2, HCDR3, LCDR1, LCDR2, and LCDR3 set forth as SEQ ID NOs: 32, 121, 34, 123, 30, 31, and the sequence of HFR3 Kabat positions 72-76 is QLSQDPDDPDWG (SEQ ID NO: 36). The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 101 and 103, respectively, wherein the $V_H$ and the $V_L$ comprise the HCDR1, HCDR2, HCDR3, LCDR1, LCDR2, and LCDR3 set forth as SEQ ID NOs: 32, 122, 34, 29, 30, 31, respectively, and the sequence of HFR3 Kabat positions 72-76 is QLSQDPDDPDWG (SEQ ID NO: 36). The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 101 and 104, respectively, wherein the $V_H$ and the $V_L$ comprise the HCDR1, HCDR2, HCDR3, LCDR1, LCDR2, and LCDR3 set forth as SEQ ID NOs: 32, 122, 34, 123, 30, 31, respectively, and the sequence of HFR3 Kabat positions 72-76 is QLSQDPDDPDWG (SEQ ID NO: 36). The antibody or antigen binding fragment specifically binds to HIV-1 Env and neutralizes HIV-1.

In some embodiments, the parent VRC01-class antibody is VRC07-523, and the light chain variable region comprises a R24D substitution, a N72Q substitution, or a R24D substitution and a N72Q substitution, according to Kabat positioning.

In some embodiments, the $V_H$ and the $V_L$ of the monoclonal antibody or antigen binding fragment comprise the amino acid sequences set forth as SEQ ID NOs: 101 and 7, respectively, 101 and 103, respectively, 101 and 104, respectively, 102 and 7, respectively, 102 and 103, respectively, or 102 and 104, respectively, and specifically binds to HIV-1 Env and neutralizes HIV-1.

VRC-PG04 70-03

In some embodiments, the antibody or antigen binding fragment is based on a VRC-PG04 antibody or antigen binding fragment. For example, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 59, 60, 61, 62, 63, and 64, respectively, and a modification of a HFR3 compared to the VRC-PG04 HFR3, wherein the modification is a substitution of the amino acids of Kabat positions 72-76 of VRC-PG04 HFR3 with the sequence set forth as QLSQDPDDPDWG (SEQ ID NO: 36). The antibody or antigen binding fragment specifically binds to HIV-1 Env and neutralizes HIV-1.

In some embodiments, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 59, 60, 61, 62, 63, and 64, respectively, and a modification of a heavy chain framework region (HFR) 3 compared to the VRC-PG04 antibody, wherein the modification is a substitution of the amino acids of Kabat positions 72-76 of VRC-PG04 HFR3 with the sequence set forth as QLSQDPDDPDWG (SEQ ID NO: 36), and wherein a HFR1, a HFR2, the HFR3, and a HFR4 of the monoclonal antibody comprise, in aggregate and not including the modification, no more than 10 (such as no more than 5, no more than 4, no more than 3, no more than 2, or no more than 1) amino acid substitutions compared to the corresponding VRC-PG04 sequences, and a LFR1, a LFR2, a LFR3, and a LFR4 of the monoclonal antibody comprise, in aggregate and not including the modification, no more than 10 (such as no more than 5, no more than 4, no more than 3, no more than 2, or no more than 1) amino acid substitutions (such as conservative amino acid substitutions) compared to the corresponding VRC-PG04 sequences. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 58 and 57, respectively, wherein the $V_H$ and the $V_L$ comprise the HCDR1, HCDR2, HCDR3, LCDR1, LCDR2, and LCDR3 set forth as SEQ ID NOs: 59, 60, 61, 62, 63, and 64, respectively, and the HFR3 modification of the substitution of Kabat positions 72-76 for QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 58 and 57, respectively, and specifically binds to HIV-1 Env and neutralizes HIV-1.

In some embodiments, the $V_H$ of the monoclonal antibody or antigen binding fragment based on the VRC-PG04 antibody further comprises a phenylalanine, tyrosine, or tryptophan substitution (such as a phenylalanine or tryptophan substitution) at Kabat position 54, such as a T54F substitution or a T54W substitution, and/or the N-terminus of the $V_L$ of the monoclonal antibody or antigen binding fragment based on the VRC-PG04 antibody further comprises a two or three-amino acid deletion, such as a deletion of the EI or EIV residues at the N-terminus of the $V_L$. In some embodiments, the $V_H$ of the monoclonal antibody or antigen binding fragment based on the VRC-PG04 antibody further comprises a T54W substitution (Kabat numbering) and the N-terminus of the $V_L$ of the monoclonal antibody or antigen binding fragment based on the VRC-PG04 antibody further comprises a deletion of the EIV residues at the N-terminus of the $V_L$.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 58 and 57, respectively, wherein the $V_H$ and the $V_L$ comprise the HCDR1, HCDR2, HCDR3, LCDR1, LCDR2, and LCDR3 set forth as SEQ ID NOs: 59, 60, 61, 62, 63, and 64, respectively, the HCDR2 (SEQ ID NO: 60) further comprises the T54W or T54H substitution, the HFR3 comprises the substitution of Kabat positions 72-76 for QLSQDPDDPDWG (SEQ ID NO: 36), and the N-terminus of the $V_L$ further comprises the two or three-amino acid deletion relative to the VRC-PG04 $V_L$. The antibody or antigen binding fragment specifically binds to HIV-1 Env and neutralizes HIV-1.

N49P7 70-03

In some embodiments, the antibody or antigen binding fragment is based on a N49P7 antibody or antigen binding fragment. For example, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 72, 73, 74, 75, 76, and 77, respectively, and a modification of a HFR3 compared to the N49P7 HFR3, wherein the modification is a substitution of the amino acids of Kabat positions 72-76 of N49P7 HFR3 with the sequence set forth as QLSQDPDDPDWG (SEQ ID NO: 36). The antibody or antigen binding fragment specifically binds to HIV-1 Env and neutralizes HIV-1.

In some embodiments, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 72, 73, 74, 75, 76, and 77, respectively, and a modification of a heavy chain framework region (HFR) 3 compared to the N49P7 antibody, wherein the modification is a substitution of the amino acids of Kabat positions 72-76 of N49P7 HFR3 with the sequence set forth as QLSQDPDDPDWG (SEQ ID NO: 36), and wherein a HFR1, a HFR2, the HFR3, and a HFR4 of the monoclonal antibody comprise, in aggregate and not including the modification, no more than 10 (such as no more than 5, no more than 4, no more than 3, no more than 2, or no more than 1) amino acid substitutions compared to the corresponding N49P7 sequences, and a LFR1, a LFR2, a LFR3, and a LFR4 of the monoclonal antibody comprise, in aggregate and not including the modification, no more than 10 (such as no more than 5, no more than 4, no more than 3, no more than 2, or no more than 1) amino acid substitutions (such as conservative amino acid substitutions) compared to the corresponding N49P7 sequences. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 87 and 88, respectively, wherein the $V_H$ and the $V_L$ comprise the HCDR1, HCDR2, HCDR3, LCDR1, LCDR2, and LCDR3 set forth as SEQ ID NOs: 72, 73, 74, 75, 76, and 77, respectively, and the HFR3 modification of the substitution of Kabat positions 72-76 for QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 87 and 88, respectively, and specifically binds to HIV-1 Env and neutralizes HIV-1.

In some embodiments, the $V_H$ of the monoclonal antibody or antigen binding fragment based on the N49P7 antibody further comprises a phenylalanine, tyrosine, or tryptophan substitution (such as a phenylalanine or tryptophan substitution) at Kabat position 54, such as a G54F substitution or a G54W substitution, and/or the N-terminus of the $V_L$ of the monoclonal antibody or antigen binding fragment based on the N49P7 antibody further comprises a two or three amino acid deletion, such as a deletion of the QS or QSA residues at the N-terminus of the $V_L$. In some embodiments, the $V_H$ of the monoclonal antibody or antigen binding fragment based on the N49P7 antibody further comprises a G54W substitution (Kabat numbering) and the N-terminus of the $V_L$ of the monoclonal antibody or antigen binding fragment based on the N49P7 antibody further comprises a deletion of the QSA residues at the N-terminus of the $V_L$.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 87 and 88, respectively, wherein the $V_H$ and the $V_L$ comprise the HCDR1, HCDR2, HCDR3, LCDR1, LCDR2, and LCDR3 set forth as SEQ ID NOs: 72, 73, 74, 75, 76, and 77, respectively, with the HCDR2 (SEQ ID NO: 73) further comprising the G54W or G54H substitution, the HFR3 comprising the substitution of Kabat positions 72-76 for QLSQDPDDPDWG (SEQ ID NO: 36), and the N-terminus of the $V_L$ further comprises the two or three-amino acid deletion relative to the N49P7 $V_L$. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 105 and 106, respectively, wherein the $V_H$ and the $V_L$ comprise the HCDR1, HCDR2, HCDR3, LCDR1, LCDR2, and LCDR3 set forth as SEQ ID NOs: 72, 120, 74, 75, 76, 77, and the sequence of HFR3 Kabat positions 72-76 is QLSQDPDDPDWG (SEQ ID NO: 36). The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 105 and 107, respectively, wherein the $V_H$ and the $V_L$ comprise the HCDR1, HCDR2, HCDR3, LCDR1, LCDR2, and LCDR3 set forth as SEQ ID NOs: 72, 120, 74, 75, 76, 77, and the sequence of HFR3 Kabat positions 72-76 is QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 105 and 88, respectively, 105 and 106, respectively, or 105 and 107, respectively, and specifically binds to HIV-1 Env and neutralizes HIV-1.

VRC08 70-03

In some embodiments, the antibody or antigen binding fragment is based on a VRC08 antibody or antigen binding fragment. For example, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 78, 79, 80, 81, 82, and 83, respectively, and a modification of a HFR3 compared to the VRC08 HFR3, wherein the modification is a substitution of the amino acids of Kabat positions 72-76 of VRC08 HFR3 with the sequence set forth as QLSQDPDDPDWG (SEQ ID NO: 36). The antibody or antigen binding fragment specifically binds to HIV-1 Env and neutralizes HIV-1.

In some embodiments, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 78, 79, 80, 81, 82, and 83, respectively, and a modification of a heavy chain framework region (HFR) 3 compared to the VRC08 antibody, wherein the modification is a substitution of the amino acids of Kabat positions 72-76 of VRC08 HFR3 with the sequence set forth as QLSQDPDDPDWG (SEQ ID NO: 36), and wherein a HFR1, a HFR2, the HFR3, and a HFR4 of the monoclonal antibody comprise, in aggregate and not including the modification, no more than 10 (such as no more than 5, no more than 4, no more than 3, no more than 2, or no more than 1) amino acid substitutions compared to the corresponding VRC08 sequences, and a LFR1, a LFR2, a LFR3, and a LFR4 of the monoclonal antibody comprise, in aggregate and not including the modification, no more than 10 (such as no more than 5, no more than 4, no more than 3, no more than 2, or no more than 1) amino acid substitutions (such as conservative amino acid substitutions) compared to the corresponding VRC08 sequences. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 89 and 90, respectively, wherein the $V_H$ and the $V_L$ comprise the HCDR1, HCDR2, HCDR3, LCDR1, LCDR2, and LCDR3 set forth as SEQ ID NOs: 78, 79, 80, 81, 82, and 83, respectively, and the HFR3 modification of the substitution of Kabat positions 72-76 for QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 89 and 90, respectively, and specifically binds to HIV-1 Env and neutralizes HIV-1.

In some embodiments, the $V_H$ of the monoclonal antibody or antigen binding fragment based on the VRC08 antibody further comprises a phenylalanine, tyrosine, or tryptophan substitution (such as a phenylalanine or tryptophan substitution) at Kabat position 54, such as a G54F substitution or a G54W substitution, and/or the N-terminus of the $V_L$ of the monoclonal antibody or antigen binding fragment based on the VRC08 antibody further comprises a two or three-amino acid deletion, such as a deletion of the YI or YIG residues at the N-terminus of the $V_L$. In some embodiments, the $V_H$ of the monoclonal antibody or antigen binding fragment based on the VRC08 antibody further comprises a G54W substitution (Kabat numbering) and the N-terminus of the $V_L$ of the monoclonal antibody or antigen binding fragment based on the VRC08 antibody further comprises a deletion of the YIG residues at the N-terminus of the $V_L$.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 89 and 90, respectively, wherein the $V_H$ and the $V_L$ comprise the HCDR1, HCDR2, HCDR3, LCDR1, LCDR2, and LCDR3 set forth as SEQ ID NOs: 78, 79, 80, 81, 82, and 83, respectively, the HCDR2 (SEQ ID NO: 79) further comprises the G54W or G54H substitution, the HFR3 comprises the substitution of Kabat positions 72-76 for QLSQDPDDPDWG (SEQ ID NO: 36) and the N-terminus of the $V_L$ further comprises the two or three amino acid deletion relative to the VRC08 $V_L$. The antibody or antigen binding fragment specifically binds to HIV-1 Env and neutralizes HIV-1.

In some embodiments, the $V_H$ and the $V_L$ of the monoclonal antibody or antigen binding fragment comprise the amino acid sequences set forth as SEQ ID NOs: 108 and 90, respectively, 108 and 109, respectively, or 108 and 110, respectively, and specifically binds to HIV-1 Env and neutralizes HIV-1.

3BNC117

In some embodiments, the antibody or antigen binding fragment is based on a 3BNC117 antibody or antigen binding fragment. For example, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 66, 67, 68, 69, 70, and 71, respectively, and a modification of a HFR3 compared to the 3BNC117 HFR3, wherein the modification is a substitution of the amino acids of Kabat positions 72-76 of 3BNC117 HFR3 with the sequence set forth as QLSQDPDDPDWG (SEQ ID NO: 36). The antibody or antigen binding fragment specifically binds to HIV-1 Env and neutralizes HIV-1.

In some embodiments, the monoclonal antibody or antigen binding fragment comprises a $V_H$ and a $V_L$ comprising a HCDR1, a HCDR2, a HCDR3, a LCDR1, a LCDR2, and a LCDR3 set forth as SEQ ID NOs: 66, 67, 68, 69, 70, and 71, respectively, and a modification of a heavy chain framework region (HFR) 3 compared to the 3BNC117 antibody, wherein the modification is a substitution of the amino acids of Kabat positions 72-76 of 3BNC117 HFR3 with the sequence set forth as QLSQDPDDPDWG (SEQ ID NO: 36), and wherein a HFR1, a HFR2, the HFR3, and a HFR4 of the monoclonal antibody comprise, in aggregate and not including the modification, no more than 10 (such as no more than 5, no more than 4, no more than 3, no more than 2, or no more than 1) amino acid substitutions compared to the corresponding VRC08 sequences, and a LFR1, a LFR2, a LFR3, and a LFR4 of the monoclonal antibody comprise, in aggregate and not including the modification, no more than 10 (such as no more than 5, no more than 4, no more than 3, no more than 2, or no more than 1) amino acid substitutions (such as conservative amino acid substitutions) compared to the corresponding 3BNC117 sequences. The antibody or antigen binding fragment specifically binds to HIV-1 Env and neutralizes HIV-1.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 86 and 9, respectively, wherein the $V_H$ and the $V_L$ comprise the HCDR1, HCDR2, HCDR3, LCDR1, LCDR2, and LCDR3 set forth as SEQ ID NOs: 66, 67, 68, 69, 70, and 71, respectively, and the HFR3 modification of the substitution of Kabat positions 72-76 for QLSQDPDDPDWG (SEQ ID NO: 36). The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 86 and 9, respectively, and specifically binds to HIV-1 Env and neutralizes HIV-1.

In some embodiments, the $V_H$ of the monoclonal antibody or antigen binding fragment based on the 3BNC117 antibody further comprises a phenylalanine, tyrosine, or tryptophan substitution (such as a phenylalanine or tryptophan substitution) at Kabat position 54, such as a T54F substitution or a T54W substitution, and/or the N-terminus of the $V_L$ of the monoclonal antibody or antigen binding fragment based on the 3BNC117 antibody further comprises a two or three-amino acid deletion, such as a deletion of the DI or DIQ residues at the N-terminus of the $V_L$. In some embodiments, the $V_H$ of the monoclonal antibody or antigen binding fragment based on the 3BNC117 antibody further comprises a T54W substitution (Kabat numbering) and the N-terminus of the $V_L$ of the monoclonal antibody or antigen binding fragment based on the 3BNC117 antibody further comprises a deletion of the DIQ residues at the N-terminus of the $V_L$.

In some embodiments, the $V_H$ and the $V_L$ of the monoclonal antibody or antigen binding fragment comprise amino acid sequences that are at least 90% (such as at least 95%, at least 98%, or at least 99%) identical to the amino acid sequences set forth as SEQ ID NOs: 86 and 9, respectively, wherein the $V_H$ and the $V_L$ comprise the HCDR1, HCDR2, HCDR3, LCDR1, LCDR2, and LCDR3 set forth as SEQ ID NOs: 66, 67, 68, 69, 70, and 71, respectively, the HCDR2 (SEQ ID NO: 67) further comprises the T54W or T54H substitution, the HFR3 comprises the substitution of Kabat positions 72-76 for QLSQDPDDPDWG (SEQ ID NO: 36), and the N-terminus of the $V_L$ further comprises the two or three-amino acid deletion relative to the 3BNC117 $V_L$. The antibody or antigen binding fragment specifically binds to HIV-1 Env and neutralizes HIV-1.

In further embodiments, the $V_H$ and the $V_L$ of the monoclonal antibody or antigen binding fragment comprise the amino acid sequences set forth as SEQ ID NOs: 111 and 9, respectively, 111 and 113, respectively, 111 and 114, respectively, 112 and 9, respectively, 112 and 113, respectively, 112 and 114, respectively, 115 and 9, respectively, 115 and 113, respectively, or 115 and 114, respectively, and specifically binds to HIV-1 Env and neutralizes HIV-1.

1. Additional Description of Antibodies and Antigen Binding Fragments

The antibody or antigen binding fragment can be a human antibody or fragment thereof. Chimeric antibodies are also provided. The antibody or antigen binding fragment can include any suitable framework region, such as (but not limited to) a human framework region. Human framework regions, and mutations that can be made in human antibody framework regions, are known in the art (see, for example, in U.S. Pat. No. 5,585,089, which is incorporated herein by reference). Alternatively, a heterologous framework region, such as, but not limited to a mouse or monkey framework region, can be included in the heavy or light chain of the antibodies. (See, for example, Jones et al., *Nature*, 321 (6069):522-525, 1986; Riechmann et al., *Nature*, 332(6162): 323-327, 1988; Verhoeyen et al., *Science* 239(4847):1534-1536, 1988; Carter et al., *Proc. Natl. Acad. Sci. U.S.A.* 89(10):4285-4289, 1992; Sandhu, *Crit. Rev. Biotechnol.* 12(5-6):437-462, 1992; and Singer et al., *J. Immunol.* 150 (7):2844-2857, 1993.)

The antibody can be of any isotype. The antibody can be, for example, an IgM or an IgG antibody, such as IgG$_1$, IgG$_2$, IgG$_3$, or IgG$_4$. The class of an antibody that specifically binds HIV-1 Env can be switched with another. In one aspect, a nucleic acid molecule encoding V$_L$ or V$_H$ is isolated using methods well-known in the art, such that it does not include any nucleic acid sequences encoding the constant region of the light or heavy chain, respectively. A nucleic acid molecule encoding V$_L$ or V$_H$ is then operatively linked to a nucleic acid sequence encoding a C$_L$ or C$_H$ from a different class of immunoglobulin molecule. This can be achieved using a vector or nucleic acid molecule that comprises a C$_L$ or C$_H$ chain, as known in the art. For example, an antibody that specifically binds HIV-1 Env, that was originally IgG may be class switched to an IgM. Class switching can be used to convert one IgG subclass to another, such as from IgG$_1$ to IgG$_2$, IgG$_3$, or IgG$_4$.

In some examples, the disclosed antibodies are oligomers of antibodies, such as dimers, trimers, tetramers, pentamers, hexamers, septamers, octomers and so on.

The antibody or antigen binding fragment can be derivatized or linked to another molecule (such as another peptide or protein). In general, the antibody or antigen binding fragment is derivatized such that the binding to HIV-1 Env is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

(a) Binding Affinity

In several embodiments, the antibody or antigen binding fragment specifically binds HIV-1 Env with an affinity (e.g., measured by K$_D$) of no more than 1.0×10$^{-8}$M, no more than 5.0×10$^{-8}$M, no more than 1.0×10$^{-9}$M, no more than 5.0×10$^{-9}$M, no more than 1.0×10$^{-10}$ M, no more than 5.0×10$^{-10}$ M, or no more than 1.0×10$^{-11}$M. K$_D$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293(4):865-881, 1999). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc™ Catalog #269620), 100 μM or 26 μM [$^{125}$I]-antigen are mixed with serial dilutions of a Fab of interest (e.g., consistent with assessment of the anti-VEGF antibody, Fab-12, in Presta et al., *Cancer Res.* 57(20):4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MicroScint™-20; PerkinEmler) is added, and the plates are counted on a TOPCOUNT™ gamma counter (PerkinEmler) for ten minutes. Concentrations of each Fab that give less than or equal to 20% of maximal binding are chosen for use in competitive binding assays.

(b) Neutralization

In some embodiments, the antibody or antigen binding fragment can also be distinguished by neutralization breadth. In some embodiments, the antibody or antigen binding fragment neutralizes at least 80% (such as at least 85%, least 90%, or at least 95%) of the HIV-1 isolates included in a standardized panel of HIV-1 pseudoviruses (such as the panel shown in FIG. 3B) with an IC$_{50}$ of less than 50 μg/ml. Exemplary pseudovirus neutralization assays and panels of HIV-1 pseudovirus are described for example, in Li et al., J Virol 79, 10108-10125, 2005, incorporated by reference herein. The person of ordinary skill in the art is familiar with methods of measuring neutralization breadth and potency, for example such methods include the single-round HIV-1 Env-pseudoviruses infection of TZM-bl cells (see, e.g., Li et al., *J Virol* 79, 10108-10125, 2005, incorporated by reference herein; see also, PCT Pub. No. WO2011/038290, incorporated by reference herein).

An additional method to assay for neutralization activity includes a single-cycle infection assay as described in Martin et al. (2003) *Nature Biotechnology* 21:71-76. In this assay, the level of viral activity is measured via a selectable marker whose activity is reflective of the amount of viable virus in the sample, and the IC$_{50}$ is determined. In other assays, acute infection can be monitored in the PM1 cell line or in primary cells (normal PBMC). In this assay, the level of viral activity can be monitored by determining the p24 concentrations using ELISA. See, for example, Martin et al. (2003) *Nature Biotechnology* 21:71-76.

(c) Multispecific Antibodies

In some embodiments, the antibody or antigen binding fragment is included on a multispecific antibody, such as a bi-specific antibody or a tri-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available, for example, from Thermo Fisher Scientific, Waltham, Mass., and MilliporeSigma Corporation, St. Louis, Mo.

In some embodiments, a trispecific antibody is provided that includes at least one antibody or antigen binding fragment as disclosed herein (e.g., comprising a modified heavy chain variable region containing the 70-03 insertion as described herein). For example, the tri-specific antibody contains an antibody or antigen binding fragment including heavy and light chain variable regions set forth as SEQ ID NOs: 16 and 2, respectively (N6 70-03) or 84 and 85, respectively (VRC01.23). In some embodiments, the trispecific antibody comprising the antigen binding fragment as disclosed herein contains three different antigen binding fragments that target HIV-1 Env, such as trispecific antibody format described in Xu et al., "Trispecific broadly neutralizing HIV antibodies mediate potent SHIV protection in macaques," Science, 358(6359): 85-90, 2017, which is incorporated by reference herein in its entirety.

In some embodiments, the antibody or antigen binding fragment is included on a bispecific antibody that that specifically binds to HIV-1 Env and further specifically binds to CD3. Examples of CD3 binding domains that can be included on the bispecific antibody or antigen binding fragment are known and include those disclosed in PCT Pub. No. WO2013/163427, which is incorporated by reference herein in its entirety.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack et al., *J. Immunol.*, 158(8):3965-3970, 1997; Mack et al., *Proc. Natl. Acad. Sci. U.S.A.*, 92(15): 7021-7025, 1995; Kufer et al., *Cancer Immunol. Immunother.*, 45(3-4):193-197, 1997; Löffler et al., *Blood*, 95(6): 2098-2103, 2000; and Brühl et al., *J. Immunol.*, 166(4): 2420-2426, 2001. Production of bispecific Fab-scFv ("bibody") molecules are described, for example, in Schoonjans et al. (*J. Immunol.*, 165(12):7050-7057, 2000) and Willems et al. (*J. Chromatogr. B Analyt. Technol. Biomed Life Sci.* 786(1-2):161-176, 2003). For bibodies, a scFv molecule can be fused to one of the VL-CL (L) or VH-CH1 chains, e.g., to produce a bibody one scFv is fused to the C-term of a Fab chain.

(d) Fragments

Antigen binding fragments are encompassed by the present disclosure, such as Fab, F(ab')$_2$, and Fv which include a heavy chain and V$_L$ and specifically bind HIV-1 Env. These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the V$_H$ and V$_L$ expressed as two chains; and (5) Single chain antibody (such as scFv), defined as a genetically engineered molecule containing the V$_H$ and the V$_L$ linked by a suitable polypeptide linker as a genetically fused single chain molecule (see, e.g., Ahmad et al., *Clin. Dev. Immunol.*, 2012, doi:10.1155/2012/980250; Marbry and Snavely, *IDrugs*, 13(8):543-549, 2010). The intramolecular orientation of the V$_H$-domain and the V$_L$-domain in a scFv, is not decisive for the provided antibodies (e.g., for the provided multispecific antibodies). Thus, scFvs with both possible arrangements (V$_H$-domain-linker domain-V$_L$-domain; V$_L$-domain-linker domain-V$_H$-domain) may be used.

(6) A dimer of a single chain antibody (scFV$_2$), defined as a dimer of a scFV. This has also been termed a "miniantibody."

Methods of making these fragments are known in the art (see for example, Greenfield (Ed.), *Antibodies: A Laboratory Manual*, 2$^{nd}$ ed. New York: Cold Spring Harbor Laboratory Press, 2014).

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. In some examples, the antibody heavy chain can include an engineered protease cleave site (such as an HRV3C protease cleavage site) in place of or in addition to the typical papain cleavage site to facilitate cleavage by proteases other than papain.

(e) Additional Description of Antibody Variants

In some embodiments, amino acid sequence variants of the antibodies provided herein are provided. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. In a non-limiting example, sites of interest for substitutional mutagenesis include the framework regions. Amino acid substitutions may be introduced into an antibody of interest and the products screened for a desired activity, e.g., retained/improved antigen binding, increased HIV-1 neutralization breadth or potency, decreased immunogenicity, or improved antibody dependent cellular cytotoxicity (ADCC) or complement dependent cytotoxicity (CDC).

The variants typically retain amino acid residues necessary for correct folding and stabilizing between the $V_H$ and the $V_L$ regions, and will retain the charge characteristics of the residues in order to preserve the low pI and low toxicity of the molecules Amino acid substitutions can be made in the $V_H$ and the $V_L$ regions to increase yield.

In some embodiments, the $V_H$ and $V_L$ of the antibody each comprise up to 10 (such as up to 1, up to 2, up to 3, up to 4, up to 5, up to 6, up to 7, up to 8, or up to 9) amino acid substitutions (such as conservative amino acid substitutions) compared to the amino acid sequences set forth as SEQ ID NOs: 16 and 2, respectively, SEQ ID NOs: 17 and 4, respectively, SEQ ID NOs: 18 and 4, respectively, SEQ ID NOs: 19 and 7, respectively, SEQ ID NOs: 84 and 85, respectively, SEQ ID NOs: 86 and 9, respectively, SEQ ID NOs: 87 and 88, respectively, or SEQ ID NOs: 89 and 90, respectively.

In some embodiments, the framework regions of the $V_H$ and $V_L$ of the antibody each comprise up to 10 (such as up to 1, up to 2, up to 3, up to 4, up to 5, up to 6, up to 7, up to 8, or up to 9) amino acid substitutions (such as conservative amino acid substitutions) compared to the amino acid sequences set forth as SEQ ID NOs: 16 and 2, respectively, SEQ ID NOs: 17 and 4, respectively, SEQ ID NOs: 18 and 4, respectively, SEQ ID NOs: 19 and 7, respectively, SEQ ID NOs: 84 and 85, respectively, SEQ ID NOs: 86 and 9, respectively, SEQ ID NOs: 87 and 88, respectively, or SEQ ID NOs: 89 and 90, respectively.

In some embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *Trends Biotechnol.* 15(1):26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO 2002/031140; Okazaki et al., *J. Mol. Biol.,* 336(5):1239-1249, 2004; Yamane-Ohnuki et al., *Biotechnol. Bioeng.* 87(5):614-622, 2004. Examples of cell lines capable of producing defucosylated antibodies include Lec 13 CHO cells deficient in protein fucosylation (Ripka et al., *Arch. Biochem. Biophys.* 249(2):533-545, 1986; US Pat. Appl. No. US 2003/0157108 and WO 2004/056312, especially at Example 11), and knockout cell lines, such as alpha-1,6-fucosyltransferase gene, FUT8, knockout CHO cells (see, e.g., Yamane-Ohnuki et al., *Biotechnol. Bioeng.,* 87(5): 614-622, 2004; Kanda et al., *Biotechnol. Bioeng.,* 94(4): 680-688, 2006; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

In several embodiments, the constant region of the antibody comprises one or more amino acid substitutions to optimize in vivo half-life of the antibody. The serum half-life of IgG Abs is regulated by the neonatal Fc receptor (FcRn). Thus, in several embodiments, the antibody comprises an amino acid substitution that increases binding to the FcRn. Several such substitutions are known, such as substitutions at IgG constant regions T250Q and M428L (see, e.g., Hinton et al., *J Immunol.,* 176(1):346-356, 2006); M428L and N434S (the "LS" mutation, see, e.g., Zalevsky, et al., *Nature Biotechnol.,* 28(2):157-159, 2010); N434A (see, e.g., Petkova et al., *Int. Immunol.,* 18(12):1759-1769, 2006); T307A, E380A, and N434A (see, e.g., Petkova et al., *Int. Immunol.,* 18(12):1759-1769, 2006); and M252Y, S254T, and T256E (see, e.g., Dall'Acqua et al., *J. Biol. Chem.,* 281(33):23514-23524, 2006). The disclosed antibodies and antigen binding fragments can be linked to or comprise a Fc polypeptide including any of the substitutions listed above, for example, the Fc polypeptide can include the M428L and N434S substitutions. An exemplary sequence of an IgG1 constant region containing the M428L and N434S substitutions is provided as SEQ ID NO: 118. This heavy chain constant region can be paired with an appropriate light chain constant region (such as SEQ ID NO: 119), and appropriate $V_H$ and $V_L$ regions as provided herein to generate a monoclonal antibody. In a non-limiting example, the monoclonal antibody comprises heavy and light chains comprising the amino acid sequences set forth as SEQ ID NOs: 91 and 92, respectively, or 99 and 100, respectively. As used herein, reference to an antibody with the "LS" substitution (or similar language) indicates that the antibody heavy chain is an IgG with M428L and N434S substitutions.

In some embodiments, the constant region of the antibody comprises one or more amino acid substitutions to optimize ADCC. ADCC is mediated primarily through a set of closely related Fcγ receptors. In some embodiments, the antibody comprises one or more amino acid substitutions that increase binding to FcγRIIIa. Several such substitutions are known, such as substitutions at IgG constant regions S239D and I332E (see, e.g., Lazar et al., *Proc. Natl., Acad. Sci. U.S.A.*, 103(11):4005-4010, 2006); and S239D, A330L, and I332E (see, e.g., Lazar et al., *Proc. Natl., Acad. Sci. U.S.A.*, 103(11):4005-4010, 2006).

Combinations of the above substitutions are also included, to generate an IgG constant region with increased binding to FcRn and FcγRIIIa. The combinations increase antibody half-life and ADCC. For example, such combinations include antibodies with the following amino acid substitutions in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E. In some examples, the antibodies, or an antigen binding fragment thereof is modified such that it is directly cytotoxic to infected cells, or uses natural defenses such as complement, ADCC, or phagocytosis by macrophages.

In some embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in an application under defined conditions, etc.

(f) Additional Description of Antibodies and Related Methods

Clause 1. A monoclonal antibody, comprising:

a heavy chain variable region ($V_H$) comprising a heavy chain complementarity determining region (HCDR) 1, a HCDR2, and a HCDR3 of a parent VRC01-class antibody;

a light chain variable region ($V_L$) comprising a light chain complementarity determining region (LCDR) 1, a LCDR2, and a LCDR3 of the parent VRC01-class antibody;

a modification of a heavy chain framework region (HFR) 3 compared to the parent VRC01-class antibody, wherein the modification is a substitution of the amino acids of Kabat positions 72-76 of the parent VRC01-class antibody with the sequence set forth as QLSQDPDDPDWG (SEQ ID NO: 36);

wherein the parent VRC01-class antibody does not contain an amino acid insertion between Kabat positions 75 and 76 compared to an IGHV1-2*02 germline sequence; and wherein the antibody specifically binds to HIV-1 Env and neutralizes HIV-1.

Clause 2. The monoclonal antibody of Clause 1, wherein a HFR 1, a HFR2, the HFR3, and a HFR4 of the monoclonal antibody comprise, in aggregate and not including the modification, no more than 10 amino acid substitutions compared to the corresponding sequences of the parent VRC01-class antibody; and a light chain framework region (LFR) 1, a LFR2, a LFR3, and a LFR4 of the monoclonal antibody comprise, in aggregate, no more than 10 amino acid substitutions compared to the corresponding sequences of the parent VRC01-class antibody.

Clause 3. The monoclonal antibody of Clause 2, wherein the amino acid substitutions are conservative amino acid substitutions.

Clause 4. The monoclonal antibody of any one of the prior Clauses, wherein the parent VRC01-class antibody is any one of N6, VRC01, VRC07, VRC07-523, or VRC-PG04.

Clause 5. The monoclonal antibody of any one of the prior Clauses, wherein the parent VRC01-class antibody is N6, and the HCDR1, the HCDR2, the HCDR3, the LCDR1, the LCDR2, and the LCDR3 comprise the amino acids sequences set forth as SEQ ID NOs: 20, 21, 22, 23, 24, and 25, respectively.

the parent VRC01-class antibody is VRC01, and the HCDR1, the HCDR2, the HCDR3, the LCDR1, the LCDR2, and the LCDR3 comprise the amino acids sequences set forth as SEQ ID NOs: 26, 27, 28, 29, 30, and 31, respectively;

the parent VRC01-class antibody is VRC07, and the HCDR1, the HCDR2, the HCDR3, the LCDR1, the LCDR2, and the LCDR3 comprise the amino acids sequences set forth as SEQ ID NOs: 32, 33, 34, 29, 30, and 31, respectively;

the parent VRC01-class antibody is VRC07-523, and the HCDR1, the HCDR2, the HCDR3, the LCDR1, the LCDR2, and the LCDR3 comprise the amino acids sequences set forth as SEQ ID NOs: 32, 35, 34, 29, 30, and 31, respectively; or the parent VRC01-class antibody is VRC-PG04, and the HCDR1, the HCDR2, the HCDR3, the LCDR1, the LCDR2, and the LCDR3 comprise the amino acids sequences set forth as SEQ ID NOs: 59, 60, 61, 62, 63, and 64, respectively.

Clause 6. The monoclonal antibody of any one of the prior Clauses, wherein the parent VRC01-class antibody is N6, and the amino acid sequences of the $V_H$ and $V_L$ are at least 90% identical to SEQ ID NOs: 16 and 2, respectively;

the parent VRC01-class antibody is VRC01, and the amino acid sequences of the $V_H$ and $V_L$ are at least 90% identical to SEQ ID NOs: 17 and 4, respectively;

the parent VRC01-class antibody is VRC07, and the amino acid sequences of the $V_H$ and $V_L$ are at least 90% identical to SEQ ID NOs: 18 and 4, respectively;

the parent VRC01-class antibody is VRC07-523, and the amino acid sequences of the $V_H$ and $V_L$ are at least 90% identical to SEQ ID NOs: 19 and 7, respectively; or the parent VRC01-class antibody is VRC-PG04, and the amino acid sequences of the $V_H$ and $V_L$ are at least 90% identical to SEQ ID NOs: 58 and 57, respectively.

Clause 7. The monoclonal antibody of Clause 1, wherein
the $V_H$ and $V_L$ comprise the amino acid sequences set forth as SEQ ID NOs: 16 and 2, respectively (N6 70-03);

the $V_H$ and $V_L$ comprise the amino acid sequences set forth as SEQ ID NOs: 17 and 4, respectively (VRC01 70-03);

the $V_H$ and $V_L$ comprise the amino acid sequences set forth as SEQ ID NOs: 18 and 4, respectively (VRC07 70-03);

the $V_H$ and $V_L$ comprise the amino acid sequences set forth as SEQ ID NOs: 19 and 7, respectively (VRC07-523 70-03); or the $V_H$ and $V_L$ comprise the amino acid sequences set forth as SEQ ID NOs: 58 and 57, respectively (VRC-PG04 70-03).

Clause 8. The monoclonal antibody of any one or the prior Clauses, further comprising a tryptophan, tyrosine, or phenylalanine substitution at Kabat position 54.

Clause 9. The monoclonal antibody of Clause 8, comprising the tryptophan substitution at Kabat position 54.

Clause 10. The monoclonal antibody of any one of the prior Clauses, further comprising a two or three amino acid deletion at the N-terminus of the $V_L$.

Clause 11. The monoclonal antibody of Clause 10, comprising the three-amino acid deletion at the N-terminus of the $V_L$.

Clause 12. The monoclonal antibody of any one of the prior Clauses, wherein the parent VRC01-class antibody is any one of VRC01, VRC07, or VRC07-523, and the $V_L$ of the monoclonal antibody further comprises a R24D substitution according to the Kabat numbering system.

Clause 13. The monoclonal antibody of any one of the prior Clauses, wherein the parent VRC01-class antibody is any one of N6, VRC01, VRC07, or VRC07-523, and the $V_L$ of the monoclonal antibody further comprises a N72Q substitution according to the Kabat numbering system.

Clause 14. The monoclonal antibody of any one of the prior Clauses, wherein the parent VRC01-class antibody is VRC07-523, and the monoclonal antibody further comprises a one amino acid deletion at the N-terminus of the $V_L$.

Clause 15. The monoclonal antibody of any one of Clauses 8-13, wherein the HCDR1, the HCDR2, the HCDR3, the LCDR1, the LCDR2, and the LCDR3 comprise the amino acids sequences set forth as SEQ ID NOs: 26, 65, 28, 29, 30, and 31, respectively (VRC01.23 CDRs).

Clause 16. The monoclonal antibody of any one of Clauses 8-13 or 15, wherein the $V_H$ and $V_L$ of the antibody comprise amino acid sequences at least 90% identical to SEQ ID NOs: 84 and 85, respectively (VRC01.23 $V_H$ and $V_L$).

Clause 17. The monoclonal antibody of Clause 16, wherein the $V_H$ and $V_L$ comprise the amino acid sequences set forth as SEQ ID NOs: 84 and 85, respectively (VRC01.23 $V_H$ and $V_L$).

Clause 18. The monoclonal antibody of any one of Clauses 8-11, wherein the HCDR1, the HCDR2, the HCDR3, the LCDR1, the LCDR2, and the LCDR3 comprise the amino acids sequences set forth as SEQ ID NOs: 72, 120, 74, 75, 76, 77, respectively (N49P7.v2 and .v3 CDRs).

Clause 19. The monoclonal antibody of any one of Clauses 8-11 or 18, wherein the $V_H$ and $V_L$ of the antibody comprise amino acid sequences at least 90% identical to SEQ ID NOs: 105 and 106, respectively (N49P7.v2 $V_H$ and $V_L$), or SEQ ID NOs: 105 and 107, respectively (N49P7.v3 $V_H$ and $V_L$).

Clause 20. The monoclonal antibody of Clause 19, wherein the $V_H$ and $V_L$ comprise the amino acid sequences set forth as SEQ ID NOs: 105 and 106, respectively (N49P7.v2 $V_H$ and $V_L$), or SEQ ID NOs: 105 and 107, respectively (N49P7.v3 $V_H$ and $V_L$).

Clause 21. The monoclonal antibody of any one of Clauses 8-14, wherein the HCDR1, the HCDR2, the HCDR3, the LCDR1, the LCDR2, and the LCDR3 comprise the amino acids sequences set forth as:

SEQ ID NOs: 32, 121, 34, 29, 30, 31, respectively (VRC07-523.v1 CDRs);

SEQ ID NOs: 32, 121, 34, 123, 30, 31, respectively (VRC07-523.v2 CDRs);

SEQ ID NOs: 32, 122, 34, 29, 30, 31, respectively (VRC07-523.v3 CDRs); or

SEQ ID NOs: 32, 122, 34, 123, 30, 31, respectively (VRC07-523.v4 CDRs).

Clause 22. The monoclonal antibody of any one of Clauses 8-14 or 21, wherein the $V_H$ and $V_L$ of the antibody comprise amino acid sequences at least 90% identical to SEQ ID NOs: 102 and 103, respectively (VRC07-523v.1 $V_H$ and $V_L$), SEQ ID NOs: 102 and 104, respectively (VRC07-523v.2 $V_H$ and $V_L$), SEQ ID NOs: 101 and 103, respectively (VRC07-523v.3 $V_H$ and $V_L$), or SEQ ID NOs: 101 and 104, respectively (VRC07-523v.4 $V_H$ and $V_L$).

Clause 23. The monoclonal antibody of Clause 22, wherein the $V_H$ and $V_L$ comprise the amino acid sequences set forth as SEQ ID NOs: 102 and 103, respectively (VRC07-523v.1 $V_H$ and $V_L$), SEQ ID NOs: 102 and 104, respectively (VRC07-523v.2 $V_H$ and $V_L$), SEQ ID NOs: 101 and 103, respectively (VRC07-523v.3 $V_H$ and $V_L$), or SEQ ID NOs: 101 and 104, respectively (VRC07-523v.4 $V_H$ and $V_L$).

Clause 24. The monoclonal antibody of any one of the prior Clauses, wherein the antibody is an IgG, IgM or IgA.

Clause 25. The monoclonal antibody of any one of the prior Clauses, comprising a recombinant constant domain comprising a modification that increases binding to the neonatal Fc receptor.

Clause 26. The monoclonal antibody of Clause 25, wherein the recombinant constant domain is an IgG1 constant domain comprising M428L and N434S mutations.

Clause 27. The monoclonal antibody of Clause 26, wherein the heavy and light chains of the antibody comprise the amino acid sequences set forth as SEQ ID NOs: 91 and 92, respectively (VRC01.23-LS).

Clause 28. An antigen binding fragment of the monoclonal antibody of any one of the prior Clauses.

Clause 29. The antigen binding fragment of Clause 28, wherein the antigen binding fragment is a Fv, Fab, F(ab')$_2$, scFV or a scFV$_2$ fragment.

Clause 30. The monoclonal antibody or antigen binding fragment of any of the prior Clauses, wherein the antibody or antigen binding fragment neutralizes HIV-1 Env with an IC$_{50}$ of less than 0.4 µg/ml.

Clause 31. A multispecific antibody comprising the isolated monoclonal antibody or antigen binding fragment of any of the prior Clauses.

Clause 32. The multispecific antibody of Clause 31, wherein the multispecific antibody is a bispecific antibody or a trispecific antibody.

Clause 33. The monoclonal antibody or antigen binding fragment or multispecific antibody of any of the prior Clauses, linked to an effector molecule or a detectable marker.

Clause 34. The monoclonal antibody or antigen binding fragment or multispecific antibody of Clause 33, wherein the detectable marker is a fluorescent, enzymatic, or radioactive marker.

Clause 35. An isolated nucleic acid molecule encoding the monoclonal antibody or antigen binding fragment or multispecific antibody of any of Clauses 1-34.

Clause 36. An isolated nucleic acid molecule encoding the $V_H$ and/or the $V_L$ of the monoclonal antibody or antigen binding fragment of any of Clauses 1-34.

Clause 37. The isolated nucleic acid molecule of any of Clauses 35 or 36, operably linked to a promoter.

Clause 38. An expression vector comprising the nucleic acid molecule of any of Clauses 35-37.

Clause 39. The expression vector of Clause 38, wherein the expression vector is a viral vector.

Clause 40. A pharmaceutical composition, comprising:

a therapeutically effective amount of the antibody, antigen binding fragment, nucleic acid molecule, or expression vector of any one of the prior Clauses; and a pharmaceutically acceptable carrier.

Clause 41. A method of producing an antibody that specifically binds to HIV-1 Env, comprising:

expressing the nucleic acid molecule or expression vector of any of Clauses 35-39 in a host cell to produce the antibody in the host cell; and purifying the antibody.

Clause 42. A method of detecting an HIV-1 infection in a subject, comprising:

contacting a biological sample from the subject with the antibody or antigen binding fragment of any of Clauses 1-34 under conditions sufficient to form an immune complex; and detecting the presence of the immune complex in the sample, wherein the presence of the immune complex in the sample indicates that the subject has the HIV-1 infection.

Clause 43. A method of inhibiting an HIV-1 infection in a subject, comprising administering to the subject a therapeutically effective amount of the antibody, antigen binding fragment, nucleic acid molecule, expression vector, or pharmaceutical composition of any of Clauses 1-40, thereby preventing or treating the HIV-1 infection.

Clause 44. The method of Clause 43, wherein the subject is at risk of or has an HIV-1 infection.

Clause 45. Use of the antibody, antigen binding fragment, nucleic acid molecule, expression vector, host cell, or pharmaceutical composition of any of Clauses 1-40 to inhibit HIV-1 infection in a subject.

B. Conjugates

The antibodies and antigen binding fragments that specifically bind to an epitope on gp120 can be conjugated to an agent, such as an effector molecule or detectable marker. Both covalent and noncovalent attachment means may be used. Various effector molecules and detectable markers can be conjugated to the antibody or antigen binding fragment, including (but not limited to) toxins and radioactive agents such as $^{125}I$, $^{32}P$, $^{14}C$, $^{3}H$ and $^{35}S$ and other labels, target moieties and ligands, etc. The choice of a particular effector molecule or detectable marker depends on the particular target molecule or cell, and the desired biological effect.

The choice of a particular effector molecule or detectable marker depends on the particular target molecule or cell, and the desired biological effect. Thus, for example, the effector molecule can be a cytotoxin that is used to bring about the death of a particular target cell (such as an HIV-1 infected cell). In other embodiments, the effector molecule can be a cytokine, such as IL-15; conjugates including the cytokine can be used, e.g., to stimulate immune cells locally.

The procedure for attaching an effector molecule or detectable marker to an antibody or antigen binding fragment varies according to the chemical structure of the effector. Polypeptides typically contain a variety of functional groups, such as carboxyl (—COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules, such as those available from Thermo Fisher Scientific, Waltham, Mass. and MilliporeSigma Corporation, St. Louis, Mo. The linker is capable of forming covalent bonds to both the antibody or antigen binding fragment and to the effector molecule or detectable marker. Suitable linkers include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side chains (such as through a disulfide linkage to cysteine) or the alpha carbon, or through the amino, and/or carboxyl groups of the terminal amino acids.

In view of the large number of methods that have been reported for attaching a variety of radiodiagnostic compounds, radiotherapeutic compounds, labels (such as enzymes or fluorescent molecules), toxins, and other agents to antibodies, a suitable method for attaching a given agent to an antibody or antigen binding fragment or other polypeptide can be determined.

In some embodiments, the antibody or antigen binding fragment can be conjugated with effector molecules such as small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents to make an antibody drug conjugate (ADC). In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

The antibody or antigen binding fragment can be conjugated with a detectable marker; for example, a detectable marker capable of detection by ELISA, spectrophotometry, flow cytometry, microscopy or diagnostic imaging techniques (such as CT, computed axial tomography (CAT), MRI, magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1- napthalenesulfonyl chloride, phycoerythrin, lanthanide phosphors and the like. Bioluminescent markers are also of use, such as luciferase, green fluorescent protein (GFP), and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitope recognized by a secondary reporter (such as leucine zipper pair sequences, binding sites for secondary antibodies, metal binding domains, epitope tags).

The antibody or antigen binding fragment can be conjugated with a radiolabeled amino acid, for example, for diagnostic purposes. For instance, the radiolabel may be used to detect gp120 and gp120 expressing cells by radiography, emission spectra, or other diagnostic techniques. Examples of labels for polypeptides include, but are not limited to, the following radioisotopes: $^3$H, $^{14}$C, $^{35}$S, $^{90}$Y, $^{99m}$Tc, $^{111}$In, $^{125}$I, $^{131}$I. The radiolabels may be detected, for example, using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In some embodiments, the average number of effector molecules or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule per antibody ratio) of a conjugate may be controlled in different ways, for example, by: (i) limiting the molar excess of effector molecule-linker intermediate or linker reagent relative to antibody, (ii) limiting the conjugation reaction time or temperature, (iii) partial or limiting reducing conditions for cysteine thiol modification, (iv) engineering by recombinant techniques the amino acid sequence of the antibody such that the number and position of cysteine residues is modified for control of the number or position of linker-effector molecule attachments.

C. Polynucleotides and Expression

Nucleic acid molecules (for example, cDNA or RNA molecules) encoding the amino acid sequences of antibodies, antigen binding fragments, and conjugates that specifically bind HIV-1 Env are provided. Nucleic acids encoding these molecules can readily be produced using the amino acid sequences provided herein (such as the CDR sequences and $V_H$ and $V_L$ sequences), sequences available in the art (such as framework or constant region sequences), and the genetic code. In several embodiments, nucleic acid molecules can encode the $V_H$, the $V_L$, or both the $V_H$ and $V_L$ (for example in a bicistronic expression vector) of a disclosed antibody or antigen binding fragment. In several embodiments, the nucleic acid molecules can be expressed in a host cell (such as a mammalian cell) to produce a disclosed antibody or antigen binding fragment.

The genetic code can be used to construct a variety of functionally equivalent nucleic acid sequences, such as nucleic acids which differ in sequence but which encode the same antibody sequence or a conjugate or fusion protein including the $V_L$ and/or $V_H$ of the antibody.

Nucleic acid molecules encoding the antibodies, antigen binding fragments, and conjugates that specifically bind HIV-1 Env can be prepared by any suitable method including, for example, cloning of appropriate sequences or by direct chemical synthesis by standard methods. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques can be found, for example, in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Nucleic acids can also be prepared by amplification methods. Amplification methods include the polymerase chain reaction (PCR), the ligase chain reaction (LCR), the transcription-based amplification system (TAS), and the self-sustained sequence replication system (3SR).

The nucleic acid molecules can be expressed in a recombinantly engineered cell such as bacteria, plant, yeast, insect and mammalian cells. The antibodies, antigen binding fragments, and conjugates can be expressed as individual proteins including the $V_H$ and/or $V_L$ (linked to an effector molecule or detectable marker as needed), or can be expressed as a fusion protein. Methods of expressing and purifying antibodies and antigen binding fragments are known and further described herein (see, e.g., Al-Rubeai (Ed.), *Antibody Expression and Production*, Dordrecht; New York: Springer, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence (Gly$_4$-Ser)$_3$, such that the $V_H$ and $V_L$ sequences can be expressed as a contiguous single-chain protein, with the $V_L$ and $V_H$ domains joined by the flexible linker (see, e.g., Bird et al., *Science*, 242(4877):423-426, 1988; Huston et al., *Proc. Natl. Acad. Sci. U.S.A.*, 85(16):5879-5883, 1988; McCafferty et al., *Nature*, 348:552-554, 1990; Kontermann and Dübel (Eds.), *Antibody Engineering*, Vols. 1-2, 2$^{nd}$ ed., Springer-Verlag, 2010; Greenfield (Ed.), *Antibodies: A Laboratory Manual*, 2$^{nd}$ ed. New York: Cold Spring Harbor Laboratory Press, 2014). Optionally, a cleavage site can be included in a linker, such as a furin cleavage site.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to gp120 and another antigen, such as, but not limited to CD3. The encoded $V_H$ and $V_L$ optionally can include a furin cleavage site between the $V_H$ and $V_L$ domains.

One or more DNA sequences encoding the antibodies, antigen binding fragments, or conjugates can be expressed in vitro by DNA transfer into a suitable host cell. The cell may be prokaryotic or eukaryotic. Numerous expression systems available for expression of proteins including *E. coli*, other bacterial hosts, yeast, and various higher eukaryotic cells such as the COS, CHO, HeLa and myeloma cell lines, can be used to express the disclosed antibodies and antigen binding fragments. Methods of stable transfer, meaning that the foreign DNA is continuously maintained in the host, are known in the art. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signals for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, for example, a strong promoter to direct transcription, a ribosome binding site for translational initiation (e.g., internal ribosomal binding sequences), and a transcription/translation terminator. For *E. coli*, this can include a promoter such as the T7, tip, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, GPt, neo, and hyg genes.

Modifications can be made to a nucleic acid encoding a polypeptide described herein without diminishing its biological activity. Some modifications can be made to facilitate the cloning, expression, or incorporation of the targeting molecule into a fusion protein. Such modifications include, for example, termination codons, sequences to create conveniently located restriction sites, and sequences to add a methionine at the amino terminus to provide an initiation site, or additional amino acids (such as poly His) to aid in purification steps.

Once expressed, the antibodies, antigen binding fragments, and conjugates can be purified according to standard procedures in the art, including ammonium sulfate precipitation, affinity columns, column chromatography, and the like (see, generally, Simpson et al. (Eds.), *Basic methods in Protein Purification and Analysis: A Laboratory Manual*, New York: Cold Spring Harbor Laboratory Press, 2009). The antibodies, antigen binding fragment, and conjugates need not be 100% pure. Once purified, partially or to homogeneity as desired, if to be used prophylatically, the polypeptides should be substantially free of endotoxin.

Methods for expression of antibodies, antigen binding fragments, and conjugates, and/or refolding to an appropriate active form, from mammalian cells, and bacteria such as *E. coli* have been described and are applicable to the antibodies disclosed herein. See, e.g., Greenfield (Ed.), *Antibodies: A Laboratory Manual, $2^{nd}$ ed.* New York: Cold Spring Harbor Laboratory Press, 2014, Simpson et al. (Eds.), *Basic methods in Protein Purification and Analysis: A Laboratory Manual*, New York: Cold Spring Harbor Laboratory Press, 2009, and Ward et al., *Nature* 341(6242): 544-546, 1989.

D. Methods and Compositions

1. Therapeutic Methods

Methods are disclosed herein for the inhibition of an HIV-1 infection in a subject. The methods include administering to a subject an effective amount (that is, an amount effective to inhibit HIV-1 infection in a subject) of a disclosed antibody, antigen binding fragment, conjugate, or a nucleic acid encoding such an antibody, antigen binding fragment, or conjugate, to a subject with or at risk of the HIV-1 infection. The methods can be used pre-exposure (for example, to prevent HIV-1 infection), in post-exposure prophylaxis, or for treatment of a subject with an HIV-1 infection.

In some examples, the antibody, antigen binding fragment, conjugate, or nucleic acid molecule, can be used to eliminate or reduce the viral reservoir of HIV-1 in a subject.

HIV-1 infection does not need to be completely inhibited for the method to be effective. For example, the method can decrease HIV-1 infection by at least 10%, at least 20%, at least 50%, at least 60%, at least 70%, at least 80%, at least 90%, at least 95%, at least 98%, or even at least 100% (elimination of detectable HIV-1 infected cells), as compared to HIV-1 infection in the absence of the treatment. In some embodiments, the method results in a reduction of HIV-1 replication in the subject. HIV-1 replication does not need to be completely eliminated for the method to be effective. For example, the method can reduce HIV-1 replication in the subject by at least 10%, at least 20%, at least 50%, at least 60%, at least 70%, at least 80%, at least 90%, at least 95%, at least 98%, or even at least 100% (elimination of detectable HIV-1 replication), as compared to HIV-1 replication in the absence of the treatment.

In some embodiments, administration of an effective amount of a disclosed antibody, antigen binding fragment, conjugate, or nucleic acid molecule, inhibits the establishment of HIV-1 infection and/or subsequent HIV-1 progression in a subject, which can encompass any statistically significant reduction in HIV-1 activity or symptoms of HIV-1 infection in the subject.

In one embodiment, administration of a disclosed antibody, antigen binding fragment, conjugate, or nucleic acid molecule, results in a reduction in the establishment of HIV-1 infection and/or reducing subsequent HIV-1 disease progression in a subject. A reduction in the establishment of HIV-1 infection and/or a reduction in subsequent HIV-1 disease progression encompass any statistically significant reduction in HIV-1 activity. In some embodiments, methods are disclosed for treating a subject with an HIV-1 infection. These methods include administering to the subject a effective amount of a disclosed antibody, antigen binding fragment, conjugate, or nucleic acid molecule, to preventing or treating the HIV-1 infection.

Studies have shown that the rate of HIV-1 transmission from mother to infant is reduced significantly when zidovudine is administered to HIV-infected women during pregnancy and delivery and to the offspring after birth (Connor et al., 1994 *Pediatr Infect Dis J* 14: 536-541). The present disclosure provides antibodies, antigen binding fragments, conjugates, and nucleic acid molecule that are of use in decreasing HIV-transmission from mother to infant. In some examples, an effective amount of a HIV-1 Env-specific antibody or antigen binding fragment thereof or nucleic acid encoding such antibodies or antibody antigen binding fragments, is administered to a pregnant subject in order to prevent transmission of HIV-1, or decrease the risk of transmission of HIV-1, from a mother to an infant. In some examples, an effective amount of the antibody, or an antigen binding fragment or nucleic acid encoding such antibodies or antigen binding fragment, is administered to mother and/or to the child at childbirth. In other examples, an effective amount of the antibody, antigen binding fragment, or nucleic acid encoding the antibody or antigen binding fragment is administered to the mother and/or infant prior to breast feeding in order to prevent viral transmission to the infant or decrease the risk of viral transmission to the infant.

For any application, the antibody, antigen binding fragment, conjugate, or nucleic acid molecule can be combined with anti-retroviral therapy. Antiretroviral drugs are broadly classified by the phase of the retrovirus life-cycle that the drug inhibits. The disclosed antibodies can be administered in conjunction with nucleoside analog reverse-transcriptase inhibitors (such as zidovudine, didanosine, zalcitabine, stavudine, lamivudine, abacavir, emtricitabine, entecavir, and apricitabine), nucleotide reverse transcriptase inhibitors (such as tenofovir and adefovir), non-nucleoside reverse transcriptase inhibitors (such as efavirenz, nevirapine, delavirdine, etravirine, and rilpivirine), protease inhibitors (such as saquinavir, ritonavir, indinavir, nelfinavir, amprenavir, lopinavir, fosamprenavir, atazanavir, tipranavir, and darunavir), entry or fusion inhibitors (such as maraviroc and enfuvirtide), maturation inhibitors, (such as bevirimat and vivecon), or a broad spectrum inhibitors, such as natural antivirals. In some examples, a disclosed antibody or active fragment thereof or nucleic acids encoding such is administered in conjunction with IL-15, or conjugated to IL-15.

Studies have shown that cocktails of HIV-1 neutralizing antibodies that target different epitopes of gp120 can treat macaques chronically infected with SHIV (Shingai et al., Nature, 503, 277-280, 2013; and Barouch et al., Nature, 503, 224-228, 2013). Accordingly, in some examples, a subject is further administered one or more additional antibodies that bind HIV-1 Env (e.g., that bind to gp120 or gp41), and that can neutralize HIV-1. The additional antibodies can be administrated before, during, or after administration of the novel antibodies disclosed herein. In some embodiments, the additional antibody can be an antibody that specifically binds to an epitope on HIV-1 Env such as the membrane-proximal external region (e.g., 10E8 antibody), the V1/V2 domain (e.g., PG9 antibody, CAP256-VRC26), or the V3 loop (e.g., 10-1074, PGT 121, or PGT128 antibody), or those that bind both gp120 and gp41 subunits (eg. 35022, PGT151, or 8ANC195). Antibodies that specifically bind to these regions and neutralizing HIV-1 infection are known to the person of ordinary skill in the art. Non-limiting examples can be found, for example, in PCT Pub. No. WO 2011/038290, WO/2013/086533, WO/2013/090644, WO/2012/158948, which are incorporated herein by reference in their entirety.

Antibodies and antigen binding fragments thereof are typically administered by intravenous infusion. Doses of the antibody or antigen binding fragment vary, but generally range between about 0.5 mg/kg to about 50 mg/kg, such as a dose of about 1 mg/kg, about 5 mg/kg, about 10 mg/kg, about 20 mg/kg, about 30 mg/kg, about 40 mg/kg, or about 50 mg/kg. In some embodiments, the dose of the antibody or antigen binding fragment can be from about 0.5 mg/kg to about 5 mg/kg, such as a dose of about 1 mg/kg, about 2 mg/kg, about 3 mg/kg, about 4 mg/kg or about 5 mg/kg. The antibody or antigen binding fragment is administered according to a dosing schedule determined by a medical practitioner. In some examples, the antibody or antigen binding fragment is administered weekly, every two weeks, every three weeks or every four weeks.

In some examples, a subject is administered DNA or RNA encoding a disclosed antibody to provide in vivo antibody production, for example using the cellular machinery of the subject. Administration of nucleic acid constructs is known in the art and taught, for example, in U.S. Pat. Nos. 5,643,578, 5,593,972 and 5,817,637. U.S. Pat. No. 5,880,103 describes several methods of delivery of nucleic acids encoding proteins to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof. In some embodiments, a disclosed antibody or antigen binding fragment is expressed in a subject using the pVRC8400 vector (described in Barouch et al., *J. Virol.*, 79(14), 8828-8834, 2005, which is incorporated by reference herein).

In several embodiments, a subject (such as a human subject at risk of ebolavirus infection) can be administered an effective amount of an AAV viral vector that includes one or more nucleic acid molecules encoding a disclosed antibody or antigen binding fragment. The AAV viral vector is designed for expression of the nucleic acid molecules encoding a disclosed antibody or antigen binding fragment, and administration of the effective amount of the AAV viral vector to the subject leads to expression of an effective amount of the antibody or antigen binding fragment in the subject. Non-limiting examples of AAV viral vectors that can be used to express a disclosed antibody or antigen binding fragment in a subject include those provided in Johnson et al., *Nat. Med.*, 15(8):901-906, 2009 and Gardner et al., *Nature*, 519(7541):87-91, 2015, each of which is incorporated by reference herein in its entirety.

In one embodiment, a nucleic acid encoding a disclosed antibody, or antigen binding fragment thereof, is introduced directly into tissue. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

Single or multiple administrations of a composition including a disclosed HIV-1 Env specific antibody, antigen binding fragment, conjugate, or nucleic acid molecule encoding such molecules, can be administered depending on the dosage and frequency as required and tolerated by the patient. The dosage can be administered once, but may be applied periodically until either a desired result is achieved or until side effects warrant discontinuation of therapy. Generally, the dose is sufficient to inhibit ebolavirus infection without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The effective dose can be determined from cell culture assays and animal studies.

The HIV-1 Env-specific antibody, antigen binding fragment, conjugate, or nucleic acid molecule encoding such molecules, or a composition including such molecules, can be administered to subjects in various ways, including local and systemic administration, such as, e.g., by injection subcutaneously, intravenously, intra-arterially, intraperitoneally, intramuscularly, intradermally, or intrathecally. In an embodiment, the antibody, antigen binding fragment, conjugate, or nucleic acid molecule encoding such molecules, or a composition including such molecules, is administered by a single subcutaneous, intravenous, intra-arterial, intraperitoneal, intramuscular, intradermal or intrathecal injection once a day. The antibody, antigen binding fragment, conjugate, or nucleic acid molecule encoding such molecules, or a composition including such molecules, can also be administered by direct injection at or near the site of disease. A further method of administration is by osmotic pump (e.g., an Alzet pump) or mini-pump (e.g., an Alzet mini-osmotic pump), which allows for controlled, continuous and/or slow-release delivery of the antibody, antigen binding fragment, conjugate, or nucleic acid molecule encoding such molecules, or a composition including such molecules, over a pre-determined period. The osmotic pump or mini-pump can be implanted subcutaneously, or near a target site.

2. Compositions

Compositions are provided that include one or more of the HIV-1 Env-specific antibody, antigen binding fragment, conjugate, or nucleic acid molecule encoding such molecules, that are disclosed herein in a carrier. The compositions are useful, for example, for the inhibition or detection of an HIV-1 infection. The compositions can be prepared in unit dosage forms for administration to a subject. The amount and timing of administration are at the discretion of the administering physician to achieve the desired purposes. The HIV-1 Env-specific antibody, antigen binding fragment, conjugate, or nucleic acid molecule encoding such molecules can be formulated for systemic or local administration. In one example, the HIV-1 Env-specific antibody, antigen binding fragment, conjugate, or nucleic acid molecule encoding such molecules, is formulated for parenteral administration, such as intravenous administration.

In some embodiments, the antibody, antigen binding fragment, or conjugate thereof, in the composition is at least 70% (such as at least 75%, at least 80%, at least 85%, at least 90%, at least 95%, at least 96%, at least 97%, at least 98% or at least 99%) pure. In some embodiments, the composition contains less than 10% (such as less than 5%, less than 4%, less than 3%, less than 2%, less than 1%, less than 0.5%, or even less) of macromolecular contaminants, such as other mammalian (e.g., human) proteins.

The compositions for administration can include a solution of the HIV-1 Env-specific antibody, antigen binding fragment, conjugate, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions are known and are described in more detail in such publications as *Remington: The Science and Practice of Pharmacy, 22$^{nd}$ ed.*, London, UK: Pharmaceutical Press, 2013. In some embodiments, the composition can be a liquid formulation including one or more antibodies, antigen binding fragments (such as an antibody or antigen binding fragment that specifically binds to HIV-1 Env), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of Rituximab in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30-minute period if the previous dose was well tolerated.

Controlled-release parenteral formulations can be made as implants, oily injections, or as particulate systems. For a broad overview of protein delivery systems see, Banga, *Therapeutic Peptides and Proteins: Formulation, Processing, and Delivery Systems*, Lancaster, Pa.: Technomic Publishing Company, Inc., 1995. Particulate systems include microspheres, microparticles, microcapsules, nanocapsules, nanospheres, and nanoparticles. Microcapsules contain the active protein agent, such as a cytotoxin or a drug, as a central core. In microspheres, the active protein agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, *Colloidal Drug Delivery Systems*, J. Kreuter (Ed.), New York, N.Y.: Marcel Dekker, Inc., pp. 219-342, 1994; and Tice and Tabibi, *Treatise on Controlled Drug Delivery: Fundamentals, Optimization, Applications*, A. Kydonieus (Ed.), New York, N.Y.: Marcel Dekker, Inc., pp. 315-339, 1992.

Polymers can be used for ion-controlled release of the antibody compositions disclosed herein. Various degradable and nondegradable polymeric matrices for use in controlled drug delivery are known in the art (Langer, *Acc. Chem. Res.* 26(10):537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.*, 9(3):425-434, 1992; and Pec et al., *J. Parent. Sci. Tech.*, 44(2):58-65, 1990). Alternatively, hydroxyapatite has been used as a microcarrier for controlled release of proteins (Ijntema et al., *Int. J. Pharm.* 112(3):215-224, 1994). In yet another aspect, liposomes are used for controlled release as well as drug targeting of the lipid-capsulated drug (Betageri et al., *Liposome Drug Delivery Systems*, Lancaster, Pa.: Technomic Publishing Co., Inc., 1993). Numerous additional systems for controlled delivery of active protein agent are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

3. Methods of Detection and Diagnosis

Methods are also provided for the detection of the presence of HIV-1 Env in vitro or in vivo. In one example, the presence of HIV-1 Env is detected in a biological sample from a subject, and can be used to identify a subject with HIV-1 infection. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, with an antibody or antigen binding fragment that specifically binds to HIV-1 Env, or conjugate thereof (e.g. a conjugate including a detectable marker) under conditions sufficient to form an immune complex, and detecting the immune complex (e.g., by detecting a detectable marker conjugated to the antibody or antigen binding fragment).

In one embodiment, the antibody or antigen binding fragment is directly labeled with a detectable marker. In another embodiment, the antibody that binds HIV-1 Env (the primary antibody) is unlabeled and a secondary antibody or other molecule that can bind the primary antibody is utilized for detection. The secondary antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially. Suitable labels for the antibody, antigen binding fragment or secondary antibody are known and described above, and include various enzymes, prosthetic groups, fluorescent materials, luminescent materials, magnetic agents and radioactive materials.

In some embodiments, the disclosed antibodies or antigen binding fragments thereof are used to test vaccines. For example, to test if a vaccine composition including an HIV-1 Env or fragment thereof assumes a conformation including the epitope of a disclosed antibody. Thus, provided herein is a method for testing a vaccine, wherein the method includes contacting a sample containing the vaccine, such as an HIV-1 Env immunogen, with a disclosed antibody or antigen binding fragment under conditions sufficient for formation of an immune complex, and detecting the immune complex, to detect the vaccine, such as an HIV-1 Env immunogen including the epitope, in the sample. In one example, the detection of the immune complex in the sample indicates that the vaccine component, such as an HIV-1 Env immunogen, assumes a conformation capable of binding the antibody or antigen binding fragment.

F. Kits

Kits are also provided. For example, kits for treating a subject with an HIV-1 infection, or for detecting HIV-1 Env in a sample or in a subject. The kits will typically include a disclosed HIV-1 Env-specific antibody, antigen binding fragment, conjugate, or nucleic acid molecule encoding such molecules, or compositions including such molecules. More than one of the disclosed HIV-1 Env-specific antibodies, antigen binding fragments, conjugates, or nucleic acid molecules encoding such molecules, or compositions including such molecules can be included in the kit.

In one embodiment, the kit is a diagnostic kit and includes an immunoassay. Although the details of the immunoassays may vary with the particular format employed, the method of detecting HIV-1 Env in a biological sample generally includes the steps of contacting the biological sample with an antibody which specifically reacts, under conditions sufficient to form an immune complex, to HIV-1 Env. The antibody is allowed to specifically bind under immunologically reactive conditions to form an immune complex, and the presence of the immune complex (bound antibody) is detected directly or indirectly.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments the container may have a sterile access port (for example the container may be an intravenous solution bag or a vial having a stopper pierceable by a hypodermic injection needle). A label or package insert indicates that the composition is used for treating or detecting the particular condition and typically will further include instructions for use of the antibodies, antigen binding fragments, conjugates, nucleic acid molecules, or compositions included in the kit.

The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method.

III. Examples

The following examples are provided to illustrate particular features of certain embodiments, but the scope of the claims should not be limited to those features exemplified.

Example 1

Improvement of HIV-1 Broadly Neutralizing Antibodies by Engraftment of Quaternary-Contacting HFR3 Residues Broadly neutralizing antibodies (bNAb) are a promising alternative to antiretroviral drugs for prevention and treatment of HIV infection. A number of bNAbs have been isolated from the naturally HIV-1 infected individuals, including VRC01-class antibodies, which are named for the prototypical member of the class (VRC01) and have arisen special interest in the field for their high potency and breadth. This example describes structure-based engineering to modify VRC01-class antibodies by extending the framework 3 loop of the heavy chain (HFR3), enabling the antibody to establish quaternary contact with the neighboring gp120 protomer in the HIV Env trimeric spike. The extension was replacement of the Kabat positions 72-76 of the VRC01-class antibody with the sequence set forth as QLSQDPDDPDWG (SEQ ID NO: 36), which are the Kabat positions 72-76 from VRC03 (which contains a 70s Loop insertion). This insertion is referred to as a '70-03 insertion'. Three out of four engineered VRC01-class antibodies showed an enhanced neutralizing capacity against the majority of HIV-1 strains tested. Unlike the successful engineered antibodies, the engineered VRC01-class antibody that was not improved by the 70-03 insertion already contained an amino acid insertion between Kabat positions 75/76 compared to an IGHV1-2*02 germline sequence.

Further, the crystal structure of one engineered antibody, N6 70-03, complexed with the BG505 SOSIP.664 trimer was solved. The HFR3 loop of N6 70-03 was shown to interact with the V3 base and the CD4-binding site 2 (CD4BS2) in the neighboring gp120 protomer. The quaternary contact stabilized the interaction between the modified antibody and the Env trimer by slowing down their dissociation rate. With improved potency, the disclosed modified VRC01-class antibodies are potential candidates for application in HIV-1 therapy and prevention.

Introduction

The native HIV-1-envelope (Env) spike on the surface of mature virions is the sole functional form that mediates viral attachment and entry, and thereby represents the major target for neutralizing antibodies and a central focus for vaccine development. The native spike is a trimer of gp120-gp41 heterodimers constrained into a metastable structure, which evades immunologic control by a variety of mechanisms, including antigenic variability, N-linked glycosylation, and conformational masking of the conserved receptor-binding sites. Upon binding to the primary cellular receptor, CD4, the external gp120 Env glycoprotein undergoes major conformational changes, transitioning to a state that is competent for interaction with a coreceptor, CCR5 or CXCR4. The CD4-binding site (CD4-BS) of gp120, which is a critical target of broad-spectrum neutralizing antibodies, has been finely mapped by both mutagenesis and co-crystallization in complex with soluble CD4 (sCD4). However, most studies were performed with monomeric gp120 subunits, thereby hindering the evaluation of the role of quaternary elements assembled in the pre-fusion trimeric structure that may be involved in the initial CD4 interaction. Quaternary interactions with an adjacent gp120 protomer have previously been documented by cryogenic electron microscopy (cryo-EM) and crystallography, respectively, for two monoclonal antibodies (mAbs) directed to the CD4 supersite, VRC-PG04 and VRC01. In addition, in silico docking to model quaternary trimer interactions for additional anti-CD4-BS mAbs and for sCD4 itself predicted contacts of VRC01 and sCD4 with a limited surface of the α0 helix of an adjacent protomer, as well as more extensive contacts of other mAbs with basic residues in C2 and the V3 loop; however, the functional significance of these interactions was not investigated.

Considerable progress has been made in the elucidation of the molecular anatomy of the HIV-1 Env spike, particularly with the design and crystallization of soluble truncated trimers (SOSIP.664) stabilized in a near-native configuration and the increasing resolution of cryo-EM imaging of native, membrane-bound Env spikes. Nevertheless, obtaining structural information on the initial contact of CD4 with the pre-fusion trimer has remained a challenging endeavor, primarily due to the rapid transition of the trimer toward an open configuration upon CD4 interaction. Using a combination of structural modeling, targeted mutagenesis and cryo-EM, recent evidence shows that the functional HIV-1 Env trimer interacts with CD4 through a quaternary surface formed by coalescence of the previously defined CD4-contact region in the gp120 outer domain with a second binding site (CD4-BS2) in the inner domain of a neighboring gp120 protomer (see Liu et al., "Quaternary contact in the initial interaction of CD4 with the HIV-envelope trimer," Nat. Struct. Mol. Biol., 24(4)370-378, 2017). Disruption of CD4-BS2 in diverse HIV-1 Envs was found to reduce the stability of CD4-trimer interaction and to fully abrogate HIV-1 infectivity by preventing the acquisition of coreceptor-binding competence. A corresponding reduction in HIV-1 infectivity was seen upon mutation of CD4 residues that interact with CD4-BS2. A 6.8-Å cryoEM structure of a stabilized trimer (DS-SOSIP) in complex with soluble CD4 confirmed the quaternary contact. Similar to CD4, it was also found that selected neutralizing human antibodies to the CD4 antigenic supersite, most notably VRC03, VRC06 and VRC-CH31, interact with a quaternary surface that partially overlaps with CD4-BS2, providing evidence that this region is immunogenic in vivo (see Liu et al., "Quaternary contact in the initial interaction of CD4 with the HIV-envelope trimer," Nat. Struct. Mol. Biol., 24(4)370-378, 2017).

In this Example, structure-based rational engineering was employed to modify some of the most potent VRC01-class antibodies against the CD4 supersite derived from chronically HIV-1-infected individuals by engrafting the extended heavy chain framework 3 (HFR3) loop of VRC03. The engraftment was successful and enabled the resulting chimeric antibodies to establish quaternary contacts with a second gp120 protomer in the HIV Env trimeric spike. Chimeric antibodies displayed enhanced binding affinity for the closed Env trimer and increased neutralizing potency against a majority of primary HIV-1 isolates of different clades. These results have implications for the development of increasingly effective strategies for HIV-1 treatment and prevention.

Selected Broadly Neutralizing Antibodies to the CD4 Antigenic Supersite Interact with the Quaternary Surface Through Extended HFR3 Loops CD4BS antibodies were docked to an Env trimer structure (PDB ID: 4TVP) by aligning the antibody-bound monomeric gp120 to one gp120 protomer of the trimer (see FIG. 1A). The antibody binding surface on the classic CD4BS is largely overlapping. However, some antibodies like VRC03 and VRC06 seem to also establish contact with the neighboring protomer of the Env trimer. The sequence alignment showed that the heavy chain of VRC03 and VRC06 contains an extended FR3 loop unlike the other CD4BS antibodies (FIG. 1B). This long FR3 loop is similar to a recently reported region of CD4 that contacts CD4-BS2, which is located on the inner domain of the neighboring gp120 protomer. Mutations on CD4-BS2 reduced the binding of the Env trimer to bind these antibodies. To further investigate the functional role the FR3 loops, FR3-deletion mutants of VRC03 and VRC06 were created by replacing the FR3 loop with a GPG (glycine-proline-glycine) linker (FIG. 1C), and binding to HIV-1 Env and neutralization of HIV-1 pseudovirus were assessed.

For binding assays, the BG505 SOSIP.664 Env ectodomain trimer at 2 μg/ml was coated on 96-well plates overnight at 4° C. Plates were blocked with BLOTTO buffer (PBS, 1% FBS, 5% non-fat milk) for 1 h at room temperature, followed by incubation with antibody serially diluted in disruption buffer (PBS, 5% FBS, 2% BSA, 1% Tween-20) for 1 h at room temperature. 1:10,000 dilution of horseradish peroxidase (HRP)-conjugated goat anti-human IgG antibody was added for 1 h at room temperature. Plates were washed between each step with 0.2% Tween 20 in PBS. Plates were developed using 3,3',5,5'-tetramethylbenzidine (TMB) (Sigma-Aldrich) and read at 450 nm.

Neutralization activity of the monoclonal antibodies was assessed using single-round HIV-1 Env-pseudovirus infection of TZM-bl cells as described previously (Li et al., J. Virol., 79, 10108-10125, 2005). Heat-inactivated patient serum or monoclonal antibody (mAb) was serially diluted five-fold with Dulbecco's modified Eagle medium 10% FCS (Gibco), and 10 μl of serum or mAb was incubated with 40 μl of pseudovirus in a 96-well plate at 37° C. for 30 min. TZM-bl cells were then added and plates were incubated for 48 h. Assays were then developed with a luciferase assay system (Promega, Finnboda Varvsväg, Sweden), and the relative light units (RLU) were read on a luminometer (Perkin Elmer).

As shown in FIGS. 1E and 1F, the deletion mutants lost the ability to bind to the BG505 SOSIP.664, and their neutralizing capacity was impaired as shown on two HIV-1 isolates (FIGS. 1E and 1F). These results indicate an essential role of the long FR3 loop making CD4-BS2 contact in the function of these mAbs.

Engraftment of Extended Quaternary-Contacting HFR3 Loops into VRC01

Figure 2A:
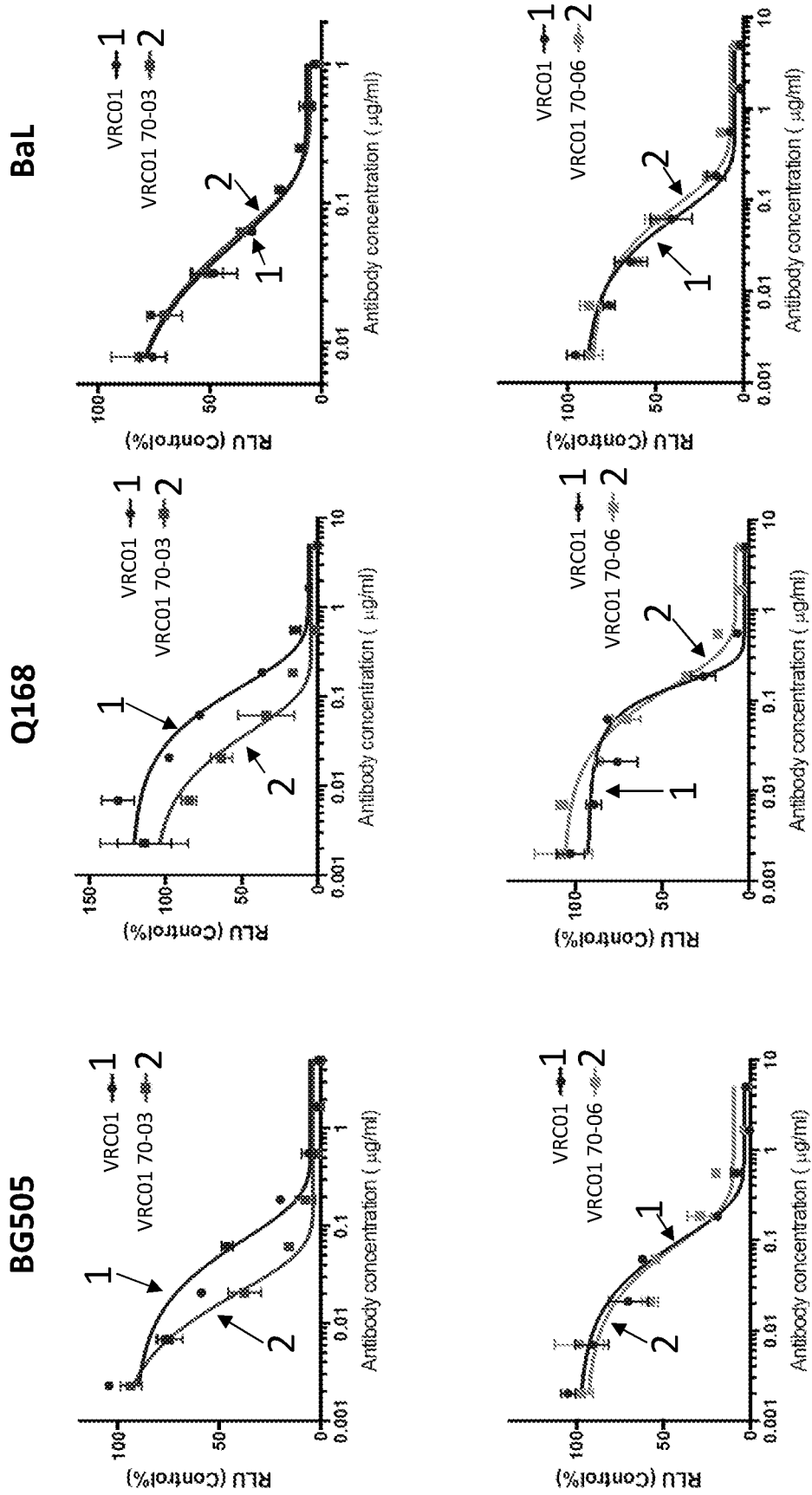

It was hypothesized that the FR3 loop of VRC03 and VRC06 could be engrafted onto other CD4-BS antibodies like VRC01, and enable them to establish quaternary contact with the Env trimer and potentially improve their potency (see sequences in FIG. 1C). To test this hypothesis, the FR3 loop (12 aa: 72-83) of VRC03 and VRC06, respectively, was introduced into VRC01 producing two chimeric antibodies that were designated VRC01 70-03 and VRC01 70-06. The antibodies were produced in mammalian cells and purified by affinity chromatography. Neutralization was assessed using the pseudovirus assay described above. The neutralizing capacity was clearly increased for VRC01 70-03 but not VRC01 70-06 when these chimeras were tested against 5 HIV isolates from different HIV-1 clades (FIG. 2). Three out of 5 isolates were more sensitive to chimeric VRC01 70-03 than to WT VRC01. Neutralization of two other isolates, BaL and C1080, was not affected or slightly reduced. Based on these results, it was concluded that VRC01 can be improved by elongation of the FR3 loop from VRC03, but not from VRC06.

Engraftment of the VRC03 HFR3 Loop into Multiple VRC01-Class Antibodies Increases the Neutralization Potency Against a Majority of Primary HIV-1 Strains Next, it was tested if FR3 engraftment could be applied to other CD4BS antibodies, especially those with very high potency and breadth (FIG. 3). Using the same strategy, chimeric antibodies based on N6, VRC07, and 3BNC117 were created. A small global panel of 12 HIV-1 isolates was used to evaluate the neutralizing capacity of the chimeric antibodies. For VRC07, 80% of the isolates were more sensitive to the chimeric antibody than to the WT form. The majority of the isolates were more sensitive to the chimeric forms of VRC01, VRC07 and N6. Antibody 3BNC117 was an exception, with a reduced neutralization against half of the isolates tested. Notably, 3BNC117 contains a longer FR3 than N6, VRC01 and VRC07, which has a potential contact with V3 from the neighboring gp120 protomer. As a result, further elongation of FR3 probably didn't strengthen but disrupt this natural contact.

Engraftment of the HFR3 Loop Enhances the Binding Affinity for the Prefusion Env Trimer The binding affinity of the chimeric antibody to soluble Env trimers was examined by ELISA (FIG. 4). Chimeric N6 70-03 showed a higher binding affinity to BG505 SOSIP.664 than the WT form. Binding of VRC01 70-03 was also slightly increased. For JRFL SOSIP.664, both of the chimeric antibodies had similar binding level compared to their WT forms. These results are corresponding to the observation that neutralization of the chimeras is improved to the BG505 but not to JRFL. Binding assay with Fabs of chimeric antibodies were also performed by surface plasmon resonance (SPR). mAb 2G12 was used to capture the BG505 SOSIP.664 trimer and the chimeric antibodies used in the flow phase. The increased binding of the two chimeras to the Env trimer was confirmed by SPR measurements. Engraftment of the FR3 loop had a limited impact on the on-rate of the chimeras but significantly slowed down the off-rate. These results demonstrated that the engrafted FR3 stabilizes the interaction of the antibody with the Env trimer.

Figures 4B, 5:
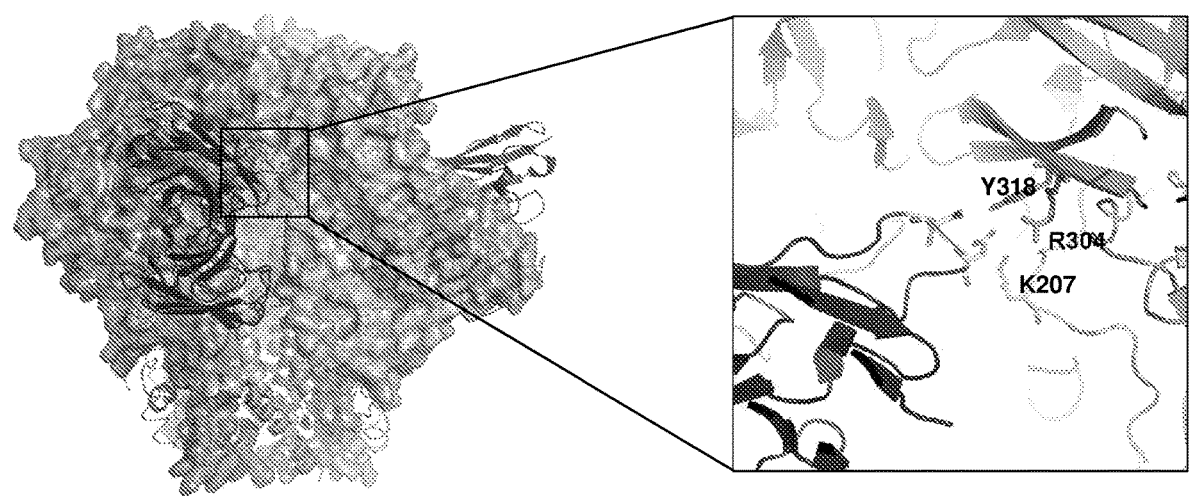

Crystal Structure of VRC03-Loop Chimeric N6 Antibody in Complex with the BG505 SOSIP-664 Trimer To gain structural insights into the interaction of the chimeric antibody with the HIV Env trimer, a crystal structure of chimeric antibody N6 70-03 complexed with the BG505 SOSIP.664 trimer was solved (FIG. 5). The elongated FR3 loop was well defined and showed a conformation similar to that of the FR3 loop in the VRC03 structure. Besides contacting CD4BS2, mostly with residue K207, the FR3 loop also seems to make contact with residues in the V3 base of the neighboring gp120 protomer, especially two amino acids with long side chains, R304 and Y318. Structure alignment showed that the overall orientation of the N6 70-03 is close to that of the WT form. It seems that the elongated FR3 loop is simply inducing an additional interaction without affecting the 'classic' binding. By stabilizing this quaternary contact, the FR3 loop confers an improved binding capacity on the chimeras.

Figure 6A:
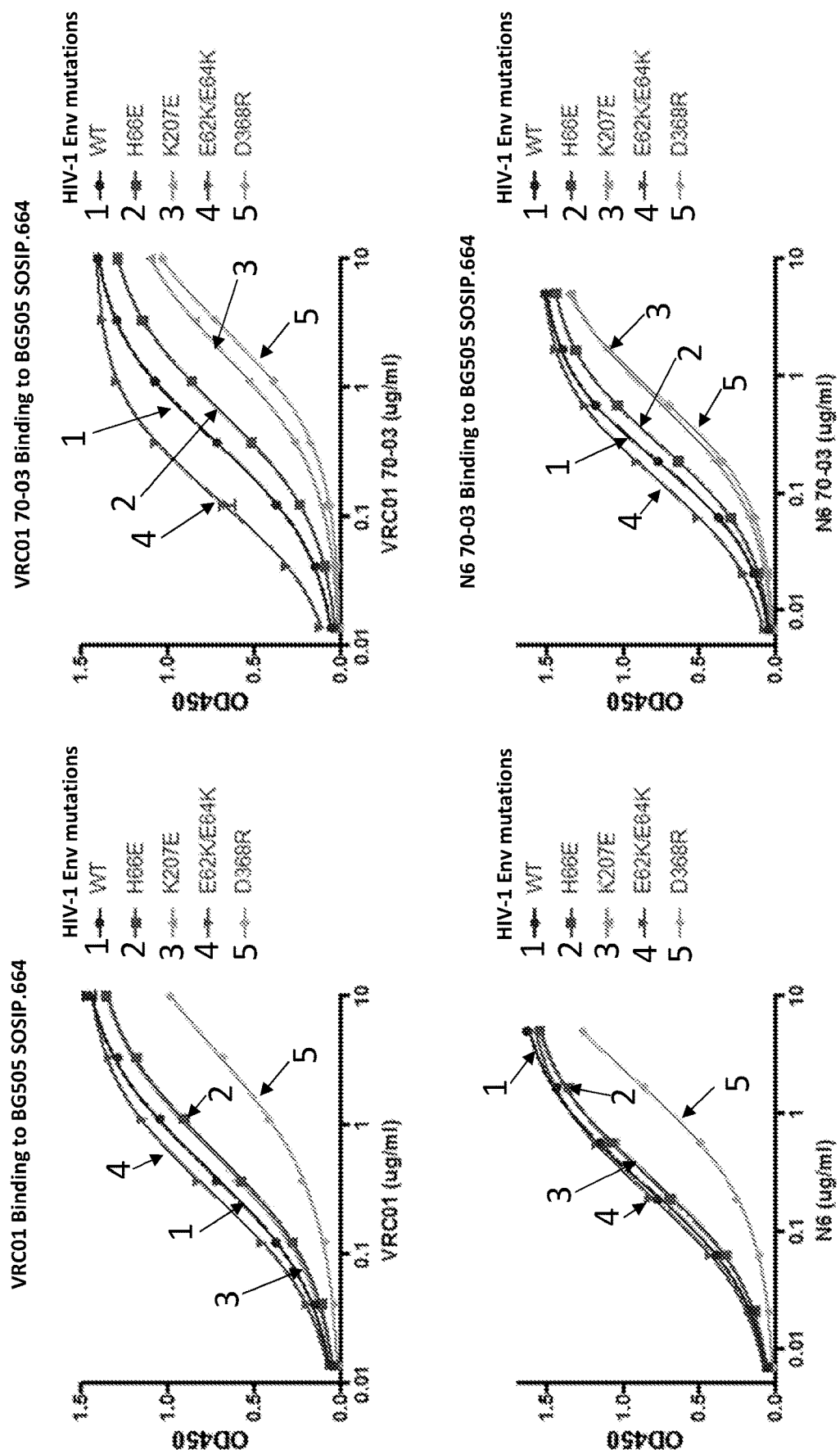
FIGS. 6A and 6B. Mapping of binding interface by mutagenesis. (6A) The binding of WT VRC01 and WT N6 to HIV-1 Env is not altered by mutations on the CD4BS2 of HIV Env trimer. However, the binding affinity of chimeric antibodies to the CD4BS2 mutant K207E is reduced, suggesting the important role of this residue in the contact with FR3 loop. Mutations at other sites has minimal or no impact. The 368R is a control mutation on primary CD4 binding site. (B) Mutations at 304 and 318 in the Env caused almost no change in the neutralization sensitivity of pseudo-particles to WT VRC01 and WT N6. But for the N6 70-03 and VRC01 70-03 antibodies, pseudoviruses carrying mutated Env especially at site 304 became less sensitive. These data indicate that the key residues in the Env trimer that account for the interaction with the transplanted FR3 loop.
Figure 6B:
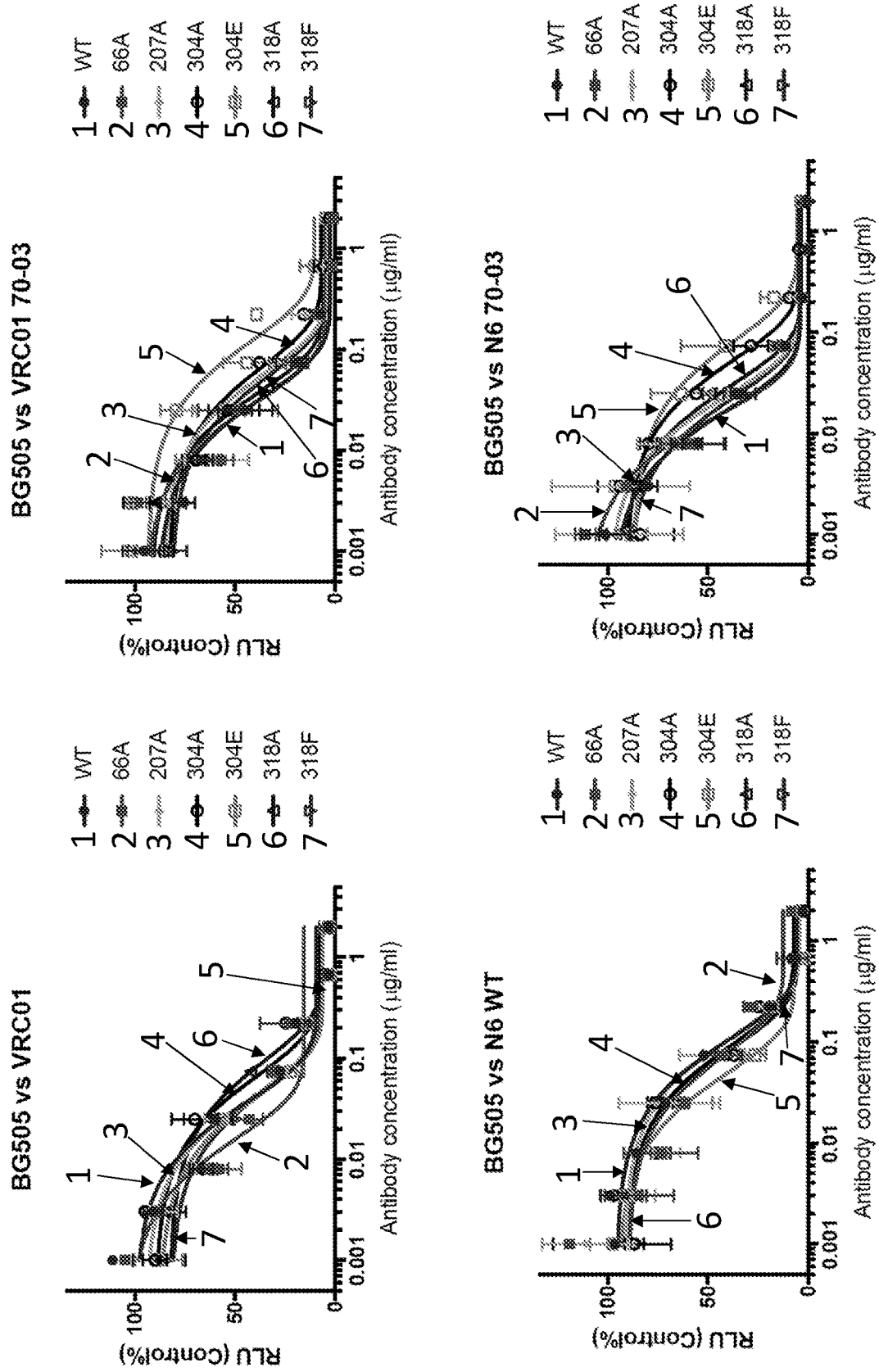

Mapping of the Chimeric Antibody Interactive Surface Reveals Quaternary Contacts within the V3-Loop Region of a Neighboring Gp120 Protomer To experimentally verify the quaternary interaction between the FR3 loop and the neighboring protomer, the key binding residues identified based on the crystal structure were mutated and the resulting HIV-1 Env assessed for binding to the antibodies with the 70-03 modification (FIG. 6). Pseudoviruses were produced bearing the mutated Env and tested for neutralization sensitivity to the WT and chimeric antibodies. If the mutation site of the Env is involved in the quaternary contact with the engrafted FR3, the corresponding pseudovirus should become less sensitive to the chimeric antibody compared the WT viruses. Mutation at sites 66 and 318 had no effect, while mutation of K207 has a moderate impact reducing the sensitivity to the chimeric antibodies. The most pronounced change was seen with the R304E mutant, with a reduction in N6 70-03 neutralization sensitivity by ~8-fold (IC50: 0.053 µg/ml) compared to the WT virus (IC50: 0.007 µg/ml). The same trend was observed with the chimeric VRC01 70-03. These results confirmed the functional role of the quaternary interaction between the chimeric antibody and the Env trimer, and confirmed that the FR3-contacting region on the Env trimer involves two key residues, K207 and R304. Other residues like Y318 may also be involved, but their role appears to be less dominant.

Modification of the VRC01 20's Loop

Figure 7A:
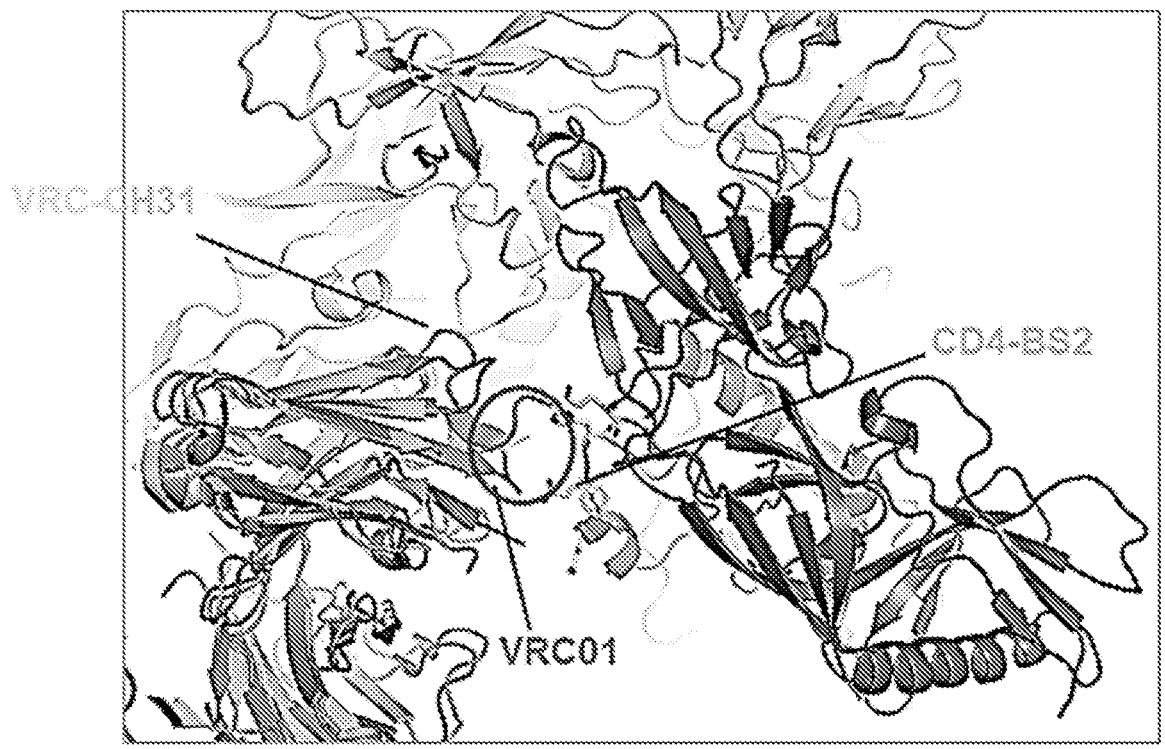

VRC-CH31 contains a longer 20s' loop in HCDR1 region than VRC01. Part of this 20s' loop was transplanted to VRC01 with linkers of various length to determine if the modification could increase HIV-1 Env binding or HIV-1 neutralization. The modified sequences are illustrated in FIG. 7A. HIV-1 neutralization was assessed by pseudovirus neutralization assay as discussed above. As shown in FIG. 7B, compared to the WT VRC01, all the 20s' loop chimeras were less potent for neutralization of the BG505 and BaL HIV-1 isolates.

Further Modification of the VRC01 HFR3 Loop

Further optimization of the 70-03 modification in chimeric VRC01 was not successful (FIG. 8). The length (8A) or the composition (8B) of the HFR3 loop in the VRC01 70-03 was varied, but all loop-modified mutants were less potent for HIV-1 neutralization than the original VRC01 70-03 design.

Example 2

Modified VRC01-Class Antibodies

This example illustrates additional modified VRC01-class antibodies, including the VRC01.23 antibody, which neutralized 96% of HIV-1 pseudoviruses with a median IC50 of 0.042 µg/ml on a 208-virus panel.

As noted above, the VRC01 antibody modified with the 70-03 mutation provided improved binding to HIV-1 Env, and increased HIV-1 neutralization, relative to the parent VRC01 antibody. A matrix of additional VRC01 variants was assessed to determine if additional modifications could further improve the properties of VRC01. The modifications in the matrix included a G54W substitution in the heavy chain variable region (e.g., as described in the context of NIH45-46 G54W antibody in Diskin et al., Science, 334 (6060): 1289-1293, 2011), the 70-03 substitution described herein, a four amino acid ARDY insertion in the HCDR3 (as present in VRC07 HCDR3), a 2 amino acid deletion at the N-terminus of the light chain variable region coupled with a serine substitution at the third position of the light chain variable region (2aa_del_V3S; e.g., as described in the context of VRC07 antibody in Rudicell et al., J. Virol., 88(21): 12669-12682, 2014), and a 3 amino acid deletion at the N-terminus of the light chain variable region (3aa_del; e.g., as described in the context of VRC07 antibody in Rudicell et al., J. Virol., 88(21): 12669-12682, 20141. The matrix of modified VRC01 antibodies included the following:

| Name | VH modifications relative to VRC01 | VL modifications relative to VRC01 |
| --- | --- | --- |
| VRC01.11 | G54W | — |
| .12 | | 2aa_del_V3S |
| .13 | | _3aa_del |
| VRC01.21 | G54W | — |
| .22 | 70-03 | 2aa_del_V3S |
| .23 | | 3aa_del |
| VRC01.31 | G54W | — |
| .32 | HCDR3 (VRC07) | 2aa_del_V3S |
| .33 | | 3aa_del |
| VRC01.41 | G54W | — |
| .42 | 70-03 | 2aa_del_V3S |
| .43 | HCDR3 (VRC07) | 3aa_del |

The antibodies were produced as an IgG1 in mammalian cells and purified by affinity chromatography, substantially as described in Rudicell et al. (J. Virol. 88(21): 12669-12682, 2014). The heavy chain is an IgG1 including the "LS" mutation to increase serum half-life.

Neutralization activity of the monoclonal antibodies was assessed using single-round HIV-1 Env-pseudovirus infection of TZM-bl cells as described previously (Li et al., J. Virol., 79, 10108-10125, 2005). Heat-inactivated patient serum or monoclonal antibody (mAb) was serially diluted five-fold with Dulbecco's modified Eagle medium 10% FCS (Gibco), and 10 µl of serum or mAb was incubated with 40 µl of pseudovirus in a 96-well plate at 37° C. for 30 min. TZM-bl cells were then added and plates were incubated for 48 h. Assays were then developed with a luciferase assay system (Promega, Finnboda Varvsväg, Sweden), and the relative light units (RLU) were read on a luminometer (Perkin Elmer).

Initial assessment included HIV-1 neutralization on a small panel of diverse HIV-1 Env pseudoviruses. As shown in FIGS. 9A and 9B, the VRC01.23 exhibited a surprising improvement in neutralization potency based on the pseudoviruses in the panel.

The sequences of the VRC01.23 $V_H$ and VL are provided as SEQ ID NOs: 84 and 85, respectively. The sequences of the full heavy and light chains are provided as SEQ ID NOs: 91 and 92, respectively.

Figure 10B:
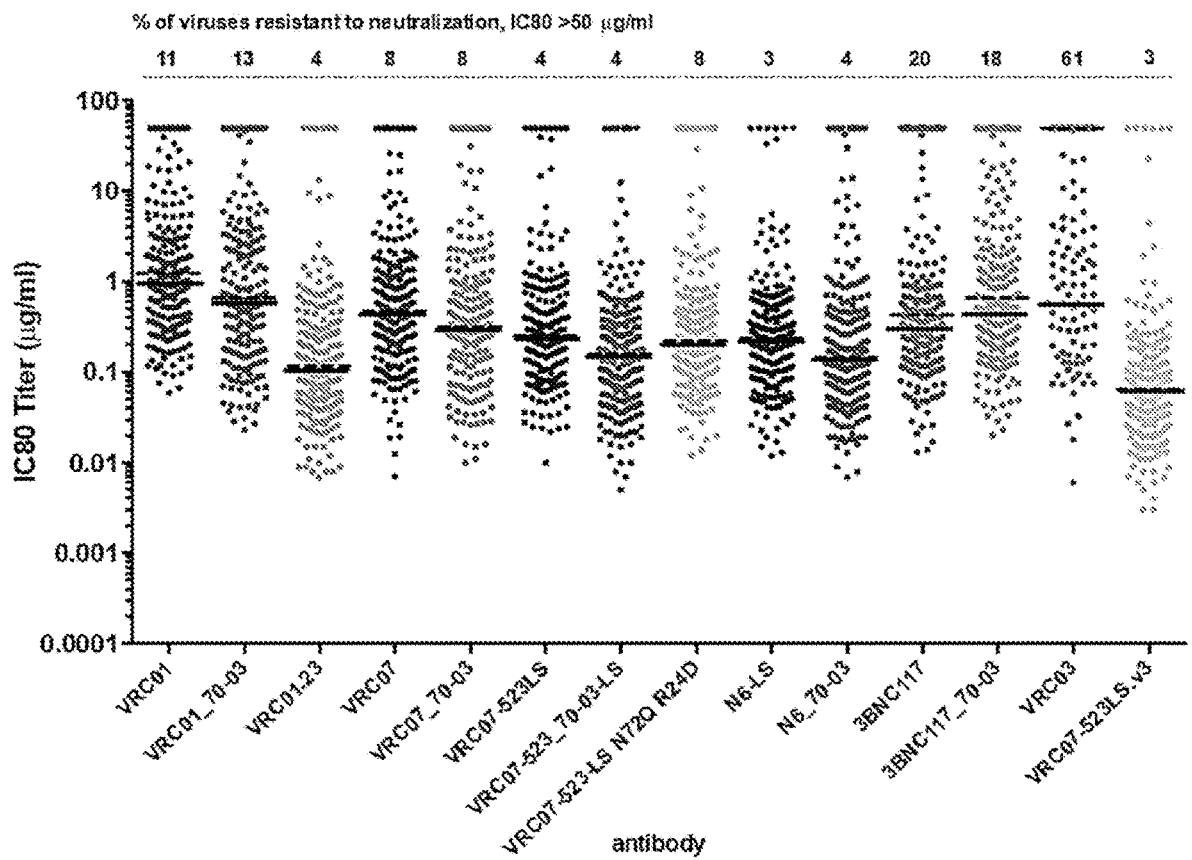

To confirm the improved potency of VRC01.23, this antibody as well as several other VRC01-class antibodies (including several with the 70-03 modification), were assessed for neutralization on a panel of 208 diverse HIV-1 Env pseudoviruses. The assay was performed substantially as described previously (see Kwon et al., Cell Reports, 22, 1798-1809, 2018). As shown in FIGS. 10A-10C, the VRC01.23 exhibited a surprising improvement in neutralization potency relative to the other antibodies assessed in the neutralization panel. It is believed that VRC01.23 is one of the most potent CD4-binding site antibody thus far identified.

Figure 11A:
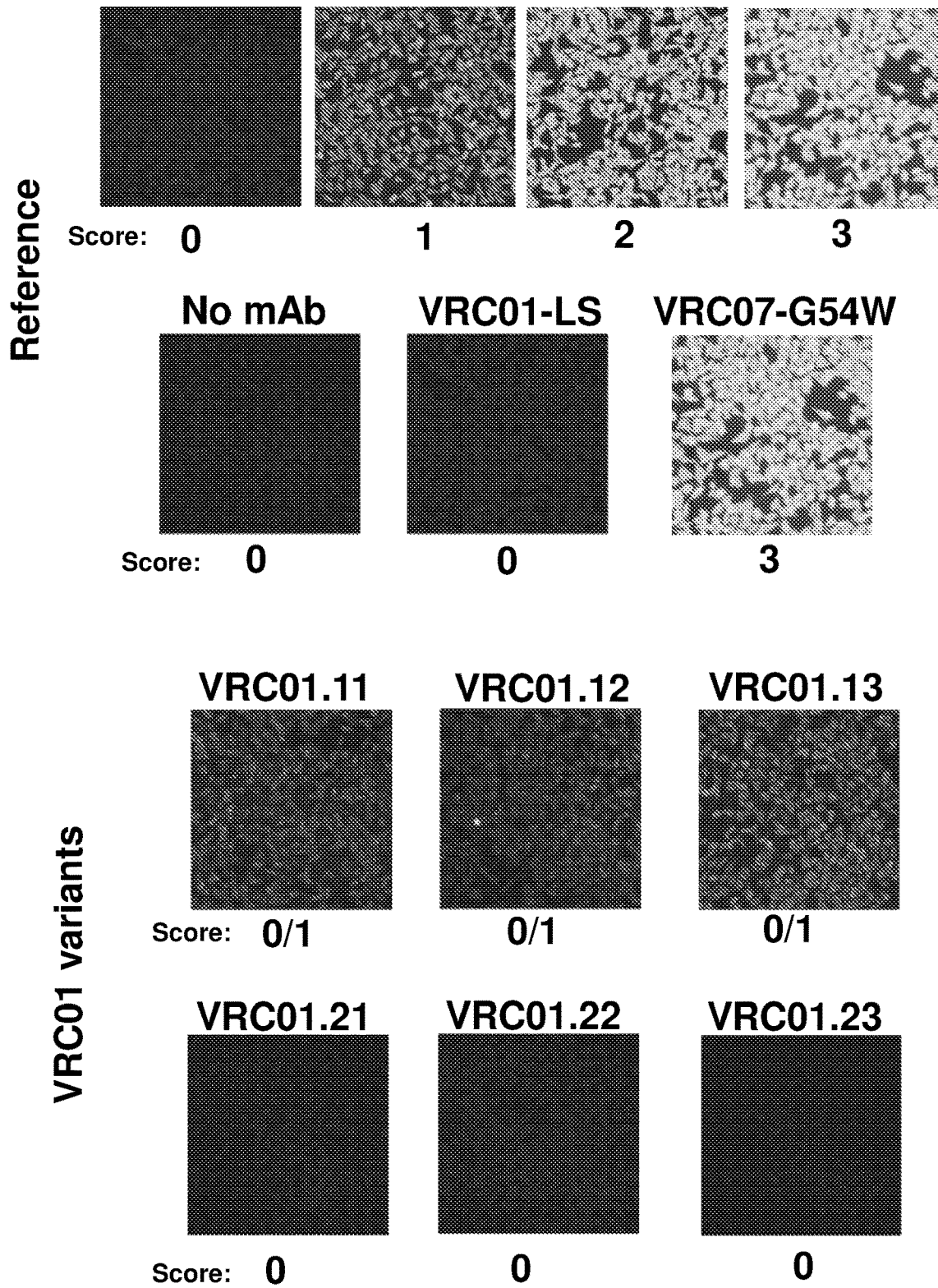
FIGS. 11A and 11B show results of an in vitro autoreactivity assay. Several different VRC01 variants were assessed for autoreactivity in a HEp-2 cell staining assay. The staining score (on a scale of 0-4) for reference antibodies, as well as the VRC01 variants is shown for assays completed at 25 μg/ml antibody (FIG. 11A) and 50 μg/ml antibody (FIG. 11B).
Figure 11B:
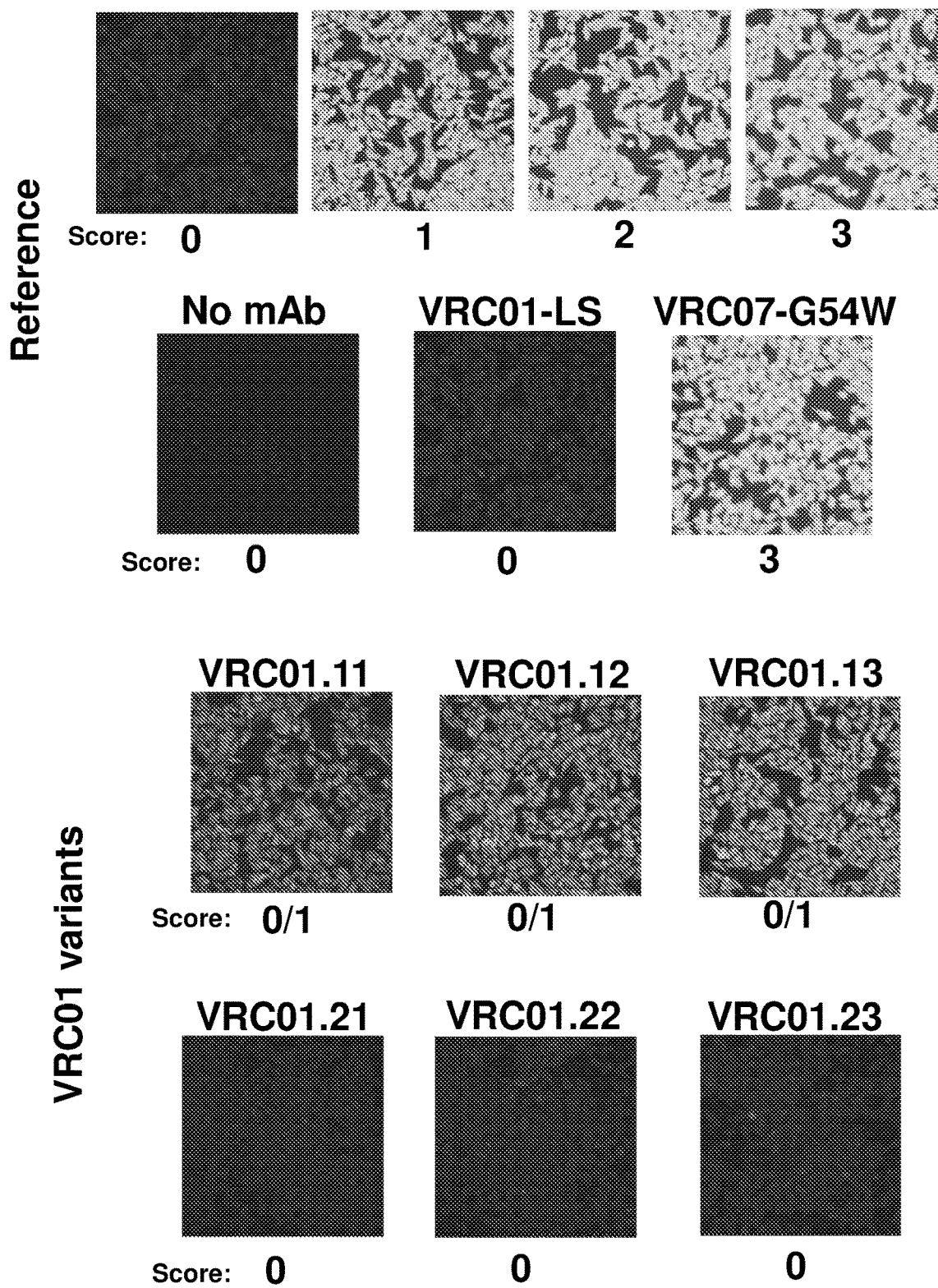

The reactivity of the VRC01 variants to HIV-1 negative human epithelial (HEp-2) cells was determined by indirect immunofluorescence on slides using Evans Blue as a counterstain and FITC-conjugated goat anti-human IgG according to previously described methods (Haynes et al., Science, 308, 1906-1908, 2005). The staining score (on a scale of 0-4) for reference antibodies, as well as the VRC01 variants is shown for assays completed at 25 µg/ml and 50 µg/ml antibody (FIG. 11). The introduction of the 70-03 modification significantly reduced autoreactivity.

The in vivo half-life of the VRC01.23LS antibody was assessed in mice with a humanized neonatal Fc receptor (FcRn) and in Rhesus macaques (FIG. 12). As shown in the figure, introduction of the G54W, 70-03, and 3-amino acid deletion in the light chain did not alter the in vivo half-life of VRC01.23LS relative to VRC01LS in mice with a humanized FcRn as well as in rhesus macaques. Additionally, the in vivo half-life of the VRC07-523LS 70-03 antibody was assessed in mice with a humanized neonatal Fc receptor (FcRn) and in Rhesus macaques (FIG. 12). As shown in the figure, introduction of the 70-03 mutation slightly increased the in vivo half-life of VRC07-523LS 70-03 relative to VRC07-523LS in these animal models.

Example 3

Modified VRC01-Class Antibodies

As discussed in Example 2, modification of VRC01 to include the G54W substitution in the HCDR2, the 70-03 substitution in the heavy chain FR3, and the deletion of the first three amino acids of the light chain variable region (ΔEIV) generated a VRC01-class antibody (VRC01.23) with exceptional potency for neutralization of HIV-1.

To further assess the impact of these modifications on VRC01-class antibodies, as well as a few additional modifications (including a phenylalanine substitution at Kabat position 54 of the heavy chain, a two-amino acid deletion at the N-terminus of the light chain, and a Y98S in the N6 light chain, and) a further matrix of VRC01-class variants was assessed. The matrix of antibodies included:

| Name | Parent antibody | $V_H$ modifications | $V_H$ SEQ ID NO | $V_L$ modifications | $V_L$ SEQ ID NO |
|---|---|---|---|---|---|
| N49P7.v1 | N49P7 | G54W | 105 | — | 88 |
| N49P7.v2 | | 70-03 | | 2aa_del | 106 |
| N49P7.v3 | | | | 3aa_del | 107 |
| VRC08.v1 | VRC08 | G54W | 108 | — | 90 |
| VRC08.v2 | | 70-03 | | 2aa_del | 109 |
| VRC08.v3 | | | | 3aa_del | 110 |
| 3BNC117.v1 | 3BNC117 | T54W | 111 | — | 9 |
| 3BNC117.v2 | | | | 2aa_del | 113 |
| 3BNC117.v3 | | | | 3aa_del | 114 |
| 3BNC117.v4 | | T54W | 112 | — | 9 |
| 3BNC117.v5 | | 70-03 | | 2aa_del | 113 |
| 3BNC117.v6 | | | | 3aa_del | 114 |
| N6.v1 | N6 | 70-03 | 16 | — | 2 |
| N6.v2 | | | | 2aa_del | 97 |
| N6.v3 | | | | 3aa_del | 98 |
| N6.v4 | | 70-03 | 96 | — | 2 |
| N6.v5 | | Y98S | | 2aa_del | 97 |
| N6.v6 | | | | 3aa_del | 98 |
| VRC07-523.v1 | VRC07-523 | 70-03 | 102 | 3aa_del | 103 |
| VRC07-523.v2 | | H54F | | 3aa_del_R24D, N72Q | 104 |
| VRC07-523.v3 | | 70-03 | 101 | 3aa_del | 103 |
| VRC07-523.v4 | | H54W | | 3aa_del_R24D, N72Q | 104 |

The antibodies were produced as an $IgG_1$ with the "LS" mutation to increase serum half-life as described above.

Neutralization activity of the monoclonal antibodies was assessed using single-round HIV-1 Env-pseudovirus infection of TZM-bl cells as described previously (Li et al., J. Virol., 79, 10108-10125, 2005). Heat-inactivated patient serum or monoclonal antibody (mAb) was serially diluted five-fold with Dulbecco's modified Eagle medium 10% FCS (Gibco), and 10 µl of serum or mAb was incubated with 40 µl of pseudovirus in a 96-well plate at 37° C. for 30 min. TZM-bl cells were then added and plates were incubated for 48 h. Assays were then developed with a luciferase assay system (Promega, Finnboda Varvsväg, Sweden), and the relative light units (RLU) were read on a luminometer (Perkin Elmer). For geometric mean and median calculation, >50's were treated as 50.

Assessment included HIV-1 neutralization on a small panel of diverse HIV-1 Env pseudoviruses; and IC50 and IC80 values were determined (FIGS. 13A-13H). The N49P7.v2 and .v3, and VRC07-523LS.v1-v4 showed improved potency in the 12-virus panel neutralization assay.

One of the antibodies (VRC07-523LS.v3) was assessed for neutralization on the panel of 208 diverse HIV-1 Env pseudoviruses described above. As shown in FIGS. 10A-10C, VRC07-523LS.v3 was found to be even more potent than VRC01.23 in this neutralization screen. Another antibody, (VRC07-523LS.v1) was assessed for neutralization on a slightly smaller panel of 140 diverse HIV-1 Env pseudoviruses as described above. As shown in FIG. 14, VRC07-523LS.v1 was also more potent than VRC01.23 in this neutralization screen (compare FIG. 14 to FIG. 10).

Figure 15A:
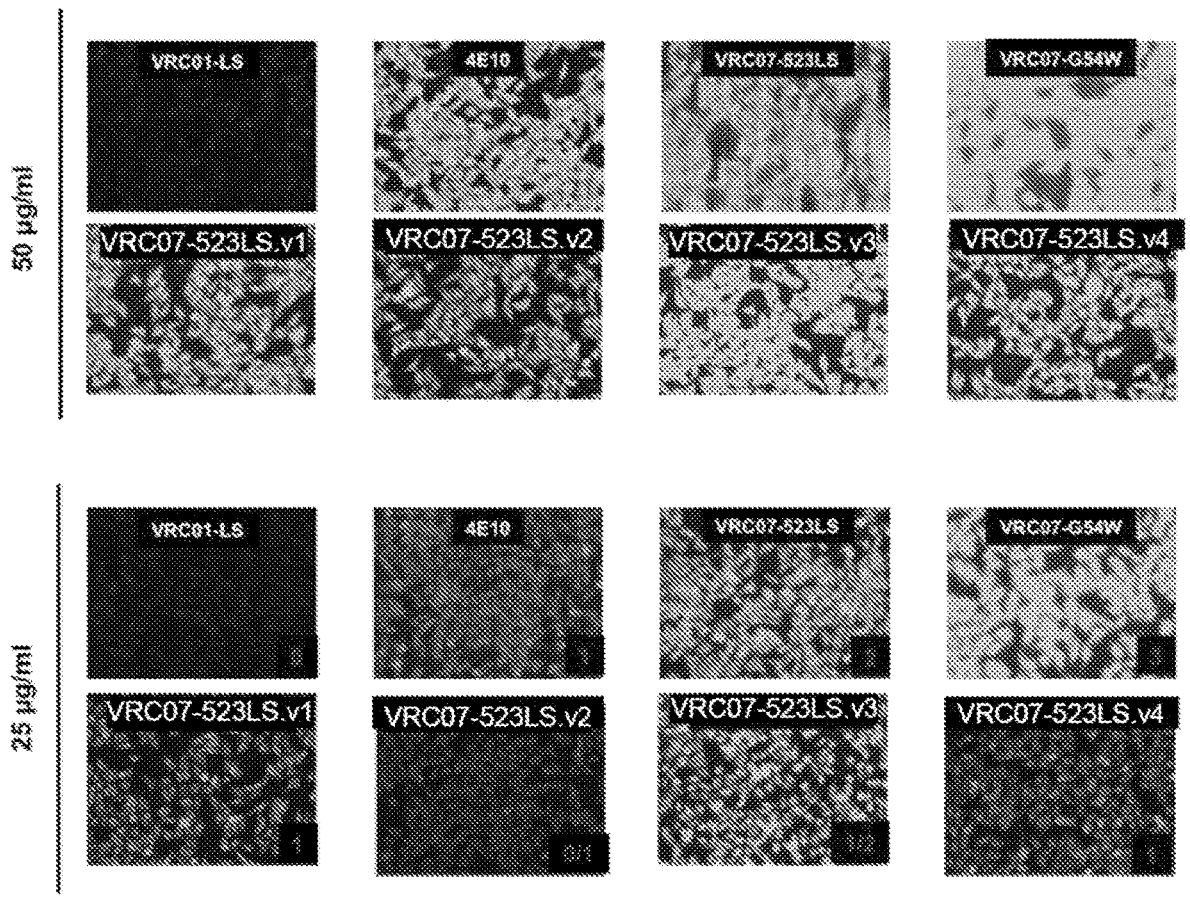
Figure 15B:
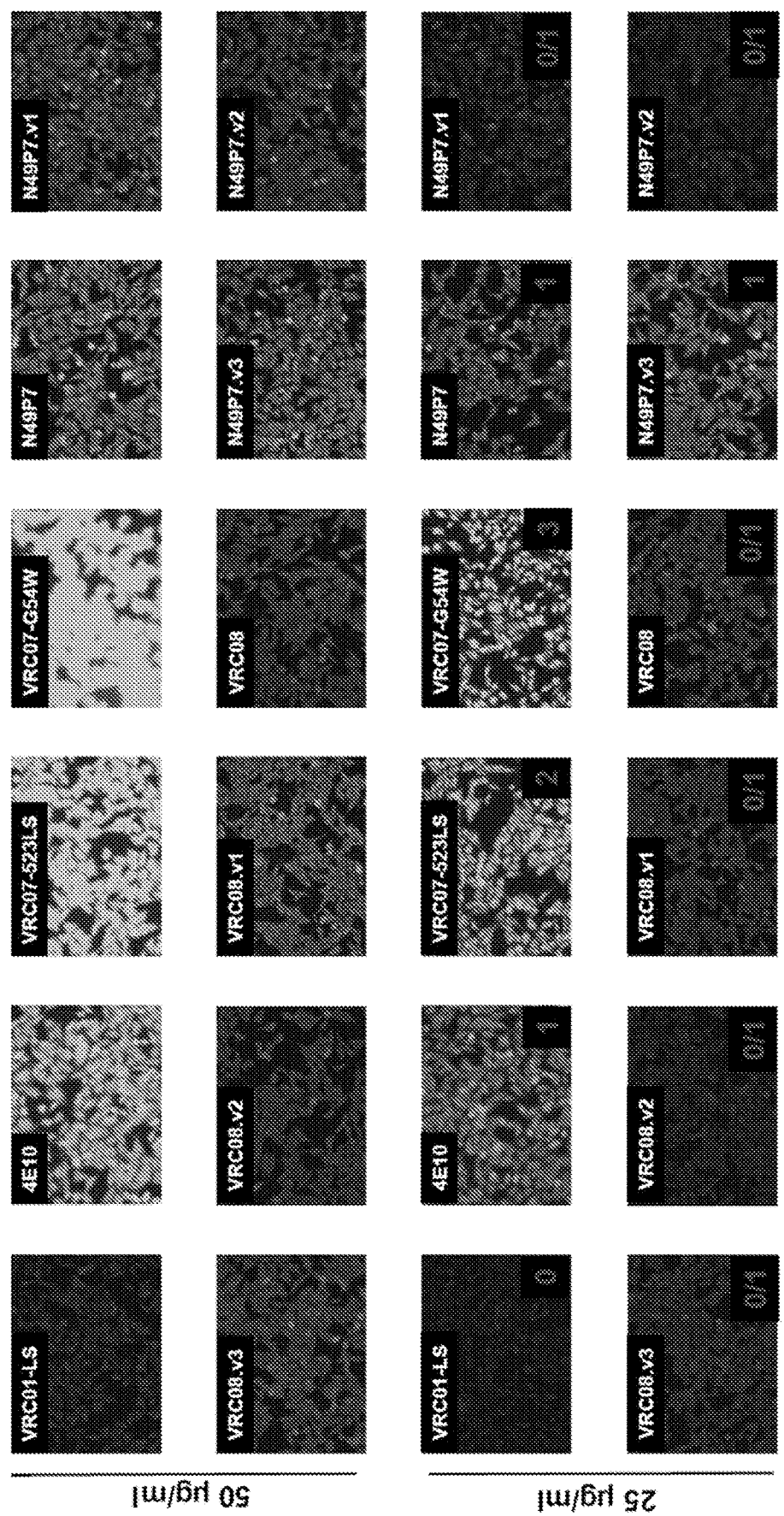

ANA HEp-2 staining analysis and anti-cardiolipin ELISA were performed to test the auto-reactivity of the VRC01- class variants. The HEp-2 staining assays were performed as described above. The anti-cardiolipin ELISA was performed as described in Asokan et al. J. Virol., doi: 10.1128/JVI.02097-15, 2015). For the HEp-2 staining analysis, the staining score (on a scale of 0-4) for reference antibodies, as well as the VRC01-class variants is shown for assays completed at 25 μg/ml and 50 μg/ml antibody (FIGS. 15A-15C). The HEp-2 staining score was assigned according to the following:

| HEp-2 Score | Reactivity | Appearance of staining intensity |
|---|---|---|
| 0 | Not reactive | Not reactive |
| 0/1 | Mild reactive | Between VRC01-LS and 4E10 |
| 1 | Reactive | Like 4E10 |
| 1/2 | Reactive | Between 4E10 and VRC07-523-LS |
| 2 | Reactive | VRC07-523-LS |
| 2/3 | Reactive | Between VRC07-523-LS and VRC07-G54W |
| 3 | Reactive | Like VRC07-G54W or greater |

The introduction of 70-03 and G54 modifications on heavy chain or two or three amino acid deletions in the light chain led to decrease in autoreactivity. The results of the anti-cardiolipin ELISA are shown in FIGS. 16A and 16B. The results were scored based on detected GPL units (negative: <20 GPL units; intermediate: 20-80 GPL units; High positive: >80 GPL units).

Example 4

Treatment of HIV-1 Using an HIV-1 Env Specific Antibody

This example describes a particular method that can be used to treat HIV-1 infection in a human subject by administration of a disclosed HIV-1 Env-specific antibody. Although particular methods, dosages, and modes of administrations are provided, one skilled in the art will appreciate that variations can be made without substantially affecting the treatment.

Based upon the teaching disclosed herein, HIV-1 infection can be treated by administering a therapeutically effective amount of one or more of the neutralizing mAbs described herein, thereby reducing or eliminating HIV-1 infection.

Screening Subjects

In particular examples, the subject is first screened to determine if they have an HIV-1 infection. Examples of methods that can be used to screen for HIV-1 infection include a combination of measuring a subject's CD4+ T cell count and the level of HIV-1 virus in serum blood levels. Additional methods using an HIV-1 Env-specific antibody described herein can also be used to screen for HIV-1 infection.

In some examples, HIV-1 testing consists of initial screening with an enzyme-linked immunosorbent assay (ELISA) to detect antibodies to HIV-1. Specimens with a nonreactive result from the initial ELISA are considered HIV-1-negative unless new exposure to an infected partner or partner of unknown HIV-1 status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV-1 infection. Specimens that are repeatedly ELISA-reactive occasionally provide an indeterminate Western blot result, which may be either an incomplete antibody response to HIV-1 in an infected person, or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV-1 in a subject's blood is indicative that the subject is infected with HIV-1 and is a candidate for receiving the therapeutic compositions disclosed herein. Moreover, detection of a CD4+ T cell count below 350 per microliter, such as 200 cells per microliter, is also indicative that the subject is likely to have an HIV-1 infection.

Pre-screening is not required prior to administration of the therapeutic compositions disclosed herein Pre-Treatment of Subjects In particular examples, the subject is treated prior to administration of a therapeutic agent that includes one or more antiretroviral therapies known to those of skill in the art. However, such pre-treatment is not always required, and can be determined by a skilled clinician.

Administration of Therapeutic Compositions

Following subject selection, a therapeutically effective dose of a HIV-1 Env-specific antibody described herein (such as the N6 70-03, VRC01 70-03, VRC07 70-03, VRC07-523 70-03, or VRC-PG04 70-03 antibody) is administered to the subject (such as an adult human or a newborn infant either at risk for contracting HIV-1 or known to be infected with HIV-1). Additional agents, such as anti-viral agents, can also be administered to the subject simultaneously or prior to or following administration of the disclosed agents. Administration can be achieved by any method known in the art, such as oral administration, inhalation, intravenous, intramuscular, intraperitoneal, or subcutaneous.

The amount of the composition administered to prevent, reduce, inhibit, and/or treat HIV-1 or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV-1) in a subject without causing a substantial cytotoxic effect in the subject. An effective amount can be readily determined by one skilled in the art, for example using routine trials establishing dose response curves. As such, these compositions may be formulated with an inert diluent or with a pharmaceutically acceptable carrier.

In one specific example, antibodies are administered at 5 mg per kg every two weeks or 10 mg per kg every two weeks. In another example, antibodies or antibody fragments are administered at 50 ng per kg given twice a week for 2 to 3 weeks.

Administration of the therapeutic compositions can be taken long term (for example over a period of months or years).

Assessment

Following the administration of one or more therapies, subjects with HIV-1 can be monitored for reductions in HIV-1 levels, increases in a subject's CD4+ T cell count, or reductions in one or more clinical symptoms associated with HIV-1 disease. In particular examples, subjects are analyzed one or more times, starting 7 days following treatment. Subjects can be monitored using any method known in the art. For example, biological samples from the subject, including blood, can be obtained and alterations in HIV-1 or CD4+ T cell levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV-1 infection, HIV-1 replication or combination thereof. A partial response may also be an increase in CD4+ T cell count such as at least 350 T cells per microliter.

It will be apparent that the precise details of the methods or compositions described may be varied or modified without departing from the spirit of the described embodiments. We claim all such modifications and variations that fall within the scope and spirit of the claims below.

We claim:

1. A monoclonal antibody, comprising:
a heavy chain variable region ($V_H$) comprising a heavy chain complementarity determining region (HCDR) 1, a HCDR2, and a HCDR3 of a parent VRC01-class antibody;
a light chain variable region ($V_L$) comprising a light chain complementarity determining region (LCDR) 1, a LCDR2, and a LCDR3 of the parent VRC01-class antibody; and
a modification of a heavy chain framework region (HFR) 3 compared to the parent VRC01-class antibody, wherein the modification is a substitution of the amino acids of Kabat positions 72-76 of the parent VRC01-class antibody with the sequence set forth as QLSQDPDDPDWG (SEQ ID NO: 36);
wherein the parent VRC01-class antibody lacks the insertion of SEQ ID NO: 36 at Kabat positions 72-76;
wherein the parent VRC01-class antibody does not contain an amino acid insertion between Kabat positions 75 and 76 compared to an IGHV1-2*02 germline sequence; and
wherein the antibody specifically binds to HIV-1 Env and neutralizes HIV-1.

2. The monoclonal antibody of claim 1, wherein the parent VRC01-class antibody is any one of VRC01, VRC07, VRC07-523, N49P7, or VRC-PG04.

3. A monoclonal antibody, comprising:
a $V_H$ comprising a HCDR 1, a HCDR2, and a HCDR3 of a parent VRC01-class antibody;
a $V_L$ comprising a LCDR 1, a LCDR2, and a LCDR3 of the parent VRC01-class antibody; and wherein:
the parent VRC01-class antibody is VRC01, and the HCDR1, the HCDR2, the HCDR3, the LCDR1, the LCDR2, and the LCDR3 comprise the amino acids sequences set forth as SEQ ID NOs: 26, 27, 28, 29, 30, and 31, respectively;
the parent VRC01-class antibody is VRC07, and the HCDR1, the HCDR2, the HCDR3, the LCDR1, the LCDR2, and the LCDR3 comprise the amino acids sequences set forth as SEQ ID NOs: 32, 33, 34, 29, 30, and 31, respectively;
the parent VRC01-class antibody is VRC07-523, and the HCDR1, the HCDR2, the HCDR3, the LCDR1, the LCDR2, and the LCDR3 comprise the amino acids sequences set forth as SEQ ID NOs: 32, 35, 34, 29, 30, and 31, respectively; or
the parent VRC01-class antibody is VRC-PG04, and the HCDR1, the HCDR2, the HCDR3, the LCDR1, the LCDR2, and the LCDR3 comprise the amino acids sequences set forth as SEQ ID NOs: 59, 60, 61, 62, 63, and 64, respectively,
wherein the monoclonal antibody further comprises a modification of a HFR3 compared to the parent VRC01-class antibody, wherein the modification is a substitution of the amino acids of Kabat positions 72-76 of the parent VRC01-class antibody with the sequence set forth as QLSQDPDDPDWG (SEQ ID NO: 36),
and wherein the antibody specifically binds to HIV-1 Env and neutralizes HIV-1.

4. The monoclonal antibody of claim 3, wherein
the parent VRC01-class antibody is VRC01, and the amino acid sequences of the $V_H$ and $V_L$ are at least 90% identical to SEQ ID NOs: 17 and 4, respectively, and wherein the HCDR1, the HCDR2, the HCDR3, the LCDR1, the LCDR2, and the LCDR3 comprise the amino acids sequences set forth as SEQ ID NOs: 26, 27, 28, 29, 30, and 31, respectively;
the parent VRC01-class antibody is VRC07, and the amino acid sequences of the $V_H$ and $V_L$ are at least 90% identical to SEQ ID NOs: 18 and 4, respectively, and wherein the HCDR1 the HCDR2, the HCDR3, the LCDR1, the LCDR2, and the LCDR3 comprise the amino acids sequences set forth as SEQ ID NOs: 32, 33, 34, 29, 30, and 31, respectively;
the parent VRC01-class antibody is VRC07-523, and the amino acid sequences of the $V_H$ and $V_L$ are at least 90% identical to SEQ ID NOs: 19 and 7, respectively, and wherein the HCDR1, the HCDR2, the HCDR3, the LCDR1, the LCDR2, and the LCDR3 comprise the amino acids sequences set forth as SEQ ID NOs: 32, 35, 34, 29, 30, and 31, respectively; or
the parent VRC01-class antibody is VRC-PG04, and the amino acid sequences of the $V_H$ and $V_L$ are at least 90% identical to SEQ ID NOs: 58 and 57, respectively, and wherein the HCDR1, the HCDR2, the HCDR3, the LCDR1, the LCDR2, and the LCDR3 comprise the amino acids sequences set forth as SEQ ID NOs: 59, 60, 61, 62, 63, and 64, respectively.

5. The monoclonal antibody of claim 1, wherein
the $V_H$ and $V_L$ comprise the amino acid sequences set forth as SEQ ID NOs: 16 and 2, respectively;
the $V_H$ and $V_L$ comprise the amino acid sequences set forth as SEQ ID NOs: 17 and 4, respectively;
the $V_H$ and $V_L$ comprise the amino acid sequences set forth as SEQ ID NOs: 18 and 4, respectively;
the $V_H$ and $V_L$ comprise the amino acid sequences set forth as SEQ ID NOs: 19 and 7, respectively; or
the $V_H$ and $V_L$ comprise the amino acid sequences set forth as SEQ ID NOs: 58 and 57, respectively.

6. The monoclonal antibody of claim 1, further comprising a tryptophan, or phenylalanine substitution at Kabat position 54, and/or a two or three-amino acid deletion at the N-terminus of the $V_L$.

7. The monoclonal antibody of claim 6, comprising the tryptophan substitution at Kabat position 54, and/or the three-amino acid deletion at the N-terminus of the $V_L$.

8. The monoclonal antibody of claim 1, wherein the parent VRC01-class antibody is VRC07-523, and the monoclonal antibody further comprises a one amino acid deletion at the N-terminus of the $V_L$.

9. A monoclonal antibody, comprising:
a $V_H$ comprising a HCDR1, a HCDR2, and a HCDR3 of a parent VRC01-class antibody; and
a $V_L$ comprising a LCDR1, a LCDR2, and a LCDR3 of the parent VRC01-class antibody;
wherein the HCDR1, the HCDR2, the HCDR3, the LCDR1, the LCDR2, and the LCDR3 comprise the amino acids sequences set forth as:
SEQ ID NOs: 26, 65, 28, 29, 30, and 31, respectively;
SEQ ID NOs: 72, 120, 74, 75, 76, and 77, respectively;
SEQ ID NOs: 32, 121, 34, 29, 30, and 31, respectively; or
SEQ ID NOs: 32, 122, 34, 29, 30, and 31, respectively,
wherein the monoclonal antibody further comprises a modification of a HFR3 compared to the parent VRC01-class antibody, wherein the modification is a substitution of the amino acids of Kabat positions 72-76 of the parent VRC01-class antibody with the sequence set forth as QLSQDPDDPDWG (SEQ ID NO: 36);
wherein the monoclonal antibody further comprises a tryptophan, or phenylalanine substitution at Kabat position 54, and/or a two or three-amino acid deletion at the N-terminus of the $V_L$;
and wherein the antibody specifically binds to HIV-1 Env and neutralizes HIV-1.

10. The monoclonal antibody of claim 9, wherein the VH and VL of the antibody further comprise amino acid sequences at least 90% identical to:
SEQ ID NOs: 84 and 85, respectively, wherein the HCDR1, the HCDR2, the HCDR3, the LCDR1, the LCDR2, and the LCDR3 comprise SEQ ID NOs: 26, 65, 28, 29, 30, and 31, respectively;
SEQ ID NOs: 105 and 106, respectively, wherein the HCDR 1, the HCDR2, the HCDR3, the LCDR1, the LCDR2, and the LCDR3 comprise SEQ ID NOs: 72, 120, 74, 75, 76, and 77, respectively;
SEQ ID NOs: 105 and 107, respectively, wherein the HCDR1, the HCDR2, the HCDR3, the LCDR1, the LCDR2, and the LCDR3 comprise SEQ ID NOs: 72, 120, 74, 75, 76, and 77, respectively;
SEQ ID NOs: 102 and 103, respectively, wherein the HCDR1, the HCDR2, the HCDR3, the LCDR1, the LCDR2, and the LCDR3 comprise SEQ ID NOs: 32, 121, 34, 29, 30, and 31, respectively; or
SEQ ID NOs: 101 and 103, respectively, wherein the HCDR1, the HCDR2, the HCDR3, the LCDR1, the LCDR2, and the LCDR3 comprise SEQ ID NOs: 32, 122, 34, 29, 30, and 31, respectively.

11. The monoclonal antibody of claim 10, wherein the $V_H$ and $V_L$ comprise the amino acid sequences set forth as:
SEQ ID NOS: 84 and 85, respectively;
SEQ ID NOs: 105 and 106, respectively;
SEQ ID NOs: 105 and 107, respectively;
SEQ ID NOs: 102 and 103, respectively; or
SEQ ID NOs: 101 and 103, respectively.

12. The monoclonal antibody of claim 1, wherein the antibody is an IgG, IgM or IgA.

13. The monoclonal antibody of claim 1, comprising a recombinant constant domain comprising a modification that increases binding to the neonatal Fc receptor.

14. The monoclonal antibody of claim 13, wherein the recombinant constant domain is an IgG1 constant domain comprising M428L and N434S mutations.

15. A monoclonal antibody comprising a heavy chain and a light chain, wherein the heavy and light chains of the antibody comprise the amino acid sequences set forth as SEQ ID NOs: 91 and 92, respectively (VRC01.23-LS), and wherein the antibody specifically binds to HIV-1 Env and neutralizes HIV-1.

16. An antigen binding fragment of the monoclonal antibody of claim 1 comprising the $V_H$ and the $V_L$.

17. The antigen binding fragment of claim 16, wherein the antigen binding fragment is a Fv, Fab, F(ab')$_2$, scFV or a scFV$_2$ fragment.

18. The monoclonal antibody or antigen binding fragment of claim 1, wherein the antibody or antigen binding fragment neutralizes HIV-1 Env with an IC$_{50}$ of less than 0.4 µg/ml.

19. A multispecific antibody comprising the isolated monoclonal antibody of claim 1 or an antigen binding fragment of the monoclonal antibody.

20. The multispecific antibody of claim 19, wherein the multispecific antibody is a bispecific antibody or a trispecific antibody.

21. The monoclonal antibody or antigen binding fragment or multispecific antibody of claim 1, linked to an effector molecule or a detectable marker, optionally wherein the detectable marker is a fluorescent, enzymatic, or radioactive marker.

22. An isolated nucleic acid molecule encoding the monoclonal antibody of claim 1, or the VH and/or the VL of the monoclonal antibody, or an antigen binding fragment of the monoclonal antibody, or a multispecific antibody comprising the isolated monoclonal antibody or antigen binding fragment.

23. The isolated nucleic acid molecule of claim 22, operably linked to a promoter.

24. An expression vector comprising the nucleic acid molecule of claim 22.

25. The expression vector of claim 24, wherein the expression vector is a viral vector.

26. A pharmaceutical composition, comprising:
a therapeutically effective amount of the monoclonal antibody of claim 1, an antigen binding fragment of the monoclonal antibody, a nucleic acid molecule encoding the monoclonal antibody, or an expression vector comprising the nucleic acid molecule; and
a pharmaceutically acceptable carrier.

27. A method of producing an antibody that specifically binds to HIV-1 Env, comprising:
expressing the nucleic acid molecule of claim 22 in a host cell to produce the antibody in the host cell; and
purifying the antibody.

28. A method of detecting an HIV-1 infection in a subject, comprising:
contacting a biological sample from the subject with the monoclonal antibody of claim 1 or an antigen binding fragment of the monoclonal antibody under conditions sufficient to form an immune complex; and
detecting the presence of the immune complex in the sample, wherein the presence of the immune complex in the sample indicates that the subject has the HIV-1 infection.

29. A method of inhibiting an HIV-1 infection in a subject, comprising administering to the subject a therapeutically effective amount of the monoclonal antibody of claim 1, an antigen binding fragment of the monoclonal antibody, a nucleic acid molecule encoding the monoclonal antibody, an expression vector comprising the nucleic acid molecule, or a pharmaceutical composition comprising the monoclonal antibody, antigen binding fragment, nucleic acid molecule, or expression vector, thereby inhibiting the HIV-1 infection.

30. The method of claim 29, wherein the subject has an HIV-1 infection.

* * * * *